US011098016B2

(12) United States Patent
Xu et al.

(10) Patent No.: US 11,098,016 B2
(45) Date of Patent: Aug. 24, 2021

(54) INDAZOLE DERIVATIVES USEFUL AS GLUCAGON RECEPTOR ANTAGONISTS

(71) Applicant: JANSSEN PHARMACEUTICA NV, Beerse (BE)

(72) Inventors: Guozhang Xu, Chesterbrook, PA (US); Micheal Gaul, Yardley, PA (US); Shyh-Ming Yang, Doylestown, PA (US); Tianbao Lu, Churchville, PA (US); Rui Zhang, Belle Mead, NJ (US); Fengbin Song, Doylestown, PA (US)

(73) Assignee: JANSSEN PHARMACEUTICA NV, Beerse (BE)

( * ) Notice: Subject to any disclaimer, the term of this patent is extended or adjusted under 35 U.S.C. 154(b) by 0 days.

(21) Appl. No.: 16/992,062

(22) Filed: Aug. 12, 2020

(65) Prior Publication Data

US 2020/0377462 A1    Dec. 3, 2020

Related U.S. Application Data

(62) Division of application No. 16/242,902, filed on Jan. 8, 2019, now Pat. No. 10,774,048, which is a division of application No. 15/695,129, filed on Sep. 5, 2017, now Pat. No. 10,214,493.

(60) Provisional application No. 62/383,622, filed on Sep. 6, 2016.

(51) Int. Cl.
| | |
|---|---|
| *C07D 409/04* | (2006.01) |
| *C07D 231/56* | (2006.01) |
| *C07D 401/06* | (2006.01) |
| *C07D 405/14* | (2006.01) |
| *C07D 405/04* | (2006.01) |
| *A61K 31/416* | (2006.01) |
| *C07D 403/04* | (2006.01) |

(52) U.S. Cl.
CPC .......... *C07D 231/56* (2013.01); *A61K 31/416* (2013.01); *C07D 401/06* (2013.01); *C07D 403/04* (2013.01); *C07D 405/04* (2013.01); *C07D 405/14* (2013.01); *C07D 409/04* (2013.01)

(58) Field of Classification Search
CPC .. C07D 401/06; C07D 403/04; C07D 409/04; C07D 407/04; C07D 407/14; A61K 31/4439; A61K 31/416
USPC ............. 514/338, 403; 546/275.7; 548/236.5
See application file for complete search history.

(56) References Cited

U.S. PATENT DOCUMENTS

| 5,739,083 A | 4/1998 | Endo et al. |
| 10,000,473 B2 | 6/2018 | Gaul et al. |
| 10,214,493 B2 | 2/2019 | Gaul et al. |

FOREIGN PATENT DOCUMENTS

| WO | WO-00/39088 A1 | 7/2000 |
| WO | WO-2007/024922 | 3/2007 |
| WO | WO-2012/162407 A1 | 11/2012 |
| WO | WO-2014/073904 | 5/2014 |

OTHER PUBLICATIONS

Barger, P.M., "p38 Mitogen-Activated Protein Kinase Activates Peroxisome Proliferator-activated Receptor α", J. Biol. Chem., 2001, pp. 44495-444501, vol. 276.
Barger, P.M., et al., "Deactivation of Peroxisome Proliferator-Activated Receptor-a During Cardiac Hypertrophic Growth", The J. of Clinical Investigation, 2000, pp. 1723-1730, vol. 105.
Bottger, I., et al., "The Effect of Exercise on Glucagon Secretion", J. Clin. Endocrinology and Metabolism, 1972, pp. 117-125, vol. 35.
Conarello, S.L., et al., "Glucagon Receptor Knockout Mice are Resistant to Diet-Induced Obesity and Streptozotocin-Mediated Beta Cell Loss and Hyperglycemia", Diabetologia, 2007, pp. 142-150, vol. 20.
Consoli, A., et al., "Predominant Role of Gluconeogenesis in Increased Hepatic Glucose Production in NIDDM", Diabetes, 1989, pp. 550-557, vol. 38.
Defronzo, R.A., et al., "Fasting Hyperglycemia in Non-Insulin-Dependent Diabetes Mellitus: Contributions of Excessive Hepatic Glucose Production and Impaired Tissue Glucose Uptake", Metabolism, 1989, pp. 387-395, vol. 38.
Gelling, R., et al., "Lower Blood Glucose, Hyperglucagonemia and Pancreatic Alpha Cell Hyperplasia in Glucagon Receptor Knockout Mice", PNAS, 2003, pp. 1438-1443, vol. 100.
*Global Report on Diabetes*, World Health Organization 2016, France.
Gu, W., et al., "Glucagon Receptor Antagonist-Mediated Improvements in Glycemic Control are Dependent on Functional Pancreatic GLP-1 Receptor", Am. J. Physiol. Endocrinol. Metab., 2010, E624-E632, vol. 299.
Guette, C., et al., "Effect of Chronic Glucagon Administration on Lipoprotein Composition in Normally Fed, Fasted and Cholesterol-Fed Rats", Lipids, 1991, pp. 451-458, vol. 26.
Hansen LH, et al., "Glucagon Receptor mRNA Expression in Rat Tissues", Peptides, 1995, pp. 1163-1166, vol. 16.
Hansen, L.H., et al., "The Gly40Ser Mutation in the Human Glucagon Receptor Gene Associated with NIDDM Results in a Receptor with Reduced Sensitivity to Glucagon", Diabetes, 1996, pp. 725-730, vol. 45.
Hippen, A.R., "Glucagon as a Potential Therapy for Ketosis and Fatty Liver", Vet. Clin. North Am. Food Anim. Pract., 2000, pp. 267-282, vol. 16.
Hippen, A.R., et al., "Alleviation of Fatty Liver in Dairy Cows with 14-Day Intravenous Infusions of Glucagon", J. Dairy Sci., 1999, pp. 1139-1152, vol. 82.
International Search Report and Written Opinion issued in related application No. PCT/US2017/050004, dated Nov. 6, 2017.

(Continued)

*Primary Examiner* — Jeffrey H Murray
(74) *Attorney, Agent, or Firm* — Arnall Golden Gregory LLP

(57) ABSTRACT

The present invention is directed to indazole derivatives, pharmaceutical compositions containing them and their use in the treatment and/or prevention of disorders and conditions ameliorated by antagonizing one or more glucagon receptors, including for example metabolic diseases such as Type II diabetes mellitus and obesity.

12 Claims, No Drawings

(56) References Cited

OTHER PUBLICATIONS

Jiang, G., et al., "Glucagon and Regulation of Glucose Metabolism", Am. J. Physiol. Endocrinol. Metab., 2003, pp. 671-678, vol. 284.

Koo, S-H, et al., "The GREB Coactivator TORC2 is a Key Regulator of Fasting Glucose Metabolism", Nature, 2005, pp. 1109-1114, vol. 437.

Liang, Y., et al., "Reduction in Glucagon Receptor Expression by an Antisense Oligonucleotide Ameliorates Diabetic Syndrome in db/db Mice", Diabetes, 2004, pp. 410-417, vol. 53.

Lin et al., "A novel series of indazole-/indole-based glucagon receptor antagonists," Bioorganic & Medicinal Chemistry Letters, 2015, pp. 4143-4147, vol. 25(19).

Longuet, C., et al., "The Glucagon Receptor is Required for the Adaptive Metabolic Response to Fasting", Cell Metabolism, 2008, pp. 359-371, vol. 8.

MacDonald, P.E., et al., "A KATP Channel-Dependent Pathway within α-Cells Regulates Glucagon Release from Both Rodent and Human Islets of Langerhans", PLOS Biology, 2007, pp. 1236-1247, vol. 5.

Mayo K.E., et al., "International Union of Pharmacology. XXXV. The Glucagon Receptor Family.", Pharmacological Reviews, 2003, pp. 167-194, vol. 55.

Parnaud, G., et al., "Proliferation of Sorted Human and Rat Beta Cells", Diabetologia, 2008, pp. 91-100, vol. 51.

Quesada, I., et al., "Physiology of the Pancreatic alpha-cell and Glucagon Secretion: Role in Glucose Homeostasis and Diabetes", Endocrinology, 2008; pp. 5-19, vol. 199.

Reaven, G., et al., "Documentation of Hyperglucagonemia Throughout the Day in Nonobese and Obese Patients with Noninsulin-Dependent Diabetes Mellitus", J Clin Endocrinol Metab, 1987; pp. 106-110, vol. 64.

Rodbell M., et al., "The Glucagon-Sensitive Adenyl Cylcase System in Plasma Membranes of Rat Liver. 3. Binging of Glucagon: Method of Assay and Specificity.", J. Biol. Chem., 1971, pp. 1861-1871, vol. 246.

Rouille, Y., et al., "Role of the Prohormone Convertase PC2 in the processing of Proglucagon to Glucagon", FEBS Letters, 1997, pp. 119-123, vol. 413.

Shah, P. et al., "Lack of Suppression of Glucagon Contributes to Postprandial Hyperglycemia in Subjects with Type 2 Diabetes Mellitus", J Clin Endocrinol Metab. 2000, pp. 4053-4059, vol. 85.

Sloop, K.W., et al., "Hepatic and Glucagon-Like Peptide-1-Mediated Reversal of Diabetes by Glucagon Receptor Antisense Oligonucleotide Inhibitors", J Clin Invest, 2004, pp. 1571-1581, vol. 113.

Trabelsi, F., et al., "Arginine-Induced Pancreatic Hormone Secretion During Exercise in Rats", J. Appl. Physiol., 1996, pp. 2528-2533, vol. 81.

Xiong, Y., et al., "p38 Mitogen-activated Protein Kinase Plays an Inhibitory Role in Hepatic Lipogenesis", J. Biol. Chem., 2007, pp. 4975-4982, vol. 282.

Yu, R. et al., "Nesidioblastosis and Hyperplasia of a Cells, Microglucagonoma, and Nonfunctioning Islet Cell Tumor of the Pancreas", Pancreas, 2008, pp. 428-431, vol. 36.

Zhuo, C., et al., "Homozygous P86S Mutation of the Human Glucagon Receptor Is Associated with Hyperglucagonemia, a Cell Hyperplasia, and Islet Cell Tumor", Pancreas, 2009, pp. 941-946, vol. 38.

INDAZOLE DERIVATIVES USEFUL AS GLUCAGON RECEPTOR ANTAGONISTS

CROSS-REFERENCE TO RELATED APPLICATIONS

This application is a Division of U.S. application Ser. No. 16/242,902, filed Jan. 8, 2019, which is a Division of U.S. application Ser. No. 15/695,129, filed on Sep. 5, 2017, now U.S. Pat. No. 10,214,493, which claims priority to U.S. Provisional Patent Application No. 62/383,622, filed Sep. 6, 2016. The entire contents of these applications are incorporated herein by reference in their entirety.

FIELD OF THE INVENTION

The present invention is directed to indazole derivatives, pharmaceutical compositions containing them and their use in the treatment and/or prevention of disorders and conditions ameliorated by antagonizing one or more glucagon receptors, including for example metabolic diseases such as Type II diabetes mellitus and obesity.

BACKGROUND OF THE INVENTION

The World Health Organization (WHO) reports a worldwide prevalence of 177 million patients with diabetes, a number that is likely to more than double by the year 2030. TYPE II diabetes accounts for approximately 90% of all diabetes cases (World Health Organization, http://www.who.int/diabetes/global-report/en/, updated 2016). Long-term complications of TYPE II diabetes include atherosclerosis, heart disease, stroke, end-stage renal disease, retinopathy leading to blindness, nerve damage, sexual dysfunction, frequent infections and recalcitrant foot ulcers that can result in lower limb amputation. Diabetics are twice as likely to develop cardiovascular disease or have a stroke, 2 to 6 times more likely to have transient ischemic attacks, and 15 to 40 times more likely to require lower-limb amputation compared with the general population. In 2007, the total economic cost of diabetes was estimated to be US $174 billion accounting for 1 of every 8 health care dollars spent in the United States.

Hyperglycemia in patients with TYPE II diabetes mellitus (previously designated non-insulin-dependent diabetes mellitus, or NIDDM) results from a combination of peripheral insulin resistance and inadequate pancreatic insulin secretion. These abnormalities lead to decreased glucose disposal and increased endogenous glucose production. Reversal of these abnormalities, either individually or in combination, can provide an improvement in blood glucose control.

One site that is critically involved in the maintenance of euglycemia is the liver. Glucose production is maintained by the opposing actions of insulin and glucagon on hepatic glucose output. In TYPE II diabetes, the normal glucagon-insulin ratio is disrupted. Studies investigating the relationship between hepatic glucose production and plasma glucagon concentrations have suggested that in patients with TYPE II diabetes, increased glucagon action is largely responsible for the hepatic insulin resistance and increased rates of glucose production (REAVEN, G., et al., "Documentation of Hyperglucagonemia Throughout the Day in Nonobese and Obese Patients with Noninsulin-Dependent Diabetes Mellitus", *J Clin Endocrinol Metab,* 1987; pp 106-110, Vol. 64; and SHAH, P. et al., "Lack of Suppression of Glucagon Contributes to Postprandial Hyperglycemia in Subjects with TYPE II Diabetes Mellitus", *J Clin Endocrinol Metab,* 2000, pp 4053-4059, Vol. 85). Both elevated fasting glucagon levels and impaired suppression of glucagon secretion after meals result in hyperglycemia during the postabsorptive and postprandial states. A positive correlation of plasma glucagon levels and hepatic glucose output and fasting glucose levels has been documented in humans (DEFRONZO, R. A., et al., "Fasting Hyperglycemia in Non-Insulin-Dependent Diabetes Mellitus: Contributions of Excessive Hepatic Glucose Production and Impaired Tissue Glucose Uptake" *Metabolism,* 1989, pp 387-395, Vol. 38; and CONSOLI, A., et al., "Predominant Role of Gluconeogenesis in Increased Hepatic Glucose Production in NIDDM", *Diabetes,* 1989, pp 550-557, Vol. 38). Therefore, glucagon receptor antagonist provide a promising approach in reducing hepatic glucose output as a mechanism in improving glycemia in TYPE II diabetics.

Glucagon is a 29 amino-acid peptide hormone, that is encoded within the proglucagon gene, and is cleaved specifically in pancreatic α-cells by pro-hormone convertase 2 (PC2) (ROUILLE, Y., et al., "Role of the Prohormone Convertase PC2 in the processing of Proglucagon to Glucagon", *FEBS Letters,* 1997, pp 119-123, Vol. 413). Within the proglucagon gene also sequences for the glucagon-like peptide 1 (GLP1), glucagon like peptide 2 (GLP2), oxyntomodulin and glicentin are encoded. Glucagon's secretion from α-cells is tightly regulated by a number of factors with the most important being glucose and insulin (QUESADA, I., et al., "Physiology of the Pancreatic alpha-cell and Glucagon Secretion: Role in Glucose Homeostasis and Diabetes", *Endocrinology,* 2008; pp 5-19, Vol. 199). In the face of low glucose levels specific ATP-sensitive $K^+$ channels are activated generating action potentials and stimulating glucagon secretion (MACDONALD, P. E., et al., "A KATP Channel-Dependent Pathway within α-Cells Regulates Glucagon Release from Both Rodent and Human Islets of Langerhans", *PLOS Biology,* 2007, pp 1236-1247, Vol. 5). Additional stimuli such as amino acids (TRABELSI, F., et al., "Arginine-Induced Pancreatic Hormone Secretion During Exercise in Rats", *J. Appl. Physiol., pp* 2528-2533, Vol. 81) and exercise (BOTTGER, I., et al., "The Effect of Exercise on Glucagon Secretion", *J. Clin. Endocrinology and Metabolism,* 1972, pp 117-125, Vol. 35) are known to stimulate glucagon secretion but the underlying mechanisms are not well understood.

The major physiological role of glucagon is to counteract the action of insulin on hepatic glucose output. Glucagon mediates its effects by binding to and activating the glucagon receptor that was first described by Rodbell and colleagues (RODBELL M., et al., "The Glucagon-Sensitive Adenyl Cylcase System in Plasma Membranes of Rat Liver. 3. Binging of Glucagon: Method of Assay and Specificity.", *J. Biol. Chem.,* 1971, pp 1861-1871, Vol. 246). By sequence homology analysis, glucagon receptor (GCGR) is a member of the Class B family of heptahelical guanosine triphosphate (GTP)-binding protein (G protein) coupled receptors, which includes those for the related peptides, glucagon-like peptide-1 (GLP-1) and glucose-dependent insulinotropic polypeptide (MAYO K. E., et al., "International Union of Pharmacology. XXXV. The Glucagon Receptor Family.", *Pharmacological Reviews,* 2003, pp 167-194, Vol. 55). The receptor is mainly expressed in liver and in kidney with lesser amounts found in heart, adipose tissue, adrenal glands, pancreas, cerebral cortex and gastrointestinal tract (HANSEN L H, et al., "Glucagon Receptor mRNA Expression in Rat Tissues." *Peptides,* 1995, pp 1163-1166, Vol. 16).

The immediate action of glucagon is rapid and transient. Specifically on the liver one of the main actions of glucagon is to regulate glycogenolysis. The molecular basis for the action of the hormone is mediated through activation of its cognate receptor, signal transduction to Gsα subunits and activation of adenylate cyclase resulting in a rise of intracellular cAMP levels, and subsequent activation of protein kinase A (PKA). Activation of PKA results in activation of glycogen phopshorylase and inactivation of glycogen synthase resulting in a net increase in gluconeogenesis via glycogenolysis (JIANG, G., et al., "Glucagon and Regulation of Glucose Metabolism", *Am. J. Physiol. Endocrinol. Metab.*, 2003, pp 671-678, Vol. 284). In addition to glycogenolysis glucagon potentiates gluconeogenesis from precursors such as lactate, alanine, pyruvate and glycerol. The level of regulation appears to be genomic dependent on and in part through cAMP-dependent PKA activation of CREB and transcriptional activation of gluconeogenic genes including PGC1α and PEPCK (KOO, S-H, et al., "The CREB Coactivator TORC2 is a Key Regulator of Fasting Glucose Metabolism", *Nature*, 2005, pp 1109-1114, Vol. 437).

The role of GCGR in glucose homeostasis has been studied in mice lacking the receptor. GCGR null mice show slightly reduced plasma glucose and insulin levels; these mice also have improved glucose tolerance compared to wild type mice (GELLING, R., et al., "Lower Blood Glucose, Hyperglucagonemia and Pancreatic Alpha Cell Hyperplasia in Glucagon Receptor Knockout Mice", *PNAS*, 2003, pp 1438-1443, Vol. 100). The heterozygote mice have no obvious phenotype. When challenged with streptozotocin, the GCGR null mice were resistant to hyperglycemia and pancreatic R-cell destruction suggesting that inhibition of glucagon signaling promotes R-cell survival and function (CONARELLO, S. L., et al., "Glucagon Receptor Knockout Mice are Resistant to Diet-Induced Obesity and Streptozotocin-Mediated Beta Cell Loss and Hyperglycemia", *Diabetologia*, 2007, pp 142-150, Vol. 20). The GCGR null mice did not exhibit hypoglycemia for fasting periods less than 24 hours, and also recovered normally after an insulin challenge (GELLING, R., et al., "Lower Blood Glucose, Hyperglucagonemia and Pancreatic Alpha Cell Hyperplasia in Glucagon Receptor Knockout Mice", *PNAS*, 2003, pp 1438-1443, Vol. 100). This suggests presence of alternate signaling pathways from counter regulatory hormones that offset hypoglycemia in the absence of the glucagon receptor. Liver membranes from GCGR null mice were found to have an increased response to epinephrine-induced cAMP production. Additionally, null animals had a 2-fold increase of fasting corticosterone levels under prolonged fasting (12-14 hours). When fasting was extended post 24 hours, these mice developed severe hypoglycemia.

GCGR null mice exhibit α-cell hyperplasia and increased expression levels of the proglucagon gene (GELLING, R., et al., "Lower Blood Glucose, Hyperglucagonemia and Pancreatic Alpha Cell Hyperplasia in Glucagon Receptor Knockout Mice", *PNAS*, 2003, pp 1438-1443, Vol. 100). The long term safety of chronic blockade of this pathway in humans is not known but it is worth mentioning that rodents have a higher capacity of islet cell replication than humans (PARNAUD, G., et al., "Proliferation of Sorted Human and Rat Beta Cells", *Diabetologia*, 2008, pp 91-100, Vol. 51). Specifically rat β-cells can proliferate when plated on extracellular matrix and this proliferation is further enhanced in the presence of exogenous factors such as liraglutide. In contrast, human β-cells fail to proliferate in vitro. The consequence of α-cell hyperplasia in the null mouse is an increased processing of proglucagon and generation of GLP-1 derived from the pancreas. It is well established that intestinally processed forms of GLP-1 act to inhibit glucagon secretion, increase insulin secretion as well as to improve R-cell glucose sensitivity and R-cell mass. GLP-1 also inhibits food intake via the central nervous system (CNS). Therefore, the elevated pancreatic-derived GLP-1 levels in GCGR null mice may account for the enhancement of glucose-stimulated insulin secretion and glucose tolerance (SLOOP, K. W., et al., "Hepatic and Glucagon-Like Peptide-1-Mediated Reversal of Diabetes by Glucagon Receptor Antisense Oligonucleotide Inhibitors", *J Clin Invest*, 2004, pp 1571-1581, Vol. 113). This has been recently validated in an investigation by Gu et al., in which the authors evaluated a mouse GCGR neutralizing antibody in GLP-1 KO mice and found that the antibody provided no improvement in glucose tolerance during an ipGTT. Based on these results, pancreatic GLP-1 would be a significant contributor to the efficacy of glucagon receptor antagonists in rodents (GU, W., et al., "Glucagon Receptor Antagonist-Mediated Improvements in Glycemic Control are Dependent on Functional Pancreatic GLP-1 Receptor", *Am. J. Physiol. Endocrinol. Metab.*, 2010, pp E624-E632, Vol. 299).

More recent studies have focused on the function of glucagon receptor on hepatic fatty acid oxidation, lipogenesis and hepatocyte survival. Administration of glucagon promotes a hypolipidemic effect in rats (GUETTE, C., et al., "Effect of Chronic Glucagon Administration on Lipoprotein Composition in Normally Fed, Fasted and Cholesterol-Fed Rats", *Lipids*, 1991, pp 451-458, Vol. 26) and resolves steatosis in lactating dairy cows (HIPPEN, A. R., et al., "Alleviation of Fatty Liver in Dairy Cows with 14-Day Intravenous Infusions of Glucagon", *J. Dairy Sci.*, 1999, pp 1139-1152, Vol. 82). In fact, glucagon has been proposed as a treatment of hepatic steatosis (HIPPEN, A. R., "Glucagon as a Potential Therapy for Ketosis and Fatty Liver", *Vet. Clin. North Am. Food Anim. Pract.*, 2000, pp 267-282, Vol. 16). Fasting GCGR null mice for 16 hours produces a phenotype with defects in triglyceride clearance and lipid synthesis. Hepatocytes isolated from these animals have reduced capacity for fatty acid beta-oxidation (LONGUET, C., et al., "The Glucagon Receptor is Required for the Adaptive Metabolic Response to Fasting", *Cell Metabolism*, 2008, pp 359-371, Vol. 8). In some instances but not all (CONARELLO, S. L., et al., "Glucagon Receptor Knockout Mice are Resistant to Diet-Induced Obesity and Streptozotocin-Mediated Beta Cell Loss and Hyperglycemia", *Diabetologia*, 2007, pp 142-150, Vol. 20), steatosis has been observed in the GCGR knockout animals (LONGUET, C., et al., "The Glucagon Receptor is Required for the Adaptive Metabolic Response to Fasting", *Cell Metabolism*, 2008, pp 359-371, Vol. 8) and in pre-clinical models that have been pharmacologically treated with ASO's (LIANG, Y., et al., "Reduction in Glucagon Receptor Expression by an Antisense Oligonucleotide Ameliorates Diabetic Syndrome in db/db Mice", *Diabetes*, 2004, pp 410-417, Vol. 53). The mechanism is PKA independent suggesting alternate glucagon signaling pathways in the liver. The exact mechanism by which glucagon signaling in the liver increases fatty acid oxidation is unclear but part of it appears to be mediated by activation of PPARα via the mitogen activated protein kinase pathway. Glucagon can activate both p38 and ERK1/2 in hepatocytes with the former increasing (BARGER, P. M., et al., "Deactivation of Peroxisome Proliferator-Activated Receptor-α During Cardiac Hypertrophic Growth", *The J. of Clinical Investigation*, 2000, pp 1723-1730, Vol. 105) and the latter decreasing PPARα activity (BARGER, P. M., "p38 Mitogen-Activated Protein Kinase Activates Peroxisome Proliferator-activated Receptor α", *J. Biol. Chem.*, 2001, pp 44495-444501, Vol. 276). The p38 pathway also modulates hepatic lipogenesis with glucagon being inhibitory and insulin stimulatory (XIONG, Y., et al., "p38 Mitogen-activated Protein Kinase Plays an Inhibitory Role in Hepatic Lipogenesis", *J. Biol. Chem.*, 2007, pp 4975-4982, Vol. 282). These observations are suggestive that glucagon signaling is required for the regulation of fatty acid oxidation and synthesis in the liver. The fact that this mechanism is dissociated from the classical glucagon G-protein PKA signal transduction indicates a potential in developing biased antagonists that can favorably affect one signaling arm vs. others thereby alleviating potential concerns of sustained inactivation of all glucagon signaling pathways.

A heterozygous missense mutation Gly40Ser that results in a loss of function has been associated with TYPE II diabetes in a French population (HANSEN, L. H., et al., "The Gly40Ser Mutation in the Human Glucagon Receptor Gene Associated with NIDDM Results in a Receptor with Reduced Sensitivity to Glucagon", *Diabetes*, 1996, pp 725-730, Vol. 45). It is not apparent why this mutation has deleterious effects on glucose control since deletion of GCGR in rodents improves glucose tolerance. Recently a patient with a homozygous mutation, Pro86Ser, was described in the literature. This patient was presented with a benign pancreatic tumor and further examination revealed elevated glucagon levels (~60,000 pg/mL) in the presence of normal fasting glucose and insulin levels (YU, R. et al., "Nesidioblastosis and Hyperplasia of a Cells, Microglucagonoma, and Nonfunctioning Islet Cell Tumor of the Pancreas", *Pancreas*, 2008, pp 428-431, Vol. 36). The tumor was resected and histological examination revealed α-cell hyperplasia. Hyperglucagonemia persisted postoperatively which was suppressed with somatostatin treatment. The glucagon receptor gene was sequenced in this patient where she was identified to be homozygous for the Pro86Ser mutation and further characterization of this mutation revealed a 10-fold loss of functional response (ZHUO, C., et al., "Homozygous P86S Mutation of the Human Glucagon Receptor Is Associated with Hyperglucagonemia, a Cell Hyperplasia, and Islet Cell Tumor", *Pancreas*, 2009, pp 941-946, Vol. 38). The presence of elevated glucagon levels was most likely sufficient to maintain glucagon receptor signaling and euglycemia. Since the homozygous mutation was inherited from both parents it suggests the heterozygous mutation is benign. Since this is a single case report, the association of this mutation to α-cell hyperplasia remains to be determined.

Glucagon antagonism may provide therapeutic agents to control Type II diabetes mellitus, along with traditional diabetes drugs focused on increasing insulin secretion or improving insulin sensitivity. Preclinical data indicate that the anti-diabetic effects of the GCGR antagonist may be related to dual mechanisms including, 1) a reduction of hepatic glucose output that is due to attenuation of glucagon action in the liver, and 2) a secondary increase in active GLP-1, which occurs as a result of increased processing of pre-proglucagon in the pancreas.

Thus there remains a need for novel glucagon antagonists for the treatment of metabolic disorders such as Type II diabetes mellitus and obesity.

SUMMARY OF THE INVENTION

The present invention is directed to indole derivatives, compounds of formula (I)

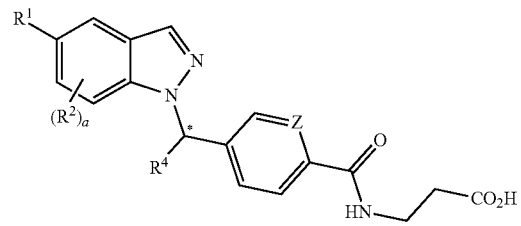

(I)

wherein
R$^1$ is selected from the group consisting of phenyl, —(C$_{1-2}$alkyl)-phenyl, naphthyl, thienyl, benzofuranyl, benzothienyl, indazolyl, quinolinyl, pyrazolyl and pyridyl;
wherein the phenyl, naphthyl, thienyl, benzofuranyl, benzothienyl, indazolyl, quinolinyl, pyrazolyl or pyridyl whether alone or as part of a substituent group is optionally substituted with one to more (preferably one to two) substituents independently selected from the group consisting of halogen, C$_{1-6}$alkyl, fluorinated C$_{1-4}$alkyl, C$_{1-4}$alkoxy and fluorinated C$_{1-4}$alkoxy;
a is in integer from 0 to 2;
each R$^2$ is independently selected from the group consisting of halogen, C$_{1-4}$alkyl, fluorinated C$_{1-4}$alkyl, C$_{1-4}$alkoxy and fluorinated C$_{1-4}$alkoxy;
R$^4$ is selected from the group consisting of C$_{1-6}$alkyl, fluorinated C$_{1-4}$alkyl, —(C$_{1-2}$alkyl)-O—(C$_{1-4}$alkyl), C$_{3-6}$cycloalkyl, —(C$_{1-2}$alkyl)-C$_{3-6}$cycloalkyl, phenyl and —(C$_{1-2}$alkyl)-phenyl;
wherein the phenyl, whether alone or as part of a substituent group is optionally substituted with one or more (preferably one to two) substituents independently selected from the group consisting of halogen, C$_{1-6}$alkyl, fluorinated C$_{1-4}$alkyl, C$_{1-4}$alkoxy and fluorinated C$_{1-4}$alkoxy;
Z is selected from the group consisting of C and N;
and stereoisomers and pharmaceutically acceptable salts thereof.

The present invention is further directed to compounds of formula (II)

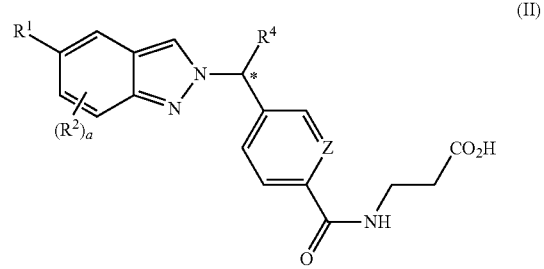

(II)

wherein
R$^1$ is selected from the group consisting of phenyl, —(C$_{1-2}$alkyl)-phenyl, naphthyl, thienyl, benzofuranyl, benzothienyl, indazolyl, quinolinyl, pyrazolyl and pyridyl;
wherein the phenyl, naphthyl, thienyl, benzofuranyl, benzothienyl, indazolyl, quinolinyl, pyrazolyl or pyridyl whether alone or as part of a substituent group is optionally substituted with one or more (preferably one to two) substituents independently selected from the group consisting of halogen, C$_{1-6}$alkyl, fluorinated C$_{1-4}$alkyl, C$_{1-4}$alkoxy and fluorinated C$_{1-4}$alkoxy;

a is in integer from 0 to 2;

each $R^2$ is independently selected from the group consisting of halogen, $C_{1-4}$alkyl, fluorinated $C_{1-4}$alkyl, $C_{1-4}$alkoxy and fluorinated $C_{1-4}$alkoxy;

$R^4$ is selected from the group consisting of $C_{1-6}$alkyl, fluorinated $C_{1-4}$alkyl, —($C_{1-2}$alkyl)-O—($C_{1-4}$alkyl), $C_{3-6}$cycloalkyl, —($C_{1-2}$alkyl)-$C_{3-6}$cycloalkyl, phenyl and —($C_{1-2}$alkyl)-phenyl;

wherein the phenyl, whether alone or as part of a substituent group is optionally substituted with one or more (preferably one to two) substituents independently selected from the group consisting of halogen, $C_{1-6}$alkyl, fluorinated $C_{1-2}$alkyl, $C_{1-4}$alkoxy and fluorinated $C_{1-4}$alkoxy;

Z is selected from the group consisting of C and N;

and stereoisomers and pharmaceutically acceptable salts thereof.

The present invention is further directed to processes for the preparation of the compounds of formula (I) and/or compounds of formula (II). The present invention is further directed to a product prepared according to the process described herein.

Illustrative of the invention is a pharmaceutical composition comprising a pharmaceutically acceptable carrier and the product prepared according to the process described herein. An illustration of the invention is a pharmaceutical composition made by mixing the product prepared according to the process described herein and a pharmaceutically acceptable carrier. Illustrating the invention is a process for making a pharmaceutical composition comprising mixing the product prepared according to the process described herein and a pharmaceutically acceptable carrier.

Exemplifying the invention are methods of treating a disorder ameliorated by antagonizing a glucagon receptor (selected from the group consisting of Type I diabetes, Type II diabetes mellitus, obesity and renal disease (including, but not limited to, renal failure as a complication of diabetes) comprising administering to a subject in need thereof a therapeutically effective amount of any of the compounds or pharmaceutical compositions described above.

In an embodiment, the present invention is directed to a compound of formula (I) or compound of formula (II) for use as a medicament. In another embodiment, the present invention is directed to a compound of formula (I) or compound of formula (II) for use in the treatment of a disorder ameliorated by antagonizing a glucagon receptor (selected from the group consisting of Type I diabetes, Type II diabetes mellitus, obesity and renal disease (including but not limited to, renal failure as a complication of diabetes). In another embodiment, the present invention is directed to a composition comprising a compound of formula (I) or compound of formula (II) for the treatment of a disorder ameliorated by a antagonizing glucagon receptor (selected from the group consisting of Type I diabetes, Type II diabetes mellitus, obesity and renal disease (including but not limited to, renal failure as a complication of diabetes).

Another example of the invention is the use of any of the compounds described herein in the preparation of a medicament for treating: (a) Type I diabetes, (b) Type II diabetes mellitus (c) obesity, (d) renal disease, in a subject in need thereof. In another example, the present invention is directed to a compound as described herein for use in a methods for treating a disorder selected from the group consisting of Type I diabetes, Type II diabetes mellitus, obesity, renal disease (for example renal failure as a complication of diabetes), in a subject in need thereof.

DETAILED DESCRIPTION OF THE INVENTION

The present invention is directed to compounds of formula (I)

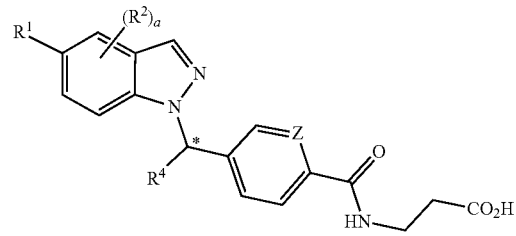

wherein $R^1$, a, $R^2$, $R^4$ and Z are as herein defined. The compounds of the present invention are useful in the treatment of conditions and disorders which are meliorated by antagonizing glucagon receptors, including but not limited to Type I diabetes, Type II diabetes mellitus, obesity and renal disease.

The present invention is further directed to compounds of formula (II)

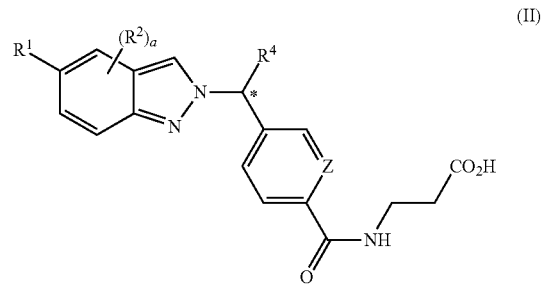

wherein $R^1$, a, $R^2$, $R^4$ and Z are as herein defined. The compounds of the present invention are useful in the treatment of conditions and disorders which are meliorated by antagonizing glucagon receptors, including but not limited to Type I diabetes, Type II diabetes mellitus, obesity and renal disease.

One skilled in the art will recognize that the compounds of formula (I) and the compounds of formula (II) are regio-isomers, wherein the

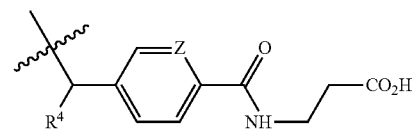

substituent group is alternatively bound to the 1-position nitrogen atom or 2-position nitrogen atom on the indazole core.

One skilled in the art will recognize that some substituent variables (e.g. $R^1$, a, $R^2$, $R^4$, Z, etc.) appear in both the compounds of formula (I) and the compounds of formula (II). One skilled in the art will further recognize that wherein a particular substituent is selected for a given variable for a compound of formula (I), said selection is not intended to limit the scope of said variable for compounds of formula (II). Similarly, the selection of a particular substituent for a given variable for a compound of formula (II), is not intended to limit the scope of said variable for compounds of formula (I).

In certain embodiments, the present invention is directed to compounds of formula (I) and/or compounds of formula (II) wherein the scope (or Markush group of possible substituents) for each variable of the compounds of formula (I) (e.g. a, $R^1$, $R^2$, $R^3$, $R^4$) is independently selected from the lists defined in the embodiments which follow hereinafter.

In another embodiment, the present invention is directed to compounds of formula (I) or compounds of formula (II) wherein $R^1$ is selected from the group consisting of phenyl, —($C_{1-2}$alkyl)-phenyl, naphthyl, thienyl, benzofuranyl, benzothienyl, indazolyl, pyrazolyl and pyridyl; wherein the phenyl, naphthyl, thienyl, benzofuranyl, benzothienyl, indazolyl, pyrazolyl or pyridyl whether alone or as part of a substituent group is optionally substituted with one to more (preferably one to two) substituents independently selected from the group consisting of halogen, $C_{1-6}$alkyl, fluorinated $C_{1-4}$alkyl, $C_{1-4}$alkoxy and fluorinated $C_{1-4}$alkoxy.

In another embodiment, the present invention is directed to compounds of formula (I) or compounds of formula (II) wherein $R^1$ is selected from the group consisting of phenyl, naphthyl, thienyl, pyridyl, benzofuranyl, benzothienyl, indazolyl, pyrazolyl and quinolinyl; wherein the phenyl, naphthyl, benzofuranyl, benzothienyl, indazolyl or pyrazolyl is optionally substituted with one to two substituents independently selected from the group consisting of halogen, $C_{1-6}$alkyl, fluorinated $C_{1-2}$alkyl and $C_{1-2}$alkoxy and fluorinated $C_{1-2}$alkoxy.

In another embodiment, the present invention is directed to compounds of formula (I) or compounds of formula (II) wherein $R^1$ is selected from the group consisting of phenyl naphthyl, thienyl, benzofuranyl, benzothienyl, indazolyl, pyrazolyl and pyridyl; wherein the phenyl, naphthyl, thienyl, benzofuranyl, benzothienyl, indazolyl, pyrazolyl or pyridyl is optionally substituted with one to more (preferably one to two) substituents independently selected from the group consisting of halogen, $C_{1-6}$alkyl, fluorinated $C_{1-4}$alkyl, $C_{1-4}$alkoxy and fluorinated $C_{1-4}$alkoxy.

In another embodiment, the present invention is directed to compounds of formula (I) or compounds of formula (II) wherein $R^1$ is selected from the group consisting of phenyl, naphthyl, thienyl, benzofuranyl, benzothienyl, pyrazolyl, indazolyl and quinolinyl; wherein the phenyl, naphthyl, benzofuranyl, benzothienyl, pyrazolyl or indazolyl is optionally substituted with one to two substituents independently selected from the group consisting of halogen, $C_{1-6}$alkyl, fluorinated $C_{1-2}$alkyl, $C_{1-2}$alkoxy and fluorinated $C_{1-2}$alkoxy.

In another embodiment, the present invention is directed to compounds of formula (I) or compounds of formula (II) wherein $R^1$ is selected from the group consisting of phenyl, 4-fluoro-phenyl, 4-isopropyl-phenyl, 4-t-butylphenyl, 4-methoxy-phenyl, 4-trifluoromethyl-phenyl, 4-trifluoromethoxy-phenyl, 2,4-dichloro-phenyl, 3,5-dichloro-phenyl, 2-chloro-4-methyl-phenyl, 2-methyl-4-chloro-phenyl, 2-methyl-4-trifluoromethyl-phenyl, 2-chloro-4-trifluoromethyl-phenyl, 3-chloro-4-trifluoromethyl-phenyl, 2,4-dimethyl-phenyl, naphth-1-yl, naphth-2-yl, 6-methoxy-naphth-2-yl, pyrid-3-yl, thien-3-yl, benzofuran-2-yl, benzothien-2-yl, 5-fluoro-benzothien-2-yl, 6-fluoro-benzothien-2-yl, 5-methyl-benzothien-2-yl, 6-methyl-benzothien-2-yl, 5-methoxy-benzothien-2-yl, 1-methyl-indazol-5-yl, 1-methyl-indazol-6-yl, 1-methyl-pyrazol-4-yl, 1-isopentyl-pyrazol-4-yl, quinolin-3-yl and quinolin-6-yl.

In another embodiment, the present invention is directed to compounds of formula (I) or compounds of formula (II) wherein $R^1$ is selected from the group consisting of 4-isopropyl-phenyl, 4-t-butylphenyl, 4-trifluoromethyl-phenyl, 2,4-dichloro-phenyl, 2-methyl-4-chloro-phenyl, 2-methyl-4-trifluoromethyl-phenyl, 2-chloro-4-trifluoromethyl-phenyl, naphth-2-yl, benzofuran-2-yl, benzothien-2-yl, 5-fluoro-benzothien-2-yl, 6-methyl-benzothien-2-yl and 5-methoxy-benzothien-2-yl. In another embodiment, the present invention is directed to compounds of formula (I) or compounds of formula (II) wherein $R^1$ is selected from the group consisting of 4-t-butylphenyl, 4-trifluoromethyl-phenyl, 2-methyl-4-chloro-phenyl, 2-methyl-4-trifluoromethyl-phenyl, 2-chloro-4-trifluoromethyl-phenyl and benzothien-2-yl.

In another embodiment, the present invention is directed to compounds of formula (I) or compounds of formula (II) wherein $R^1$ is selected from the group consisting of 2-methyl-4-trifluoromethyl-phenyl and 2-chloro-4-trifluoromethyl-phenyl. In another embodiment, the present invention is directed to compounds of formula (I) or compounds of formula (II) wherein $R^1$ is selected from the group consisting of 2-methyl-4-trifluoromethyl-phenyl and 2-chloro-4-trifluoromethyl-phenyl.

In another embodiment, the present invention is directed to compounds of formula (I) or compounds of formula (II) wherein $R^1$ is selected from the group consisting of 4-t-butyl-phenyl, 2,4-dimethyl-phenyl, 4-trifluoromethyl-phenyl, 2,4-dichloro-phenyl, 2-chloro-4-methyl-phenyl, 2-methyl-4-chloro-phenyl, 2-chloro-4-trifluoromethyl-phenyl, 2-methyl-4-trifluoromethyl-phenyl, 3-chloro-4-trifluoromethyl-phenyl, naphth-2-yl, 6-methoxy-naphth-2-yl, thien-3-yl, benzofuran-2-yl, benzothien-2-yl, 5-fluoro-benzothien-2-yl, 6-fluoro-benzothien-2-yl, 5-methyl-benzothien-2-yl, 1-isopentyl-pyrazol-4-yl, 1-methyl-indazol-5-yl, 1-methyl-indazol-6-yl, quinolin-3-yl and quinolin-6-yl.

In another embodiment, the present invention is directed to compounds of formula (I) or compounds of formula (II) wherein $R^1$ is selected from the group consisting of 4-t-butyl-phenyl, 2,4-dimethyl-phenyl, 4-trifluoromethyl-phenyl, 2,4-dichloro-phenyl, 2-chloro-4-methyl-phenyl, 2-methyl-4-chloro-phenyl, 2-chloro-4-trifluoromethyl-phenyl, 2-methyl-4-trifluoromethyl-phenyl, 3-chloro-4-trifluoromethyl-phenyl, benzofuran-2-yl, benzothien-2-yl, 5-fluoro-benzothien-2-yl and 6-fluoro-benzothien-2-yl. In another embodiment, the present invention is directed to compounds of formula (I) or compounds of formula (II) wherein $R^1$ is selected from the group consisting of 4-t-butyl-phenyl, 2,4-dimethyl-phenyl, 4-trifluoromethyl-phenyl, 2,4-dichloro-phenyl, 2-chloro-4-methyl-phenyl, 2-methyl-4-chloro-phenyl, 2-chloro-4-trifluoromethyl-phenyl, 2-methyl-4-trifluoromethyl-phenyl, 3-chloro-4-trifluoromethyl-phenyl, benzofuran-2-yl, benzothien-2-yl and 5-fluoro-benzothien-2-yl.

In another embodiment, the present invention is directed to compounds of formula (I) or compounds of formula (II) wherein $R^1$ is selected from the group consisting of 4-t-butyl-phenyl, 2,4-dimethyl-phenyl, 4-trifluoromethyl-phenyl, 2,4-dichloro-phenyl, 2-methyl-4-chloro-phenyl, 2-chloro-4-trifluoromethyl-phenyl and 2-methyl-4-trifluoromethyl-phenyl. In another embodiment, the present invention is directed to compounds of formula (I) or compounds of formula (II) wherein $R^1$ is selected from the group consisting of 2,4-dichloro-phenyl, 2-methyl-4-chloro-phenyl, 2-chloro-4-trifluoromethyl-phenyl and 2-methyl-4-trifluoromethyl-phenyl.

In an embodiment, the present invention is directed to compounds of formula (I) or compounds of formula (II) wherein a is an integer from 0 to 2. In another embodiment, the present invention is directed to compounds of formula (I) or compounds of formula (II) wherein a is an integer from 0 to 1. In another embodiment, the present invention is directed to compounds of formula (I) or compounds of formula (II) wherein a is 0. In another embodiment, the present invention is directed to compounds of formula (I) or compounds of formula (II) wherein a is 1. In another embodiment, the present invention is directed to compounds of formula (I) or compounds of formula (II) wherein a is 2.

In another embodiment, the present invention is directed to compounds of formula (I) or compounds of formula (II) wherein each $R^2$ is independently selected from the group consisting of halogen, $C_{1-4}$alkyl, fluorinated $C_{1-2}$alkyl, $C_{1-4}$alkoxy and fluorinated $C_{1-2}$alkoxy. In another embodiment, the present invention is directed to compounds of formula (I) or compounds of formula (II) wherein $R^2$ is selected from the group consisting of halogen, $C_{1-2}$alkyl, fluorinated $C_{1-2}$alkyl and $C_{1-2}$alkoxy.

In another embodiment, the present invention is directed to compounds of formula (I) or compounds of formula (II) wherein $R^2$ is selected from the group consisting of 4-chloro, 4-methyl, 4-methoxy, 4-ethoxy, 4-trifluoromethyl, 6-chloro, 6-methyl and 7-methyl. In another embodiment, the present invention is directed to compounds of formula (I) or compounds of formula (II) wherein $R^2$ is selected from the group consisting of 4-chloro, 4-methyl, 4-methoxy, 4-ethoxy, 6-chloro, 6-methyl and 7-methyl.

In another embodiment, the present invention is directed to compounds of formula (I) or compounds of formula (II) wherein $R^2$ is selected from the group consisting of 4-chloro, 4-methyl, 4-methoxy, 4-ethoxy, 6-chloro and 6-methyl. In another embodiment, the present invention is directed to compounds of formula (I) or compounds of formula (II) wherein $R^2$ is selected from the group consisting of 4-chloro, 4-methyl, 4-methoxy, 4-ethoxy and 6-methyl.

In another embodiment, the present invention is directed to compounds of formula (I) or compounds of formula (II) wherein $R^2$ is selected from the group consisting of 4-methyl, 4-methoxy, 4-ethoxy and 6-methyl. In another embodiment, the present invention is directed to compounds of formula (I) or compounds of formula (II) wherein $R^2$ is selected from the group consisting of 4-methoxy, 4-ethoxy and 6-methyl.

In another embodiment, the present invention is directed to compounds of formula (I) or compounds of formula (II) wherein a is an integer from 1 to 2; and wherein the $R^2$ group is bound at the 4-, 6- and/or 7-positions of the indole core. In another embodiment, the present invention is directed to compounds of formula (I) or compounds of formula (II) wherein a is an integer from 1 to 2, preferably a is 1; and wherein the $R^2$ group is bound at the 4- and/or 6-positions of the indole core.

In another embodiment, the present invention is directed to compounds of formula (I) or compounds of formula (II) wherein $R^4$ is selected from the group consisting of $C_{1-6}$alkyl, fluorinated $C_{1-4}$alkyl, —($C_{1-2}$alkyl)-O—($C_{1-4}$alkyl), $C_{3-6}$cycloalkyl, —($C_{1-2}$alkyl)-$C_{3-6}$cycloalkyl, phenyl and —($C_{1-2}$alkyl)-phenyl; wherein the phenyl, whether alone or as part of a substituent group is optionally substituted with one or to two substituents independently selected from the group consisting of halogen, $C_{1-6}$alkyl, fluorinated $C_{1-2}$alkyl, $C_{1-4}$alkoxy and fluorinated $C_{1-2}$alkoxy.

In another embodiment, the present invention is directed to compounds of formula (I) or compounds of formula (II) wherein $R^4$ is selected from the group consisting of $C_{1-6}$alkyl, fluorinated $C_{1-4}$alkyl, —($C_{1-2}$alkyl)-O—($C_{1-2}$alkyl), $C_{3-6}$cycloalkyl, —($C_{1-2}$alkyl)-$C_{3-6}$cycloalkyl, phenyl and —($C_{1-2}$alkyl)-phenyl; wherein the phenyl is optionally substituted with a substituent selected from the group consisting of halogen, $C_{1-2}$alkyl and fluorinated $C_{1-2}$alkyl.

In another embodiment, the present invention is directed to compounds of formula (I) or compounds of formula (II) wherein $R^4$ is selected from the group consisting of methyl, n-propyl, isobutyl, n-pentyl, isopentyl, 2,2-dimethyl-n-propyl, n-hexyl, 3,3,3-trifluoro-n-propyl, 2-fluoro-2-methyl-n-propyl, 4,4,4-trifluoro-n-butyl, 3,3,4,4,4-pentafluoro-n-butyl, methoxy-ethyl-, cyclopropyl-methyl-, cyclobutyl-methyl-, cyclobutyl-ethyl-, cyclopentyl-methyl-, cyclopentyl-ethyl-, cyclohexyl-methyl-, cyclohexyl-ethyl-, 4-trifluoromethyl-phenyl, phenylethyl- and 4-chloro-phenylethyl-.

In another embodiment, the present invention is directed to compounds of formula (I) or compounds of formula (II) wherein $R^4$ is selected from the group consisting of methyl, n-propyl, isobutyl, n-pentyl, isopentyl, 2,2-dimethyl-n-propyl, n-hexyl, 3,3,3-trifluoro-n-propyl, 3,3,4,4,4-pentafluoro-n-butyl, 2-fluoro-2-methyl-propyl, methoxy-ethyl-, cyclopropyl-methyl, cyclobutyl-methyl-, cyclobutyl-ethyl, cyclopentyl-methyl-, cyclopentyl-ethyl, cyclohexyl, cyclohexyl-methyl-, cyclohexyl-ethyl-, 4-trifluoromethyl-phenyl, phenylethyl- and 4-chloro-phenylethyl-.

In another embodiment, the present invention is directed to compounds of formula (I) or compounds of formula (II) wherein $R^4$ is selected from the group consisting of n-propyl, isobutyl, n-pentyl, isopentyl, 2,2-dimethyl-n-propyl, n-hexyl, 3,3,3-trifluoro-n-propyl, 3,3,4,4,4-pentafluoro-n-butyl, 2-fluoro-2-methyl-propyl, cyclopropyl-methyl, cyclobutyl-methyl-, cyclobutyl-ethyl, cyclopentyl-methyl-, cyclopentyl-ethyl, cyclohexyl, cyclohexyl-methyl-, cyclohexyl-ethyl, phenylethyl- and 4-chloro-phenylethyl-. In another embodiment, the present invention is directed to compounds of formula (I) or compounds of formula (II) wherein $R^4$ is selected from the group consisting of isobutyl, n-pentyl, isopentyl, 2,2-dimethyl-n-propyl, n-hexyl, 3,3,3-trifluoro-n-propyl, cyclobutyl-methyl-, cyclobutyl-ethyl-, cyclopentyl-methyl-, cyclohexyl-methyl- and cyclohexyl-ethyl-.

In another embodiment, the present invention is directed to compounds of formula (I) or compounds of formula (II) wherein $R^4$ is selected from the group consisting of isobutyl, 2,2-dimethyl-n-propyl, n-hexyl, 3,3,3-trifluoro-n-propyl, cyclobutyl-methyl-, cyclopentyl-methyl-, cyclohexyl, cyclohexyl-methyl-, cyclohexyl-ethyl and 4-chloro-phenyl-ethyl. In another embodiment, the present invention is directed to compounds of formula (I) or compounds of formula (II) wherein $R^4$ is selected from the group consisting of isobutyl, 2,2-dimethyl-n-propyl, n-hexyl, 3,3,3-trifluoro-n-propyl, cyclohexyl-methyl- and cyclohexyl-ethyl.

In another embodiment, the present invention is directed to compounds of formula (I) or compounds of formula (II) wherein $R^4$ is selected from the group consisting of isobutyl and 2,2-dimethyl-n-propyl. In another embodiment, the present invention is directed to compounds of formula (I) or compounds of formula (II) wherein $R^4$ is selected from the group consisting of isobutyl and n-hexyl. In another embodiment, the present invention is directed to compounds of formula (I) or compounds of formula (II) wherein $R^4$ is isobutyl.

In another embodiment, the present invention is directed to a compound of formula (I) or compound of formula (II) selected from the group consisting of 3-[[4-[(1R)-1-[5-[2-chloro-4-(trifluoromethyl)phenyl]-4-methoxy-indazol-2-yl]-3-methyl-butyl]benzoyl]amino]propanoic acid; 3-[[4-[(1S)-1-[5-[2-chloro-4-(trifluoromethyl)phenyl]-4-methyl-indazol-2-yl]-3-methyl-butyl]benzoyl]amino]propanoic acid; 3-[[4-[(1S)-1-[5-[2-chloro-4-(trifluoromethyl)phenyl]-6-methyl-indazol-1-yl]-3-methyl-butyl]benzoyl]amino]propanoic acid; 3-[[4-[(1S)-3-methyl-1-[6-methyl-5-[2-methyl-4-(trifluoromethyl)phenyl]indazol-1-yl]butyl]benzoyl]amino]propanoic acid; 3-[[4-[(1S)-3-methyl-1-[6-methyl-5-[2-methyl-4-(trifluoromethyl)phenyl]indazol-2-yl]butyl]benzoyl]amino]propanoic acid; and stereoisomers and pharmaceutically acceptable salts thereof.

In another embodiment, the present invention is directed to a compound of formula (I) selected from the group consisting of 3-[[4-[(1S)-1-[5-[2-chloro-4-(trifluoromethyl)phenyl]-6-methyl-indazol-1-yl]-3-methyl-butyl]benzoyl]amino]propanoic acid; 3-[[4-[(1S)-3-methyl-1-[6-methyl-5-[2-methyl-4-(trifluoromethyl)phenyl]indazol-1-yl]butyl]benzoyl]amino]propanoic acid and stereoisomers and pharmaceutically acceptable salts thereof.

In another embodiment, the present invention is directed to a compound of formula (II) selected from the group consisting of 3-[[4-[(1R)-1-[5-[2-chloro-4-(trifluoromethyl)phenyl]-4-methoxy-indazol-2-yl]-3-methyl-butyl]benzoyl]amino]propanoic acid; 3-[[4-[(1S)-1-[5-[2-chloro-4-(trifluoromethyl)phenyl]-4-methyl-indazol-2-yl]-3-methyl-butyl]benzoyl]amino]propanoic acid; 3-[[4-[(1S)-3-methyl-1-[6-methyl-5-[2-methyl-4-(trifluoromethyl)phenyl]indazol-2-yl]butyl]benzoyl]amino]propanoic acid; and stereoisomers and pharmaceutically acceptable salts thereof.

In certain embodiments, the present invention is directed to compounds of formula (I) wherein the stereo-center denoted with the "*" symbol is present as a mixture of enantiomers, preferably as a racemate. In certain embodiments, the present invention is directed to compounds of formula (I) wherein the stereo-center denoted with the "*" symbol is present in an enantiomeric excess of the corresponding S-configuration. In certain embodiments, the present invention is directed to compounds of formula (I) wherein the stereo-center denoted with the "*" symbol is present in an enantiomeric excess of the corresponding R-configuration.

In certain embodiments, the present invention is directed to compounds of formula (II) wherein the stereo-center denoted with the "*" symbol is present as a mixture of enantiomers, preferably as a racemate. In certain embodiments, the present invention is directed to compounds of formula (II) wherein the stereo-center denoted with the "*" symbol is present in an enantiomeric excess of the corresponding S-configuration. In certain embodiments, the present invention is directed to compounds of formula (II) wherein the stereo-center denoted with the "*" symbol is present in an enantiomeric excess of the corresponding R-configuration.

In certain embodiments, wherein the compound(s) of the present invention are present in an enantiomeric excess of the S- or R-stereo-configuration (at the stereo-center denoted with the "*" symbol), said enantiomeric excess is preferably in the range of from 50% to about 100%, or any amount or range therein, more preferably, the enantiomeric excess is about 75%, more preferably about 80%, more preferably about 90%, more preferably about 95%, more preferably about 97%, more preferably about 98%, more preferably about 99%.

Additional embodiments of the present invention, include those wherein the substituents selected for one or more of the variables defined herein (i.e. $R^1$, a, $R^2$, $R^4$, Z, etc.) are independently selected to be any individual substituent or any subset of substituents selected from the complete list as defined herein.

In another embodiment of the present invention is any single compound or subset of compounds selected from the representative compounds listed in Tables 1-2, below.

Representative compounds of formula (I) of the present invention are as listed in Table 1 below. Representative compounds of formula (II) are as listed in Table 2, below. Unless otherwise noted, wherein a stereogenic center is present in the listed compound, the compound was prepared as a mixture of stereo-configurations. Where a stereogenic center is present and an S* or R* designation is noted, the S* and R* designations indicate that the compound was prepared in an enantiomeric excess of one of the stereo-isomers, although the exact stereo-configuration of the center was not determined. Where a stereogenic center is present and an S or R designation is noted, the S and R designations indicate that the compound was prepared in an enantiomeric excess of one of the stereo-isomers, and further that the exact stereo-configuration of the center was determined to be S or R, as noted.

TABLE 1

Representative Compounds of Formula (I)

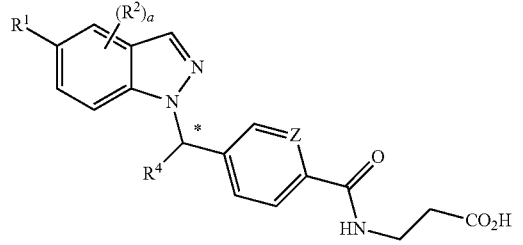

| ID No. | $(R^2)_a$ | $R^1$ | $R^4$ | Z | Stereo |
|---|---|---|---|---|---|
| 1 | a = 0 | 4-t-butyl-phenyl | isobutyl | C | |
| 4 | a = 0 | phenyl | isobutyl | C | |
| 5 | a = 0 | 4-fluoro-phenyl | isobutyl | C | |
| 7 | a = 0 | quinolin-6-yl | isobutyl | C | |
| 9 | a = 0 | 2,4-dichloro-phenyl | isobutyl | C | |
| 10 | a = 0 | 4-trifluoro-methoxy-phenyl | isobutyl | C | |
| 11 | a = 0 | benzofuran-2-yl | 3,3,3-trifluoro-n-propyl | C | |
| 12 | a = 0 | 1-methyl-indazol-5-yl | isobutyl | C | |
| 14 | a = 0 | 2-methyl-4-chloro-phenyl | isobutyl | N | |
| 21 | 4-methyl | 2-methyl-4-trifluoro-methyl-phenyl | isobutyl | C | |
| 23 | a = 0 | 4-t-butyl-phenyl | isopentyl | C | |
| 24 | a = 0 | 4-t-butyl-phenyl | cyclohexyl-methyl- | C | |
| 25 | 6-methyl | 4-trifluoro-methyl-phenyl | isobutyl | C | |
| 29 | 4-methoxy | 2-methyl-4-trifluoro-methyl-phenyl | isobutyl | C | |
| 31 | a = 0 | 4-trifluoro-methyl-phenyl | cyclobutyl-ethyl | C | |
| 32 | a = 0 | 4-trifluoro-methyl-phenyl | cyclopropyl-methyl | C | |
| 36 | a = 0 | 4-t-butyl-phenyl | isobutyl | N | |
| 37 | a = 0 | 4-t-butyl-phenyl | isobutyl | C | R* |

TABLE 1-continued

Representative Compounds of Formula (I)

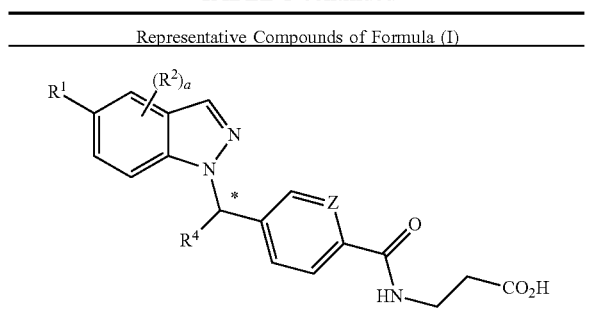

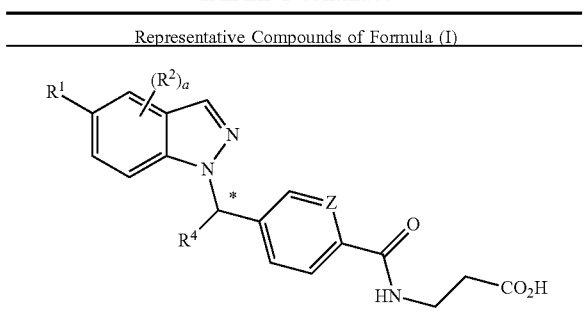

| ID No. | (R²)ₐ | R¹ | R⁴ | Z | Stereo |
|---|---|---|---|---|---|
| 38 | a = 0 | 4-methoxy-phenyl | isobutyl | C | |
| 39 | a = 0 | 2-methyl-4-chloro-phenyl | isobutyl | C | |
| 40 | a = 0 | 2-methyl-4-chloro-phenyl | 3,3,3-trifluoro-n-propyl | C | |
| 41 | a = 0 | 2-chloro-4-trifluoro-methyl-phenyl | isobutyl | C | |
| 43 | a = 0 | 2-chloro-4-trifluoro-methyl-phenyl | isobutyl | N | |
| 44 | a = 0 | 2-methyl-4-trifluoro-methyl-phenyl | 3,3,3-trifluoro-n-propyl | C | |
| 45 | a = 0 | 3,5-dichloro-phenyl | 3,3,3-trifluoro-n-propyl | C | |
| 46 | a = 0 | quinolin-3-yl | isobutyl | C | |
| 47 | 4-methyl | 4-t-butyl-phenyl | isobutyl | C | |
| 48 | a = 0 | benzothien-2-yl | isobutyl | N | |
| 55 | 4-methyl | 2-chloro-4-trifluoro-methyl-phenyl | isobutyl | C | |
| 56 | a = 0 | 4-t-butyl-phenyl | n-propyl | C | |
| 59 | a = 0 | 4-trifluoro-methyl-phenyl | isopentyl | C | |
| 60 | a = 0 | 4-trifluoro-methyl-phenyl | n-propyl | C | |
| 62 | a = 0 | 6-methyl-benzothien-2-yl | isobutyl | C | |
| 67 | 4-chloro | 4-trifluoro-methyl-phenyl | isobutyl | C | |
| 68 | a = 0 | 4-t-butyl-phenyl | methyl | C | |
| 70 | a = 0 | 4-trifluoro-methyl-phenyl | isobutyl | C | |
| 71 | a = 0 | naphth-2-yl | isobutyl | C | |
| 72 | 7-methyl | 4-t-butyl-phenyl | isobutyl | N | |
| 73 | a = 0 | benzothien-2-yl | isobutyl | C | |
| 74 | a = 0 | 4-trifluoro-methyl-phenyl | isobutyl | N | |
| 75 | a = 0 | 4-trifluoro-methyl-phenyl | 3,3,3-trifluoro-n-propyl | C | |
| 76 | a = 0 | 4-trifluoro-methoxy-phenyl | 3,3,3-trifluoro-n-propyl | C | |
| 77 | a = 0 | benzofuran-2-yl | isobutyl | C | |
| 79 | a = 0 | benzofuran-2-yl | isobutyl | N | |
| 84 | a = 0 | 2-methyl-4-trifluoro-methyl-phenyl | isobutyl | C | |
| 85 | a = 0 | 2-chloro-4-trifluoro-methyl-phenyl | isobutyl | C | R |
| 88 | a = 0 | 4-t-butyl-phenyl | n-pentyl | C | |
| 89 | a = 0 | 4-trifluoro-methyl-phenyl | n-pentyl | C | |
| 90 | a = 0 | 2-chloro-4-trifluoro-methyl-phenyl | isobutyl | C | S |
| 93 | 6-methyl | 2-methyl-4-trifluoro-methyl-phenyl | isobutyl | C | |
| 94 | 6-methyl | 2-chloro-4-trifluoro-methyl-phenyl | isobutyl | C | |
| 99 | 4-methoxy | 2-methyl-4-chloro-phenyl | isobutyl | C | |
| 100 | a = 0 | 4-trifluoro-methyl-phenyl | 3,3,4,4,4-pentafluoro-n-butyl | C | |
| 101 | a = 0 | 4-trifluoro-methyl-phenyl | 4-trifluoro-methyl-phenyl | C | |
| 102 | 6-chloro | 2-methyl-4-chloro-phenyl | isobutyl | N | |
| 103 | 4-methoxy | 2-chloro-4-trifluoro-methyl-phenyl | isobutyl | C | |
| 105 | 4-methyl | 2-chloro-4-methyl-phenyl | isobutyl | C | |
| 111 | a = 0 | 3-chloro-4-trifluoro-methyl-phenyl | 3,3,3-trifluoro-n-propyl | C | |
| 112 | a = 0 | 2,4-dichloro-phenyl | 3,3,3-trifluoro-n-propyl | C | |
| 113 | a = 0 | 2,4-dichloro-phenyl | isobutyl | N | |
| 114 | a = 0 | 4-trifluoro-methoxy-phenyl | isobutyl | N | |
| 115 | a = 0 | benzothien-2-yl | 3,3,3-trifluoro-n-propyl | C | |
| 116 | a = 0 | 1-methyl-indazol-6-yl | isobutyl | C | |
| 118 | a = 0 | 3,5-dichloro-phenyl | isobutyl | C | |
| 119 | a = 0 | 3,5-dichloro-phenyl | isobutyl | N | |
| 123 | a = 0 | 1-isopentyl-pyrazol-4-yl | isobutyl | C | |
| 126 | a = 0 | 6-fluoro-benzothien-2-yl | isobutyl | C | |
| 127 | 4-methyl | 2,4-dichloro-phenyl | isobutyl | C | |
| 128 | a = 0 | 4-t-butyl-phenyl | n-hexyl | C | |
| 131 | a = 0 | 4-trifluoro-methyl-phenyl | cyclohexyl-methyl | C | |
| 132 | a = 0 | 5-methoxy-benzothien-2-yl | isobutyl | C | |
| 135 | 4-chloro | 2-methyl-4-trifluoro-methyl-phenyl | isobutyl | C | |
| 141 | 4-chloro | 2-chloro-4-trifluoro-methyl-phenyl | isobutyl | C | |
| 142 | a = 0 | 4-trifluoro-methyl-phenyl | phenyl-ethyl | C | |
| 144 | a = 0 | 4-trifluoro-methyl-phenyl | 4-chloro-phenyl-ethyl | C | |
| 145 | 4-methoxy | 2-methyl-4-trifluoro-methyl-phenyl | isobutyl | C | R |
| 146 | 6-chloro | 2-methyl-4-trifluoro-methyl-phenyl | isobutyl | N | |
| 151 | a = 0 | 2-methyl-4-chloro-phenyl | 2,2-dimethyl-n-propyl | C | |
| 157 | a = 0 | 2-methyl-4-chloro-phenyl | cyclohexyl-ethyl | C | |
| 158 | 6-methyl | 5-fluoro-benzothien-2-yl | isobutyl | C | |
| 159 | a = 0 | 4-trifluoro-methyl-phenyl | n-hexyl | C | |
| 163 | a = 0 | 4-t-butyl-phenyl | isobutyl | C | S* |
| 164 | a = 0 | 1-methyl-pyrazol-4-yl | isobutyl | C | |
| 165 | a = 0 | naphth-1-yl | isobutyl | C | |
| 167 | a = 0 | 2-chloro-4-trifluoro-methyl-phenyl | 3,3,3-trifluoro-n-propyl | C | |
| 172 | a = 0 | 5-fluoro-benzothien-2-yl | isobutyl | C | |
| 173 | a = 0 | 4-trifluoro-methyl-phenyl | cyclohexyl-ethyl | C | |
| 174 | 6-methyl | benzothien-2-yl | isobutyl | C | |
| 175 | a = 0 | 4-trifluoro-methyl-phenyl | cyclopentyl-ethyl | C | |
| 177 | 4-methyl | 2,4-dimethyl-phenyl | isobutyl | C | |
| 179 | 4-ethoxy | 2-chloro-4-trifluoro-methyl-phenyl | isobutyl | N | |
| 183 | a = 0 | 2-methyl-4-chloro-phenyl | cyclohexyl-methyl- | N | |

TABLE 1-continued

Representative Compounds of Formula (I)

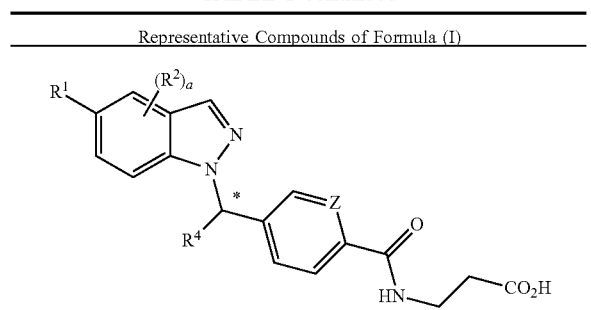

| ID No. | (R²)ₐ | R¹ | R⁴ | Z | Stereo |
|---|---|---|---|---|---|
| 185 | a = 0 | 4-trifluoro-methyl-phenyl | 2-fluoro-2-methyl-n-propyl | C | |
| 192 | 4-methoxy | 2-methyl-4-trifluoro-methyl-phenyl | isobutyl | C | S |
| 193 | a = 0 | 4-trifluoro-methyl-phenyl | n-hexyl | N | |
| 194 | a = 0 | 2-methyl-4-chloro-phenyl | cyclohexyl-methyl- | C | |
| 196 | 6-methyl | 2-chloro-4-trifluoro-methyl-phenyl | isobutyl | C | S |
| 197 | 4-ethoxy | 2-methyl-4-trifluoro-methyl-phenyl | isobutyl | N | |
| 198 | 4-methyl | 2-chloro-4-trifluoro-methyl-phenyl | isobutyl | N | |
| 199 | a = 0 | 4-trifluoro-methyl-phenyl | cyclopentyl-methyl | N | |
| 201 | 4-methoxy | 2-chloro-4-trifluoro-methyl-phenyl | isobutyl | C | S |
| 208 | a = 0 | 4-trifluoro-methyl-phenyl | cyclopentyl-methyl | C | |
| 209 | a = 0 | 4-trifluoro-methyl-phenyl | cyclohexyl-ethyl | N | |
| 210 | a = 0 | 2-methyl-4-chloro-phenyl | cyclohexyl-ethyl | N | |
| 213 | 4-methoxy | 2-methyl-4-trifluoro-methyl-phenyl | isobutyl | N | |
| 214 | 6-methyl | 2-methyl-4-trifluoro-methyl-phenyl | isobutyl | N | |
| 219 | a = 0 | pyrid-3-yl | isobutyl | C | |
| 220 | a = 0 | 4-isopropyl-phenyl | isobutyl | C | |
| 221 | a = 0 | thien-3-yl | isobutyl | C | |
| 222 | a = 0 | 6-methoxy-naphth-2-yl | isobutyl | C | |
| 223 | a = 0 | 2-chloro-4-fluoro-phenyl | 3,3,3-trifluoro-n-propyl | C | |
| 229 | 6-methyl | 4-trifluoro-methyl-phenyl | isobutyl | C | R |
| 230 | a = 0 | 5-methyl-benzothien-2-yl | isobutyl | C | |
| 231 | a = 0 | 4-trifluoro-methyl-phenyl | 2,2-dimethyl-n-propyl | C | |
| 234 | a = 0 | 4-trifluoro-methyl-phenyl | 4,4,4-trifluoro-n-butyl | C | |
| 237 | a = 0 | 4-trifluoro-methyl-phenyl | 2,2-dimethyl-n-propyl | N | |
| 238 | a = 0 | 2-methyl-4-chloro-phenyl | 2,2-dimethyl-n-propyl | N | |
| 239 | a = 0 | 4-trifluoro-methyl-phenyl | cyclobutyl-methyl | C | |
| 241 | 4-methyl | 2-chloro-4-trifluoro-methyl-phenyl | isobutyl | C | S |
| 243 | a = 0 | 4-trifluoro-methyl-phenyl | methoxy-ethyl | C | |
| 244 | a = 0 | 2-methyl-4-chloro-phenyl | n-hexyl | N | |
| 245 | a = 0 | 2-methyl-4-chloro-phenyl | n-hexyl | C | |
| 250 | 4-methoxy | 2-chloro-4-trifluoro-methyl-phenyl | isobutyl | N | |
| 251 | a = 0 | 4-trifluoro-methyl-phenyl | cyclobutyl-methyl | N | |
| 253 | 6-methyl | 2-methyl-4-trifluoro-methyl-phenyl | isobutyl | C | S |
| 255 | a = 0 | 4-trifluoro-methyl-phenyl | cyclohexyl-methyl- | N | |
| 258 | 4-methyl | 2-methyl-4-trifluoro-methyl-phenyl | isobutyl | N | |
| 259 | 6-methyl | 2-chloro-4-trifluoro-methyl-phenyl | isobutyl | N | |
| 261 | 6-chloro | 2-methyl-4-trifluoro-methyl-phenyl | isobutyl | C | |
| 262 | a = 0 | 2-methyl-4-trifluoro-methyl-phenyl | isobutyl | N | |
| 263 | 4-trifluoro-methyl | 2-chloro-4-trifluoro-methyl | isobutyl | N | |

TABLE 2

Representative Compounds of Formula (II)

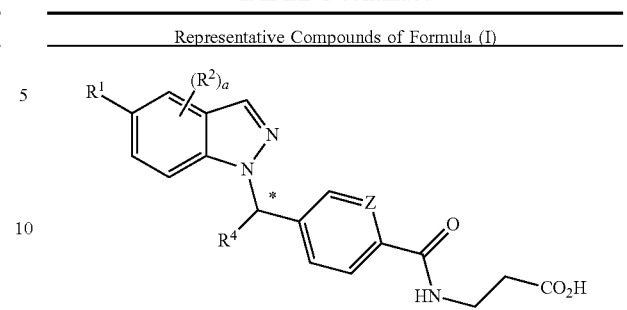

| ID No. | (R²)ₐ | R¹ | R⁴ | Z | Stereo |
|---|---|---|---|---|---|
| 2 | a = 0 | 4-t-butyl-phenyl | isobutyl | N | |
| 8 | a = 0 | 2-methyl-4-chloro-phenyl | 3,3,3-trifluoro-n-propyl | C | |
| 13 | a = 0 | benzofuran-2-yl | isobutyl | C | |
| 15 | a = 0 | naphth-2-yl | isobutyl | C | |
| 16 | a = 0 | 2-chloro-4-trifluoro-methyl-phenyl | 3,3,3-trifluoro-n-propyl | C | |
| 17 | a = 0 | 1-isopentyl-pyrazol-4-yl | isobutyl | C | |
| 18 | 4-methyl | 2-chloro-4-trifluoro-methyl-phenyl | isobutyl | C | |
| 19 | a = 0 | 2-methyl-4-trifluoro-methyl-phenyl | isobutyl | N | |
| 20 | 4-methyl | 2-methyl-4-chloro-phenyl | isobutyl | C | |
| 22 | a = 0 | 4-t-butyl-phenyl | n-propyl | C | |
| 26 | a = 0 | 4-trifluoro-methyl-phenyl | n-hexyl | C | |
| 27 | a = 0 | 4-trifluoro-methyl-phenyl | isopentyl | C | |
| 28 | a = 0 | 5-methyl-benzothien-2-yl | isobutyl | C | |
| 30 | 6-chloro | 2-methyl-4-trifluoro-methyl-phenyl | isobutyl | C | |
| 33 | 6-chloro | 2-chloro-4-trifluoro-methyl-phenyl | isobutyl | N | |
| 34 | a = 0 | 4-t-butyl-phenyl | isobutyl | C | |
| 49 | a = 0 | 1-methyl-indazol-5-yl | isobutyl | C | |

TABLE 2-continued

Representative Compounds of Formula (II)

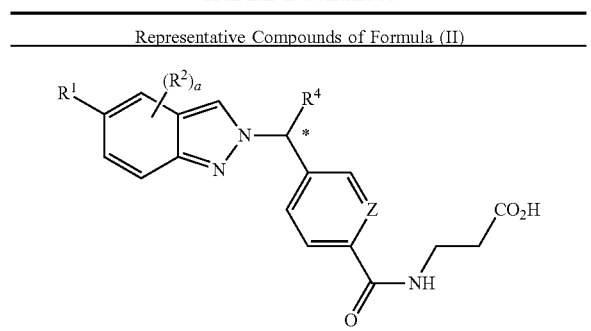

| ID No. | (R²)ₐ | R¹ | R⁴ | Z | Stereo |
|---|---|---|---|---|---|
| 50 | a = 0 | 2-methyl-4-trifluoro-methyl-phenyl | 3,3,3-trifluoro-n-propyl | C | |
| 51 | a = 0 | thien-3-yl | isobutyl | C | |
| 53 | a = 0 | 2-chloro-4-trifluoro-methyl-phenyl | isobutyl | N | |
| 54 | 4-methyl | 2-methyl-4-trifluoro-methyl-phenyl | isobutyl | C | |
| 57 | a = 0 | 6-fluoro-benzothien-2-yl | isobutyl | C | |
| 61 | a = 0 | 4-trifluoro-methyl-phenyl | 2,2-dimethyl-n-propyl | C | |
| 63 | 6-methyl | 2-methyl-4-trifluoro-methyl-phenyl | isobutyl | C | |
| 64 | 4-methoxy | 2-methyl-4-chloro-phenyl | isobutyl | C | |
| 65 | a = 0 | 4-trifluoro-methyl-phenyl | 3,3,4,4,4-pentafluoro-n-butyl | C | |
| 66 | a = 0 | 4-trifluoro-methyl-phenyl | 4-trifluoro-methyl-phenyl | C | |
| 78 | 4-methyl | 4-t-butyl-phenyl | isobutyl | C | |
| 80 | a = 0 | 1-methyl-indazol-6-yl | isobutyl | C | |
| 82 | a = 0 | 6-methoxy-naphth-2-yl | isobutyl | C | |
| 83 | a = 0 | 2,4-dichloro-phenyl | isobutyl | N | |
| 86 | a = 0 | 4-t-butyl-phenyl | n-hexyl | C | |
| 91 | a = 0 | 4-trifluoro-methyl-phenyl | n-propyl | C | |
| 92 | a = 0 | 4-trifluoro-methyl-phenyl | cyclohexyl-methyl- | C | |
| 95 | 6-methyl | 2-chloro-4-trifluoro-methyl-phenyl | isobutyl | C | |
| 96 | a = 0 | benzothien-2-yl | isobutyl | N | |
| 98 | a = 0 | 2-chloro-4-trifluoro-methyl-phenyl | cyclohexyl | C | |
| 104 | a = 0 | 4-trifluoro-methyl-phenyl | phenyl-ethyl | C | |
| 108 | 7-methyl | 4-t-butyl-phenyl | isobutyl | N | |
| 117 | a = 0 | quinolin-3-yl | isobutyl | C | |
| 120 | a = 0 | benzothien-2-yl | isobutyl | C | |
| 121 | a = 0 | quinolin-6-yl | isobutyl | C | |
| 122 | a = 0 | benzothien-2-yl | 3,3,3-trifluoro-n-propyl | C | |
| 129 | a = 0 | 5-fluoro-benzothien-2-yl | isobutyl | C | |
| 133 | a = 0 | 4-trifluoro-methyl-phenyl | cyclohexyl-ethyl | C | |
| 134 | 6-methyl | 4-trifluoro-methyl-phenyl | isobutyl | C | |
| 136 | a = 0 | 4-trifluoro-methyl-phenyl | cyclohexyl | C | |
| 137 | 4-methoxy | 2-chloro-4-trifluoro-methyl-phenyl | isobutyl | C | |
| 138 | a = 0 | 4-trifluoro-methyl-phenyl | cyclobutyl-ethyl | C | |
| 139 | a = 0 | 4-trifluoro-methyl-phenyl | cyclopropyl-methyl | C | |
| 140 | 6-chloro | 2-methyl-4-chloro-phenyl | isobutyl | N | |
| 143 | 4-methyl | 2,4-dimethyl-phenyl | isobutyl | C | |
| 147 | 4-chloro | 4-trifluoro-methyl-phenyl | isobutyl | C | |
| 148 | 4-methyl | 2-chloro-4-methyl-phenyl | isobutyl | C | |
| 149 | 4-methyl | 3-chloro-4-trifluoro-methyl-phenyl | isobutyl | C | |
| 150 | 4-methoxy | 2-chloro-4-trifluoro-methyl-phenyl | isobutyl | C | S |
| 152 | a = 0 | 4-trifluoro-methyl-phenyl | n-hexyl | N | |
| 153 | a = 0 | 2-methyl-4-chloro-phenyl | cyclohexyl-methyl- | C | |
| 154 | 4-methyl | 2-chloro-4-trifluoro-methyl-phenyl | isobutyl | N | |
| 155 | 4-methyl | 2-methyl-4-trifluoro-methyl-phenyl | isobutyl | N | |
| 156 | 4-methyl | 2-methyl-4-trifluoro-methyl-phenyl | isobutyl | C | S |
| 160 | a = 0 | 4-trifluoro-methyl-phenyl | cyclopentyl-ethyl | C | |
| 161 | a = 0 | 4-t-butyl-phenyl | methyl | C | |
| 168 | a = 0 | 2-methyl-4-chloro-phenyl | isobutyl | C | |
| 170 | a = 0 | 4-t-butyl-phenyl | n-pentyl | C | |
| 171 | a = 0 | 4-trifluoro-methyl-phenyl | n-pentyl | C | |
| 176 | 6-chloro | 2-methyl-4-trifluoro-methyl-phenyl | isobutyl | N | |
| 178 | 4-methoxy | 2-chloro-4-trifluoro-methyl-phenyl | isobutyl | N | |
| 180 | 4-methyl | 2-chloro-4-trifluoro-methyl-phenyl | isobutyl | C | S |
| 182 | 4-ethoxy | 2,4-dimethyl-phenyl | isobutyl | N | |
| 184 | a = 0 | 2-methyl-4-chloro-phenyl | cyclohexyl-ethyl | N | |
| 186 | a = 0 | 4-trifluoro-methyl-phenyl | cyclohexyl-ethyl | N | |
| 187 | 6-methyl | 2-methyl-4-trifluoro-methyl-phenyl | isobutyl | N | |
| 188 | a = 0 | 4-trifluoro-methyl-phenyl | cyclopentyl-methyl | N | |
| 189 | a = 0 | 2-methyl-4-trifluoro-methyl-phenyl | isobutyl | C | |
| 190 | 4-methyl | 2,4-dichloro-phenyl | isobutyl | C | |
| 191 | 4-methoxy | 2-chloro-4-trifluoro-methyl-phenyl | isobutyl | C | R |
| 195 | a = 0 | 2-methyl-4-chloro-phenyl | 2,2-dimethyl-n-propyl | C | |
| 200 | a = 0 | 4-trifluoro-methyl-phenyl | 4-chloro-phenyl-ethyl | C | |
| 202 | a = 0 | 4-trifluoro-methyl-phenyl | methoxy-ethyl | C | |
| 203 | a = 0 | 2-methyl-4-chloro-phenyl | n-hexyl | N | |
| 204 | a = 0 | 2-methyl-4-chloro-phenyl | n-hexyl | C | |
| 205 | 4-ethoxy | 2-chloro-4-trifluoro-methyl-phenyl | isobutyl | N | |
| 207 | 4-ethoxy | 2-methyl-4-trifluoro-methyl-phenyl | isobutyl | N | |
| 211 | a = 0 | 4-trifluoro-methyl-phenyl | cyclobutyl-methyl | C | |
| 212 | a = 0 | 4-trifluoro-methyl-phenyl | 2,2-dimethyl-n-propyl | N | |

TABLE 2-continued

Representative Compounds of Formula (II)

| ID No. | (R²)ₐ | R¹ | R⁴ | Z | Stereo |
|---|---|---|---|---|---|
| 215 | a = 0 | 4-trifluoro-methyl-phenyl | cyclobutyl-methyl | N | |
| 224 | a = 0 | 2,4-dichloro-phenyl | 3,3,3-trifluoro-n-propyl | C | |
| 225 | a = 0 | 2-chloro-4-trifluoro-methyl-phenyl | isobutyl | C | |
| 226 | a = 0 | 2,4-dichloro-phenyl | isobutyl | C | |
| 227 | a = 0 | 4-t-butyl-phenyl | isopentyl | C | |
| 228 | a = 0 | 4-t-butyl-phenyl | cyclohexyl-methyl- | C | |
| 232 | 4-chloro | 2-methyl-4-trifluoro-methyl-phenyl | isobutyl | C | |
| 233 | 4-methoxy | 2-methyl-4-trifluoro-methyl-phenyl | isobutyl | C | |
| 235 | 4-trifluoro-methyl | 2-chloro-4-trifluoro-methyl-phenyl | isobutyl | N | |
| 236 | 4-methoxy | 2-methyl-4-trifluoro-methyl-phenyl | isobutyl | N | |
| 240 | a = 0 | 4-trifluoro-methyl-phenyl | cyclohexyl-methyl- | N | |
| 242 | 6-methyl | 2-chloro-4-trifluoro-methyl-phenyl | isobutyl | N | |
| 246 | 4-trifluoro-methyl | 2-methyl-4-trifluoro-methyl-phenyl | isobutyl | N | |
| 247 | a = 0 | 2-methyl-4-chloro-phenyl | cyclohexyl-ethyl | C | |
| 248 | 6-methyl | 2-methyl-4-trifluoro-methyl-phenyl | isobutyl | C | S |
| 249 | a = 0 | 2-methyl-4-chloro-phenyl | cyclohexyl-methyl- | N | |
| 252 | a = 0 | 2-methyl-4-chloro-phenyl | isobutyl | N | |
| 254 | a = 0 | 4-trifluoro-methyl-phenyl | cyclopentyl-methyl | C | |
| 256 | a = 0 | 4-trifluoro-methyl-phenyl | 2-fluoro-2-methyl-n-propyl | C | |
| 257 | a = 0 | 2-methyl-4-chloro-phenyl | 2,2-dimethyl-n-propyl | N | |
| 260 | a = 0 | benzofuran-2-yl | isobutyl | N | |

Definitions

As used herein, "halogen" shall mean chlorine, bromine, fluorine and iodine. Preferably, the halogen is selected from the group consisting of chlorine, bromine and fluorine.

As used herein, the term "$C_{X-Y}$alkyl" wherein X and Y are integers, whether used alone or as part of a substituent group, include straight and branched chains containing between X and Y carbon atoms. For example, $C_{1-4}$alkyl radicals include straight and branched chains of between 1 and 4 carbon atoms, including methyl, ethyl, propyl, isopropyl, butyl, isobutyl, sec-butyl and t-butyl.

One skilled in the art will recognize that the term "—($C_{X-Y}$alkyl)-", wherein X and Y are integers, shall denote any straight or branched $C_{X-Y}$alkyl carbon chain as herein defined, wherein said $C_{X-Y}$alkyl chain is divalent and is further bound through two points of attachment, preferably through two terminal carbon atoms. For example, the term "—($C_{1-2}$alky)-" shall include —$CH_2$— and —$CH_2CH_2$—.

As used herein, unless otherwise noted, the term "fluorinated $C_{1-4}$alkyl" shall mean any $C_{1-4}$alkyl group as defined above substituted with at least one fluorine atom, Suitable examples include but are not limited to —$CF_3$, —$CH_2$—$CF_3$, —$CF_2$—$CF_2$—$CF_2$—$CF_3$, and the like.

As used herein, unless otherwise noted, "$C_{1-4}$alkoxy" shall denote an oxygen ether radical of the above described straight or branched chain alkyl groups containing one to four carbon atoms. For example, methoxy, ethoxy, n-propoxy, isopropoxy, sec-butoxy, t-butoxy, and the like.

As used herein, unless otherwise noted, the term "fluorinated $C_{1-4}$alkoxy" shall mean any $C_{1-4}$alkoxy group as defined above substituted with at least one fluoro atom. Suitable examples include but are not limited to —$OCF_3$, —$OCH_2$—$CF_3$, —$OCF_2$—$CF_2$—$CF_2$—$CF_3$, and the like.

As used herein, unless otherwise noted, the term "$C_{X-Y}$cycloalkyl", wherein X and Y are integers, shall mean any stable X- to Y-membered monocyclic, saturated ring system. For example, the term "$C_{3-6}$cycloalkyl" shall include cyclopropyl, cyclobutyl, cyclopentyl and cyclohexyl.

When a particular group is "substituted" (e.g. alkyl, cycloalkyl, phenyl, etc.), that group may have one or more substituents, preferably from one to five substituents, more preferably from one to three substituents, most preferably from one to two substituents, independently selected from the list of substituents.

With reference to substituents, the term "independently" means that when more than one of such substituents is possible, such substituents may be the same or different from each other.

As used herein, the notation "*" shall denote the presence of a stereogenic center.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Preferably, wherein the compound is present as an enantiomer, the enantiomer is present at an enantiomeric excess of greater than or equal to about 80%, more preferably, at an enantiomeric excess of greater than or equal to about 90%, more preferably still, at an enantiomeric excess of greater than or equal to about 95%, more preferably still, at an enantiomeric excess of greater than or equal to about 98%, most preferably, at an enantiomeric excess of greater than or equal to about 99%. Similarly, wherein the compound is present as a diastereomer, the diastereomer is present at an diastereomeric excess of greater than or equal to about 80%, more preferably, at an diastereomeric excess of greater than or equal to about 90%, more preferably still, at an diastereomeric excess of greater than or equal to about 95%, more preferably still, at an diastereomeric excess of greater than or equal to about 98%, most preferably, at an diastereomeric excess of greater than or equal to about 99%.

Furthermore, some of the crystalline forms for the compounds of the present invention may exist as polymorphs and as such are intended to be included in the present invention. In addition, some of the compounds of the present invention may form solvates with water (i.e., hydrates) or common organic solvents, and such solvates are also intended to be encompassed within the scope of this invention.

Abbreviations used in the specification, particularly the Schemes and Examples, are as follows:

AcOH or HOAc=Acetic acid
AIBN=Azobisisobutyronitrile
aq.=Aqueous
BCA=Bicinchoninic acid
$BF_3.Et_2O$=Boron trifluoride diethyl etherate
$BH_3Me_2S$ Borane dimethyl sulfide complex
BPO=Benzoyl Peroxide
BSA=Bovine Serum Albumin
$Bu_4NF$=Tetra-n-butylammonium fluoride
cAMP=Cyclic adenosine monophosphate
conc. or con.=Concentrated
DCE=1,1-Dichloroethane
DCM=Dichloromethane
DIP-Cl-(−)=(−)-B-Chlorodiisopinocampheylborane
DIPEA or DIEA=Diisopropylethylamine
DME=Dimethoxyethane
DMEM=Dulbecco's modified Eagle's medium
DMF=N,N-Dimethylformamide
DMSO=Dimethylsulfoxide
dppBz=1,2-Bis(diphenylphosphino)benzene
EA=Ethyl acetate
EDC or EDCI=1-Ethyl-3-(3-dimethylaminopropyl) carbodiimide
Et=Ethyl
$Et_3N$ or TEA=Triethylamine
$Et_2O$=Diethyl ether
EtOAc or EA=Ethyl acetate
HATU=O-(7-Azabenzotriazol-1-yl)-N,N,N",N"-Tetramethyl Uronium Hexafluorophosphate
HBSS=Hank's Buffered Saline Solution
HEPES (buffer)=4-(2-Hydroxyethyl)-1-piperizine ethane sulfonic acid
HOBt=1-Hydroxybenzotriazole
HPLC=High Pressure Liquid Chromatography
$K[N(SiMe)_3]_2$=Potassium bis(trimethylsilyl)amide
KOt-Bu=Potassium tert-Butoxide
LC-MS=Liquid Chromatography-Mass Spectroscopy
Martin's Reagent or =Dess-Martin Periodinane
Me=Methyl
MeCOH=Methanol
$Me_3SiCN$=Trimethyl silyl cyanide
$Me_3SiI$=Trimethylsilyl iodide
Mesyl or Ms=Methylsulfonyl
MOM=Methoxymethyl ether
MS=Mass Spectroscopy
MsCI=Mesyl chloride
MsO=mesylate (i.e. $-O-SO_2-CH_3$)
$NaBH(OAc)_3$=Sodium triacetoxyborohydride
NBS=N-Bromosuccinimide
NIS=N-Iodosuccinimide
NMM=N-methylmorpholine
NMP=N-methyl-2-pyrrolidone
$^1H$ NMR=Hydrogen Nuclear Magnetic Resonance
OTf=Trifluoromethanesulfonate (i.e. $-O-SO_2-CF_3$)
PCC=Pyridinium chlorochromate
$PdCl_2(PPh_3)_2$=Bis(triphenylphosphine) Palladium (II) dichloride
$Pd(OAc)_2$=Palladium(II) acetate
$Pd(dba)_2$=Tris(dibenzylideneacetone) dipalladium(0)
$Pd_2(dba)_3$=Tris(dibenzylideneacetone) dipallaium (0)
$Pd(dppf)Cl_2$=1,1'-Bis(diphenylphosphino) ferrocenepalladium dichloride
$Pd(PPh_3)_4$=tetrakis(triphenylphosphine) palladium (0)
PE=Petroleum ether
PEI=Polyethyleneimine
$PPh_3$=Tri-phenyl Phosphine
(S)-Methyl-CBS or =(S)-2-Methyl-CBS-oxaboborolidine
(S)—$CH_3$—CBS
TEA=Triethylamine
tert-BuOH=tert-Butanol
TFA=Trifluoroacetic Acid
THE=Tetrahydrofuran
THP=Tetrahydopyran
TLC=Thin Layer Chromatography
TMS=Trimethylsilyl
Tosyl=p-Toluenesulfonyl As used herein, unless otherwise noted, the term "isolated form" shall mean that the compound is present in a form which is separate from any solid mixture with another compound(s), solvent system or biological environment. In an embodiment of the present invention, the compound of formula (I) is present in an isolated form. In an embodiment of the present invention, the compound of formula (I) is present in an isolated form.

As used herein, unless otherwise noted, the term "substantially pure form" shall mean that the mole percent of impurities in the isolated compound is less than about 5 mole percent, preferably less than about 2 mole percent, more preferably, less than about 0.5 mole percent, most preferably, less than about 0.1 mole percent. In an embodiment of the present invention, the compound of formula (I) is present as a substantially pure form.

As used herein, unless otherwise noted, the term "substantially free of a corresponding salt form(s)" when used to described the compound of formula (I) shall mean that mole percent of the corresponding salt form(s) in the isolated compound of formula (I) is less than about 5 mole percent, preferably less than about 2 mole percent, more preferably, less than about 0.5 mole percent, most preferably less than about 0.1 mole percent. In an embodiment of the present invention, the compound of formula (I) is present in a form which is substantially free of corresponding salt form(s).

As used herein, unless otherwise noted the term "condition, disease or disorder ameliorated by antagonizing a glucagon receptor" shall mean and condition, disease or disorders wherein at least one symptom of said condition, disease or disorder is alleviated or eliminated when one or more glucagon receptors are antagonized. Suitable examples include, but are not limited to Type I diabetes, Type II diabetes mellitus, obesity and renal disease, for example renal failure as a complication of diabetes. Preferably, the condition, disease or disorder ameliorated by antagonizing a glucagon receptor is selected from the group consisting of Type II diabetes mellitus and obesity.

As used herein, unless otherwise noted, the term "renal disease" shall include renal disease relating to renal hypertrophy, glomerular injury and microalbuminuria in glucose intolerant individuals characterized by persistent hyperglucagonemia.

As used herein, unless otherwise noted, the terms "treating", "treatment" and the like, shall include the management and care of a subject or patient (preferably mammal, more preferably human) for the purpose of combating a disease, condition, or disorder and includes the administration of a compound of the present invention to prevent the onset of the symptoms or complications, alleviate the symptoms or complications, or eliminate the disease, condition, or disorder.

As used herein, unless otherwise noted, the term "prevention" shall include (a) reduction in the frequency of one or more symptoms; (b) reduction in the severity of one or more symptoms; (c) the delay or avoidance of the development of additional symptoms; and/or (d) delay or avoidance of the development of the disorder or condition.

One skilled in the art will recognize that wherein the present invention is directed to methods of prevention, a subject in need of thereof (i.e. a subject in need of prevention) shall include any subject or patient (preferably a mammal, more preferably a human) who has experienced or exhibited at least one symptom of the disorder, disease or condition to be prevented. Further, a subject in need thereof may additionally be a subject (preferably a mammal, more preferably a human) who has not exhibited any symptoms of the disorder, disease or condition to be prevented, but who has been deemed by a physician, clinician or other medical profession to be at risk of developing said disorder, disease or condition. For example, the subject may be deemed at risk of developing a disorder, disease or condition (and therefore in need of prevention or preventive treatment) as a consequence of the subject's medical history, including, but not limited to, family history, pre-disposition, co-existing (co-morbid) disorders or conditions, genetic testing, and the like.

The term "subject" as used herein, refers to an animal, preferably a mammal, most preferably a human, who has been the object of treatment, observation or experiment. Preferably, the subject has experienced and/or exhibited at least one symptom of the disease or disorder to be treated and/or prevented.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

As used herein, the term "composition" is intended to encompass a product comprising the specified ingredients in the specified amounts, as well as any product which results, directly or indirectly, from combinations of the specified ingredients in the specified amounts.

To provide a more concise description, some of the quantitative expressions given herein are not qualified with the term "about". It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value.

To provide a more concise description, some of the quantitative expressions herein are recited as a range from about amount X to about amount Y. It is understood that wherein a range is recited, the range is not limited to the recited upper and lower bounds, but rather includes the full range from about amount X through about amount Y, or any amount or range therein.

As more extensively provided in this written description, terms such as "reacting" and "reacted" are used herein in reference to a chemical entity that is any one of: (a) the actually recited form of such chemical entity, and (b) any of the forms of such chemical entity in the medium in which the compound is being considered when named.

One skilled in the art will recognize that, where not otherwise specified, the reaction step(s) is performed under suitable conditions, according to known methods, to provide the desired product. One skilled in the art will further recognize that, in the specification and claims as presented herein, wherein a reagent or reagent class/type (e.g. base, solvent, etc.) is recited in more than one step of a process, the individual reagents are independently selected for each reaction step and may be the same of different from each other. For example wherein two steps of a process recite an organic or inorganic base as a reagent, the organic or inorganic base selected for the first step may be the same or different than the organic or inorganic base of the second step. Further, one skilled in the art will recognize that wherein a reaction step of the present invention may be carried out in a variety of solvents or solvent systems, said reaction step may also be carried out in a mixture of the suitable solvents or solvent systems. One skilled in the art will further recognize that wherein two consecutive reaction or process steps are run without isolation of the intermediate product (i.e. the product of the first of the two consecutive reaction or process steps), then the first and second reaction or process steps may be run in the same solvent or solvent system; or alternatively may be run in different solvents or solvent systems following solvent exchange, which may be completed according to known methods.

Examples of suitable solvents, bases, reaction temperatures, and other reaction parameters and components are provided in the detailed description which follows herein. One skilled in the art will recognize that the listing of said examples is not intended, and should not be construed, as limiting in any way the invention set forth in the claims which follow thereafter.

As used herein, unless otherwise noted, the term "leaving group" shall mean a charged or uncharged atom or group which departs during a substitution or displacement reaction. Suitable examples include, but are not limited to, Br, Cl, I, mesylate, tosylate, triflate, and the like.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

As used herein, unless otherwise noted, the term "nitrogen protecting group" shall mean a group which may be attached to a nitrogen atom to protect said nitrogen atom from participating in a reaction and which may be readily removed following the reaction. Suitable nitrogen protecting groups include, but are not limited to carbamates—groups of the formula —C(O)O—R wherein R is for example methyl, ethyl, t-butyl, benzyl, phenylethyl, $CH_2$=CH—$CH_2$—, and the like; amides—groups of the formula —C(O)—R' wherein R' is for example methyl, phenyl, trifluoromethyl, and the like; N-sulfonyl derivatives—groups of the formula —$SO_2$—R" wherein R" is for example tolyl, phenyl, trifluoromethyl, 2,2,5,7,8-pentamethylchroman-6-yl-, 2,3,6-trimethyl-4-methoxybenzene, and the like. Other suitable nitrogen protecting groups may be found in texts such as T. W. Greene & P. G. M. Wuts, *Protective Groups in Organic Synthesis*, John Wiley & Sons, 1991.

As used herein, unless otherwise noted, the term "oxygen protecting group" shall mean a group which may be attached to an oxygen atom to protect said oxygen atom from participating in a reaction and which may be readily removed following the reaction. Suitable oxygen protecting groups include, but are not limited to, acetyl, benzoyl, t-butyl-dimethylsilyl, trimethylsilyl (TMS), MOM, THP, and the like. Other suitable oxygen protecting groups may be found in texts such as T. W. Greene & P. G. M. Wuts, *Protective Groups in Organic Synthesis*, John Wiley & Sons, 1991.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-D-tartaric acid and/or (+)-di-p-toluoyl-L-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

Additionally, chiral HPLC against a standard may be used to determine percent enantiomeric excess (% ee). The enantiomeric excess may be calculated as follows

[(Rmoles−Smoles)/(Rmoles+Smoles)]×100% where Rmoles and Smoles are the R and S mole fractions in the resulting mixture such that Rmoles+Smoles=1. The enantiomeric excess may alternatively be calculated from the specific rotations of the desired enantiomer and the prepared mixture as follows:

ee=([α−obs]/[α−max])×100.

The present invention includes within its scope prodrugs of the compounds of this invention. In general, such prodrugs will be functional derivatives of the compounds which are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs", ed. H. Bundgaard, Elsevier, 1985.

For use in medicine, the salts of the compounds of this invention refer to non-toxic "pharmaceutically acceptable salts." Other salts may, however, be useful in the preparation of compounds according to this invention or of their pharmaceutically acceptable salts. Suitable pharmaceutically acceptable salts of the compounds include acid addition salts which may, for example, be formed by mixing a solution of the compound with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts. Thus, representative pharmaceutically acceptable salts include, but are not limited to, the following: acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate.

Representative acids which may be used in the preparation of pharmaceutically acceptable salts include, but are not limited to, the following: acids including acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, (+)-camphoric acid, camphorsulfonic acid, (+)-(1S)-camphor-10-sulfonic acid, capric acid, caproic acid, caprylic acid, cinnamic acid, citric acid, cyclamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucoronic acid, L-glutamic acid, α-oxo-glutaric acid, glycolic acid, hipuric acid, hydrobromic acid, hydrochloric acid, (+)-L-lactic acid, (±)-DL-lactic acid, lactobionic acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinc acid, nitric acid, oleic acid, orotic acid, oxalic acid, palmitic acid, pamoic acid, phosphoric acid, L-pyroglutamic acid, salicylic acid, 4-amino-salicylic acid, sebaic acid, stearic acid, succinic acid, sulfuric acid, tannic acid, (+)-L-tartaric acid, thiocyanic acid, p-toluenesulfonic acid and undecylenic acid.

Representative bases which may be used in the preparation of pharmaceutically acceptable salts include, but are not limited to, the following: bases including ammonia, L-arginine, benethamine, benzathine, calcium hydroxide, choline, deanol, diethanolamine, diethylamine, 2-(diethylamino)-ethanol, ethanolamine, ethylenediamine, N-methyl-glucamine, hydrabamine, 1H-imidazole, L-lysine, magnesium hydroxide, 4-(2-hydroxyethyl)-morpholine, piperazine, potassium hydroxide, 1-(2-hydroxyethyl)-pyrrolidine, secondary amine, sodium hydroxide, triethanolamine, tromethamine and zinc hydroxide.

General Synthesis Methods

Compounds of formula (I) and formula (II) may be prepared according to the process outlined in Scheme 1.

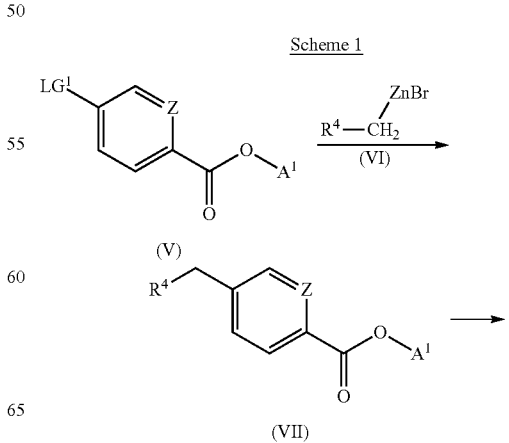

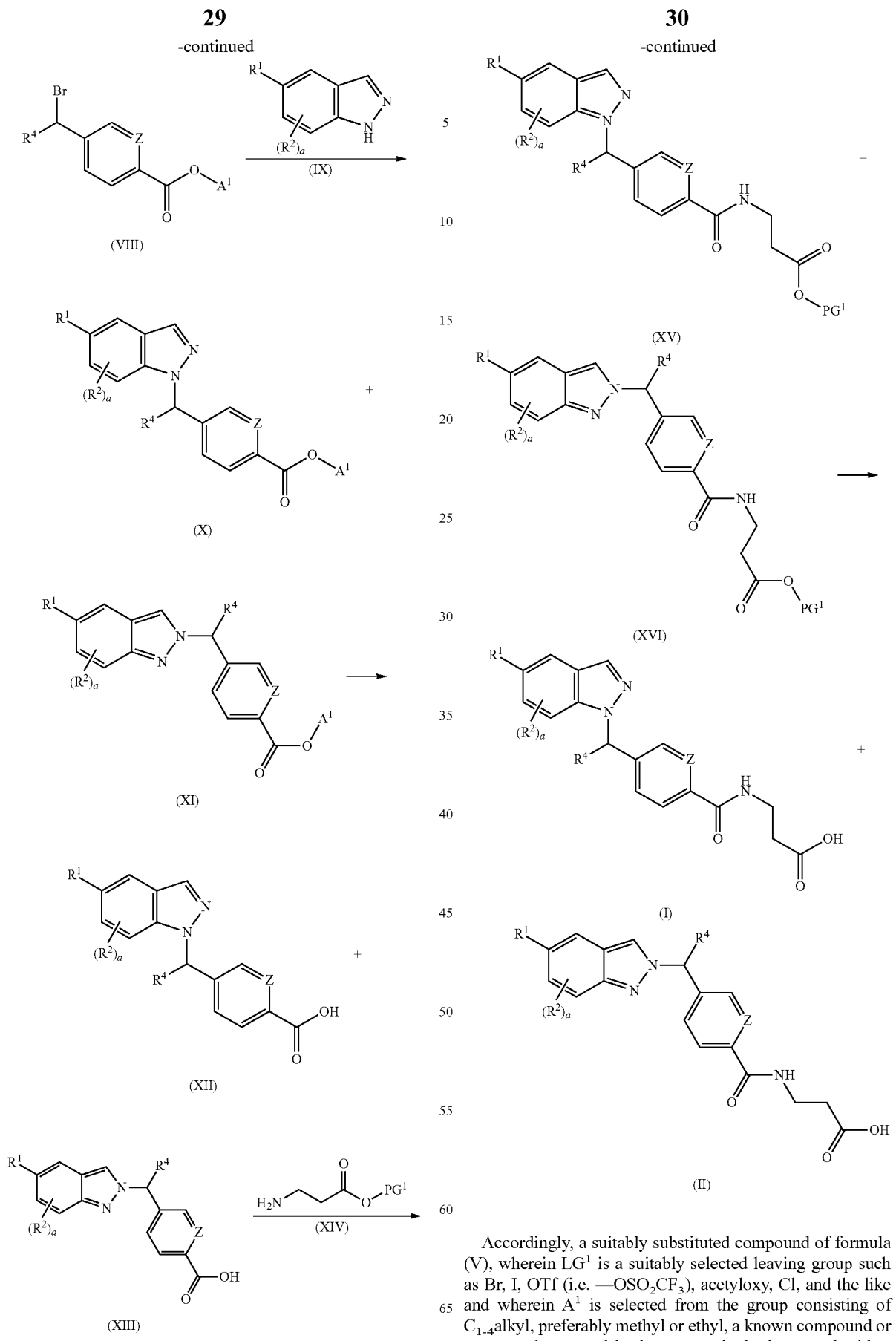
Accordingly, a suitably substituted compound of formula (V), wherein $LG^1$ is a suitably selected leaving group such as Br, I, OTf (i.e. —$OSO_2CF_3$), acetyloxy, Cl, and the like and wherein $A^1$ is selected from the group consisting of $C_{1-4}$alkyl, preferably methyl or ethyl, a known compound or compound prepared by known methods, is reacted with a suitably selected compound of formula (VI), a known compound or compound prepared by known methods; in the presence of a suitably selected coupling catalyst such as Pd(PPh$_3$)$_4$, Pd$_2$(dba)$_3$, Pd(OAc)$_2$; in a suitably selected organic solvent such as THF, 1,4-dioxane, toluene, and the like; to yield the corresponding compound of formula (VII).

The compound of formula (VII) is reacted with a suitably selected brominating agent such as NBS, Br$_2$, HBr, and the like; in the presence of a radical initiator such as benzoyl peroxide, AIBN, and the like; in a suitably selected organic solvent such as carbon tetrachloride, DCM, ClCH$_2$CH$_2$Cl, and the like; to yield the corresponding compound of formula (VIII).

The compound of formula (VIII) is reacted with a suitably substituted compound of formula (IX), a known compound or compound prepared by known methods (for example, by reacting 5-bromo-indazole with a suitably substituted boronic acid, a compound of the formula R$^1$—B(OH)$_2$, a known compound or compound prepared by known method; in the presence of a suitably selected coupling agent such as Pd(PPh$_3$)$_4$, and the like, in the presence of suitably selected base such as K$_2$CO$_3$, in a suitably selected solvent or mixture of solvent such as 1,4-dioxane/water), in the presence of a suitably selected base such as Cs$_2$CO$_3$, K$_2$CO$_3$, NaH, and the like; in a suitably selected organic solvent such as DMF, acetonitrile, NMP (N-methyl-2-pyrrolidone), and the like; to yield a mixture of the corresponding compound of formula (X) and the corresponding compound of formula (XI).

The mixture of compounds of formula (X) and formula (XI) is hydrolyzed to according to known methods, to convert the A$^1$-alkyl ester to the corresponding carboxylic acid; to yield a mixture of the corresponding compounds of formula (XII) and formula (XIII). For example, wherein A$^1$ is methyl, the mixture of compounds of formula (X) and formula (XI) is reacted with LiOH/THF in an alcohol such as methanol. In another example, the mixture of compounds of formula (X) and formula (XI) is reacted with a suitably selected acid or base such as NaOH, TFA, and the like; in a suitably selected solvent or mixture of solvents such as THF/methanol, DCE, DCM, and the like.

The mixture of compounds of formula (XII) and formula (XIII) is reacted with a suitably protected beta-alanine, a compound of formula (XIV) wherein PG$^1$ is a suitably selected protecting group such as C$_{1-4}$alkyl (preferably methyl or ethyl), tert-butyl, and the like, a known compound; in the presence of a suitably selected organic base such as DIPEA, TEA, pyridine, and the like, preferably DIPEA; in the presence of a suitably selected coupling agent such as HATU, HOBt in combination with EDCI, and the like; to yield a mixture of the corresponding compounds of formula (XV) and formula (XVI).

The mixture of compounds of formula (XV) and formula (XVI) is de-protected according to known methods, to yield the corresponding compounds of formula (I) and formula (II), respectively. For example, wherein the PG$^1$ group is t-butyl, the mixture of compounds of formula (XV) and (XVI) is de-protected by reacting with a suitably selected acid such as TFA, (CH$_3$)$_3$SiI, HCl, and the like; in a suitably selected organic solvent such as DCM, Et$_2$O, H$_2$O, and the like. In another example, wherein PG$^1$ is C$_{1-4}$alkyl, the mixture of compounds of formula (XV) and (XVI) is de-protected by hydrolysis with a suitably selected base such as NaOH, LiH, KOH, and the like; in a suitably selected organic solvent or mixture of solvents such as MeCOH/THF, MeOH/1,4-dioxane, and the like.

One skilled in the art will recognize that in an alternative, the compounds of formula (X) and formula (XI) are separated, according to known methods (for example by flash chromatography on silica gel or HPLC) and the individual compounds of formula (X) and formula (XI) are then reacted as described above (to sequentially (a) remove the A$^1$ group, (b) react with the compound of formula (XIV) to attach the protected β-alanine and (c) remove the β-alanine PG$^1$ protecting group) to individually prepare the corresponding compounds of formula (I) and formula (II).

One skilled in the art will further recognize that wherever a reaction step yields a mixture of regio-isomers, said mixture of regio-isomers may be separated into its individual compounds, which individual compounds may be further reacted as described above, to yield the corresponding compound of formula (I) or formula (II).

Compounds of formula (I) and formula (II) may alternatively be prepared according to the process outlined in Scheme 2.

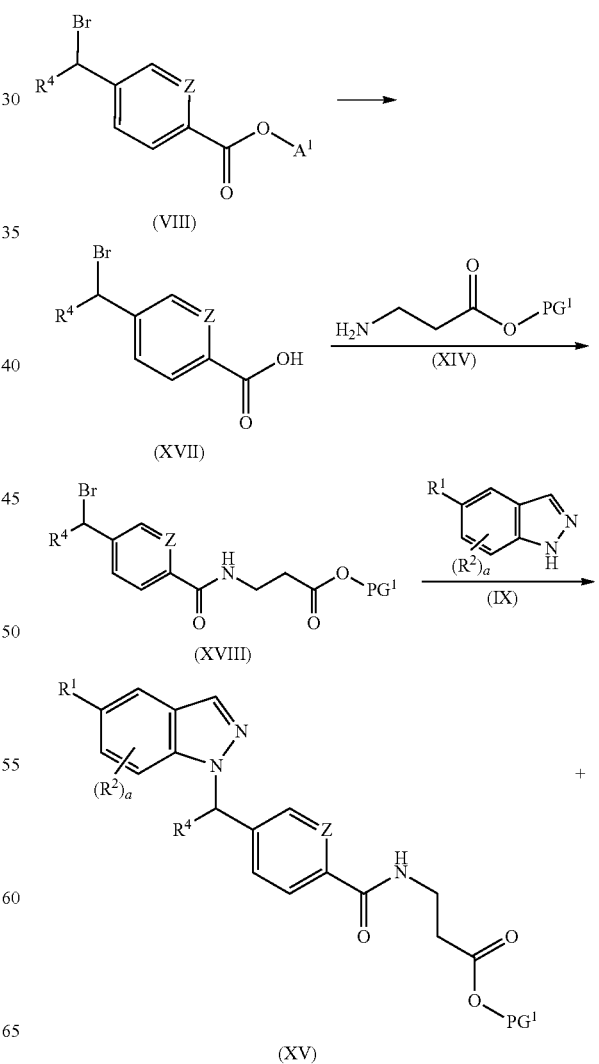

Scheme 2

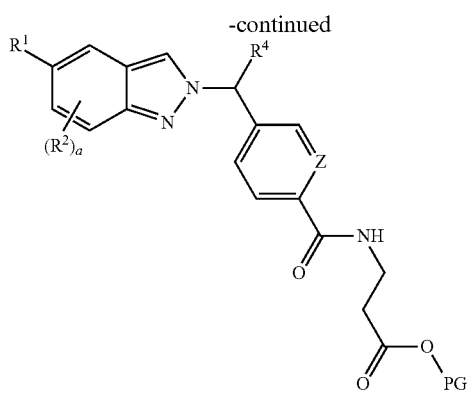

(XVI)

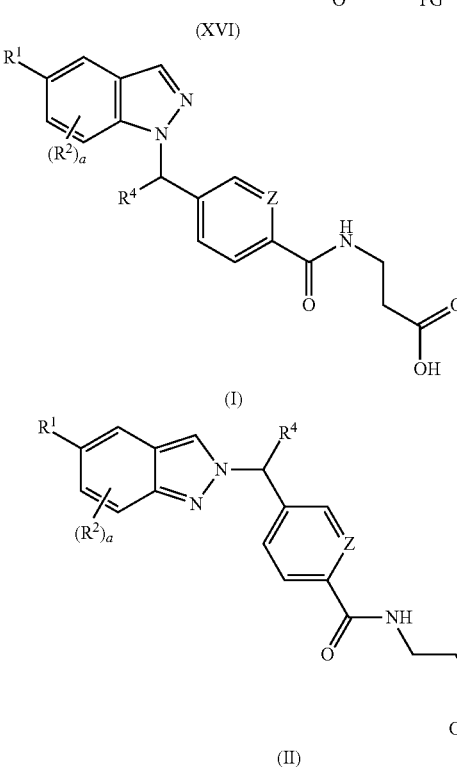

(I)

(II)

Accordingly, a suitably substituted compound of formula (VIII), prepared for example as describe in Scheme 1 above, is hydrolyzed according to known methods, to convert the $A^1$-alkyl ester to the corresponding carboxylic acid; to yield the corresponding compound of formula (XVII). For example, wherein $A^1$ is methyl, the compound of formula (VIII) is reacted with LiOH/THF in an alcohol such as methanol. In another example, the compound of formula (VIII) is reacted with a suitably selected acid or base such as NaOH, TFA, and the like; in a suitably selected solvent or mixture of solvents such as THF/methanol, DCE, DCM, and the like.

The compound of formula (XVII) is reacted with a suitably protected beta-alanine, a compound of formula (XIV), wherein $PG^1$ is a suitably selected protecting group such as $C_{1-4}$alkyl (preferably methyl or ethyl), tert-butyl, and the like, a known compound; in the presence of a suitably selected organic base such as DIPEA, TEA, pyridine, and the like, preferably DIPEA; in the presence of a suitably selected coupling agent such as HATU, HOBt in combination with EDCI, and the like; to yield the corresponding compound of formula (XVIII).

The compound of formula (XVIII) is reacted with a suitably substituted compound of formula (IX), a known compound or compound prepared for example as described in Scheme 1 above, in the presence of a suitably selected base such as $Cs_2CO_3$, $K_2CO_3$, NaH, and the like; in a suitably selected organic solvent such as DMF, acetonitrile, NMP, and the like; to yield a mixture of the corresponding compound of formula (XV) and the corresponding compound of formula (XVI).

The mixture of compounds of formula (XV) and formula (XVI) is de-protected according to known methods, to yield the corresponding compounds of formula (I) and formula (II), respectively. For example, wherein the $PG^1$ group is t-butyl, the mixture of compounds of formula (XV) and (XVI) is de-protected by reacting with a suitably selected acid such as TFA, $(CH_3)_3SiI$, HCl, and the like; in a suitably selected organic solvent such as DCM, $Et_2O$, $H_2O$, and the like. In another example, wherein $PG^1$ is $C_{1-4}$alkyl, the mixture of compounds of formula (XV) and (XVI) is de-protected by hydrolysis with a suitably selected base such as NaOH, LiH, KOH, and the like; in a suitably selected organic solvent or mixture of solvents such as MeCOH/THF, MeOH/1,4-dioxane, and the like.

Alternatively, the mixture of the compounds of formula (XV) and formula (XVI) is separated into its individual compounds, each of which is then reacted to remove the $PG^1$ group, as described herein; to yield the corresponding compound of formula (I) and formula (II), respectively.

Compounds of formula (I) and formula (II) may alternatively be prepared according to the process outlined in Scheme 3.

Scheme 3

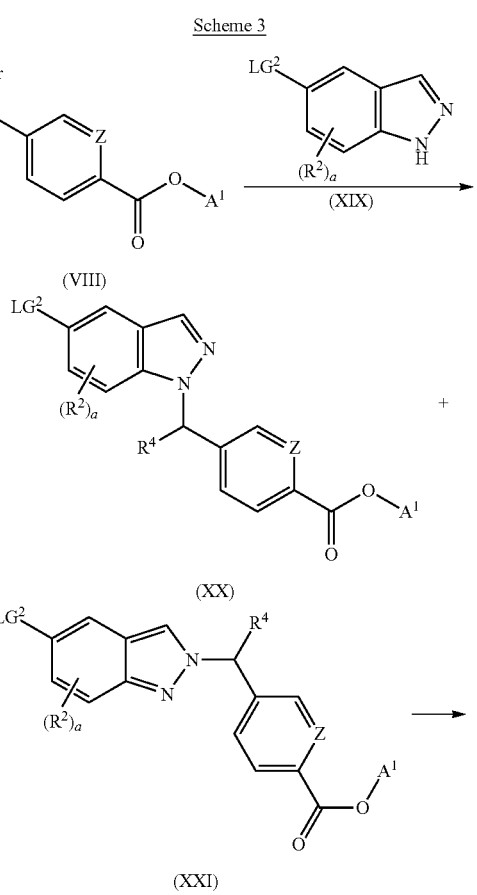

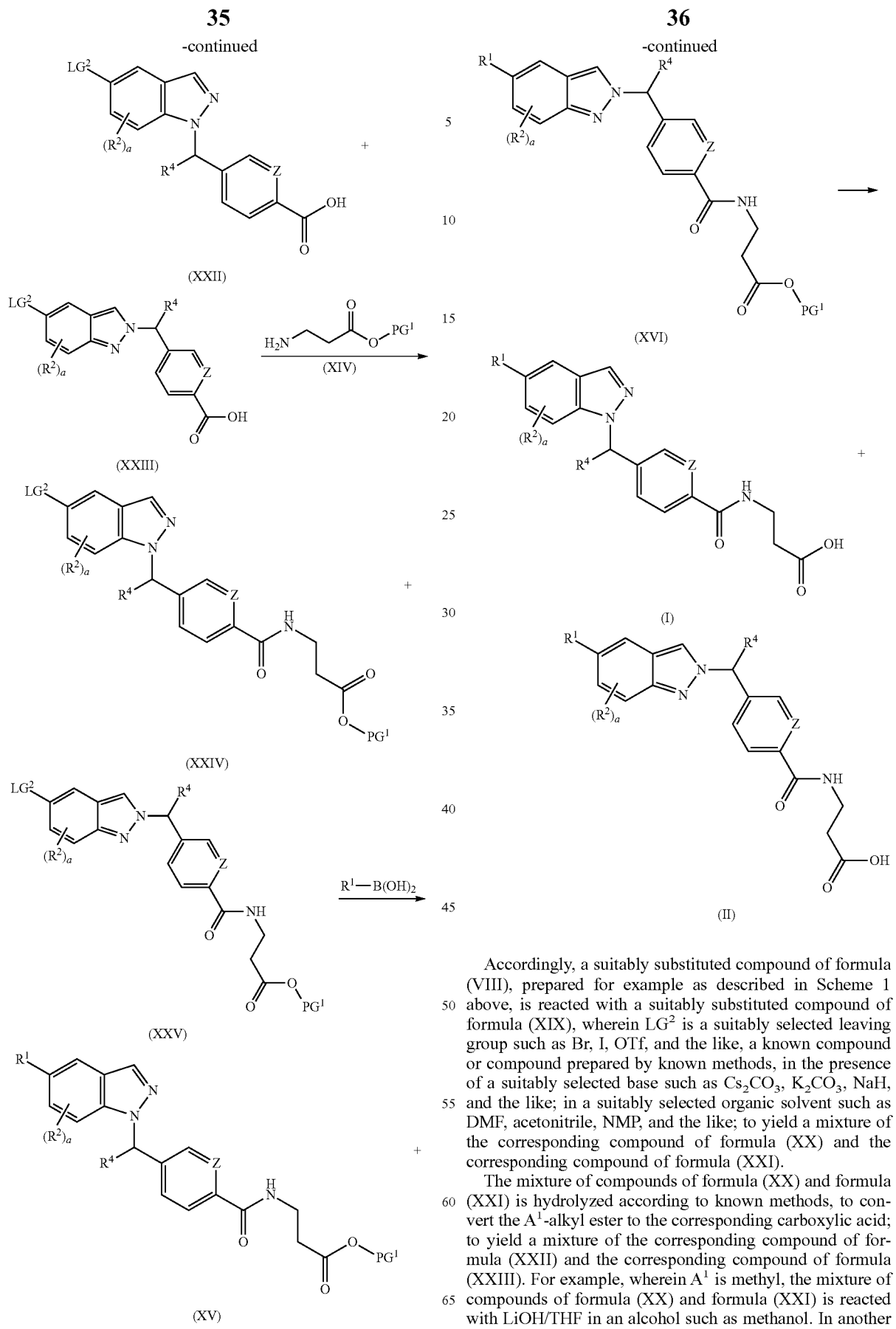

Accordingly, a suitably substituted compound of formula (VIII), prepared for example as described in Scheme 1 above, is reacted with a suitably substituted compound of formula (XIX), wherein LG² is a suitably selected leaving group such as Br, I, OTf, and the like, a known compound or compound prepared by known methods, in the presence of a suitably selected base such as $Cs_2CO_3$, $K_2CO_3$, NaH, and the like; in a suitably selected organic solvent such as DMF, acetonitrile, NMP, and the like; to yield a mixture of the corresponding compound of formula (XX) and the corresponding compound of formula (XXI).

The mixture of compounds of formula (XX) and formula (XXI) is hydrolyzed according to known methods, to convert the A¹-alkyl ester to the corresponding carboxylic acid; to yield a mixture of the corresponding compound of formula (XXII) and the corresponding compound of formula (XXIII). For example, wherein A¹ is methyl, the mixture of compounds of formula (XX) and formula (XXI) is reacted with LiOH/THF in an alcohol such as methanol. In another example, the mixture of compounds of formula (XX) and formula (XXI) is reacted with a suitably selected acid or base such as NaOH, TFA, and the like; in a suitably selected solvent or mixture of solvents such as THF/methanol, DCE, DCM, and the like.

The mixture of compounds of formula (XXII) and formula (XXIII) is reacted with a suitably protected beta-alanine, a compound of formula (XIV) wherein $PG^1$ is a suitably selected protecting group such as $C_{1-4}$alkyl (preferably methyl or ethyl), tert-butyl, and the like, a known compound; in the presence of a suitably selected organic base such as DIPEA, TEA, pyridine, and the like, preferably DIPEA; in the presence of a suitably selected coupling agent such as HATU, HOBt in combination with EDCI, and the like; to yield a mixture of the corresponding compound of formula (XXIV) and the corresponding compound of formula (XXV).

The mixture of compounds of formula (XXIV) and formula (XXV) is reacted with a suitably substituted boronic acid, a compound of formula (XXVI), a known compound or compound prepared by known methods, in the presence of a suitably selected palladium catalyst such as Pd(dppf)Cl$_2$, Pd(dba)$_2$, Pd(OAc)$_2$, and the like; in the presence of a suitably selected inorganic base such as K$_2$CO$_3$, Na$_2$CO$_3$, and the like; in a suitably selected solvent or mixture of solvents, such as THF/water, 1,4-dioxane/water, ethanol/toluene, DME/water, and the like; to yield the corresponding compound of formula (XV) and the corresponding compound of formula (XVI).

The mixture of compounds of formula (XV) and formula (XVI) is de-protected according to known methods, to yield the corresponding compounds of formula (I) and formula (II), respectively. For example, wherein the $PG^1$ group is t-butyl, the mixture of compounds of formula (XV) and (XVI) is de-protected by reacting with a suitably selected acid such as TFA, (CH$_3$)$_3$SiI, HCl, and the like; in a suitably selected organic solvent such as DCM, Et$_2$O, H$_2$O, and the like. In another example, wherein $PG^1$ is $C_{1-4}$alkyl, the mixture of compounds of formula (XV) and (XVI) is de-protected by hydrolysis with a suitably selected base such as NaOH, LiH, KOH, and the like; in a suitably selected organic solvent or mixture of solvents such as MeCOH/THF, MeOH/1,4-dioxane, and the like.

One skilled in the art will recognize that whenever a reaction step as described in Scheme 3 above yields a mixture of regio-isomers, said mixture of regio-isomers may be separated into its individual compounds, and the individual compounds may then be further reacted as described above, to yield the corresponding compound of formula (I) or formula (II), as desired.

Compounds of formula (VIII) are known compounds or compounds which may be prepared according to known methods. Compounds of formula (VIII) may be prepared as described in Scheme 1 above. Alternatively, compounds of formula (VIII) may be prepared according to the process as outlined in Scheme 4.

Scheme 4

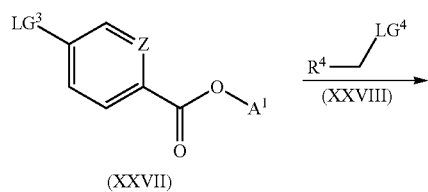

(XXVII)

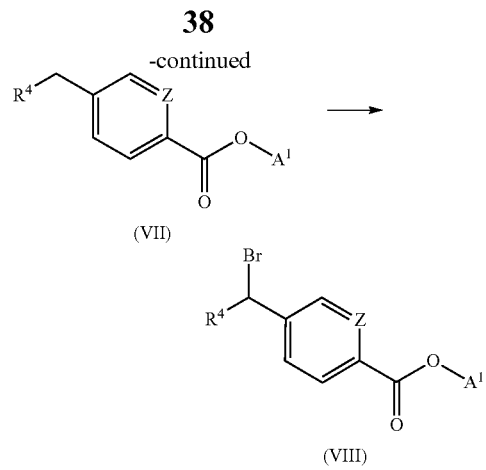

Accordingly, a suitably substituted compound of formula (XXVII), wherein $LG^3$ is a suitably selected leaving group such as Br, I, OTf, and the like and wherein $A^1$ is $C_{1-4}$alkyl, preferably methyl or ethyl, a known compound or compound prepared by known methods, is reacted with a suitably substituted compound of formula (XXVIII), wherein $LG^4$ is a suitably selected leaving group such as Br, I, OTf, and the like, a known compound or compound prepared by known methods; in the presence of a suitably selected catalyst such as NiI$_2$.H$_2$O, and the like; in the presence of a suitably selected ligand such as 1,2-bis(diphenylphosphino)benzene (dppBz), and the like; in the presence of a suitably selected nitrogen based bidentated ligand such as 4,4-di-t-butyl-2,2'-dipyridyl, and the like; in the presence of metal such as manganese (Mn); to yield the corresponding compound of formula (VII).

Alternatively, a suitably substituted compound of formula (XXVII) wherein $LG^3$ is a suitably selected leaving groups such as Br, I, OTf, and the like, and wherein $A^1$ is $C_{1-4}$alkyl, preferably methyl or ethyl, a known compound or compound prepared by known methods, is reacted with a suitably substituted compound of formula (XXVIII) wherein $LG^4$ is $BF_3^-K^+$, and the like, a known compound or compound prepared by known methods; in the presence of a suitably selected catalyst such as Pd(dppf)Cl$_2$, Pd(PPh$_3$)$_4$, and the like; in the presence of a suitably selected base such as Cs$_2$CO$_3$, K$_2$CO$_3$, Na$_3$PO$_4$, and the like; in a suitably selected organic solvent such as DMF, 1,4-dioxane, toluene, and the like; to yield the corresponding compound of formula (VII).

The compound of formula (VII) is reacted with a suitably selected brominating agent such as NBS, Br$_2$, HBr, and the like; in the presence of a radical initiator such as benzoyl peroxide, AIBN, and the like; in a suitably selected organic solvent such as carbon tetrachloride, DCM, ClCH$_2$CH$_2$Cl, and the like; to yield the corresponding compound of formula (VIII).

Compounds of formula (VIII) may alternatively be prepared according to the process as outlined in Scheme 5.

Scheme 5

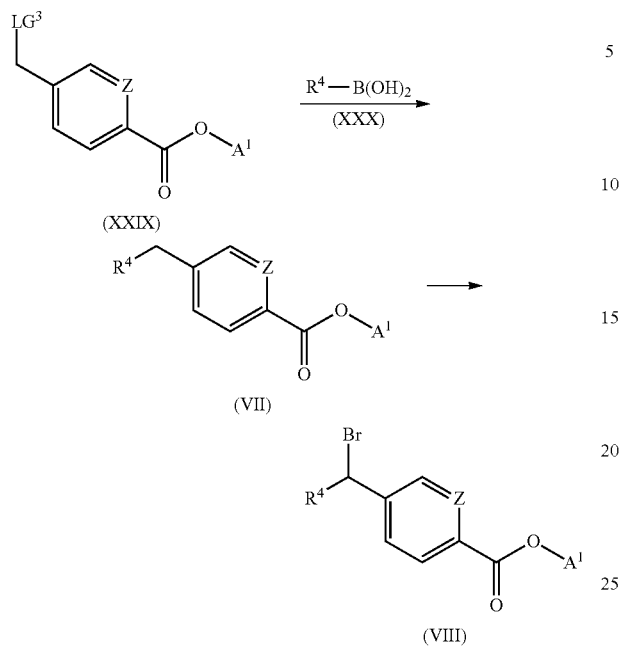

Scheme 6

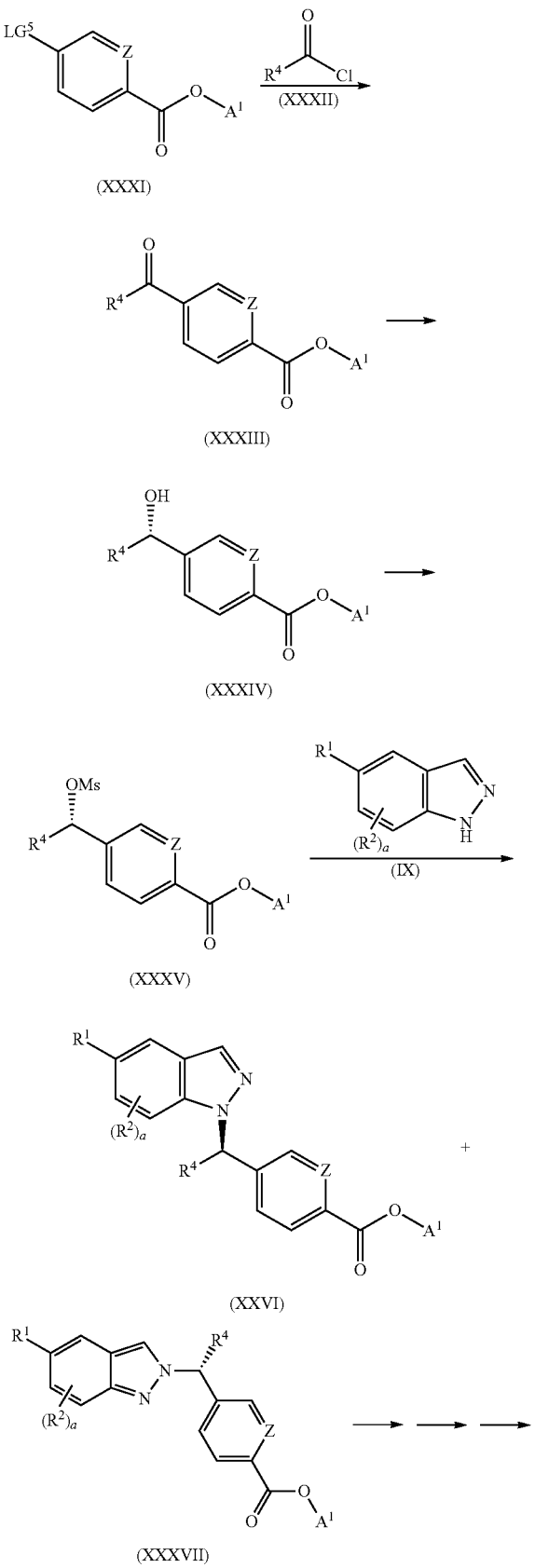

Accordingly, a suitably substituted compound of formula (XXIX), wherein $LG^3$ is a suitably selected leaving group such as Br, I, OTf, and the like and wherein $A^1$ is $C_{1-4}$alkyl, preferably methyl or ethyl, a known compound or compound prepared by known methods, is reacted with a suitably substituted boronic acid, a compound of the formula (XXX), a known compound or compound prepared by known methods; in the presence of a suitably selected coupling agent such as Pd(PPh$_3$)$_4$, Pd(dppf)Cl$_2$, and the like; in the presence of a suitably selected base such as CsF, and the like; in a suitably selected solvent or mixture of solvents, such as THF/water, 1,4-dioxane/water, ethanol/toluene, DME/water, and the like; to yield the corresponding compound of formula (VII).

The compound of formula (VII) is reacted with a suitably selected brominating agent such as NBS, Br$_2$, HBr, and the like; in the presence of a radical initiator such as benzoyl peroxide, AIBN, and the like; in a suitably selected organic solvent such as carbon tetrachloride, DCM, ClCH$_2$CH$_2$Cl, and the like; to yield the corresponding compound of formula (VIII).

Compounds of formula (VIII) may alternatively be prepared according to the procedures as described in the Examples which follow herein, modifying reagents, starting materials and conditions, as would be readily recognized and understood by those skilled in the art.

Compounds of formula (I) and formula (II), particularly enantiomerically enriched compounds of formula (I) and formula (II) may be prepared according to the process as outlined in Scheme 6.

-continued

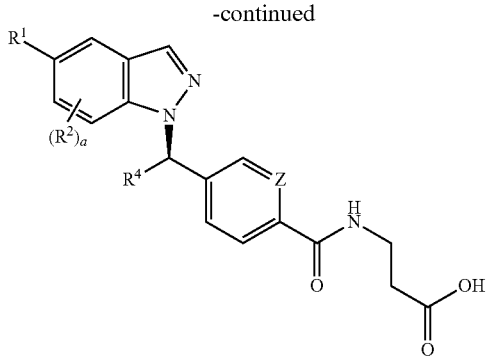

(Ia)

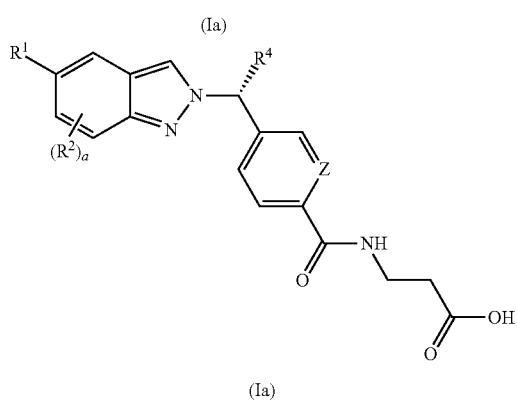

(Ia)

Accordingly, a suitably substituted compound of formula (XXXI), wherein $LG^5$ is ZnBr or ZnI, a known compound or compound prepared by known methods, is reacted with a suitably substituted acid chloride, a compound of formula (XXXII), a known compound or compound prepared by known methods; in the presence of a suitably selected coupling agent such as $PdCl_2(dppf)$; in a suitably selected organic solvent such as THF, 1,4-dioxane, and the like; to yield the corresponding compound of formula (XXXIII).

The compound of formula (XXXIII) is reacted with a suitably selected enantioselective reducing agent such as a mixture of (S)-methyl-CBS and $BH_3Me_2S$, and the like; in a suitably selected organic solvent such as THF, toluene, and the like; to yield the corresponding enantiomerically enriched compound of formula (XXXIV).

The compound of formula (XXXIV) is reacted with mesyl chloride, a known compound; in the presence of a suitably selected organic base such as TEA, DIPEA, pyridine, and the like; in a suitably selected organic solvent such as DCM, toluene, THF, and the like; to yield the corresponding compound of formula (XXXV).

The compound of formula (XXXV) is reacted with a suitably substituted compound of formula (IX), a known compound or compound prepared for example as described in Scheme 1 above, in the presence of a suitably selected base such as $Cs_2CO_3$, $K_2CO_3$, NaH, and the like; in a suitably selected organic solvent such as DMF, acetonitrile, NMP, and the like; to yield a mixture of the corresponding compound of formula (XXXVI) and the corresponding compound of formula (XXXVII).

The mixture of compounds of formula (XXXVI) and formula (XXXVII) are substituted, for example, for the compounds of formula (X) and formula (XI) in Scheme 1, and reacted as described therein; to yield the corresponding, enantiomerically enriched compounds of formula (Ia) and formula (IIa).

One skilled in the art will recognize that the reactions on the enantiomerically enriched compound of formula (XXXIV) and subsequent compounds are not expected to result in any significant amount of racemization. Therefore the process of Scheme 6 results in enantiomerically enriched compounds of formula (I) and formula (II).

One skilled in the art will further recognize that the compound of formula (XXXIII) may alternatively be reacted with, for example, a mixture of (R)-methyl-CBS and $BH_3Me_2S$ as described above, to yield the corresponding compound of formula (XXXIV) of the opposite stereo-orientation, i.e. a compound of formula (XXXIV-A)

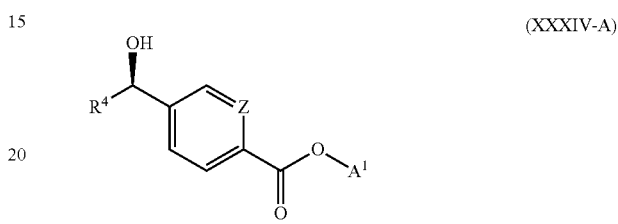

(XXXIV-A)

which compound of formula (XXXIV-A) is then reacted as described in Scheme 6, to yield the corresponding compounds of formula (Ib) and (IIb):

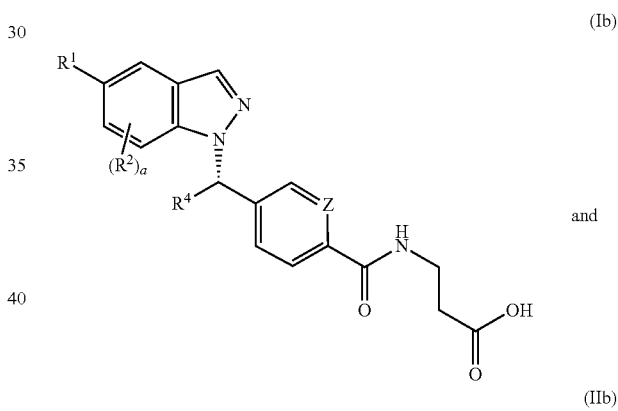

(Ib)

and

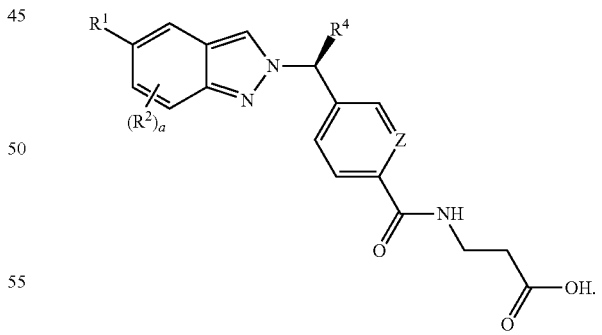

(IIb)

One skilled in the art will further recognize that whenever a reaction step as described in Scheme 6 above yields a mixture of regio-isomers, said mixture of regio-isomers may be separated into its individual compounds, and the individual compounds may then be further reacted as described above, to yield the corresponding enantiomerically enriched compound of formula (I) or formula (II), as desired.

Compounds of formula (XXXIII) may alternatively be prepared according to the process as outlined in Scheme 7.

Scheme 7

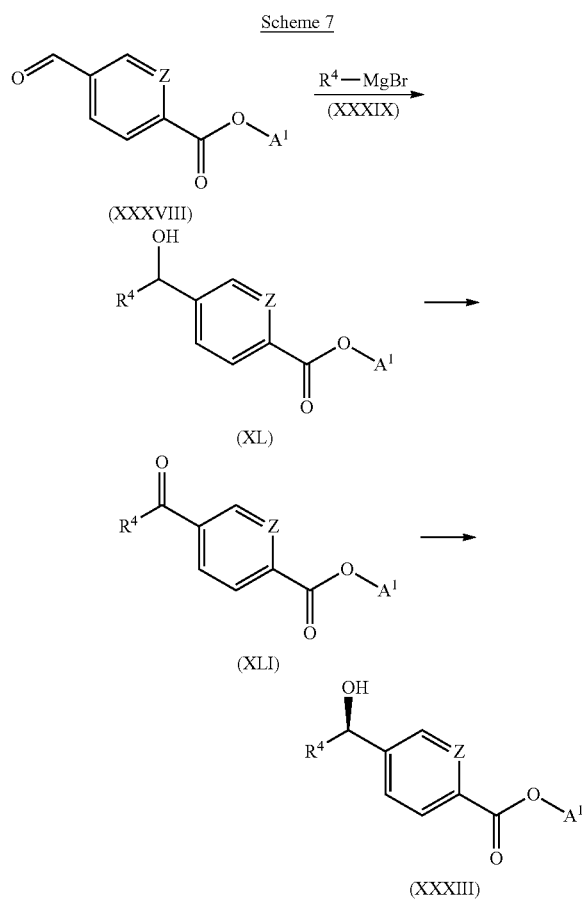

Accordingly, a suitably substituted compound of formula (XXXVIII), wherein $A^1$ is $C_{1-4}$alkyl, preferably methyl or ethyl, a known compound or compound prepared by known methods; is reacted with a suitably substituted compound of formula (XXXIX), a known compound or compound prepared by known methods; under Grignard conditions (in a suitably selected anhydrous solvent such as THF); to yield the corresponding compound of formula (XL).

The compound of formula (XL) is reacted with a suitably selected oxidants such as PCC, Martin's reagent, $MnO_2$, and the like; in a suitably selected organic solvent such as DCM, acetonitrile, and the like; to yield the corresponding compound of formula (XLI).

The compound of formula (XLI) is reacted with chloro ((1R,2R,3S,5R)-2,6,6-trimethylbicyclo[3.1.1]heptan-3-yl) ((1R,2S,3S,5R)-2,6,6-trimethylbicyclo[3.1.1]heptan-3-yl) borane (also known as (+)-diisopinocampheyl chloroborane), a known compound; in a suitably selected organic solvent such as THF, toluene, $Et_2O$, and the like; to yield the corresponding, enantiomerically enriched compound of formula (XXXIII).

Pharmaceutical Compositions

The present invention further comprises pharmaceutical compositions containing one or more compounds of formula (I) or formula (II) with a pharmaceutically acceptable carrier. Pharmaceutical compositions containing one or more of the compounds of the invention described herein as the active ingredient can be prepared by intimately mixing the compound or compounds with a pharmaceutical carrier according to conventional pharmaceutical compounding techniques. The carrier may take a wide variety of forms depending upon the desired route of administration (e.g., oral, parenteral). Thus for liquid oral preparations such as suspensions, elixirs and solutions, suitable carriers and additives include water, glycols, oils, alcohols, flavoring agents, preservatives, stabilizers, coloring agents and the like; for solid oral preparations, such as powders, capsules and tablets, suitable carriers and additives include starches, sugars, diluents, granulating agents, lubricants, binders, disintegrating agents and the like. Solid oral preparations may also be coated with substances such as sugars or be enteric-coated so as to modulate major site of absorption. For parenteral administration, the carrier will usually consist of sterile water and other ingredients may be added to increase solubility or preservation. Injectable suspensions or solutions may also be prepared utilizing aqueous carriers along with appropriate additives.

To prepare the pharmaceutical compositions of this invention, one or more compounds of the present invention as the active ingredient is intimately admixed with a pharmaceutical carrier according to conventional pharmaceutical compounding techniques, which carrier may take a wide variety of forms depending of the form of preparation desired for administration, e.g., oral or parenteral such as intramuscular. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules, caplets, gelcaps and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, through other ingredients, for example, for purposes such as aiding solubility or for preservation, may be included. Injectable suspensions may also be prepared, in which case appropriate liquid carriers, suspending agents and the like may be employed. The pharmaceutical compositions herein will contain, per dosage unit, e.g., tablet, capsule, powder, injection, teaspoonful and the like, an amount of the active ingredient necessary to deliver an effective dose as described above. The pharmaceutical compositions herein will contain, per unit dosage unit, e.g., tablet, capsule, powder, injection, suppository, teaspoonful and the like, of from about 0.01 mg to about 1000 mg or any amount or range therein, and may be given at a dosage of from about 0.01 mg/kg/day to about 300 mg/kg/day, or any amount or range therein, preferably from about 0.1 mg/kg/day to about 50 mg/kg/day, or any amount or range therein, preferably from about 0.05 mg/kg/day to about 15 mg/kg/day, or any amount or range therein. The dosages, however, may be varied depending upon the requirement of the patients, the severity of the condition being treated and the compound being employed. The use of either daily administration or post-periodic dosing may be employed.

Preferably these compositions are in unit dosage forms from such as tablets, pills, capsules, powders, granules, sterile parenteral solutions or suspensions, metered aerosol or liquid sprays, drops, ampoules, autoinjector devices or suppositories; for oral parenteral, intranasal, sublingual or rectal administration, or for administration by inhalation or insufflations. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from about 0.01 mg to about 1,000 mg, or any amount or range therein, of the active ingredient of the present invention. The tablets or pills of the novel composition can be coated or otherwise compounded to provide a dosage form yielding the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of material can be used for such enteric layers or coatings, such materials including a number of polymeric acids with such materials as shellac, cetyl alcohol and cellulose acetate.

The liquid forms in which the novel compositions of the present invention may be incorporated for administration orally or by injection include, aqueous solutions, suitably flavored syrups, aqueous or oil suspensions, and flavored emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone or gelatin.

The method of treating conditions, diseases or disorders described in the present invention may also be carried out using a pharmaceutical composition comprising any of the compounds as defined herein and a pharmaceutically acceptable carrier. The pharmaceutical composition may contain between about 0.01 mg and about 1000 mg of the compound, or any amount or range therein; preferably from about 1.0 mg to about 500 mg of the compound, or any amount or range therein, and may be constituted into any form suitable for the mode of administration selected. Carriers include necessary and inert pharmaceutical excipients, including, but not limited to, binders, suspending agents, lubricants, flavorants, sweeteners, preservatives, dyes, and coatings. Compositions suitable for oral administration include solid forms, such as pills, tablets, caplets, capsules (each including immediate release, timed release and sustained release formulations), granules, and powders, and liquid forms, such as solutions, syrups, elixers, emulsions, and suspensions. Forms useful for parenteral administration include sterile solutions, emulsions and suspensions.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those of ordinary skill in that art. To be administered in the form of a transdermal delivery system, the dosage administration will, of course, be continuous rather than intermittent throughout the dosage regimen.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders; lubricants, disintegrating agents and coloring agents can also be incorporated into the resulting mixture. Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms in suitably flavored suspending or dispersing agents such as the synthetic and natural gums, for example, tragacanth, acacia, methyl-cellulose and the like. For parenteral administration, sterile suspensions and solutions are desired. Isotonic preparations which generally contain suitable preservatives are employed when intravenous administration is desired.

To prepare a pharmaceutical composition of the present invention, a compound of formula (I) as the active ingredient is intimately admixed with a pharmaceutical carrier according to conventional pharmaceutical compounding techniques, which carrier may take a wide variety of forms depending of the form of preparation desired for administration (e.g. oral or parenteral). Suitable pharmaceutically acceptable carriers are well known in the art. Descriptions of some of these pharmaceutically acceptable carriers may be found in *The Handbook of Pharmaceutical Excipients*, published by the American Pharmaceutical Association and the Pharmaceutical Society of Great Britain.

Methods of formulating pharmaceutical compositions have been described in numerous publications such as *Pharmaceutical Dosage Forms: Tablets, Second Edition, Revised and Expanded*, Volumes 1-3, edited by Lieberman et al; *Pharmaceutical Dosage Forms: Parenteral Medications*, Volumes 1-2, edited by Avis et al; and *Pharmaceutical Dosage Forms: Disperse Systems*, Volumes 1-2, edited by Lieberman et al; published by Marcel Dekker, Inc.

Compounds of this invention may be administered in any of the foregoing compositions and according to dosage regimens established in the art whenever treatment of conditions, disorders or diseases, which are ameliorated by antagonizing a glucagon receptor is required.

The daily dosage of the products may be varied over a wide range from about 0.01 mg to about 10,000 mg per adult human per day, or any amount or range therein. For oral administration, the compositions are preferably provided in the form of tablets containing, 0.01, 0.05, 0.1, 0.5, 1.0, 2.5, 5.0, 10.0, 15.0, 25.0, 50.0, 100, 150, 200, 250 and 500 milligrams of the active ingredient for the symptomatic adjustment of the dosage to the patient to be treated. An effective amount of the drug is ordinarily supplied at a dosage level of from about 0.01 mg/kg to about 300 mg/kg of body weight per day, or any amount or range therein. Preferably, the range is from about 0.1 to about 1000.0 mg/kg of body weight per day, or any amount or range therein. More preferably, from about 0.1 to about 50.0 mg/kg of body weight per day, or any amount or range therein. More preferably, from about 0.5 to about 25.0 mg/kg of body weight per day, or any amount or range therein. More preferably, from about 0.5 to about 15 mg/kg of body weight per day, or any amount or range therein. More preferably, from about 0.75 to about 7.5 mg/kg of body weight per day, or any amount or range therein. The compounds may be administered on a regimen of 1 to 4 times per day.

Optimal dosages to be administered may be readily determined by those skilled in the art, and will vary with the particular compound used, the mode of administration, the strength of the preparation, the mode of administration, and the advancement of the disease condition. In addition, factors associated with the particular patient being treated, including patient age, weight, diet and time of administration, will result in the need to adjust dosages.

One skilled in the art will recognize that, both in vivo and in vitro trials using suitable, known and generally accepted cell and/or animal models are predictive of the ability of a test compound to treat or prevent a given disorder.

One skilled in the art will further recognize that human clinical trials including first-in-human, dose ranging and efficacy trials, in healthy patients and/or those suffering from a given disorder, may be completed according to methods well known in the clinical and medical arts.

SYNTHESIS EXAMPLES

The following Examples are set forth to aid in the understanding of the invention, and are not intended and should not be construed to limit in any way the invention set forth in the claims which follow thereafter.

In the Examples which follow, some synthesis products are listed as having been isolated as a residue. It will be understood by one of ordinary skill in the art that the term "residue" does not limit the physical state in which the product was isolated and may include, for example, a solid, an oil, a foam, a gum, a syrup, and the like.

In the Examples which follow, some synthesis step result in the coupling of a substituent group to a N-atom on the indazole core of the compounds of the present invention. One skilled in the art will recognize that such coupling reactions generally result in the preparation of two regio-isomers, bound at the N-1 and N-2 nitrogen atoms of the indazole. Said regio-isomers are denoted in the Examples which follow as the "N-1 substituted compound" and the N-2 substituted compound" respectively.

Example 1—Compound #1

3-(4-(1-(5-(4-(tert-Butyl)phenyl)-1H-indazol-1-yl)-3-methylbutyl)benzamido)propanoic Acid

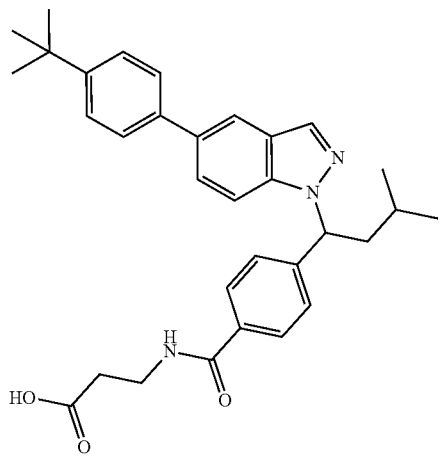 [SMILES: CC(C)CC(c1ccc(C(=O)NCCC(=O)O)cc1)n1ncc2cc(-c3ccc(C(C)(C)C)cc3)ccc21]

Step A:

A reaction mixture of 5-bromo-1H-indazole (1.00 g, 5.08 mmol), (4-(tert-butyl)phenyl)boronic acid (1.08 g, 6.09 mmol), $K_2CO_3$ (1.68 g, 12.18 mmol) and tetrakis(triphenylphosphine)palladium (0.59 g, 0.51 mmol) in 1,4-dioxane (15 mL) and $H_2O$ (5 mL) was heated under $N_2$ at 120° C. in a microwave for 3 h. The cooled mixture was diluted with EtOAc and washed with $H_2O$. The organic phase was dried over $Na_2SO_4$. Filtration and concentration yielded a solid. The solid was triturated with 10 mL of $CH_2Cl_2$ and filtered. The resulting off-white solid was collected. The filtrate was purified by chromatography on silica gel (20% to 30% EtOAc in heptane) to yield a white solid. The solid collected after filtration and after column (5-(4-tert-butyl-phenyl)-indazole) were combined and used in the next step. $^1$H NMR (CDCl$_3$, 400 MHz) δ 10.06 (br s, 1H)), 8.13 (s, 1H), 7.94 (s, 1H), 7.67 (d, J=8.5 Hz, 1H), 7.58 (d, J=8.3 Hz, 2H), 7.56 (d, J=8.5 Hz, 1H), 7.49 (d, J=8.3 Hz, 2H), 1.38 (s, 9H).

Step B:

A mixture of (5-(4-tert-butyl-phenyl)-indazole) (0.43 g, 1.72 mmol), 4-(1-bromo-3-methylbutyl)benzoic acid (0.54 g, 1.89 mmol) and $Cs_2CO_3$ (0.67 g, 2.06 mmol) in DMF (15 mL) under $N_2$ was heated in an oil bath at 68° C. for 16 h. The reaction mixture was diluted with $CH_2Cl_2$ and filtered. The filtrate was concentrated under high vacuum. The residue was purified by chromatography on silica gel (heptane to 10% EtOAc in heptane) to yield the N-1 substituted compound as an off-white foam solid. $^1$H NMR (CHLOROFORM-d) δ 8.13 (s, 1H), 7.96 (d, J=8.1 Hz, 2H), 7.89 (s, 1H), 7.38-7.60 (m, 8H), 5.74 (dd, J=9.8, 5.4 Hz, 1H), 3.87 (s, 3H), 2.66-2.75 (m, 1H), 2.03-2.12 (m, 1H), 1.42-1.53 (m, 1H), 1.37 (s, 9H), 0.99 (d, J=6.0 Hz, 3H), 0.97 (d, J=6.0 Hz, 3H);

followed by N-2 substituted compound as a white foam solid. $^1$H NMR (CHLOROFORM-d) δ 8.03 (s, 1H), 7.99 (d, J=8.1 Hz, 2H), 7.77-7.82 (m, 2H), 7.53-7.60 (m, 3H), 7.47 (d, J=8.1 Hz, 2H), 7.43 (d, J=8.1 Hz, 2H), 5.74 (dd, J=9.2, 6.5 Hz, 1H), 3.89 (s, 3H), 2.57 (ddd, J=14.3, 8.9, 5.9 Hz, 1H), 2.13 (dt, J=14.1, 7.2 Hz, 1H), 1.42-1.51 (m, 1H), 1.37 (s, 9H), 1.01 (br d, J=6.6 Hz, 3H), 0.97 (br d, J=6.6 Hz, 3H).

Step C:

A solution of N-1 substituted compound (off-white foam solid) (184 mg, 0.41 mmol) in THF/MeOH/H$_2$O (4:1:1 v/v/v) (12 mL) was treated with LiH (1 M in H$_2$O) (2 mL, 2 mmol). The mixture was stirred at room temperature for 2 h and then at 50° C. for 1 h. After neutralization with 1N HCl, brine was added and the mixture was extracted with EtOAc twice. The combined extracts were washed with brine and dried over Na$_2$SO$_4$. Filtration and concentration of the filtrate yielded an off-white foam solid. $^1$H NMR (CHLOROFORM-d) δ 8.13 (s, 1H), 8.02 (d, J=8.3 Hz, 2H), 7.89 (s, 1H), 7.58 (dd, J=8.8, 1.7 Hz, 1H), 7.50-7.56 (m, 2H), 7.40-7.49 (m, 5H), 5.75 (dd, J=9.8, 5.4 Hz, 1H), 2.66-2.76 (m, 1H), 2.05-2.12 (m, 1H), 1.41-1.54 (m, 1H), 1.36 (s, 9H), 0.99 (t, J=6.2 Hz, 3H), 0.98 (t, J=6.2 Hz, 3H).

Step D:

To a mixture of the off-white foam of Step C (303 mg, 0.69 mmol) and N-(3-dimethylaminopropyl)-N'-ethylcarbodiimide hydrochloride (198 mg, 1.03 mmol) in CH$_2$Cl$_2$ (5 mL) at room temperature were added tert-butyl 3-aminopropanoate hydrochloride (150 mg, 0.82 mmol) and triethylamine (0.19 mL, 1.37 mmol). The solution was stirred at room temperature for 48 h. The reaction mixture was concentrated and purified by chromatography on silica gel (20% to 50% EtOAc in heptane) to yield a white solid. $^1$H NMR (CHLOROFORM-d) δ 8.12 (s, 1H), 7.89 (s, 1H), 7.68 (d, J=7.8 Hz, 2H), 7.50-7.59 (m, 3H), 7.38-7.50 (m, 5H), 6.81 (br t, J=5.7 Hz, 1H), 5.73 (dd, J=9.8, 5.6 Hz, 1H), 3.64 (q, J=5.8 Hz, 2H), 2.64-2.73 (m, 1H), 2.51 (t, J=5.8 Hz, 2H), 2.08 (ddd, J=14.0, 7.9, 6.2 Hz, 1H), 1.44 (s, 9H), 1.36 (s, 9H), 0.99 (t, J=5.9 Hz, 3H), 0.97 (t, J=5.9 Hz, 3H); MS (ES, m/z) 568 [M+H$^+$].

Step E:

A solution of the white solid prepared in Step D (272 mg, 0.48 mmol) in 4 N HCl/dioxane (10 mL) was stirred at room temperature for 2 h. After concentration of the reaction mixture, the residue was purified by chromatography on silica gel (CH$_2$Cl$_2$ to 10% MeCOH in CH$_2$Cl$_2$) yielded the title compound as a white foam solid.

$^1$H NMR (METHANOL-d$_4$) δ 8.14 (s, 1H), 7.95 (s, 1H), 7.73 (d, J=8.3 Hz, 2H), 7.66 (s, 2H), 7.56 (d, J=8.3 Hz, 2H), 7.47 (br d, J=8.3 Hz, 2H), 7.44 (br d, J=8.3 Hz, 2H), 5.93 (dd, J=10.5, 5.1 Hz, 1H), 3.55-3.62 (m, 2H), 2.64-2.73 (m, 1H), 2.59 (t, J=6.8 Hz, 2H), 2.05 (ddd, J=13.9, 8.7, 5.3 Hz, 1H), 1.36-1.44 (m, 1H), 1.35 (s, 9H), 1.00 (d, J=6.6 Hz, 3H), 0.95 (d, J=6.6 Hz, 3H); MS (ES, m/z) 512 [M+H$^+$].

Separation, by chiral HPLC, of the material prepared in Example 1 yielded the corresponding enantiomerically enriched Compound #37, which was assigned an R* orientation, and the corresponding enantiomerically enriched Compound #163, which was assigned the S* orientation.

Example 2—Compound #34

3-(4-(1-(5-(4-(tert-butyl)phenyl)-2H-indazol-2-yl)-3-methylbutyl)benzamido)propanoic Acid

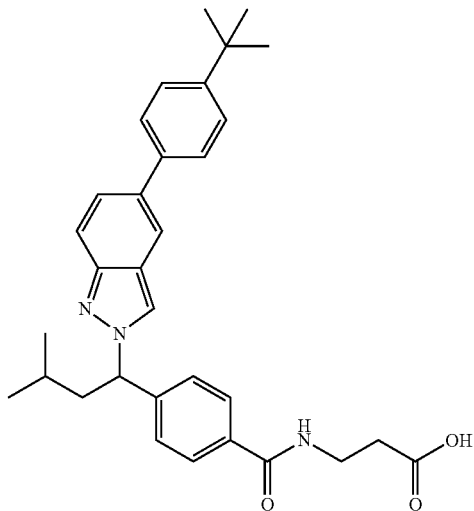 [SMILES: CC(C)CC(c1ccc(C(=O)NCCC(=O)O)cc1)n1cc2cc(-c3ccc(C(C)(C)C)cc3)ccc2n1]

Step A:

A solution of the N-2 substituted white foam solid prepared in Example 1, Step B (104 mg, 0.23 mmol) in THF/MeOH/H$_2$O (4:1:1 v/v/v) (12 mL) was treated with LiH (1 M in H$_2$O) (2 mL, 2 mmol). The mixture was stirred at room temperature for 2 h and then at 50° C. for 1 h. After neutralization with 1N HCl, brine was added and the mixture was extracted with EtOAc thrice. The combined extracts were washed with brine and dried over Na$_2$SO$_4$. Filtration and concentration of the filtrate to yield an off-white foam solid. $^1$H NMR (CHLOROFORM-d) δ 8.00-8.10 (m, 3H), 7.76-7.82 (m, 2H), 7.54-7.59 (m, 3H), 7.42-7.50 (m, 4H), 5.76 (br dd, J=8.8, 6.6 Hz, 1H), 2.53-2.62 (m, 1H), 2.09-2.18 (m, 1H), 1.40-1.53 (m, 1H), 1.37 (s, 9H), 1.02 (d, J=6.6 Hz, 3H), 0.98 (d, J=6.6 Hz, 3H).

Step B:

To a mixture of the off-white foam prepared in Step A (161 mg, 0.37 mmol) and N-(3-dimethylaminopropyl)-N'-ethylcarbodiimide hydrochloride (105 mg, 0.55 mmol) in CH$_2$C$_2$ (4 mL) at room temperature were added tert-butyl 3-aminopropanoate hydrochloride (80 mg, 0.44 mmol) and triethylamine (0.10 mL, 0.73 mmol). The solution was stirred at room temperature for 48 h. The reaction mixture was concentrated and purified by chromatography on silica gel (20% to 50% EtOAc in heptane) yielded a white solid. $^1$H NMR (CHLOROFORM-d) δ 8.02 (s, 1H), 7.77-7.81 (m, 2H), 7.72 (d, J=8.1 Hz, 2H), 7.56 (d, J=8.3 Hz, 3H), 7.47 (d, J=8.3 Hz, 2H), 7.43 (d, J=8.1 Hz, 2H), 6.83 (br t, J=5.5 Hz, 1H), 5.72 (dd, J=8.9, 6.5 Hz, 1H), 3.66 (q, J=6.1 Hz, 2H), 2.50-2.59 (m, 3H), 2.14 (dt, J=14.2, 7.1 Hz, 1H), 1.41-1.50 (m, 10H), 1.37 (s, 9H), 1.01 (d, J=6.6 Hz, 3H), 0.97 (d, J=6.6 Hz, 3H).

Step C:

A solution of the white solid prepared in Step B above (143 mg, 0.25 mmol) in 4 N HCl/dioxane (5 mL) was stirred at room temperature for 2 h. After concentration of the reaction mixture, the residue was purified by chromatography on silica gel (CH$_2$Cl$_2$ to 10% MeCOH in CH$_2$Cl$_2$) to yield the title compound as a white foam solid.

$^1$H NMR (METHANOL-d$_4$) δ 8.44 (s, 1H), 7.87 (s, 1H), 7.77 (d, J=7.3 Hz, 2H), 7.65-7.69 (m, 1H), 7.54-7.62 (m, 3H), 7.43-7.52 (m, 4H), 5.85 (dd, J=10.0, 5.9 Hz, 1H), 3.60 (t, J=6.8 Hz, 2H), 2.53-2.63 (m, 3H), 2.12 (ddd, J=14.1, 8.2, 5.9 Hz, 1H), 1.33-1.41 (m, 10H), 1.02 (d, J=6.6 Hz, 3H), 0.96 (d, J=6.6 Hz, 3H); MS (ES, m/z) 512 [M+H$^+$].

Example 3—Compound #68

3-(4-(1-(5-(4-(tert-Butyl)phenyl)-1H-indazol-1-yl)ethyl)benzamido) propanoic Acid

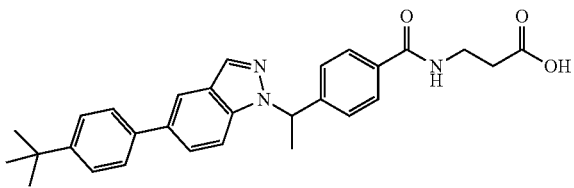 [SMILES: CC(c1ccc(C(=O)NCCC(=O)O)cc1)n1ncc2cc(-c3ccc(C(C)(C)C)cc3)ccc21]

Step A:

To a mixture of the 4-(1-bromoethyl)benzoic acid (2.29 g, 10.0 mmol) and N-(3-dimethylaminopropyl)-N'-ethylcarbodiimide hydrochloride (2.01 g, 10.5 mmol) in CH$_2$Cl$_2$ (30 mL) at room temperature were added methyl 3-aminopropanoate hydrochloride (1.40 g, 10.0 mmol) and diisopropylethylamine (1.95 mL, 11.0 mmol). The solution was stirred at room temperature for 16 h. The resulting mixture was diluted with CH$_2$Cl$_2$ and washed successively with 1N aqueous HCl, H$_2$O (twice), brine and then dried over Na$_2$SO$_4$. Filtration and concentration of the filtrate resulted in a residue which was purified by chromatography on silica gel (20% to 50% EtOAc in heptane) to yield a white solid. $^1$H NMR (CDCl$_3$, 400 MHz) δ 7.75 (d, J=8.3 Hz, 0.9H), 7.74 (d, J=8.1 Hz, 1.1H) (two rotamers 0.9H+1.1H=2H), 7.49 (d, J=8.1 Hz, 1.1H), 7.48 (d, J=8.3 Hz, 0.9H) (two rotamers 0.9H+1.1H=2H), 6.86 (br s, 1H), 5.20 (q, J=6.9 Hz, 0.55H), 5.20 (q, J=6.9 Hz, 0.45H) (two rotamers 0.55H+0.45H=1H), 3.73 (t, J=5.9 Hz, 2H), 3.71 (s, 3H), 2.66 (t, J=5.9 Hz, 2H), 2.04 (d, J=6.9 Hz, 1.65H), 1.84 (d, J=6.9 Hz, 1.35H) (two rotamers 1.65H+1.35H=3H); MS (ES, m/z) 314, 316 [M+H$^+$].

Step B:

A mixture of the white solid of Step A and methyl 3-(4-(1-bromo-3-methylbutyl)benzamido)propanoate (0.36 g, 1.1 mmol) and Cs$_2$CO$_3$ (0.39 g, 1.2 mmol) in DMF (6 mL) under N$_2$ was heated in an oil bath at 68° C. for 18 h. The reaction mixture was diluted with CH$_2$Cl$_2$ and filtered. The filtrate was concentrated in vacuo to yield a residue, which was purified by chromatography on silica-gel (20% to 80% EtOAc in heptane) to yield the N-1 substituted compound as an off-white foam solid.

$^1$H NMR (CDCl$_3$, 400 MHz) δ 8.11 (s, 1H), 7.90 (s, 1H), 7.70 (d, J=8.1 Hz, 2H), 7.45-7.56 (m, 5H), 7.28-7.33 (m, 3H), 6.77 (br t, J=5.6 Hz, 1H), 5.86 (q, J=6.8 Hz, 1H), 3.66-3.72 (m, 5H), 2.62 (t, J=5.9 Hz, 2H), 2.07 (d, J=6.8 Hz, 3H), 1.36 (s, 9H); MS (ES, m/z) 484 [M+H$^+$];

followed by the N-2 substituted compound as a colorless film stuck on flask wall. $^1$H NMR (CDCl$_3$, 400 MHz) δ 7.98 (s, 1H), 7.71-7.81 (m, 4H), 7.54-7.60 (m, 3H), 7.47 (d, J=8.3 Hz, 2H), 7.31 (d, J=8.3 Hz, 2H), 6.84 (br t, J=5.7 Hz, 1H), 5.86 (q, J=7.0 Hz, 1H), 3.67-3.73 (m, 5H), 2.64 (t, J=5.7 Hz, 2H), 2.03-2.10 (m, 3H), 1.37 (s, 9H); MS (ES, m/z) 484 [M+H$^+$].

Step C:

The off-white foam solid prepared in Step B (the N-1 substituted compound 199 mg, 0.41 mmol) in THF/MeOH/H$_2$O (4:1:1 v/v/v) (12 mL) was treated with LiH (1 M in H$_2$O) (2 mL, 2 mmol). The mixture was stirred at room temperature for 3 h. Saturated NH$_4$Cl aqueous solution was added and the resulting mixture was extracted with EtOAc thrice. The combined extracts were washed with brine and dried over Na$_2$SO$_4$. Filtration and concentration of the filtrate resulted in a residue, which was purified by chromatography on silica-gel (10% MeCOH in CH$_2$Cl$_2$) to yield the title compound as a white foam solid.

$^1$H NMR (CDCl$_3$, 400 MHz) δ 8.11 (s, 1H), 7.89 (s, 1H), 7.67 (d, J=8.1 Hz, 2H), 7.44-7.56 (m, 5H), 7.27-7.32 (m, 3H), 6.79 (br t, J=5.9 Hz, 1H), 5.85 (q, J=6.8 Hz, 1H), 3.67 (dt, J=5.8 Hz, 2H), 2.65 (br t, J=5.8 Hz, 2H), 2.04 (d, J=6.8 Hz, 3H), 1.36 (s, 9H).

Example 4—Compound #161

3-(4-(1-(5-(4-(tert-butyl)phenyl)-2H-indazol-2-yl)ethyl)benzamido) propanoic Acid

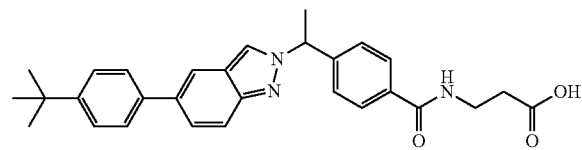 [SMILES: CC(c1ccc(C(=O)NCCC(=O)O)cc1)n1cc2cc(-c3ccc(C(C)(C)C)cc3)ccc2n1]

The colorless film prepared in Example 3, Step B (the N-2 substituted compound, 108 mg, 0.22 mmol) in THF/MeOH/H$_2$O (4:1:1 v/v/v) (12 mL) was treated with LiH (1 M in H$_2$O) (2 mL, 2 mmol). The mixture was stirred at room temperature for 3 h. Saturated NH$_4$Cl aqueous solution was added and the resulting mixture was extracted with EtOAc thrice. The combined extracts were washed with brine and dried over Na$_2$SO$_4$. Filtration and concentration of the filtrate resulted in a residue, which was purified by chromatography on silica-gel (10% MeCOH in CH$_2$Cl$_2$) to yield the title compound as a yellowish foam solid.

$^1$H NMR (CDCl$_3$, 400 MHz) δ 8.00 (s, 1H), 7.67-7.81 (m, 4H), 7.45-7.60 (m, 5H), 7.29 (br d, J=8.1 Hz, 2H), 6.90 (br s, 1H), 5.89 (q, J=7.0 Hz, 1H), 3.68 (br dt, J=4.9 Hz, 2H), 2.65 (t, J=4.9 Hz, 2H), 2.04 (br d, J=7.0 Hz, 3H), 1.37 (s, 9H).

Example 5—Compound #9

3-(4-(1-(5-(2,4-Dichlorophenyl)-1H-indazol-1-yl)-3-methylbutyl)benzamido)propanoic Acid

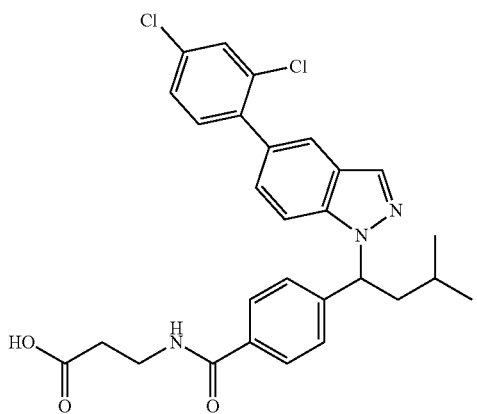 [SMILES: CC(C)CC(c1ccc(C(=O)NCCC(=O)O)cc1)n1ncc2cc(-c3ccc(Cl)cc3Cl)ccc21]

Step A:

A mixture of 5-bromo-1H-indazole (2.10 g, 10.68 mmol), methyl 4-(1-bromo-3-methylbutyl)benzoate (3.05 g, 10.68 mmol), and $Cs_2CO_3$ (4.18 g, 12.82 mmol) in DMF (40 mL) under $N_2$ was heated in an oil bath at 68° C. for 6 hr. The reaction mixture was diluted with $CH_2Cl_2$ and filtered through CELITE. The filtrate was concentrated under high vacuum to yield a residue, which was purified by chromatography on silica gel (heptane to 10% EtOAc in heptane) to yield the N-1 substituted compound as a yellow oil. $^1$H NMR (CHLOROFORM-d) δ 8.02 (s, 1H), 7.95 (d, J=8.3, 2H), 7.87 (d, J=1.7 Hz, 1H), 7.39 (dd, J=8.8, 1.7 Hz, 1H), 7.35 (d, J=8.3 Hz, 2H), 7.25 (d, J=8.8 Hz, 1H), 5.67 (dd, J=9.9, 5.5 Hz, 1H), 3.88 (s, 3H), 2.66 (ddd, J=14.0, 9.9, 5.5 Hz, 1H), 2.06 (ddd, J=14.0, 8.5, 5.5 Hz, 1H), 1.35-1.47 (m, 1H), 0.96 (d, J=6.6 Hz, 3H), 0.94 (d, J=6.6 Hz, 3H);

followed by the N-2 substituted compound as a brownish oil. $^1$H NMR (CHLOROFORM-d) δ 7.99 (d, J=8.3 Hz, 2H), 7.93 (s, 1H), 7.79 (d, J=1.7 Hz, 1H), 7.61 (d, J=9.3 Hz, 1H), 7.40 (d, J=8.3 Hz, 2H), 7.33 (dd, J=9.3, 1.7 Hz, 1H), 5.70 (dd, J=9.3, 6.6 Hz, 1H), 3.89 (s, 3H), 2.48-2.57 (m, 1H), 2.12 (dt, J=14.0, 7.1 Hz, 1H), 1.35-1.46 (m, 1H), 0.99 (d, J=6.6 Hz, 3H), 0.96 (d, J=6.6 Hz, 3H).

Step B:

A solution of the yellow oil prepared in Step A above (the N-1 substituted compound, 1.25 g, 3.12 mmol) in THF/MeOH/$H_2O$ (4:1:1 v/v/v, 48 mL) was treated with LiH aqueous solution (1 M in $H_2O$, 8 mL, 8 mmol). The reaction mixture was stirred in an oil bath at 50° C. for 2 h. Hydrochloric acid (1 M in $H_2O$) was added to neutralize the mixture. Brine was added and the resulting mixture was extracted with EtOAc thrice. The combined extracts were washed with brine and dried over $Na_2SO_4$. Filtration and concentration of the filtrate yielded a slightly yellowish foam solid. $^1$H NMR (CHLOROFORM-d) δ: 7.94-8.07 (m, 3H), 7.87 (s, 1H), 7.33-7.43 (m, 3H), 7.25 (d, J=8.8 Hz, 1H), 5.68 (dd, J=9.8, 5.6 Hz, 1H), 2.61-2.71 (m, 1H), 2.01-2.10 (m, 1H), 1.36-1.49 (m, 1H), 0.96 (d, J=6.6 Hz, 3H), 0.95 (d, J=6.6 Hz, 3H).

Step C:

To a mixture of the slightly yellowish foam solid of Step B (1.11 g, 2.87 mmol), tert-butyl 3-aminopropanoate hydrochloride (0.46 g, 2.53 mmol) and HATU (1.05 g, 2.76 mmol) in DMF (25 mL) at room temperature was added diisopropylethylamine (1.19 mL, 6.89 mmol). The solution was stirred at room temperature for 16 h. Water was added and the resulting mixture was extracted with EtOAc thrice. The combined extracts were washed with $H_2O$, brine and dried over $Na_2SO_4$. Filtration and concentration of the filtrate resulted in a residue, which was purified by chromatography on silica gel (heptane to 30% EtOAc in heptane) to yield a yellow solid. $^1$H NMR (CHLOROFORM-d) δ: 8.01 (s, 1H), 7.86 (d, J=1.5 Hz, 1H), 7.67 (d, J=8.3 Hz, 2H), 7.39 (dd, J=8.9, 1.5 Hz, 1H), 7.34 (d, J=8.3 Hz, 2H), 7.25 (d, J=8.9 Hz, 1H), 6.80 (br t, J=5.9 Hz, 1H), 5.66 (dd, J=9.8, 5.6 Hz, 1H), 3.65 (q, J=5.9 Hz, 2H), 2.57-2.68 (m, 1H), 2.51 (t, J=5.9 Hz, 2H), 2.06 (ddd, J=14.0, 8.3, 5.9 Hz, 1H), 1.37-1.46 (m, 10H), 0.96 (d, J=6.6 Hz, 3H), 0.95 (d, J=6.6 Hz, 3H); MS (ES, m/z) 458, 460 [M-tBu].

Step D:

A mixture of the yellow solid of Step C (77 mg, 0.15 mmol), (2,4-dichlorophenyl)boronic acid (38 mg, 0.20 mmol), $PdCl_2(dppf)\cdot CH_2Cl_2$ (12 mg, 0.015 mmol) and $K_2CO_3$ (55 mg, 0.40 mmol) in 1,4dioxane (1.5 mL)/water (0.5 mL) was heated under $N_2$ at 90° C. for 3 h. The cooled reaction mixture was diluted with $CH_2Cl_2$, dried over $Na_2SO_4$ and filtered through CELITE. The filtrate was concentrated and the residue was purified by chromatography on silica gel (heptane to 40% EtOAc in heptane) to yield a white solid. $^1$H NMR (CHLOROFORM-d) δ 8.12 (s, 1H), 7.74 (s, 1H), 7.69 (d, J=8.3 Hz, 2H), 7.50 (d, J=1.5 Hz, 1H), 7.35-7.44 (m, 5H), 7.28-7.30 (m, 2H), 6.80 (br t, J=6.1 Hz, 1H), 5.73 (dd, J=9.5, 5.9 Hz, 1H), 3.65 (q, J=6.1 Hz, 2H), 2.68 (ddd, J=13.9, 9.5, 5.6 Hz, 1H), 2.52 (t, J=6.1 Hz, 2H), 2.10 (ddd, J=13.9, 8.3, 5.9 Hz, 1H), 1.41-1.52 (m, 10H), 0.99 (d, J=6.6 Hz, 3H), 0.98 (d, J=6.6 Hz, 3H); MS (ES, m/z) 580 [M+H$^+$].

Step E:

A solution of the white solid prepared in Step D (72 mg, 0.12 mmol) in TFA/$CH_2Cl_2$ (1:1 v/v, 4 mL) was stirred at room temperature for 1h. After concentration, the residue was purified by chromatography on silica gel (2% to 10% MeCOH in $CH_2Cl_2$) to yield the title compound as a white solid.

$^1$H NMR (CHLOROFORM-d) δ 8.12 (s, 1H), 7.73 (s, 1H), 7.67 (d, J=8.1 Hz, 2H), 7.49 (s, 1H), 7.35-7.44 (m, 4H), 7.24-7.31 (m, 2H), 6.79 (br t, J=5.6 Hz, 1H), 5.73 (dd, J=9.5, 5.9 Hz, 1H), 3.67 (q, J=5.5 Hz, 2H), 2.61-2.70 (m, 3H), 2.08 (ddd, J=14.0, 8.0, 5.9 Hz, 1H), 1.46 (dt, J=13.4, 6.6 Hz, 1H), 0.98 (d, J=6.6 Hz, 3H), 0.96 (d, J=6.6 Hz, 3H); MS (ES, m/z) 524 [M+H$^+$].

Example 6—Compound #226

3-(4-(1-(5-(2,4-Dichlorophenyl)-2H-indazol-2-yl)-3-methylbutyl)benzamido)propanoic Acid

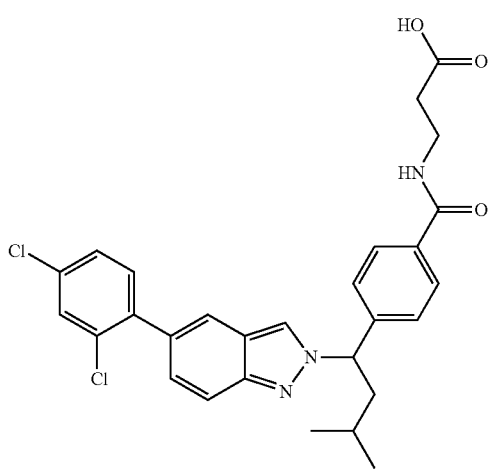 [SMILES: CC(C)CC(c1ccc(C(=O)NCCC(=O)O)cc1)n1cc2cc(-c3ccc(Cl)cc3Cl)ccc2n1]

Step A:

A solution of the brownish oil prepared in Example 5, Step A (the N-2 substituted compound, 0.71 g, 1.77 mmol) in THF/MeOH/H$_2$O (4:1:1 v/v/v, 12 mL) was treated with LiH aqueous solution (1 M in H$_2$O, 2 mL, 2 mmol). The reaction mixture was stirred in an oil bath at 50° C. for 2 h. Hydrochloric acid (1 M in H$_2$O) was added to neutralize the mixture. Brine was added and the resulting mixture was extracted with EtOAc thrice. The combined extracts were washed with brine and dried over Na$_2$SO$_4$. Filtration and concentration of the filtrate yielded a yellowish foam solid.

$^1$H NMR (CHLOROFORM-d) δ 8.02 (br d, J=7.8 Hz, 2H), 7.93 (s, 1H), 7.79 (s, 1H), 7.62 (d, J=9.3 Hz, 1H), 7.39 (br d, J=7.8 Hz, 2H), 7.33 (dd, J=9.3, 1.7 Hz, 1H), 5.70 (dd, J=8.8, 6.6 Hz, 1H), 2.51 (ddd, J=14.2, 8.8, 6.1 Hz, 1H), 2.10 (dt, J=14.2, 7.2 Hz, 1H), 1.34-1.45 (m, 1H), 0.99 (br d, J=6.6 Hz, 3H), 0.95 (br d, J=6.6 Hz, 3H).

Step B:

To a mixture of the yellowish foam solid prepared in Step A (0.63 g, 1.63 mmol), methyl 3-aminopropanoate hydrochloride (0.25 g, 1.79 mmol) and HATU (0.74 g, 1.95 mmol) in DMF (15 mL) at room temperature was added diisopropylethylamine (0.84 mL, 4.88 mmol). The solution was stirred at room temperature for 16 h. Water was added and the resulting mixture was extracted with EtOAc thrice. The combined extracts were washed with H$_2$O, brine and dried over Na$_2$SO$_4$. Filtration and concentration of the filtrate resulted in a residue, which was purified by chromatograph on silica gel (10% to 40% EtOAc in heptane) to yield a gray solid. $^1$H NMR (CHLOROFORM-d) δ 7.92 (s, 1H), 7.78 (s, 1H), 7.72 (d, J=8.3 Hz, 2H), 7.61 (d, J=9.0 Hz, 1H), 7.41 (d, J=8.3 Hz, 2H), 7.32 (dd, J=9.0, 1.5 Hz, 1H), 6.80 (br t, J=5.5 Hz, 1H), 5.68 (dd, J=8.7, 7.0 Hz, 1H), 3.67-3.73 (m, 5H), 2.64 (t, J=5.7 Hz, 2H), 2.45-2.55 (m, 1H), 2.04-2.17 (m, 1H), 1.40 (ddd, J=6.6, 6.6, 6.6 Hz, 1H), 0.99 (br d, J=6.6 Hz, 3H), 0.95 (br d, J=6.6 Hz, 3H)

Step C:

A mixture of the gray solid prepared in Step B (47 mg, 0.10 mmol), (2,4-dichlorophenyl)boronic acid (21 mg, 0.11 mmol), PdCl$_2$(dppf).CH$_2$Cl$_2$ (8 mg, 0.01 mmol) and K$_2$CO$_3$ (30 mg, 0.22 mmol) in dioxane (1 mL)/water (0.3 mL) was heated at 85° C. under N$_2$ for 4 h. The cooled reaction mixture was diluted with CH$_2$Cl$_2$, dried over Na$_2$SO$_4$ and filtered through CELITE. The filtrate was concentrated and the residue was purified by chromatography on silica gel (10% to 50% EtOAc in heptane) to yield a white solid. $^1$H NMR (CHLOROFORM-d) δ 8.04 (s, 1H), 7.77 (d, J=9.0 Hz, 1H), 7.73 (d, J=8.3 Hz, 2H), 7.63 (s, 1H), 7.42-7.51 (m, 3H), 7.28-7.34 (m, 3H), 6.79 (br t, J=5.9 Hz, 1H), 5.73 (dd, J=8.8, 6.6 Hz, 1H), 3.68-3.73 (m, 5H), 2.64 (t, J=5.9 Hz, 2H), 2.55 (ddd, J=14.4, 8.8, 6.2 Hz, 1H), 2.11-2.19 (m, 1H), 1.38-1.51 (m, 1H), 1.01 (d, J=6.6 Hz, 3H), 0.98 (d, J=6.6 Hz, 3H); MS (ES, m/z) 538 [M+H$^+$].

Step D:

The white solid prepared in Step C (23 mg, 0.04 mmol) in THF/MeOH/H$_2$O (4:1:1 v/v/v) (6 mL) was treated with LiH (1 M in H$_2$O) (1 mL, 1 mmol). The mixture was stirred at room temperature for 2 h. After the reaction was with 1N HCl aqueous solution, the mixture was extracted with EtOAc thrice. The combined extracts were washed with brine and dried over Na$_2$SO$_4$. Filtration and concentration of the filtrate yielded the title compound as a white solid.

$^1$H NMR (CHLOROFORM-d) δ 8.05 (s, 1H), 7.75 (br d, J=9.0 Hz, 1H), 7.71 (br d, J=7.8 Hz, 2H), 7.63 (s, 1H), 7.49 (s, 1H), 7.43 (br d, J=7.8 Hz, 2H), 7.32 (d, J=9.0 Hz, 1H), 7.25-7.30 (m, 2H), 6.95 (br s, 1H), 5.79 (br t, J=7.7 Hz, 1H), 3.65-3.73 (m, 2H), 2.67 (m, 2H), 2.45-2.60 (m, 1H), 2.06-2.16 (m, 1H), 1.43 (m, 1H), 0.99 (br d, J=6.6 Hz, 3H), 0.96 (br d, J=6.6 Hz, 3H); MS (ES, m/z) 524 [M+H$^+$].

The following compounds (as shown in Examples 7-15 below) were similarly prepared according to the procedures described in Examples 5 and 6, selecting and substituting a suitably substituted boronic acid in the Suzuki coupling step.

Example 7—Compound #39

3-(4-(1-(5-(4-Chloro-2-methylphenyl)-1H-indazol-1-yl)-3-methylbutyl)benzamido)propanoic Acid

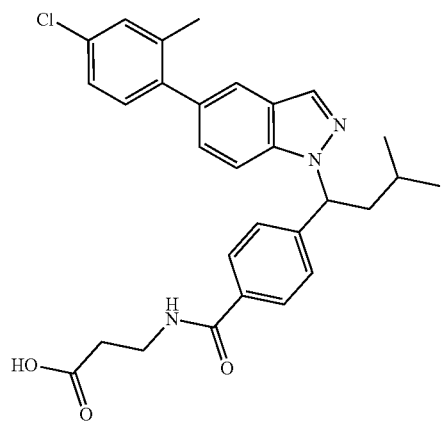

$^1$H NMR (CHLOROFORM-d) δ 8.10 (s, 1H), 7.68 (br d, J=8.1 Hz, 2H), 7.59 (s, 1H), 7.37-7.43 (m, 3H), 7.13-7.24 (m, 4H), 6.78 (br t, J=5.5 Hz, 1H), 5.73 (dd, J=9.5, 5.9 Hz, 1H), 3.63-3.73 (m, 2H), 2.61-2.72 (m, 3H), 2.23 (s, 3H), 2.09 (ddd, J=13.9, 8.2, 6.0 Hz, 1H), 1.47 (dt, J=13.9, 6.7 Hz, 1H), 0.98 (d, J=5.9 Hz, 3H), 0.96 (d, J=5.9 Hz, 3H).

Example 8—Compound #168

3-(4-(1-(5-(4-Chloro-2-methylphenyl)-2H-indazol-2-yl)-3-methylbutyl)benzamido)propanoic Acid

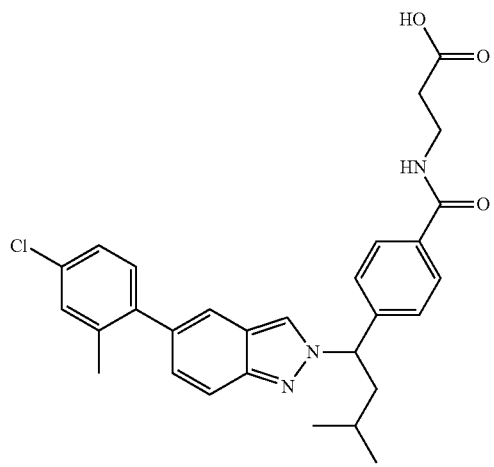 [SMILES: Cc1cc(Cl)ccc1-c1ccc2nn(C(CC(C)C)c3ccc(C(=O)NCCC(=O)O)cc3)cc2c1]

¹H NMR (CHLOROFORM-d) δ 8.03 (s, 1H), 7.73 (br d, J=7.8 Hz, 3H), 7.40-7.52 (m, 3H), 7.14-7.26 (m, 4H), 6.97 (br t, J=5.6 Hz, 1H), 5.81 (br dd, J=8.3, 7.1 Hz, 1H), 3.70 (q, J=5.5 Hz, 2H), 2.67 (br t, J=5.5 Hz, 2H), 2.46-2.55 (m, 1H), 2.23 (s, 3H), 2.06-2.20 (m, J=14.0, 7.1, 7.1 Hz, 1H), 1.37-1.49 (m, 1H), 1.00 (br d, J=6.6 Hz, 3H), 0.96 (br d, J=6.6 Hz, 3H); MS (ES, m/z) 504 [M+H⁺].

Example 9—Compound #41

3-(4-(1-(5-(2-Chloro-4-(trifluoromethyl)phenyl)-1H-indazol-1-yl)-3-methylbutyl)benzamido)propanoic Acid

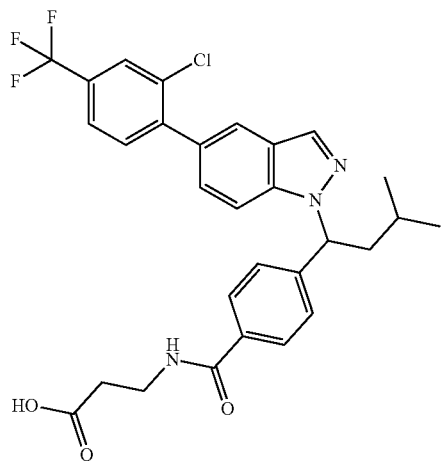

¹H NMR (CHLOROFORM-d) δ: 8.15 (s, 1H), 7.77 (s, 1H), 7.75 (s, 1H), 7.68 (br d, J=8.1 Hz, 2H), 7.57 (br d, J=8.1 Hz, 1H), 7.37-7.49 (m, 5H), 6.80 (br t, J=5.6 Hz, 1H), 5.74 (br dd, J=9.7, 5.7 Hz, 1H), 3.68 (q, J=5.2 Hz, 2H), 2.62-2.71 (m, 3H), 2.04-2.13 (m, 1H), 1.41-1.51 (m, 1H), 0.98 (d, J=5.9 Hz, 3H), 0.97 (d, J=5.9 Hz, 3H); MS (ES, m/z) 558 [M+H⁺].

Example 10—Compound #225

3-(4-(1-(5-(2-Chloro-4-(trifluoromethyl)phenyl)-2H-indazol-2-yl)-3-methylbutyl)benzamido)propanoic Acid

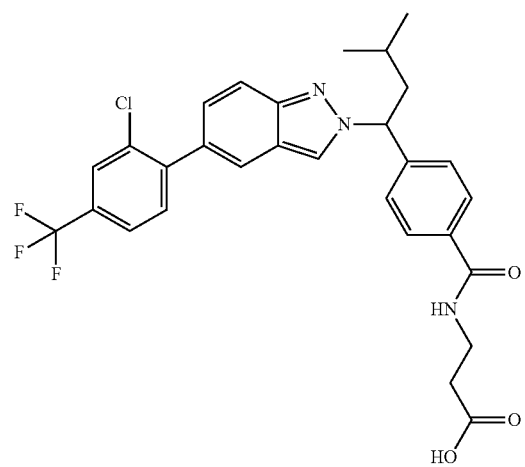 [SMILES: CC(C)CC(c1ccc(C(=O)NCCC(=O)O)cc1)n1cc2cc(-c3ccc(C(F)(F)F)cc3Cl)ccc2n1]

¹H NMR (CHLOROFORM-d) δ 8.08 (s, 1H), 7.66-7.80 (m, 5H), 7.53-7.60 (m, 1H), 7.48 (d, J=8.1 Hz, 1H), 7.44 (d, J=8.1 Hz, 2H), 7.35 (d, J=9.8 Hz, 1H), 6.93 (br t, J=5.5 Hz, 1H), 5.77-5.83 (m, 1H), 3.70 (q, J=5.4 Hz, 2H), 2.68 (br t, J=5.4 Hz, 2H), 2.52 (ddd, J=14.4, 8.6, 5.9 Hz, 1H), 2.13 (dt, J=14.4, 7.2 Hz, 1H), 1.38-1.48 (m, 1H), 1.00 (d, J=6.6 Hz, 3H), 0.96 (d, J=6.6 Hz, 3H); MS (ES, m/z) 558 [M+H⁺].

Example 11—Compound #84

3-((4-(3-Methyl-1-(5-(2-methyl-4-(trifluoromethyl)phenyl)-1H-indazol-1-yl)butyl)benzyl)amino)propanoic Acid

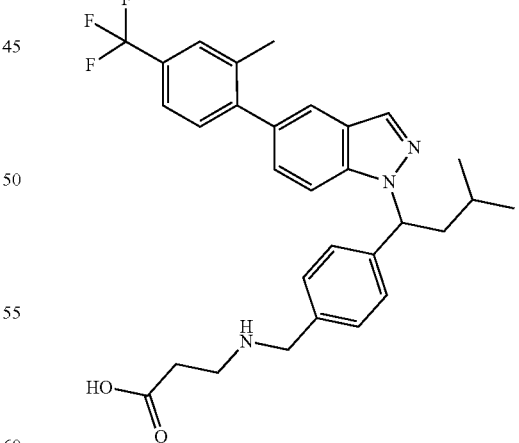

¹H NMR (CHLOROFORM-d) δ 8.14 (br s, 1H), 7.65-7.73 (m, 2H), 7.63 (s, 1H), 7.39-7.54 (m, 5H), 7.28-7.36 (m, 2H), 6.73-6.81 (m, 1H), 5.75 (br d, J=9.0, 5.6 Hz, 1H), 3.70 (br d, J=5.4 Hz, 2H), 2.64-2.75 (m, 3H), 2.30 (s, 3H), 2.05-2.14 (m, 1H), 1.43-1.53 (m, 1H), 0.99 (t, J=6.0 Hz, 3H), 0.98 (t, J=6.0 Hz, 3H); MS (ES, m/z) 538 [M+H⁺].

Example 12—Compound #189

3-(4-(3-Methyl-1-(5-(2-methyl-4-(trifluoromethyl)phenyl)-2H-indazol-2-yl)butyl)benzamido)propanoic Acid

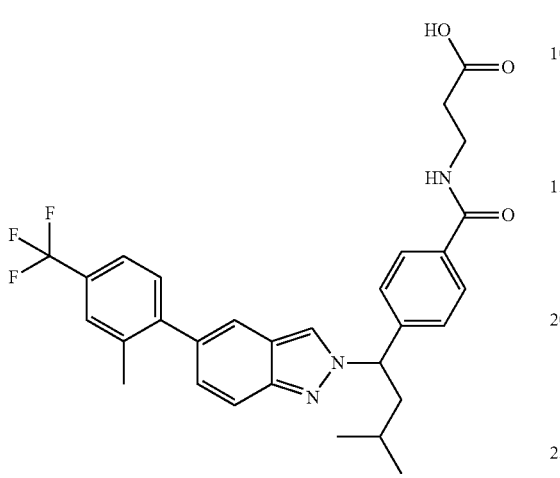

$^1$H NMR (CHLOROFORM-d) δ 8.05 (s, 1H), 7.68-7.80 (m, 3H), 7.43-7.55 (m, 5H), 7.34 (d, J=8.1 Hz, 1H), 7.23 (d, J=8.9 Hz, 1H), 6.94 (br t, J=5.7 Hz, 1H), 5.81 (br t, J=7.7 Hz, 1H), 3.70 (q, J=5.8 Hz, 2H), 2.68 (br t, J=5.8 Hz, 2H), 2.47-2.57 (m, 1H), 2.32 (s, 3H), 2.14 (dt, J=13.8, 7.0 Hz, 1H), 1.37-1.50 (m, 1H), 1.01 (d, J=6.4 Hz, 3H), 0.97 (d, J=6.6 Hz, 3H); MS (ES, m/z) 538 [M+H$^+$].

Example 13—Compound #38

3-((4-(1-(5-(4-Methoxyphenyl)-1H-indazol-1-yl)-3-methylbutyl)benzyl)amino)propanoic Acid

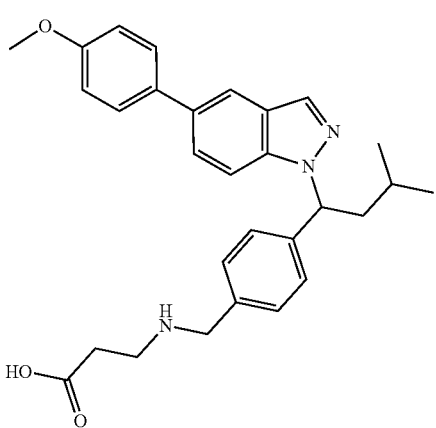 [SMILES: COc1ccc(-c2ccc3c(cnn3C(CC(C)C)c3ccc(CNCCC(=O)O)cc3)c2)cc1]

$^1$H NMR (CHLOROFORM-d) δ 8.11 (s, 1H), 7.84 (s, 1H), 7.66 (d, J=8.1 Hz, 2H), 7.47-7.56 (m, 3H), 7.34-7.42 (m, 3H), 6.98 (d, J=8.8 Hz, 2H), 6.78 (br t, J=6.0 Hz, 1H), 5.73 (dd, J=9.8, 5.6 Hz, 1H), 3.85 (s, 3H), 3.61-3.73 (m, 2H), 2.61-2.71 (m, 3H), 2.06 (ddd, J=13.8, 8.4, 5.7 Hz, 1H), 1.45 (dt, J=13.8, 6.7 Hz, 1H), 0.97 (t, J=6.6 Hz, 3H), 0.95 (t, J=6.6 Hz, 3H); MS (ES, m/z) 486 [M+H$^+$].

Example 14—Compound #10

3-((4-(3-Methyl-1-(5-(4-(trifluoromethoxy)phenyl)-1H-indazol-1-yl)butyl)benzyl)amino)propanoic Acid

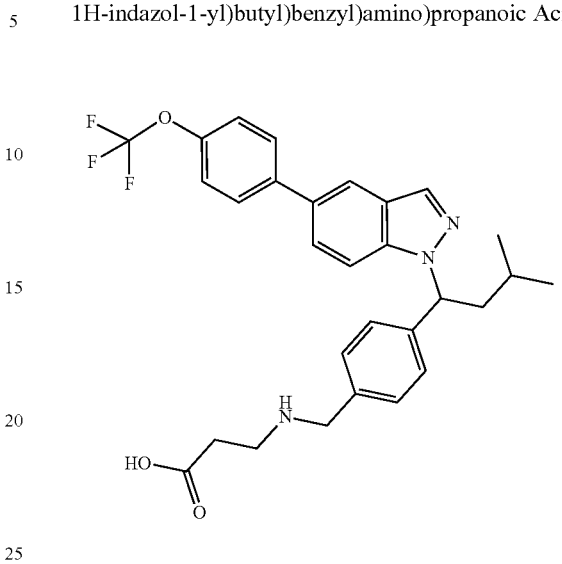

$^1$H NMR (CHLOROFORM-d) δ 8.13 (s, 1H), 7.86 (s, 1H), 7.67 (d, J=8.3 Hz, 2H), 7.51-7.60 (m, 3H), 7.41-7.46 (m, 1H), 7.38 (d, J=8.3 Hz, 2H), 7.28 (dd, J=8.8, 2H), 6.74 (t, J=6.1 Hz, 1H), 5.73 (dd, J=9.8, 5.6 Hz, 1H), 3.67 (q, J=6.0 Hz, 2H), 2.62-2.71 (m, 3H), 2.07 (ddd, J=14.0, 8.5, 5.6 Hz, 1H), 1.40-1.51 (m, 1H), 0.98 (t, J=6.5 Hz, 3H) 0.96 (t, J=6.5 Hz, 3H); MS (ES, m/z) 540 [M+H$^+$].

Example 15—Compound #118

3-((4-(1-(5-(3,5-Dichlorophenyl)-1H-indazol-1-yl)-3-methylbutyl)benzyl)amino)propanoic Acid

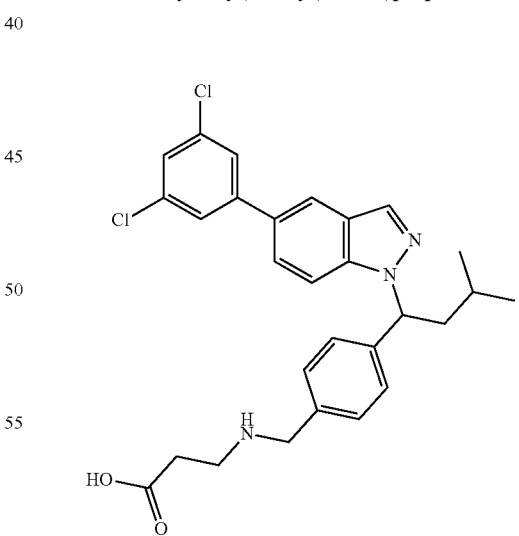

$^1$H NMR (CHLOROFORM-d) δ 8.13 (s, 1H), 7.87 (s, 1H), 7.65-7.71 (m, 2H), 7.36-7.52 (m, 6H), 7.32 (t, J=1.8 Hz, 1H), 6.66-6.74 (m, 1H), 5.73 (dd, J=9.4, 5.5 Hz, 1H), 3.64-3.75 (m, 2H), 2.62-2.74 (m, 3H), 2.03-2.13 (m, 1H), 1.41-1.51 (m, 1H), 0.98 (t, J=6.0 Hz, 3H), 0.97 (t, J=6.0 Hz, 3H); MS (ES, m/z) 524 [M+H$^+$].

Example 16—Compound #113

3-(5-(1-(5-(2,4-Dichlorophenyl)-1H-indazol-1-yl)-3-methylbutyl)picolinamido)propanoic Acid

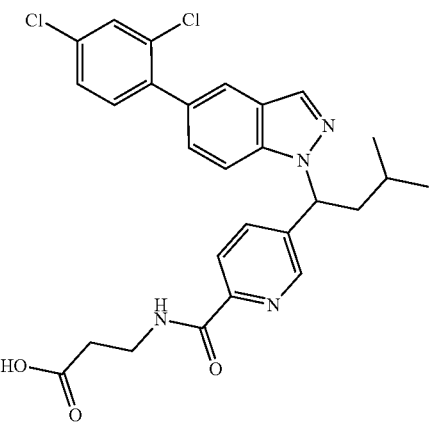

Step A:

A mixture of 5-bromo-1H-indazole (2.69 g, 13.65 mmol), methyl 5-(1-bromo-3-methylbutyl)picolinate (3.55 g, 12.42 mmol), and $Cs_2CO_3$ (5.34 g, 16.38 mmol) in DMF (50 mL) under $N_2$ was heated in an oil bath at 68° C. for 60 hr. The reaction mixture was diluted with $CH_2Cl_2$ and filtered through CELITE. The filtrate was concentrated under high vacuum to yield a residue, which was purified by chromatography on silica gel (10% to 40% EtOAc in heptane) to yield a yellow oil (the N-1 substituted compound). $^1$H NMR (CHLOROFORM-d) δ 8.71 (d, J=2.2 Hz, 1H), 8.03 (s, 1H), 8.04 (d, J=8.6 Hz, 1H), 7.88 (d, J=1.5 Hz, 1H), 7.79 (dd, J=8.6, 2.2 Hz, 1H), 7.43 (dd, J=8.9, 1.5 Hz, 1H), 7.28 (d, J=8.9 Hz, 1H), 5.71 (dd, J=10.0, 5.6 Hz, 1H), 3.98 (s, 3H), 2.68 (ddd, J=13.9, 10.0, 5.6 Hz, 1H), 2.04 (ddd, J=14.0, 8.4, 5.6 Hz, 1H), 1.35-1.47 (m, 1H), 0.97 (d, J=5.4 Hz, 3H), 0.95 (d, J=5.4 Hz, 3H);

followed by a second yellow oil (the N-2 substituted compound). $^1$H NMR (CHLOROFORM-d) δ 8.75 (d, J=2.2 Hz, 1H), 8.09 (d, J=8.3 Hz, 1H), 7.97 (s, 1H), 7.87 (dd, J=8.3, 2.2 Hz, 1H), 7.80 (d, J=1.8 Hz, 1H), 7.60 (d, J=9.2 Hz, 1H), 7.34 (dd, J=9.2, 1.8 Hz, 1H), 5.68-5.75 (m, 1H), 3.99 (s, 3H), 2.58 (ddd, J=13.9, 9.4, 6.0 Hz, 1H), 2.04-2.15 (m, 1H), 1.34-1.43 (m, 1H), 1.01 (d, J=6.6 Hz, 3H), 0.96 (d, J=6.6 Hz, 3H);

Step B:

A solution of the first yellow oil (the N-1 substituted compound, 1.85 g, 4.61 mmol) in THF/MeOH/$H_2O$ (4:1:1 v/v/v, 60 mL) was treated with LiH aqueous solution (1 M in $H_2O$, 10 mL, 10 mmol). The reaction mixture was stirred in an oil bath at 50° C. for 2 h. Hydrochloric acid (1 M in $H_2O$) was added to neutralize the mixture. Brine was added and the resulting mixture was extracted with EtOAc thrice. The combined extracts were washed with brine and dried over $Na_2SO_4$. Filtration and concentration of the filtrate yielded a white foam solid. $^1$H NMR (CHLOROFORM-d) δ 8.59 (s, 1H), 8.15 (d, J=8.1 Hz, 1H), 8.05 (s, 1H), 7.86-7.96 (m, 2H), 7.46 (dd, J=9.0, 1.7 Hz, 1H), 7.29 (d, J=8.8 Hz, 1H), 5.74 (dd, J=10.1, 5.4 Hz, 1H), 2.71 (ddd, J=14.1, 10.1, 5.4 Hz, 1H), 1.99-2.08 (m, 1H), 1.35-1.46 (m, 1H), 0.98 (t, J=6.8 Hz, 3H), 0.96 (t, J=6.8 Hz, 3H).

Step C:

To a mixture of the white foam prepared in Step B (1.79 g, 4.60 mmol), tert-butyl 3-aminopropanoate hydrochloride (0.92 g, 5.06 mmol) and HATU (1.05 g, 2.76 mmol) in DMF (30 mL) at room temperature was added diisopropylethylamine (2.38 mL, 13.8 mmol). The solution was stirred at room temperature for 16 h. Water was added and the resulting mixture was extracted with EtOAc thrice. The combined extracts were washed with $H_2O$, brine and dried over $Na_2SO_4$. Filtration and concentration of the filtrate yielded a residue, which was purified by chromatography on silica gel (10% to 40% EtOAc in heptane) to yield a white solid. $^1$H NMR (CHLOROFORM-d) δ: 8.51 (d, J=2.1 Hz, 1H), 8.37 (br t, J=6.1 Hz, 1H), 8.10 (d, J=8.1 Hz, 1H), 8.03 (s, 1H), 7.88 (d, J=1.5 Hz, 1H), 7.80 (dd, J=8.1, 2.1 Hz, 1H), 7.43 (dd, J=8.8, 1.5 Hz, 1H), 7.29 (d, J=8.8 Hz, 1H), 5.70 (dd, J=9.9, 5.5 Hz, 1H), 3.67 (q, J=6.1 Hz, 2H), 2.63-2.72 (m, 1H), 2.53 (t, J=6.1 Hz, 2H), 2.05 (ddd, J=14.0, 8.5, 5.6 Hz, 1H), 1.36-1.48 (m, 10H), 0.96 (t, J=6.1 Hz, 3H), 0.95 (t, J=6.1 Hz, 3H); MS (ES, m/z) 515, 517 [M+H$^+$].

Step D:

A mixture of the white solid prepared in Step C (77 mg, 0.15 mmol), (2,4-dichlorophenyl)boronic acid (38 mg, 0.20 mmol), $PdCl_2$(dppf)-$CH_2Cl_2$ (12 mg, 0.015 mmol) and $K_2CO_3$ (55 mg, 0.40 mmol) in 1,4-dioxane (1.5 mL)/water (0.5 mL) was heated under $N_2$ at 90° C. for 16 h. The cooled reaction mixture was diluted with $CH_2Cl_2$, dried over $Na_2SO_4$ and filtered through CELITE. The filtrate was concentrated and the residue was purified by chromatography on silica gel (heptane to 40% EtOAc in heptane) to yield a as white solid. $^1$H NMR (CHLOROFORM-d) δ 8.56 (d, J=2.0 Hz, 1H), 8.37 (br t, J=5.9 Hz, 1H), 8.13 (s, 1H), 8.11 (d, J=8.1 Hz, 1H), 7.86 (dd, J=8.1, 2.0 Hz, 1H), 7.75 (s, 1H), 7.37-7.52 (m, 3H), 7.27-7.33 (m, 2H), 5.77 (dd, J=9.9, 5.7 Hz, 1H), 3.68 (q, J=6.4 Hz, 2H), 2.63-2.77 (m, 1H), 2.53 (t, J=6.1 Hz, 2H), 2.08 (ddd, J=14.0, 8.4, 5.7 Hz, 1H), 1.43-1.51 (m, 10H), 1.00 (t, J=7.0 Hz, 3H), 0.98 (t, J=7.0 Hz, 3H); MS (ES, m/z) 581, 583 [M+H$^+$].

Step E:

A solution of the white solid prepared in Step D (78 mg, 0.13 mmol) in 4 N HCl in 1,4-dioxane (5 mL) was stirred at room temperature for 16h. After concentration, the residue was purified by chromatography on silica gel (2% to 10% MeCOH in $CH_2Cl_2$) to yield the title compound as a white solid.

$^1$H NMR (METHANOL-$d_4$) δ 8.66 (br s, 1H), 8.19 (s, 1H), 7.95-8.06 (m, 2H), 7.74-7.81 (m, 2H), 7.56 (s, 1H), 7.34-7.48 (m, 3H), 6.07 (br dd, J=10.4, 4.5 Hz, 1H), 3.64 (br t, J=6.6 Hz, 2H), 2.68-2.79 (m, 1H), 2.61 (br t, J=6.6 Hz, 2H), 2.05 (ddd, J=13.8, 8.9, 5.0 Hz, 1H), 1.28-1.46 (m, 1H), 1.01 (d, J=6.6 Hz, 3H), 0.96 (d, J=6.6 Hz, 3H); MS (ES, m/z) 525, 527 [M+H$^+$].

Example 17—Compound #83

3-(5-(1-(5-(2,4-Dichlorophenyl)-2H-indazol-2-yl)-3-methylbutyl)picolinamido)propanoic Acid

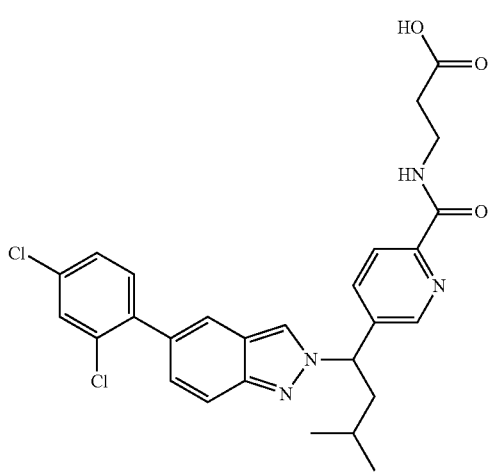

Step A:

A solution of the second yellow oil prepared in Example 16, Step A (the N-2 substituted compound, 1.08 g, 2.69 mmol) in THF/MeOH/H$_2$O (4:1:1 v/v/v, 18 mL) was treated with LiH aqueous solution (1 M in H$_2$O, 3 mL, 3 mmol). The reaction mixture was stirred in an oil bath at 50° C. for 2 h. Hydrochloric acid (1 M in H$_2$O) was added to neutralize the mixture. Brine was added and the resulting mixture was extracted with EtOAc thrice. The combined extracts were washed with brine and dried over Na$_2$SO$_4$. Filtration and concentration of the filtrate yielded a yellow foam solid. $^1$H NMR (CHLOROFORM-d) δ 8.64 (s, 1H), 8.19 (d, J=8.1 Hz, 1H), 8.01 (s, 1H), 7.98 (d, J=8.1 Hz, 1H), 7.81 (s, 1H), 7.61 (d, J=9.0 Hz, 1H), 7.36 (dd, J=9.0, 1.7 Hz, 1H), 5.74 (dd, J=9.7, 6.0 Hz, 1H), 2.57-2.66 (m, 1H), 2.03-2.13 (m, 1H), 1.34-1.45 (m, 1H), 1.02 (d, J=6.6 Hz, 3H), 0.97 (d, J=6.6 Hz, 3H).

Step B:

To a mixture of the yellow foam prepared in Step A (1.04 g, 2.68 mmol), methyl 3-aminopropanoate hydrochloride (0.41 g, 2.95 mmol) and HATU (1.22 g, 3.21 mmol) in DMF (25 mL) at room temperature was added diisopropylethylamine (1.39 mL, 8.04 mmol). The solution was stirred at room temperature for 16 h. Water was added and the resulting mixture was extracted with EtOAc thrice. The combined extracts were washed with H$_2$O, brine and dried over Na$_2$SO$_4$. Filtration and concentration of the filtrate yielded a residue, which was purified by chromatography on silica gel (20% to 50% EtOAc in heptane) to yield a yellowish solid. $^1$H NMR (CHLOROFORM-d) δ: 8.56 (s, 1H), 8.39 (br t, J=5.9 Hz, 1H), 8.14 (d, J=8.1 Hz, 1H), 7.96 (s, 1H), 7.85 (d, J=8.1 Hz, 1H), 7.79 (s, 1H), 7.60 (d, J=9.3 Hz, 1H), 7.34 (d, J=9.3 Hz, 1H), 5.70 (dd, J=9.3, 6.6 Hz, 1H), 3.68-3.75 (m, 5H), 2.64 (t, J=6.1 Hz, 2H), 2.52-2.61 (m, 1H), 2.11 (dt, J=14.1, 7.2 Hz, 1H), 1.33-1.43 (m, 1H), 1.01 (d, J=6.6 Hz, 3H), 0.96 (d, J=6.6 Hz, 3H).

Step C:

A mixture of the yellowish solid prepared in Step B (47 mg, 0.10 mmol), (2,4-dichlorophenyl)boronic acid (21 mg, 0.11 mmol), PdCl$_2$(dppf)-CH$_2$Cl$_2$ (8 mg, 0.01 mmol) and K$_2$CO$_3$ (30 mg, 0.22 mmol) in dioxane (1 mL)/water (0.3 mL) was heated at 85° C. under N$_2$ for 4 h. The cooled reaction mixture was diluted with CH$_2$Cl$_2$, dried over Na$_2$SO$_4$ and filtered through CELITE. The filtrate was concentrated and the residue was purified by chromatography on silica gel (10% to 50% EtOAc in heptane) to yield a white solid. $^1$H NMR (CHLOROFORM-d) δ 8.58 (s, 1H), 8.39 (br t, J=5.7 Hz, 1H), 8.14 (d, J=8.1 Hz, 1H), 8.07 (s, 1H), 7.89 (dd, J=8.1, 1.6 Hz, 1H), 7.77 (d, J=9.0 Hz, 1H), 7.64 (s, 1H), 7.50 (s, 1H), 7.29-7.35 (m, 3H), 5.75 (dd, J=9.5, 6.4 Hz, 1H), 3.68-3.76 (m, 5H), 2.57-2.67 (m, 3H), 2.09-2.17 (m, 1H), 1.39-1.53 (m, 1H), 1.03 (d, J=6.6 Hz, 3H), 0.98 (d, J=6.6 Hz, 3H); MS (ES, m/z) 581, 583 [M+H$^+$].

Step D:

The white solid prepared in Step C (43 mg, 0.08 mmol) in THF/MeOH/H$_2$O (4:1:1 v/v/v) (6 mL) was treated with LiH (1 M in H$_2$O) (1 mL, 1 mmol). The mixture was stirred at room temperature for 2 h. After the reaction was neutralized with 1N HCl aqueous solution, the mixture was extracted with EtOAc thrice. The combined extracts were washed with brine and dried over Na$_2$SO$_4$. Filtration and concentration of the filtrate yielded the title compound as an off-white solid.

$^1$H NMR (CHLOROFORM-d) δ: 8.60 (br s, 1H), 8.44 (br s, 1H), 8.05-8.19 (m, 2H), 7.88 (br d, J=7.6 Hz, 1H), 7.76 (br d, J=9.0 Hz, 1H), 7.64 (s, 1H), 7.49 (s, 1H), 7.28-7.35 (m, 3H), 5.80 (br t, J=7.2 Hz, 1H), 3.75 (br d, J=5.5 Hz, 2H), 2.71 (br t, J=5.5 Hz, 2H), 2.49-2.66 (m, 1H), 2.04-2.19 (m, 1H), 1.38-1.48 (m, 1H), 1.02 (d, J=6.4 Hz, 3H), 0.98 (d, J=6.6 Hz, 3H); MS (ES, m/z) 525, 527 [M+H$^+$].

The following compounds (as shown in Examples 18-27 below) were similarly prepared according to the procedures described in Examples 16 and 17, selecting and substituting a suitably substituted boronic acid in the Suzuki coupling step.

Example 18—Compound #36

3-(5-(1-(5-(4-(tert-Butyl)phenyl)-1H-indazol-1-yl)-3-methylbutyl)picolinamido)propanoic Acid

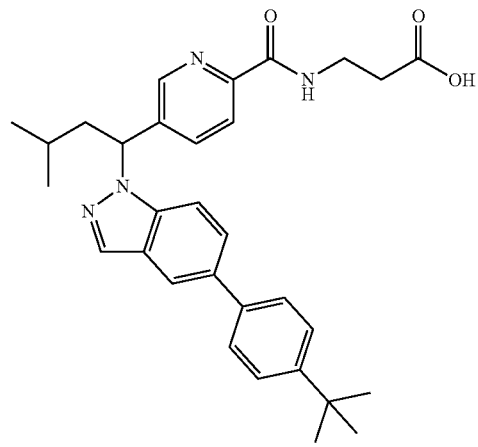 [SMILES: CC(C)CC(c1ccc(C(=O)NCCC(=O)O)nc1)n1ncc2cc(-c3ccc(C(C)(C)C)cc3)ccc21]

$^1$H NMR (METHANOL-d$_4$) δ 8.63 (s, 1H), 8.17 (s, 1H), 7.90-8.02 (m, 3H), 7.63-7.77 (m, 2H), 7.56 (br d, J=8.3 Hz, 2H), 7.46 (br d, J=8.1 Hz, 2H), 6.03 (br dd, J=10.5, 4.6 Hz, 1H), 3.63 (br t, J=6.6 Hz, 2H), 2.65-2.76 (m, 1H), 2.60 (br t, J=6.6 Hz, 2H), 2.04 (ddd, J=13.6, 8.7, 5.0 Hz, 1H), 1.34

(s, 10H), 1.00 (br d, J=6.4 Hz, 3H), 0.94 (br d, J=6.6 Hz, 3H); MS (ES, m/z) 513 [M+H⁺].

Example 19—Compound #14

3-(5-(1-(5-(4-Chloro-2-methylphenyl)-1H-indazol-1-yl)-3-methylbutyl)picolinamido)propanoic Acid

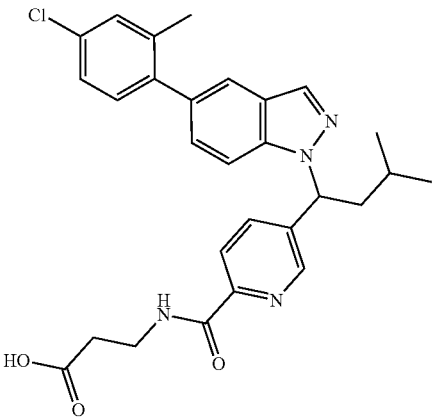 [SMILES: Cc1cc(Cl)ccc1-c1ccc2c(cnn2C(CC(C)C)c2ccc(C(=O)NCCC(=O)O)nc2)c1]

¹H NMR (CHLOROFORM-d) δ 8.55 (d, J=2.0 Hz, 1H), 8.39 (t, J=6.2 Hz, 1H), 8.11 (s, 1H), 8.12 (d, J=7.5 Hz, 1H), 7.87 (dd, J=8.1, 2.2 Hz, 1H), 7.61 (s, 1H), 7.42 (d, J=8.8 Hz, 1H), 7.23-7.29 (m, 3H), 7.18-7.23 (m, 1H), 7.14-7.18 (m, 1H), 5.77 (dd, J=9.8, 5.6 Hz, 1H), 3.74 (q, J=6.3 Hz, 2H), 2.67-2.76 (m, 3H), 2.22 (s, 3H), 1.99-2.13 (m, 1H), 1.42-1.55 (m, 1H), 1.00 (d, J=7.1 Hz, 3H) 0.98 (d, J=7.1 Hz, 3H); MS (ES, m/z) 505 [M+H⁺].

Example 20—Compound #252

3-(5-(1-(5-(4-Chloro-2-methylphenyl)-2H-indazol-2-yl)-3-methylbutyl)picolinamido)propanoic Acid

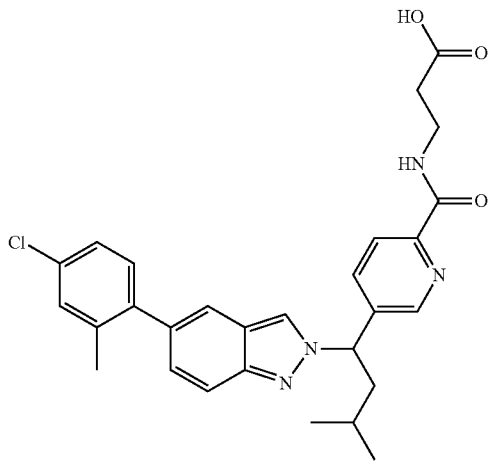

¹H NMR (CHLOROFORM-d) δ 8.61 (s, 1H), 8.45 (br t, J=6.0 Hz, 1H), 8.15 (d, J=8.1 Hz, 1H), 8.05 (s, 1H), 7.89 (br d, J=8.1 Hz, 1H), 7.74 (d, J=8.8 Hz, 1H), 7.49 (s, 1H), 7.15-7.24 (m, 4H), 5.80 (dd, J=9.0, 6.4 Hz, 1H), 3.75 (q, J=6.0 Hz, 2H), 2.71 (br t, J=6.0 Hz, 2H), 2.53-2.66 (m, 1H), 2.25 (s, 3H), 2.07-2.20 (m, 1H), 1.39-1.51 (m, 1H), 1.03 (d, J=6.4 Hz, 3H), 0.98 (d, J=6.6 Hz, 3H); MS (ES, m/z) 505 [M+H⁺].

Example 21—Compound #43

3-(5-(1-(5-(2-Chloro-4-(trifluoromethyl)phenyl)-1H-indazol-1-yl)-3-methylbutyl)picolinamido)propanoic Acid

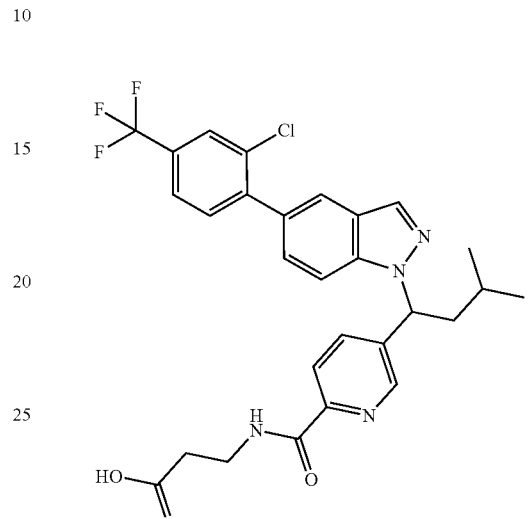

¹H NMR (METHANOL-d₄) δ: 8.69 (s, 1H), 8.22 (s, 1H), 8.06 (br s, 2H), 7.79-7.87 (m, 3H), 7.65-7.71 (m, 1H), 7.59-7.65 (m, 1H), 7.51 (d, J=8.9 Hz, 1H), 6.10 (br dd, J=10.4, 4.8 Hz, 1H), 3.61-3.68 (m, 2H), 2.70-2.80 (m, 1H), 2.59-2.65 (m, 2H), 2.01-2.11 (m, 1H), 1.33-1.46 (m, 1H), 0.99-1.06 (m, 3H), 0.96 (dd, J=6.6, 1.7 Hz, 3H); MS (ES, m/z) 559 [M+H⁺].

Example 22—Compound #53

3-(5-(1-(5-(2-Chloro-4-(trifluoromethyl)phenyl)-2H-indazol-2-yl)-3-methylbutyl)picolinamido)propanoic Acid

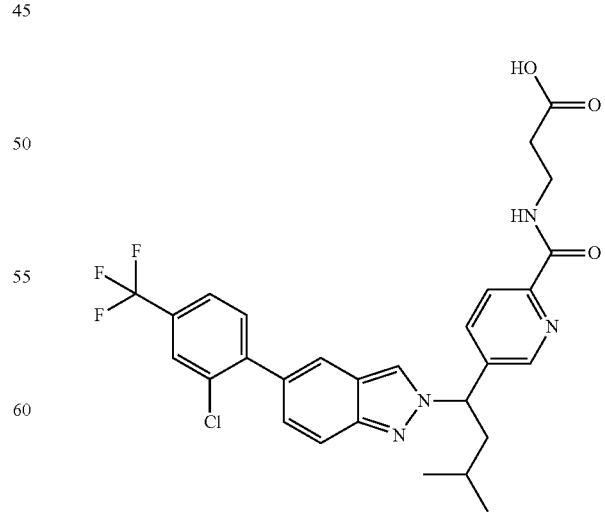

¹H NMR (CHLOROFORM-d) δ 8.57-8.62 (m, 1H), 8.44 (br t, J=6.0 Hz, 1H), 8.15 (br d, J=8.9 Hz, 1H), 8.11 (s, 1H), 7.89 (br d, J=8.2 Hz, 1H), 7.79 (d, J=8.9 Hz, 1H), 7.75 (s, 1H), 7.68 (s, 1H), 7.54-7.59 (m, 1H), 7.50 (d, J=8.2 Hz, 1H), 7.36 (d, J=9.3 Hz, 1H), 5.77-5.83 (m, 1H), 3.69-3.79 (m, 2H), 2.66-2.75 (m, 2H), 2.55-2.67 (m, 1H), 2.08-2.17 (m, 1H), 1.39-1.49 (m, 1H), 1.03 (d, J=6.4 Hz, 3H), 0.98 (d, J=6.6 Hz, 3H); MS (ES, m/z) 559 [M+H$^+$].

Example 23—Compound #79

3-(5-(1-(5-(Benzofuran-2-yl)-1H-indazol-1-yl)-3-methylbutyl)picolinamido)propanoic Acid

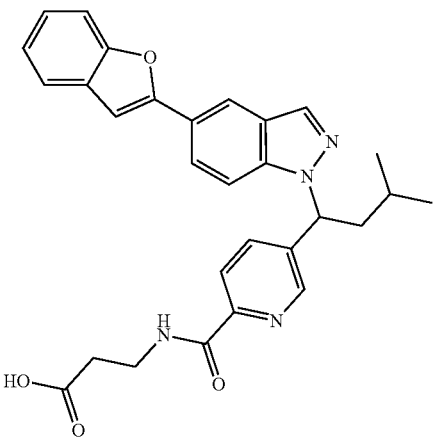 [SMILES: CC(C)CC(c1ccc(C(=O)NCCC(=O)O)nc1)n1ncc2cc(-c3cc4ccccc4o3)ccc21]

$^1$H NMR (CHLOROFORM-d) δ 8.52-8.58 (m, 1H), 8.40 (br t, J=6.1 Hz, 1H), 8.26 (s, 1H), 8.16 (s, 1H), 8.12 (d, J=7.6 Hz, 1H), 7.81-7.89 (m, 2H), 7.58 (d, J=7.2 Hz, 1H), 7.52 (d, J=8.2 Hz, 1H), 7.45 (d, J=8.8 Hz, 1H), 7.21-7.31 (m, 3H), 6.98 (s, 1H), 5.76 (dd, J=9.9, 5.5 Hz, 1H), 3.73 (q, J=6.0 Hz, 2H), 2.64-2.75 (m, 3H), 2.06 (ddd, J=14.1, 8.3, 5.5 Hz, 1H), 1.38-1.51 (m, 1H), 0.97 (br d, J=8.3 Hz, 3H), 0.98 (br d, J=8.3 Hz, 3H); MS (ES, m/z) 497 [M+H$^+$].

Example 24—Compound #260

3-(5-(1-(5-(Benzofuran-2-yl)-2H-indazol-2-yl)-3-methylbutyl)picolinamido)propanoic Acid

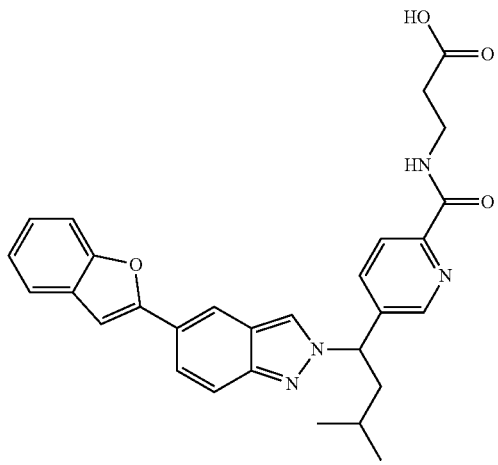 [SMILES: CC(C)CC(c1ccc(C(=O)NCCC(=O)O)nc1)n1cc2cc(-c3cc4ccccc4o3)ccc2n1]

$^1$H NMR (CHLOROFORM-d) δ 8.60 (br s, 1H), 8.44 (br s, 1H), 8.11-8.21 (m, 2H), 8.09 (s, 1H), 7.88 (br d, J=7.6 Hz, 1H), 7.70-7.81 (m, 2H), 7.58 (d, J=7.3 Hz, 1H), 7.52 (d, J=8.1 Hz, 1H), 7.27-7.30 (m, 1H), 7.20-7.25 (m, 1H), 6.99 (s, 1H), 5.77 (br dd, J=8.6, 6.8 Hz, 1H), 3.66-3.81 (m, 2H), 2.71 (br s, 2H), 2.44-2.66 (m, 1H), 2.07-2.21 (m, 1H), 1.36-1.48 (m, 1H), 1.02 (d, J=6.4 Hz, 3H), 0.97 (d, J=6.6 Hz, 3H); MS (ES, m/z) 497 [M+H$^+$].

Example 25—Compound #262

3-(5-(3-Methyl-1-(5-(2-methyl-4-(trifluoromethyl)phenyl)-1H-indazol-1-yl)butyl)picolinamido)propanoic Acid

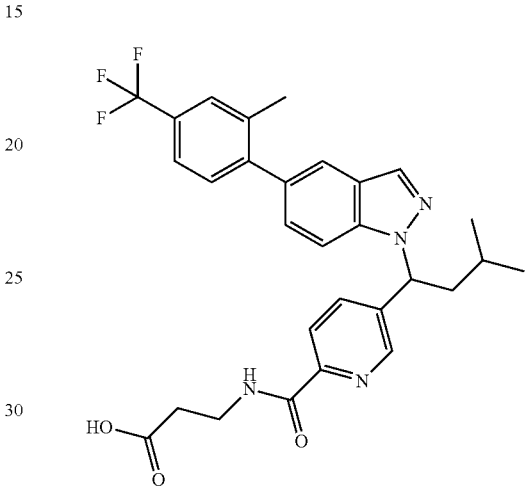

$^1$H NMR (CHLOROFORM-d) δ 8.61 (d, J=2.0 Hz, 1H), 8.44 (br t, J=6.2 Hz, 1H), 8.16 (d, J=8.3 Hz, 1H), 8.07 (s, 1H), 7.90 (dd, J=8.1, 2.2 Hz, 1H), 7.77 (d, J=9.0 Hz, 1H), 7.53 (s, 2H), 7.49 (br d, J=8.1 Hz, 1H), 7.35 (d, J=7.8 Hz, 1H), 7.24 (d, J=8.9 Hz, 1H), 5.81 (dd, J=9.4, 6.2 Hz, 1H), 3.75 (q, J=6.2 Hz, 2H), 2.71 (t, J=6.2 Hz, 2H), 2.55-2.67 (m, 1H), 2.32 (s, 3H), 2.08-2.18 (m, 1H), 1.40-1.51 (m, 1H), 1.03 (d, J=6.6 Hz, 3H), 0.99 (d, J=6.6 Hz, 3H); MS (ES, m/z) 539 [M+H$^+$].

Example 26—Compound #114

3-(5-(3-Methyl-1-(5-(4-(trifluoromethoxy)phenyl)-1H-indazol-1-yl)butyl)picolinamido)propanoic Acid

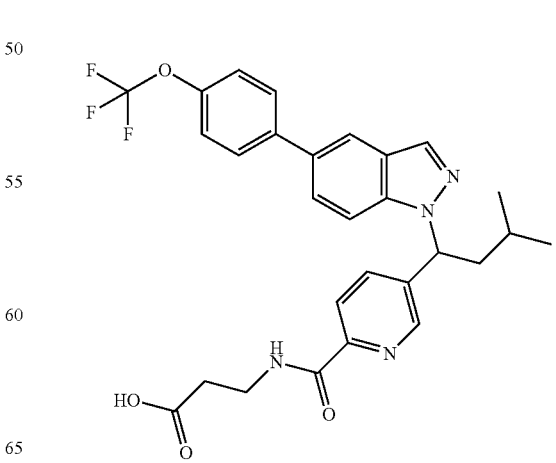

¹H NMR (CHLOROFORM-d) δ 8.55 (d, J=2.0 Hz, 1H), 8.46 (br t, J=6.2 Hz, 1H), 8.16 (s, 1H), 8.11 (d, J=8.3 Hz, 1H), 7.84-7.90 (m, 2H), 7.55-7.61 (m, 3H), 7.47 (d, J=8.8 Hz, 1H), 7.27-7.30 (m, 2H), 5.78 (dd, J=10.0, 5.6 Hz, 1H), 3.74 (q, J=6.2 Hz, 2H), 2.67-2.76 (m, 3H), 2.07 (ddd, J=14.1, 8.6, 5.5 Hz, 1H), 1.39-1.51 (m, 1H), 0.99 (d, J=6.6 Hz, 3H), 0.97 (br d, J=6.8 Hz, 3H); MS (ES, m/z) 541 [M+H$^+$].

Example 27—Compound #70

3-(5-(3-Methyl-1-(5-(4-(trifluoromethyl)phenyl)-1H-indazol-1-yl)butyl)picolinamido)propanoic Acid

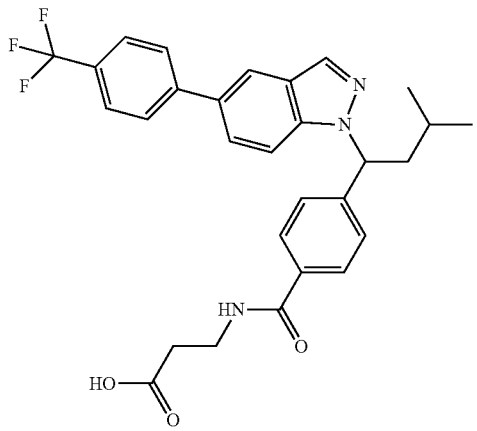 [SMILES: CC(C)CC(c1ccc(C(=O)NCCC(=O)O)cc1)n1ncc2cc(-c3ccc(C(F)(F)F)cc3)ccc21]

¹H NMR (METHANOL-d$_4$) δ 8.76 (br s, 1H), 8.21-8.26 (m, 2H), 8.08-8.17 (m, 2H), 7.82-7.87 (m, 3H), 7.72-7.79 (m, 3H), 6.15 (br dd, J=10.4, 4.3 Hz, 1H), 3.65 (br t, J=6.5 Hz, 2H), 2.66-2.78 (m, 1H), 2.60-2.66 (m, 2H), 2.06 (ddd, J=13.8, 9.0, 4.9 Hz, 1H), 1.32-1.43 (m, 1H), 1.02 (d, J=6.6 Hz, 3H), 0.95 (d, J=6.6 Hz, 3H); MS (ES, m/z) 525 [M+H$^+$].

Example 28—Compound #47

3-(4-(1-(5-(4-(tert-Butyl)phenyl)-4-methyl-1H-indazol-1-yl)-3-methylbutyl)benzamido)Propanoic Acid

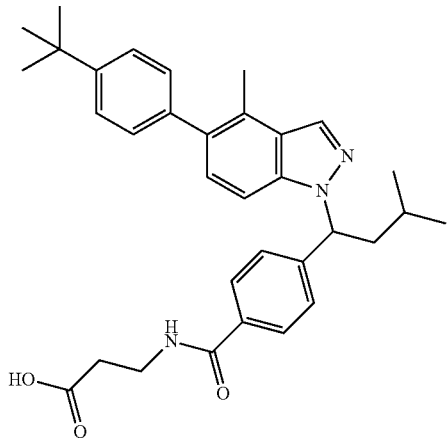 [SMILES: Cc1c(-c2ccc(C(C)(C)C)cc2)ccc2c1cnn2C(CC(C)C)c1ccc(C(=O)NCCC(=O)O)cc1]

Step A:

A mixture of 5-bromo-4-methyl-1H-indazole (0.49 g, 2.31 mmol), methyl 4-(1-bromo-3-methylbutyl)benzoate (0.59 g, 2.08 mmol) and Cs$_2$CO$_3$ (0.90 g, 2.77 mmol) in DMF (9 mL) under N$_2$ was heated in an oil bath at 68° C. for 16 h. The reaction mixture was diluted with CH$_2$Cl$_2$ and filtered. The filtrate was concentrated under high vacuum. The residue was purified by chromatography on silica gel (heptane to 10% EtOAc in heptane) to yield a yellowish solid (the N-1 substituted compound). ¹H NMR (CHLOROFORM-d) δ: 8.07 (s, 1H), 7.94 (d, J=8.3 Hz, 2H), 7.43 (d, J=8.8 Hz, 1H), 7.34 (d, J=8.3 Hz, 2H), 7.08 (d, J=8.8 Hz, 1H), 5.66 (dd, J=9.9, 5.5 Hz, 1H), 3.87 (s, 3H), 2.63-2.70 (m, 1H), 2.62 (s, 3H), 2.00-2.09 (m, 1H), 1.34-1.47 (m, 1H), 0.95 (d, J=6.5 Hz, 3H), 0.94 (d, J=6.5 Hz, 3H);

followed a second yellowish solid (the N-2 substituted compound). ¹H NMR (CHLOROFORM-d) δ: 7.93-8.02 (m, 3H), 7.35-7.50 (m, 4H), 5.69 (dd, J=9.0, 6.6 Hz, 1H), 3.90 (s, 3H), 2.49-2.56 (m, 1H), 2.53 (s, 3H), 2.13 (dt, J=14.2, 7.1 Hz, 1H), 1.36-1.48 (m, 1H), 1.00 (d, J=6.6 Hz, 3H), 0.96 (d, J=6.8 Hz, 3H).

Step B:

A solution of the first yellowish solid prepared in Step A (the N-1 substituted compound, 0.22 g, 0.54 mmol) in THF/MeOH/H$_2$O (4:1:1 v/v/v, 12 mL) was treated with LiH aqueous solution (1 M in H$_2$O, 2 mL, 2 mmol). The reaction mixture was stirred in an oil bath at 60° C. for 2 h. Hydrochloric acid (1 M in H$_2$O) was added to neutralize the mixture. Brine was added and the resulting mixture was extracted with EtOAc thrice. The combined extracts were washed with brine and dried over Na$_2$SO$_4$. Filtration and concentration of the filtrate yielded a yellowish foam solid. ¹H NMR (CHLOROFORM-d) δ 8.07-8.09 (m, 1H), 8.00 (d, J=8.3 Hz, 2H), 7.44 (d, J=8.8 Hz, 1H), 7.37 (d, J=8.3 Hz, 2H), 7.09 (d, J=8.8 Hz, 1H), 5.67 (dd, J=10.3, 5.4 Hz, 1H), 2.63-2.72 (m, 1H), 2.62 (s, 3H), 2.00-2.09 (m, 2H), 1.37-1.47 (m, 1H), 0.96 (d, J=6.5, Hz, 3H), 0.95 (d, J=6.5, Hz, 3H).

Step C:

To a mixture of the yellowish foam solid prepared in Step B (0.23 g, 0.45 mmol), tert-butyl 3-aminopropanoate hydrochloride (0.09 g, 0.49 mmol) and HATU (0.21 g, 0.54 mmol) in DMF (5 mL) at room temperature was added diisopropylethylamine (0.23 mL, 1.36 mmol). The solution was stirred at room temperature for 16 h. Water was added and the resulting mixture was extracted with EtOAc thrice. The combined extracts were washed with H$_2$O, brine and dried over Na$_2$SO$_4$. Filtration and concentration of the filtrate yielded a residue which was purified by chromatograph on silica gel (10% to 40% EtOAc in heptane) to yield a yellow solid. ¹H NMR (CHLOROFORM-d) δ 8.06 (s, 1H), 7.67 (d, J=8.3 Hz, 2H), 7.42 (d, J=8.8 Hz, 1H), 7.34 (d, J=8.3 Hz, 2H), 7.08 (d, J=8.8 Hz, 1H), 6.80 (br t, J=5.9 Hz, 1H), 5.65 (dd, J=9.8, 5.4 Hz, 1H), 3.64 (q, J=5.9 Hz, 2H), 2.63-2.68 (m, 1H), 2.62 (s, 3H), 2.51 (t, J=5.9 Hz, 2H), 2.05 (ddd, J=13.9, 8.3, 5.6 Hz, 1H), 1.36-1.45 (m, 1H), 1.44 (s, 9H), 0.95 (d, J=6.6 Hz, 3H), 0.95 (d, J=6.6 Hz, 3H).

Step D:

A mixture of the yellow solid prepared in Step C (42 mg, 0.08 mmol), (4-(tert-butyl)phenyl)boronic acid (17 mg, 0.10 mmol), Pd(PPh$_3$)$_4$ (9 mg, 0.008 mmol) and CsF (73 mg, 0.48 mmol) in dioxane (1 mL) was heated at 120° C. in microwave for 2h. The cooled reaction mixture was diluted with CH$_2$Cl$_2$ and filtered through CELITE. The filtrate was concentrated and the residue was purified by chromatography on silica gel (heptane to 30% EtOAc in heptane) to yield a yellowish solid. ¹H NMR (CHLOROFORM-d) δ 8.12 (s, 1H), 7.68 (d, J=7.2 Hz, 2H), 7.42-7.45 (m, 2H), 7.40 (d, J=8.3 Hz, 2H), 7.22-7.30 (m, 4H), 6.80 (br t, J=5.9 Hz, 1H), 5.71 (dd, J=9.8, 5.6 Hz, 1H), 3.65 (q, J=6.0 Hz, 2H), 2.70 (ddd, J=13.9, 10.0, 5.4 Hz, 1H), 2.49-2.58 (m, 5H), 2.03-2.11 (m, 1H), 1.47-1.54 (m, 1H), 1.44 (s, 9H), 1.37 (s, 9H), 0.97 (d, J=6.6 Hz, 3H), 0.98 (d, J=6.6 Hz, 3H).

Step E:

A solution of the yellowish solid prepared in Step D (36 mg, 0.06 mmol) in TFA/CH$_2$Cl$_2$ (1:1 v/v, 4 mL) was stirred at room temperature for 1h. After concentration, the residue was dissolved in EtOAc and brine was added. The mixture was neutralized by addition of saturated NaHCO$_3$ aqueous solution. The neutralized mixture was extracted with EtOAc thrice. The combined extracts were dried over Na$_2$SO$_4$. Filtration and concentration of the filtrate yielded a residue, which was purified by chromatography on silica gel (5% to 10% MeCOH in CH$_2$Cl$_2$) to yield the title compound as a slightly yellowish foam solid.

$^1$H NMR (CHLOROFORM-d) δ 8.13 (s, 1H), 7.67 (d, J=8.3 Hz, 2H), 7.43 (br d, J=8.1 Hz, 2H), 7.40 (br d, J=8.1 Hz, 2H), 7.28 (s, 1H), 7.22-7.28 (m, 3H), 6.72 (br t, J=6.0 Hz, 1H), 5.72 (dd, J=10.1, 5.5 Hz, 1H), 3.69 (q, J=6.0 Hz, 2H), 2.63-2.73 (m, 3H), 2.53 (s, 3H), 2.02-2.11 (m, 1H), 1.42-1.53 (m, 1H), 1.37 (s, 9H), 0.98 (t, J=6.0 Hz, 3H), 0.97 (t, J=6.0 Hz, 3H); MS (ES, m/z) 526 [M+H$^+$].

Example 29—Compound #78

3-(4-(1-(5-(4-(tert-Butyl)phenyl)-4-methyl-2H-indazol-2-yl)-3-methylbutyl)benzamido)propanoic Acid

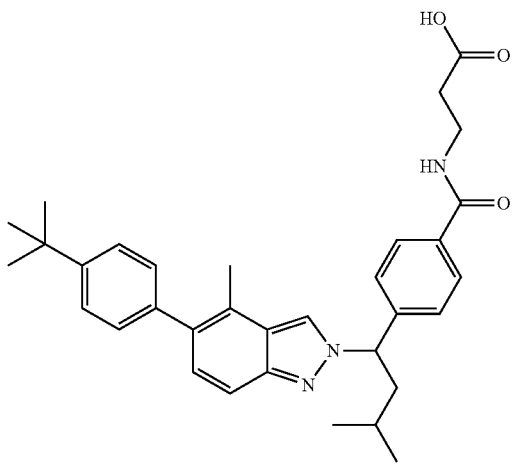 [SMILES: Cc1c(-c2ccc(C(C)(C)C)cc2)ccc2nn(C(CC(C)C)c3ccc(C(=O)NCCC(=O)O)cc3)cc12]

Step A:

A solution of the second yellowish solid prepared in Example 28, Step A (the N-2 substituted compound, 0.18 g, 0.44 mmol) in THF/MeOH/H$_2$O (4:1:1 v/v/v, 12 mL) was treated with LiH aqueous solution (1 M in H$_2$O, 2 mL, 2 mmol). The reaction mixture was stirred at room temperature for 16 h. Hydrochloric acid (1 M in H$_2$O) was added to neutralize the mixture. Brine was added and the resulting mixture was extracted with EtOAc thrice. The combined extracts were washed with brine and dried over Na$_2$SO$_4$. Filtration and concentration of the filtrate yielded an off-white solid.

Step B:

To a mixture of the off-white solid prepared in Step A (0.18 g, 0.36 mmol), tert-butyl 3-aminopropanoate hydrochloride (0.07 g, 0.39 mmol) and HATU (0.16 g, 0.42 mmol) in DMF (5 mL) at room temperature was added diisopropylethylamine (0.18 mL, 1.07 mmol). The solution was stirred at room temperature for 16 h. Water was added and the resulting mixture was extracted with EtOAc thrice. The combined extracts were washed with H$_2$O, brine and dried over Na$_2$SO$_4$. Filtration and concentration of the filtrate yielded a residue, which was purified by chromatograph on silica gel (10% to 40% EtOAc in heptane) to yield a white solid. $^1$H NMR (CHLOROFORM-d) δ 7.92 (s, 1H), 7.72 (d, J=8.3 Hz, 2H), 7.34-7.46 (m, 4H), 6.84 (br t, J=5.9 Hz, 1H), 5.68 (dd, J=8.9, 7.0 Hz, 1H), 3.66 (q, J=5.9 Hz, 2H), 2.47-2.58 (m, 6H), 2.14 (dt, J=14.1, 7.2 Hz, 1H), 1.40-1.47 (m, 10H), 1.00 (d, J=6.6 Hz, 3H), 0.96 (d, J=6.6 Hz, 3H).

Step C:

A mixture of the white solid prepared in Step B (42 mg, 0.08 mmol), (4-(tert-butyl)phenyl)boronic acid (17 mg, 0.10 mmol), Pd(PPh$_3$)$_4$ (9 mg, 0.008 mmol) and Na$_2$CO$_3$ aqueous solution (2M, 0.24 mL, 0.48 mmol) in toluene (0.75 mL) was heated at 120° C. in microwave for 1h. The cooled reaction mixture was filtered through Na$_2$SO$_4$ and CELITE. The filtrate was concentrated and the residue was purified by chromatography on silica gel (heptane to 30% EtOAc in heptane) to yield a yellowish solid. $^1$H NMR (CHLOROFORM-d) δ 7.99 (s, 1H), 7.72 (d, J=8.1 Hz, 2H), 7.60 (d, J=8.8 Hz, 1H), 7.44 (d, J=8.3 Hz, 4H), 7.29 (d, J=8.3 Hz, 2H), 7.25 (d, J=8.8 Hz, 1H), 6.84 (br t, J=6.0 Hz, 1H), 5.73 (dd, J=9.2, 6.5 Hz, 1H), 3.67 (q, J=5.9 Hz, 2H), 2.47-2.60 (m, 3H), 2.46 (s, 3H), 2.14 (dt, J=14.1, 7.0 Hz, 1H), 1.45 (s, 10H), 1.37 (s, 9H), 1.02 (d, J=6.6 Hz, 3H), 0.98 (d, J=6.6 Hz, 3H).

Step D:

A solution of the yellowish solid prepared in Step C (41 mg, 0.07 mmol) in TFA/CH$_2$Cl$_2$ (1:1 v/v, 4 mL) was stirred at room temperature for 1h. After concentration, the residue was dissolved in EtOAc and brine was added. The mixture was neutralized by addition of saturated NaHCO$_3$ aqueous solution. The neutralized mixture was extracted with EtOAc thrice. The combined extracts were dried over Na$_2$SO$_4$. Filtration and concentration of the filtrate yielded a residue which was purified by chromatography on silica gel (5% to 10% MeCOH in CH$_2$Cl$_2$) to yield the title compound as a white foam solid.

$^1$H NMR (CHLOROFORM-d) δ 8.00 (s, 1H), 7.73 (d, J=8.3 Hz, 2H), 7.58 (d, J=8.8 Hz, 1H), 7.41-7.48 (m, 4H), 7.24-7.29 (m, 3H), 6.90 (br t, J=6.1 Hz, 1H), 5.83 (dd, J=9.0, 6.6 Hz, 1H), 3.72 (q, J=5.6 Hz, 2H), 2.69 (t, J=5.6 Hz, 2H), 2.53 (ddd, J=14.3, 9.0, 5.7 Hz, 1H), 2.45 (s, 3H), 2.09-2.17 (m, 1H), 1.41-1.51 (m, 1H), 1.37 (s, 9H), 1.01 (d, J=6.6 Hz, 3H), 0.97 (d, J=6.6 Hz, 3H); MS (ES, m/z) 526 [M+H$^+$].

The following compounds (as shown in Examples 30-66 below) were similarly prepared according to the procedures described in Examples 28 and 29, selecting and substituting a suitably substituted indazoles as the starting material.

Example 30—Compound #55

3-(4-(1-(5-(2-Chloro-4-(trifluoromethyl)phenyl)-4-methyl-1H-indazol-1-yl)-3-methylbutyl)benzamido)propanoic Acid

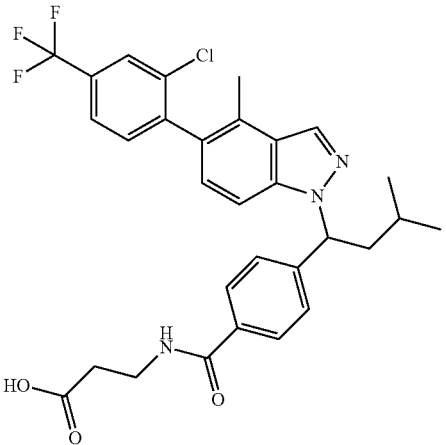 [SMILES: Cc1c(-c2ccc(C(F)(F)F)cc2Cl)ccc2c1cnn2C(CC(C)C)c1ccc(C(=O)NCCC(=O)O)cc1]

$^1$H NMR (CHLOROFORM-d) δ: 8.15 (s, 1H), 7.73-7.77 (m, 1H), 7.65-7.70 (m, 2H), 7.53-7.59 (m, 1H), 7.25-7.44 (m, 4H), 707-7.12 (m, 1H), 6.83 (br t, J=5.7 Hz, 1H), 5.71 (dd, J=9.3, 5.9 Hz, 1H), 3.67 (q, J=5.6 Hz, 2H), 2.60-2.71 (m, 3H), 2.35 (d, J=1.7 Hz, 3H), 2.00-2.14 (m, 1H), 1.38-1.54 (m, 1H), 0.92-1.01 (m, 6H); MS (ES, m/z) 572 [M+H$^+$].

Example 31—Compound #18

3-(4-(1-(5-(2-Chloro-4-(trifluoromethyl)phenyl)-4-methyl-2H-indazol-2-yl)-3-methylbutyl)benzamido)propanoic Acid

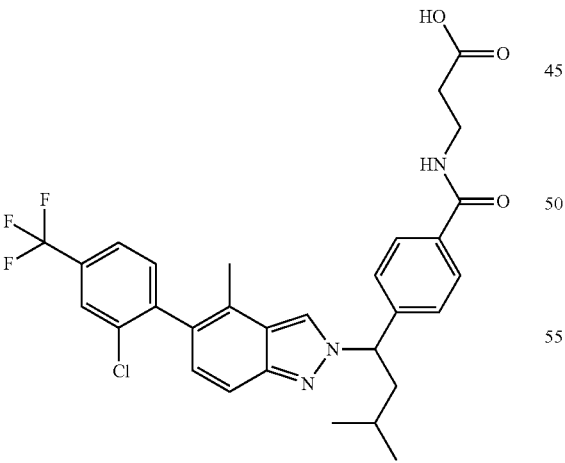

$^1$H NMR (CHLOROFORM-d) δ: 8.04 (d, J=5.1 Hz, 1H), 7.71-7.78 (m, 3H), 7.61 (br d, J=8.8 Hz, 1H), 7.57 (br d, J=7.8 Hz, 1H), 7.47 (d, J=8.3 Hz, 2H), 7.38 (br d, J=7.8 Hz, 1H), 7.06 (d, J=8.3 Hz, 1H), 6.97 (br t, J=6.0 Hz, 1H), 5.82 (br t, J=7.8 Hz, 1H), 3.71 (q, J=5.9 Hz, 2H), 2.68 (t, J=5.9 Hz, 2H), 2.47-2.57 (m, 1H), 2.27 (s, 3H), 2.09-2.19 (m, 1H), 1.40-1.51 (m, 1H), 1.01 (d, J=6.6 Hz, 3H), 0.97 (d, J=6.6 Hz, 3H); MS (ES, m/z) 572 [M+H$^+$].

Example 32—Compound #21

3-(4-(3-Methyl-1-(4-methyl-5-(2-methyl-4-(trifluoromethyl)phenyl)-1H-indazol-1-yl)butyl)benzamido)propanoic Acid

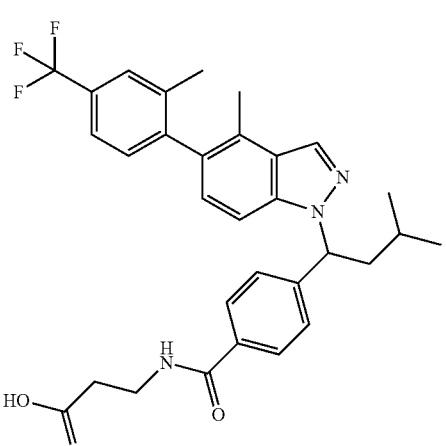

$^1$H NMR (CHLOROFORM-d) δ: 8.13 (s, 1H), 7.65-7.72 (m, 2H), 7.38-7.54 (m, 4H), 7.17-7.28 (m, 2H), 7.03-7.08 (m, 1H), 6.77-6.85 (m, 1H), 5.72 (br dd, J=9.5, 5.9 Hz, 1H), 3.63-3.72 (m, 2H), 2.61-2.72 (m, 3H), 2.28 (s, 3H), 2.02-2.15 (m, 4H), 1.39-1.54 (m, 1H), 0.94-1.02 (m, 6H); MS (ES, m/z) 552 [M+H$^+$].

Example 33—Compound #63

3-(4-(3-Methyl-1-(4-methyl-5-(2-methyl-4-(trifluoromethyl)phenyl)-2H-indazol-2-yl)butyl)benzamido)propanoic Acid

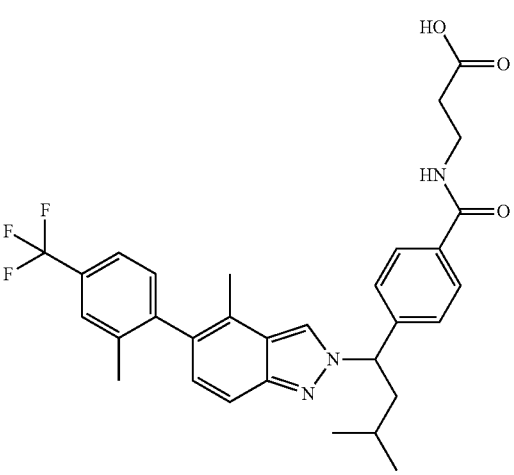

$^1$H NMR (CHLOROFORM-d) δ 8.03 (br d, J=3.4 Hz, 1H), 7.75 (br d, J=7.8 Hz, 2H), 7.61 (br d, J=8.6 Hz, 1H), 7.53 (s, 1H), 7.48 (br d, J=7.8 Hz, 3H), 7.18-7.25 (m, 1H), 7.05 (d, J=8.6 Hz, 1H), 6.86-6.93 (m, 1H), 5.82-5.89 (m,

1H), 3.69-3.76 (m, 2H), 2.67-2.73 (m, 2H), 2.47-2.57 (m, 1H), 2.18-2.24 (m, 4H), 2.12 (s, 3H), 1.43-1.53 (m, 1H), 1.02 (d, J=6.6 Hz, 3H), 0.99 (d, J=6.6 Hz, 3H); MS (ES, m/z) 552 [M+H$^+$].

Example 34—Compound #127

3-(4-(1-(5-(2,4-Dichlorophenyl)-4-methyl-1H-indazol-1-yl)-3-methylbutyl)benzamido)propanoic Acid

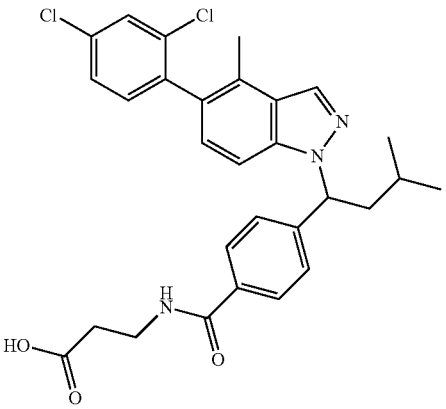 [SMILES: Cc1c(-c2ccc(Cl)cc2Cl)ccc2c1cnn2C(CC(C)C)c1ccc(C(=O)NCCC(=O)O)cc1]

$^1$H NMR (CHLOROFORM-d) δ 8.14 (s, 1H), 7.67 (br d, J=5.1 Hz, 2H), 7.49 (br d, J=5.6 Hz, 1H), 7.42 (br d, J=7.8 Hz, 1H), 7.38 (br d, J=8.1 Hz, 1H), 7.07-7.32 (m, 4H), 6.76-6.85 (m, 1H), 5.67-5.75 (m, 1H), 3.67 (br d, J=5.4 Hz, 2H), 2.60-2.71 (m, 3H), 2.34 (s, 3H), 2.07 (tt, J=14.8, 7.3 Hz, 1H), 1.36-1.54 (m, 1H), 0.92-1.01 (m, 6H); MS (ES, m/z) 538, 540 [M+H$^+$].

Example 35—Compound #20

3-(4-(1-(5-(4-Chloro-2-methylphenyl)-4-methyl-2H-indazol-2-yl)-3-methylbutyl)benzamido)propanoic Acid

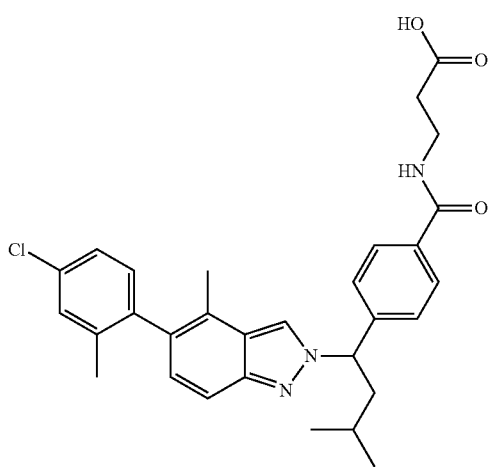 [SMILES: Cc1cc(Cl)ccc1-c1ccc2nn(C(CC(C)C)c3ccc(C(=O)NCCC(=O)O)cc3)cc2c1C]

$^1$H NMR (CHLOROFORM-d) δ 7.96-8.04 (m, 1H), 7.74 (br d, J=7.8 Hz, 2H), 7.53-7.61 (m, 1H), 7.48 (br d, J=7.8 Hz, 2H), 7.27 (s, 1H), 7.20 (dd, J=8.2, 2.1 Hz, 1H), 7.01-7.07 (m, 2H), 6.85-6.91 (m, 1H), 5.79-5.87 (m, 1H), 3.72 (br d, J=6.1 Hz, 2H), 2.67-2.73 (m, 2H), 2.48-2.57 (m, 1H), 2.12-2.24 (m, 4H), 2.04 (s, 3H), 1.42-1.52 (m, 1H), 1.02 (d, J=6.6 Hz, 3H), 0.98 (d, J=6.6 Hz, 3H); MS (ES, m/z) 518 [M+H$^+$].

Example 36—Compound #135

3-(4-(1-(4-Chloro-5-(2-methyl-4-(trifluoromethyl)phenyl)-1H-indazol-1-yl)-3-methylbutyl)benzamido)propanoic Acid

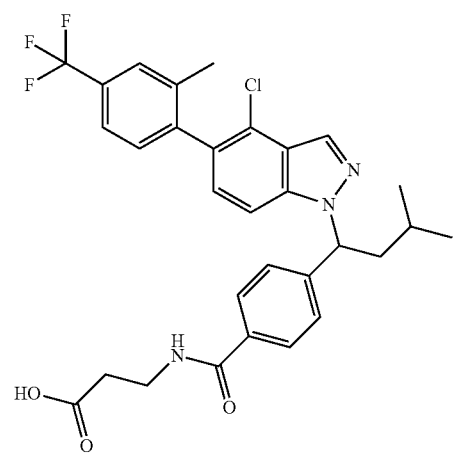 [SMILES: Cc1cc(C(F)(F)F)ccc1-c1ccc2c(cnn2C(CC(C)C)c2ccc(C(=O)NCCC(=O)O)cc2)c1Cl]

$^1$H NMR (CHLOROFORM-d) δ: 8.20 (s, 1H), 7.70 (dd, J=8.2, 4.8 Hz, 2H), 7.21-7.55 (m, 7H), 7.13 (dd, J=8.6, 3.7 Hz, 1H), 6.73-6.80 (m, 1H), 5.71 (dd, J=9.7, 5.7 Hz, 1H), 3.70 (q, J=5.9 Hz, 2H), 2.63-2.73 (m, 3H), 2.04-2.20 (m, 4H), 1.39-1.50 (m, 1H), 0.94-1.02 (m, 6H); MS (ES, m/z) 572 [M+H$^+$].

Example 37—Compound #232

3-(4-(1-(4-Chloro-5-(2-chloro-4-(trifluoromethyl)phenyl)-2H-indazol-2-yl)-3-methylbutyl)benzamido)propanoic Acid

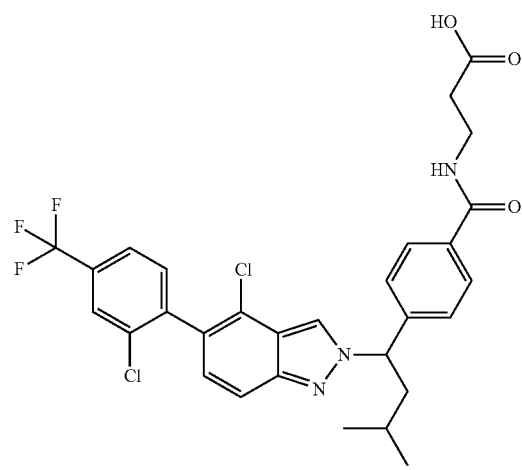 [SMILES: CC(C)CC(c1ccc(C(=O)NCCC(=O)O)cc1)n1cc2c(Cl)c(-c3ccc(C(F)(F)F)cc3Cl)ccc2n1]

$^1$H NMR (CHLOROFORM-d) δ: 8.11 (d, J=2.7 Hz, 1H), 7.75 (d, J=8.1 Hz, 2H), 7.67 (d, J=8.8 Hz, 1H), 7.44-7.57 (m,

4H), 7.26-7.30 (m, 1H), 7.08 (d, J=8.8 Hz, 1H), 6.89 (br t, J=4.8 Hz, 1H), 5.77 (br t, J=6.8 Hz, 1H), 3.65-3.77 (m, 2H), 2.69 (br t, J=5.5 Hz, 2H), 2.53 (dt, J=13.9, 7.2 Hz, 1H), 2.11-2.21 (m, 4H), 1.39-1.50 (m, 1H), 1.02 (br d, J=6.4 Hz, 3H), 0.98 (br d, J=6.6 Hz, 3H); MS (ES, m/z) 572 [M+H⁺].

Example 38—Compound #67

3-(4-(1-(4-Chloro-5-(4-(trifluoromethyl)phenyl)-1H-indazol-1-yl)-3-methylbutyl)benzamido)propanoic Acid

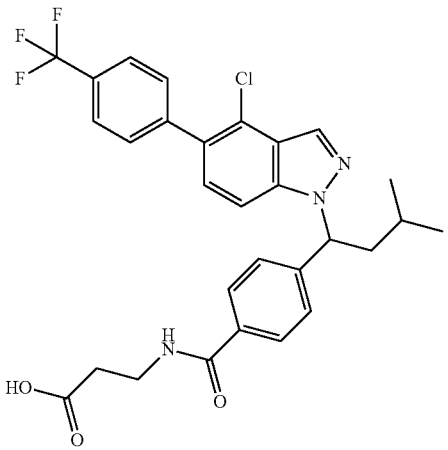 [SMILES: CC(C)CC(c1ccc(C(=O)NCCC(=O)O)cc1)n1ncc2c(Cl)c(-c3ccc(C(F)(F)F)cc3)ccc21]

¹H NMR (CHLOROFORM-d) δ 8.22 (s, 1H), 7.65-7.75 (m, 4H), 7.56 (d, J=8.1 Hz, 2H), 7.27-7.41 (m, 4H), 6.75-6.83 (m, 1H), 5.71 (dd, J=10.0, 5.6 Hz, 1H), 3.63-3.72 (m, 1H), 2.59-2.74 (m, 3H), 2.03-2.11 (m, 1H), 1.39-1.50 (m, 1H), 0.98 (t, J=5.9 Hz, 3H), 0.96 (t, J=5.9 Hz, 3H).

Example 39—Compound #147

3-(4-(1-(4-Chloro-5-(4-(trifluoromethyl)phenyl)-2H-indazol-2-yl)-3-methylbutyl)benzamido)prop-anoic Acid

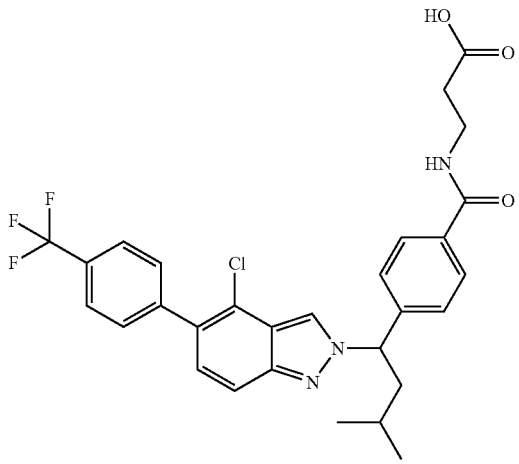

¹H NMR (CHLOROFORM-d) δ: 8.14 (s, 1H), 7.67-7.76 (m, 6H), 7.59 (d, J=8.1 Hz, 2H), 7.45 (d, J=8.3 Hz, 2H), 7.23-7.26 (m, 1H), 6.90 (br t, J=5.9 Hz, 1H), 5.76 (dd, J=8.8, 6.8 Hz, 1H), 3.70 (q, J=5.9 Hz, 2H), 2.68 (br t, J=5.9 Hz, 2H), 2.45-2.57 (m, 1H), 2.15 (dt, J=14.0, 7.1 Hz, 1H), 1.37-1.49 (m, 1H), 1.01 (d, J=6.6 Hz, 3H), 0.97 (d, J=6.6 Hz, 3H).

Example 40—Compound #141

3-(4-(1-(4-Chloro-5-(2-chloro-4-(trifluoromethyl)phenyl)-1H-indazol-1-yl)-3-methylbutyl)benzamido)propanoic Acid

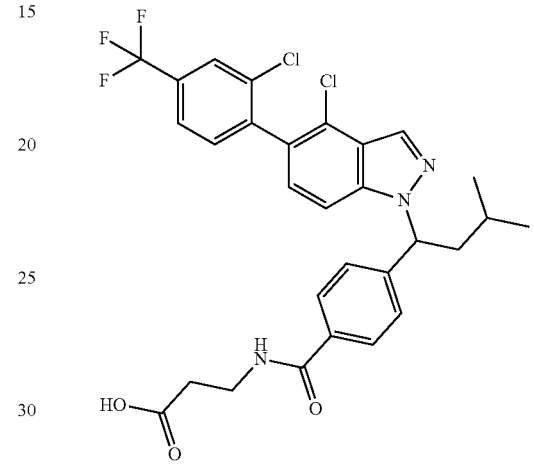

¹H NMR (CHLOROFORM-d) δ: 8.21 (s, 1H), 7.77 (d, J=5.6 Hz, 1H), 7.69 (dd, J=8.1, 4.2 Hz, 2H), 7.56-7.62 (m, 1H), 7.32-7.48 (m, 4H), 7.19 (dd, J=8.5, 5.6 Hz, 1H), 6.73-6.81 (m, 1H), 5.71 (dd, J=9.5, 5.6 Hz, 1H), 3.62-3.72 (m, 2H), 2.61-2.72 (m, 3H), 2.02-2.14 (m, 1H), 1.36-1.54 (m, 1H), 0.92-1.01 (m, 6H); MS (ES, m/z) 592, 594 [M+H⁺].

Example 41—Compound #29

3-(4-(1-(4-Methoxy-5-(2-methyl-4-(trifluoromethyl)phenyl)-1H-indazol-1-yl)-3-methylbutyl)benzamido)propanoic Acid

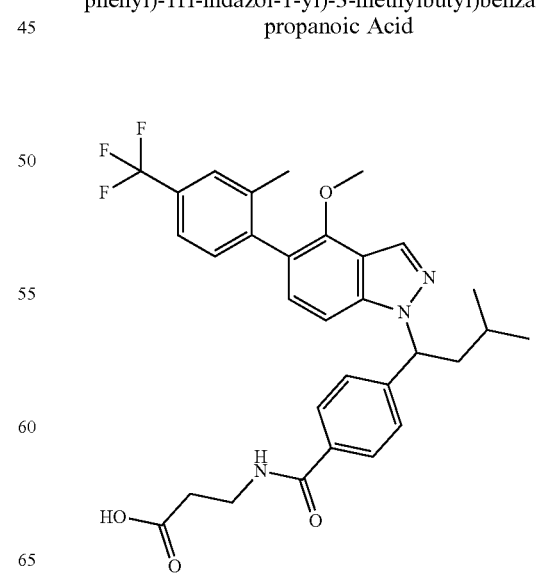

¹H NMR (CHLOROFORM-d) δ 8.27 (s, 1H), 7.70 (d, J=8.3 Hz, 2H), 7.51 (s, 1H), 7.38-7.49 (m, 3H), 7.23-7.32 (m, 1H), 7.07 (s, 2H), 6.71-6.80 (m, 1H), 5.69 (dd, J=9.7, 5.7 Hz, 1H), 4.00 (s, 3H), 3.70 (br d, J=5.9 Hz, 2H), 2.62-2.73 (m, 3H), 2.02-2.25 (m, 4H), 1.40-1.59 (m, 1H), 0.96-1.02 (m, 6H); MS (ES, m/z) 568 [M+H⁺].

Example 42—Compound #233

3-(4-(1-(4-Methoxy-5-(2-methyl-4-(trifluoromethyl)phenyl)-2H-indazol-2-yl)-3-methylbutyl)benzamido)propanoic Acid

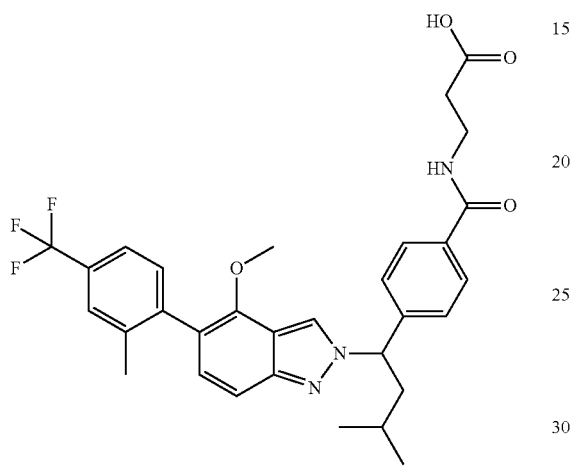

¹H NMR (CHLOROFORM-d) δ 8.14 (s, 1H), 7.74 (d, J=8.1 Hz, 2H), 7.43-7.54 (m, 5H), 7.34 (d, J=7.8 Hz, 1H), 7.02 (d, J=8.8 Hz, 1H), 6.89 (br s, 1H), 5.73-5.80 (m, 1H), 3.69-3.76 (m, 2H), 3.73 (s, 3H), 2.69 (br s, 2H), 2.48-2.58 (m, 1H), 2.23 (s, 3H), 2.11-2.21 (m, 1H), 1.41-1.51 (m, 1H), 1.01 (d, J=6.6 Hz, 3H), 0.98 (d, J=6.6 Hz, 3H); MS (ES, m/z) 568 [M+H⁺].

Example 43—Compound #103

3-(4-(1-(5-(2-Chloro-4-(trifluoromethyl)phenyl)-4-methoxy-1H-indazol-1-yl)-3-methylbutyl)benzamido)propanoic Acid

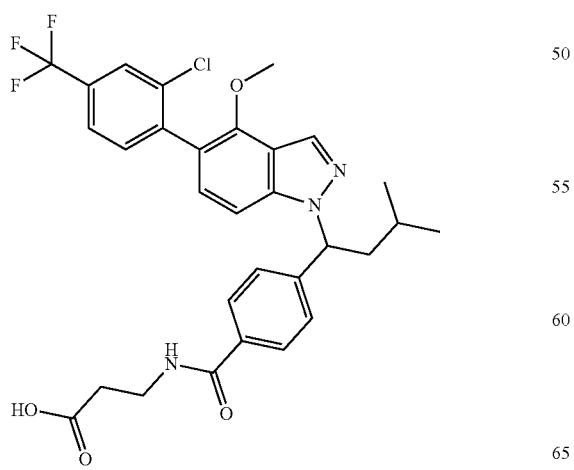

¹H NMR (CHLOROFORM-d) δ 8.28 (s, 1H), 7.73 (s, 1H), 7.67 (br d, J=7.8 Hz, 2H), 7.54 (br d, J=8.1 Hz, 1H), 7.35-7.45 (m, 3H), 7.05-7.13 (m, 2H), 6.75-6.84 (m, 1H), 5.68 (dd, J=9.7, 6.0 Hz, 1H), 4.09 (s, 3H), 3.60-3.72 (m, 2H), 2.57-2.69 (m, 3H), 2.01-2.12 (m, 1H), 1.39-1.54 (m, 1H), 0.91-1.00 (m, 6H); MS (ES, m/z) 588 [M+H⁺].

Example 44—Compound #137

3-(4-(1-(5-(2-Chloro-4-(trifluoromethyl)phenyl)-4-methoxy-2H-indazol-2-yl)-3-methylbutyl)benzamido)propanoic Acid

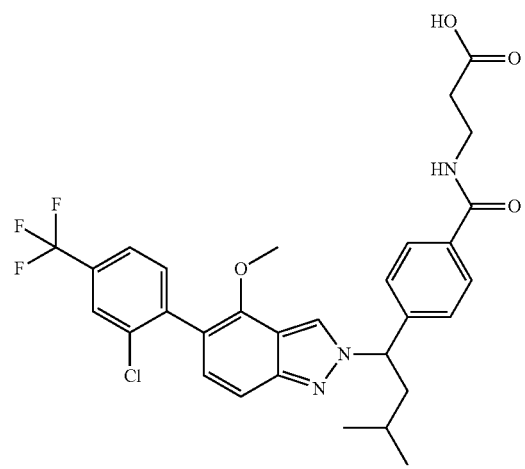 [SMILES: COc1c(-c2ccc(C(F)(F)F)cc2Cl)ccc2nn(C(CC(C)C)c3ccc(C(=O)NCCC(=O)O)cc3)cc12]

¹H NMR (CHLOROFORM-d) δ: 8.17 (s, 1H), 7.69-7.77 (m, 3H), 7.56 (d, J=7.8 Hz, 1H), 7.41-7.49 (m, 4H), 7.07 (d, J=8.8 Hz, 1H), 6.84-6.96 (m, 1H), 5.73 (br t, J=7.8 Hz, 1H), 3.86 (s, 3H), 3.63-3.72 (m, 2H), 2.58-2.73 (m, 2H), 2.47-2.58 (m, 1H), 2.08-2.19 (m, 1H), 1.39-1.50 (m, 1H), 1.00 (d, J=6.6 Hz, 3H), 0.97 (d, J=6.6 Hz, 3H); MS (ES, m/z) 588 [M+H⁺].

Example 45—Compound #99

3-(4-(1-(5-(4-Chloro-2-methylphenyl)-4-methoxy-1H-indazol-1-yl)-3-methylbutyl)benzamido)propanoic Acid

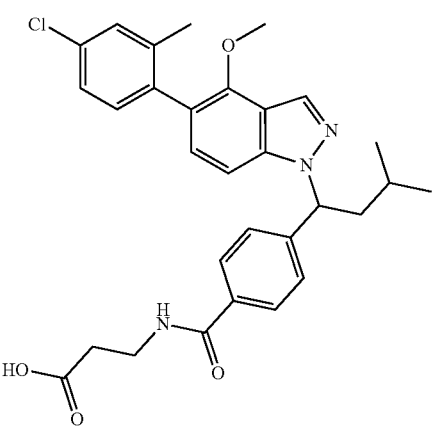 [SMILES: COc1c(-c2ccc(Cl)cc2C)ccc2c1cnn2C(CC(C)C)c1ccc(C(=O)NCCC(=O)O)cc1]

¹H NMR (CHLOROFORM-d) δ 8.25 (s, 1H), 7.69 (br d, J=7.8 Hz, 2H), 7.37-7.46 (m, 2H), 7.02-7.28 (m, 5H), 6.78-6.84 (m, 1H), 5.68 (br dd, J=8.6, 5.9 Hz, 1H), 3.96 (s, 3H), 3.63-3.74 (m, 2H), 2.59-2.73 (m, 3H), 2.01-2.16 (m, 4H), 1.40-1.54 (m, 1H), 0.98 (br d, J=4.2 Hz, 6H); MS (ES, m/z) 534 [M+H⁺].

Example 46—Compound #64

3-(4-(1-(5-(4-Chloro-2-methylphenyl)-4-methoxy-2H-indazol-2-yl)-3-methylbutyl)benzamido)propanoic Acid

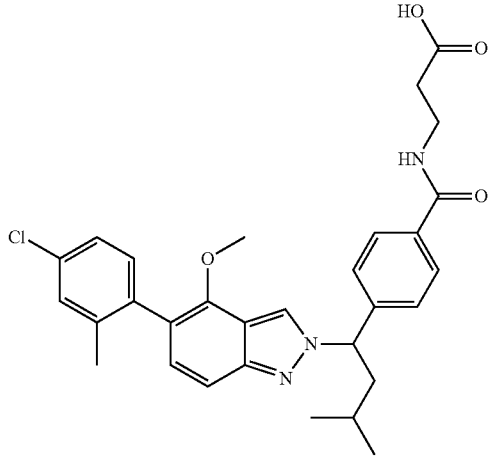 [SMILES: COc1c(-c2ccc(Cl)cc2C)ccc2nn(C(CC(C)C)c3ccc(C(=O)NCCC(=O)O)cc3)cc12]

¹H NMR (CHLOROFORM-d) δ 8.12 (s, 1H), 7.74 (br d, J=8.1 Hz, 2H), 7.47 (br d, J=8.1 Hz, 2H), 7.43 (br d, J=8.8 Hz, 1H), 7.13-7.23 (m, 3H), 7.02 (d, J=8.8 Hz, 1H), 6.91-6.98 (m, 1H), 5.77 (br t, J=7.7 Hz, 1H), 3.70 (s, 3H), 3.67-3.75 (m, 2H), 2.68 (br s, 2H), 2.46-2.57 (m, 1H), 2.10-2.18 (m, 1H), 2.15 (s, 3H), 1.40-1.50 (m, 1H), 1.01 (d, J=6.6 Hz, 3H), 0.97 (d, J=6.6 Hz, 3H); MS (ES, m/z) 534 [M+H⁺].

Example 47—Compound #258

3-(5-(3-Methyl-1-(4-methyl-5-(2-methyl-4-(trifluoromethyl)phenyl)-1H-indazol-1-yl)butyl)picolinamido)propanoic Acid

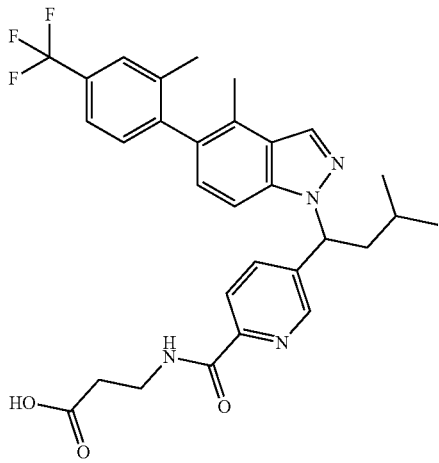 [SMILES: Cc1cc(C(F)(F)F)ccc1-c1ccc2c(cnn2C(CC(C)C)c2ccc(C(=O)NCCC(=O)O)nc2)c1C]

¹H NMR (METHANOL-d₄) δ: 8.60-8.72 (m, 1H), 8.24 (s, 1H), 7.93-8.04 (m, 2H), 7.49-7.62 (m, 3H), 7.25-7.34 (m, 1H), 7.11-7.16 (m, 1H), 6.04 (dd, J=10.5, 4.9 Hz, 1H), 3.64 (t, J=6.7 Hz, 2H), 2.70-2.79 (m, 1H), 2.61 (t, J=6.7 Hz, 2H), 2.30 (s, 3H), 1.98-2.16 (m, 4H), 1.35-1.49 (m, 1H), 0.93-1.05 (m, 6H); MS (ES, m/z) 553 [M+H⁺].

Example 48—Compound #155

3-(5-(3-Methyl-1-(4-methyl-5-(2-methyl-4-(trifluoromethyl)phenyl)-2H-indazol-2-yl)butyl)picolinamido)propanoic Acid

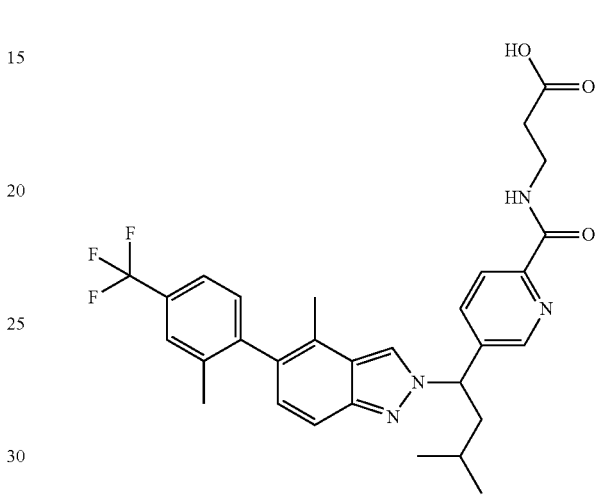

¹H NMR (CHLOROFORM-d) δ 8.63 (br s, 1H), 8.51-8.42 (m, 1H), 8.16 (br d, J=7.8 Hz, 1H), 8.04 (d, J=4.2 Hz, 1H), 7.86-7.94 (m, 1H), 7.45-7.61 (m, 3H), 7.22-7.28 (m, 1H), 7.02 (d, J=9.0 Hz, 1H), 5.77-5.86 (m, 1H), 3.70-3.82 (m, 2H), 2.65-2.78 (m, 2H), 2.55-2.65 (m, 1H), 2.21 (s, 3H), 2.08-2.18 (m, 4H), 1.40-1.53 (m, 1H), 1.04 (br d, J=6.4 Hz, 3H), 0.99 (br d, J=6.6 Hz, 3H).

Example 49—Compound #198

3-(5-(1-(5-(2-Chloro-4-(trifluoromethyl)phenyl)-4-methyl-1H-indazol-1-yl)-3-methylbutyl)picolinamido)propanoic Acid

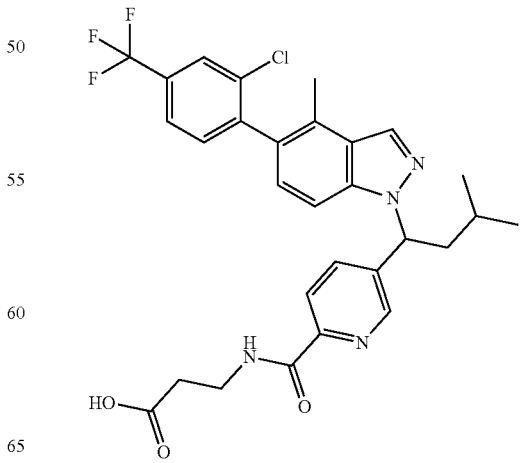

¹H NMR (METHANOL-d₄) δ: 8.58-8.74 (br s, 1H), 8.26 (s, 1H), 7.92-8.06 (m, 2H), 7.84 (d, J=5.5 Hz, 1H), 7.45-7.70 (m, 3H), 7.17 (dd, J=8.7, 4.5 Hz, 1H), 6.04 (dd, J=10.5, 4.9 Hz, 1H), 3.64 (t, J=6.7 Hz, 2H), 2.69-2.79 (m, 1H), 2.61 (t, J=6.7 Hz, 2H), 2.35 (s, 3H), 2.00-2.10 (m, 1H), 1.31-1.49 (m, 1H), 0.93-1.05 (m, 6H); MS (ES, m/z) 573 [M+H⁺].

Example 50—Compound #154

3-(5-(1-(5-(2-Chloro-4-(trifluoromethyl)phenyl)-4-methyl-2H-indazol-2-yl)-3-methylbutyl)picolinamido)propanoic Acid

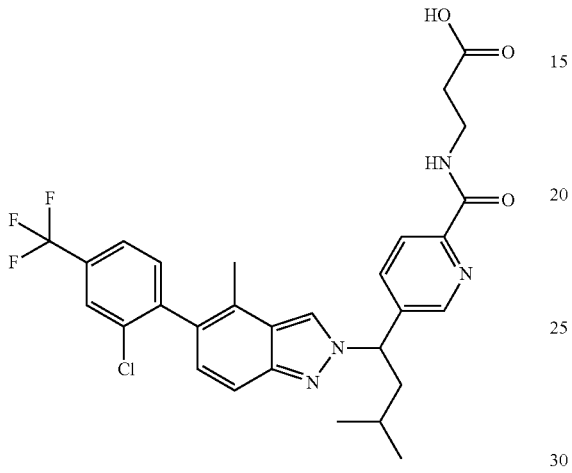

¹H NMR (CHLOROFORM-d) δ: 8.62 (br s, 1H), 8.43-8.49 (m, 1H), 8.16 (br d, J=8.1 Hz, 1H), 8.07 (d, J=4.2 Hz, 1H), 7.91 (br d, J=8.1 Hz, 1H), 7.76 (s, 1H), 7.55-7.64 (m, 2H), 7.39 (t, J=7.2 Hz, 1H), 7.07 (d, J=9.0 Hz, 1H), 5.81 (br t, J=7.7 Hz, 1H), 3.72-3.80 (m, 2H), 2.71 (br t, J=5.0 Hz, 2H), 2.55-2.67 (m, 1H), 2.28 (s, 3H), 2.10-2.19 (m, 1H), 1.41-1.53 (m, 1H), 1.03 (br d, J=6.6 Hz, 3H), 0.99 (br d, J=6.6 Hz, 3H); MS (ES, m/z) 573 [M+H⁺].

Example 51—Compound #250

3-(5-(1-(5-(2-Chloro-4-(trifluoromethyl)phenyl)-4-methoxy-1H-indazol-1-yl)-3-methylbutyl)picolinamido)propanoic Acid

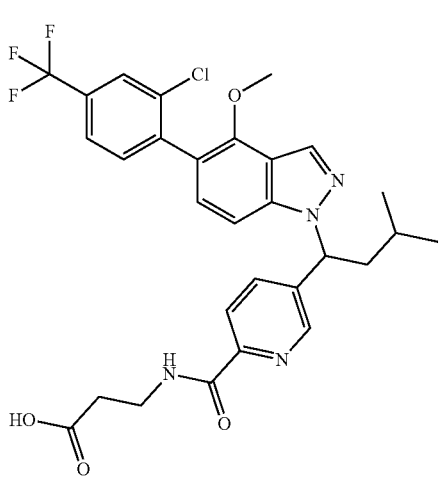 [SMILES: COc1c(-c2ccc(C(F)(F)F)cc2Cl)ccc2c1cnn2C(CC(C)C)c1ccc(C(=O)NCCC(=O)O)nc1]

¹H NMR (METHANOL-d₄) δ 8.67 (br s, 1H), 8.43 (s, 1H), 7.94-8.05 (m, 2H), 7.78 (s, 1H), 7.62 (br d, J=7.8 Hz, 1H), 7.51 (br s, 1H), 7.40 (br d, J=8.6 Hz, 1H), 7.19 (d, J=8.6 Hz, 1H), 6.02 (br dd, J=10.5, 4.9 Hz, 1H), 4.11 (s, 3H), 3.64 (br t, J=6.6 Hz, 2H), 2.67-2.78 (m, 1H), 2.61 (br t, J=6.6 Hz, 2H), 1.97-2.08 (m, 1H), 1.36-1.51 (m, 1H), 1.01 (br d, J=6.4 Hz, 3H), 0.97 (br d, J=6.6 Hz, 3H); MS (ES, m/z) 589 [M+H⁺].

Example 52—Compound #178

3-(5-(1-(5-(2-Chloro-4-(trifluoromethyl)phenyl)-4-methoxy-2H-indazol-2-yl)-3-methylbutyl)picolinamido)propanoic Acid

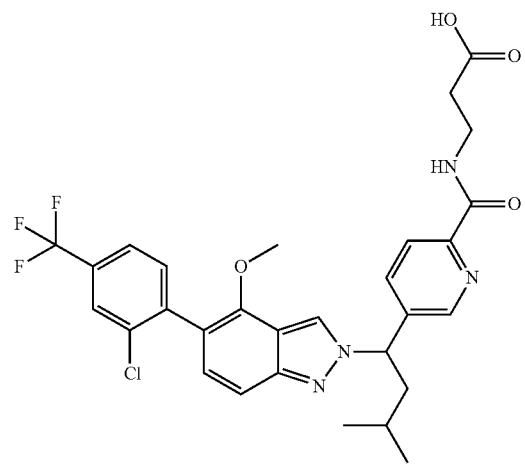 [SMILES: COc1c(-c2ccc(C(F)(F)F)cc2Cl)ccc2nn(C(CC(C)C)c3ccc(C(=O)NCCC(=O)O)nc3)cc12]

¹H NMR (CHLOROFORM-d) δ 8.62 (s, 1H), 8.44 (br t, J=6.1 Hz, 1H), 8.15-8.22 (m, 2H), 7.93 (br d, J=7.8 Hz, 1H), 7.75 (s, 1H), 7.56 (d, J=8.1 Hz, 1H), 7.47 (br d, J=8.8 Hz, 2H), 7.09 (d, J=8.8 Hz, 1H), 5.76 (dd, J=9.0, 6.6 Hz, 1H), 3.86 (s, 3H), 3.75 (q, J=5.9 Hz, 2H), 2.71 (t, J=5.9 Hz, 2H), 2.55-2.65 (m, 1H), 2.14 (dt, J=13.9, 7.1 Hz, 2H), 1.40-1.50 (m, 1H), 1.03 (d, J=6.6 Hz, 3H), 0.99 (d, J=6.6 Hz, 3H); MS (ES, m/z) 589 [M+H⁺].

Example 53—Compound #213

3-(5-(1-(4-Methoxy-5-(2-methyl-4-(trifluoromethyl)phenyl)-1H-indazol-1-yl)-3-methylbutyl)picolinamido)propanoic Acid

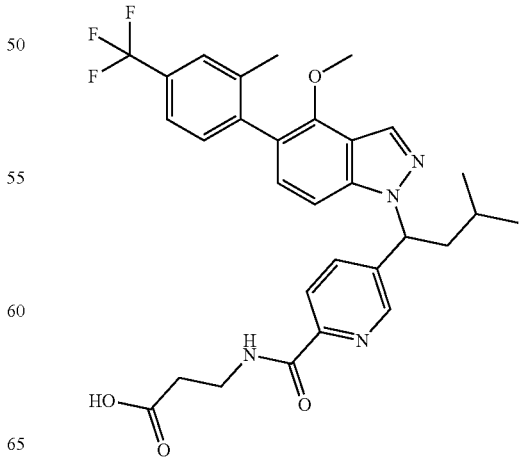

¹H NMR (METHANOL-d₄) δ: 8.67 (br s, 1H), 8.40 (s, 1H), 7.95-8.05 (m, 2H), 7.45-7.55 (m, 2H), 7.41 (br d, J=8.6 Hz, 1H), 7.27-7.36 (m, 1H), 7.15 (d, J=8.6 Hz, 1H), 6.02 (dd, J=10.5, 4.9 Hz, 1H), 4.00 (s, 3H), 3.64 (t, J=6.6 Hz, 2H), 2.69-2.79 (m, 1H), 2.61 (t, J=6.6 Hz, 2H), 2.12-2.23 (m, 3H), 1.98-2.12 (m, 1H), 1.38-1.50 (m, 1H), 1.02 (d, J=6.4 Hz, 3H), 0.97 (br d, J=6.4 Hz, 3H); MS (ES, m/z) 569 [M+H⁺].

Example 54—Compound #236

3-(5-(1-(4-Methoxy-5-(2-methyl-4-(trifluoromethyl)phenyl)-2H-indazol-2-yl)-3-methylbutyl)picolinamido)propanoic Acid

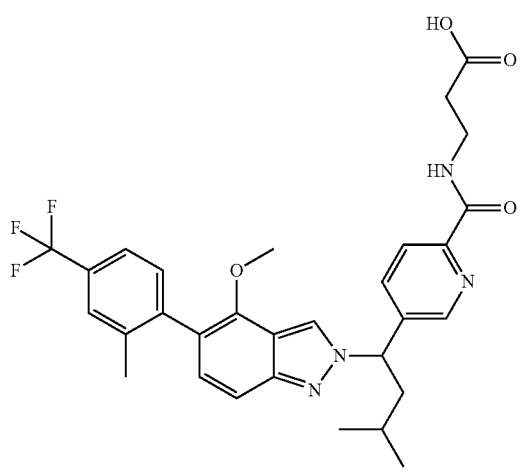 [SMILES: COc1c(-c2ccc(C(F)(F)F)cc2C)ccc2nn(C(CC(C)C)c3ccc(C(=O)NCCC(=O)O)nc3)cc12]

¹H NMR (METHANOL-d₄) δ 8.76 (s, 1H), 8.72 (br s, 1H), 8.06 (br s, 2H), 7.55 (br s, 1H), 7.49 (br s, 1H), 7.34-7.41 (m, 2H), 7.03-7.08 (m, 1H), 5.95-6.02 (m, 1H), 3.86 (br s, 3H), 3.61-3.69 (m, 2H), 2.58-2.72 (m, 3H), 2.22 (br s, 3H), 2.09-2.19 (m, 1H), 1.31-1.42 (m, 1H), 1.03-1.09 (m, 3H), 0.93-1.03 (m, 3H); MS (ES, m/z) 569 [M+H⁺].

Example 55—Compound #179

3-(5-(1-(5-(2-Chloro-4-(trifluoromethyl)phenyl)-4-ethoxy-1H-indazol-1-yl)-3-methylbutyl)picolinamido)propanoic Acid

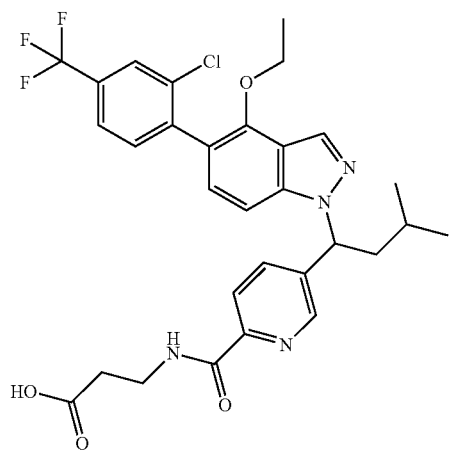 [SMILES: CCOc1c(-c2ccc(C(F)(F)F)cc2C)ccc2c1cnn2C(CC(C)C)c1ccc(C(=O)NCCC(=O)O)nc1]

¹H NMR (METHANOL-d₄) δ 8.66 (s, 1H), 8.35 (s, 1H), 7.95-8.04 (m, 2H), 7.79 (s, 1H), 7.63 (br d, J=8.1 Hz, 1H), 7.49-7.58 (m, 1H), 7.41 (d, J=8.6 Hz, 1H), 7.20 (d, J=8.6 Hz, 1H), 6.02 (dd, J=10.5, 4.9 Hz, 1H), 4.31-4.42 (m, 2H), 3.64 (t, J=6.7 Hz, 2H), 2.69-2.78 (m, 1H), 2.61 (t, J=6.7 Hz, 2H), 2.00-2.08 (m, 1H), 1.39-1.50 (m, 1H), 1.23 (t, J=7.0 Hz, 3H), 1.02 (d, J=6.6 Hz, 3H), 0.97 (d, J=6.6 Hz, 3H); MS (ES, m/z) 603 [M+H⁺].

Example 56—Compound #205

3-(5-(1-(5-(2-Chloro-4-(trifluoromethyl)phenyl)-4-ethoxy-2H-indazol-2-yl)-3-methylbutyl)picolinamido)propanoic Acid

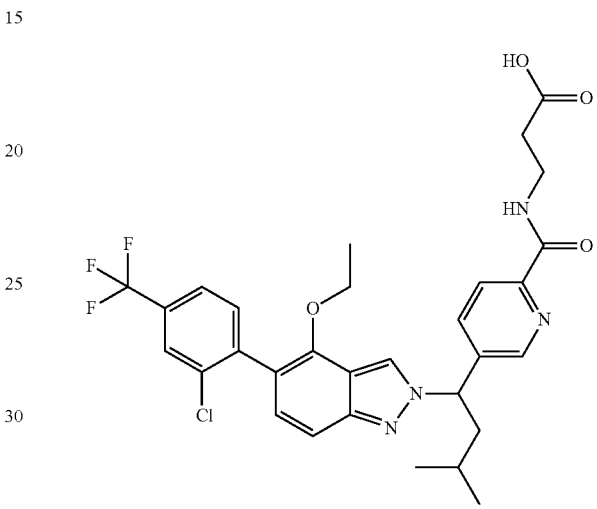

¹H NMR (METHANOL-d₄) δ 8.76 (s, 1H), 8.70 (s, 1H), 8.05 (s, 2H), 7.80 (s, 1H), 7.64 (d, J=8.1 Hz, 1H), 7.55 (d, J=8.1 Hz, 1H), 7.38 (d, J=8.8 Hz, 1H), 7.10 (d, J=8.8 Hz, 1H), 5.98 (dd, J=10.1, 5.5 Hz, 1H), 4.18-4.28 (m, 2H), 3.65 (t, J=6.6 Hz, 2H), 2.64-2.71 (m, 1H), 2.62 (t, J=6.6 Hz, 2H), 2.13 (ddd, J=13.9, 8.1, 5.9 Hz, 1H), 1.29-1.39 (m, 1H), 1.19 (t, J=7.0 Hz, 3H), 1.05 (d, J=6.6 Hz, 3H), 0.97 (d, J=6.4 Hz, 3H); MS (ES, m/z) 603 [M+H⁺].

Example 57—Compound #197

3-(5-(1-(4-Ethoxy-5-(2-methyl-4-(trifluoromethyl)phenyl)-1H-indazol-1-yl)-3-methylbutyl)picolinamido)propanoic Acid

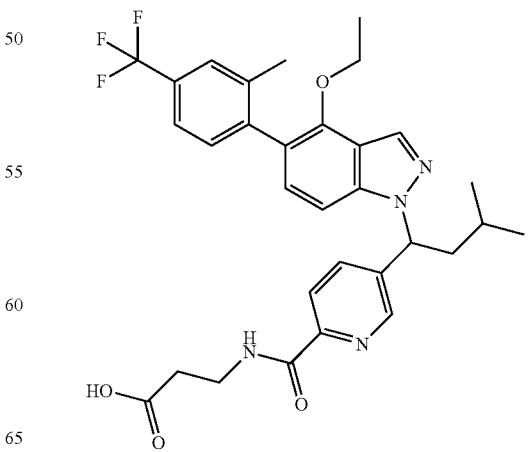

¹H NMR (METHANOL-d₄) δ 8.66 (br s, 1H), 8.31 (s, 1H), 7.95-8.04 (m, 2H), 7.54 (s, 1H), 7.27-7.50 (m, 3H), 7.16 (d, J=8.6 Hz, 1H), 6.02 (br dd, J=10.4, 4.8 Hz, 1H), 4.13-4.28 (m, 2H), 3.64 (t, J=6.6 Hz, 2H), 2.69-2.78 (m, 1H), 2.61 (t, J=6.6 Hz, 2H), 2.14-2.26 (m, 3H), 1.99-2.09 (m, 1H), 1.36-1.50 (m, 1H), 1.16 (t, J=6.8 Hz, 3H), 1.02 (d, J=6.6 Hz, 3H), 0.97 (br d, J=6.6 Hz, 3H); MS (ES, m/z) 583 [M+H⁺].

Example 58—Compound #207

3-(5-(1-(4-Ethoxy-5-(2-methyl-4-(trifluoromethyl)phenyl)-2H-indazol-2-yl)-3-methylbutyl)picolinamido)propanoic Acid

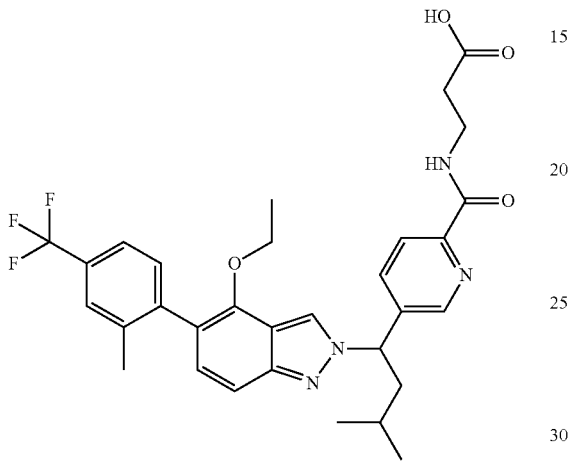

¹H NMR (METHANOL-d₄) δ 8.71 (s, 1H), 8.70 (br s, 1H), 8.06 (s, 2H), 7.47-7.57 (m, 2H), 7.35-7.41 (m, 2H), 7.07 (d, J=8.8 Hz, 1H), 5.99 (br dd, J=10.1, 5.5 Hz, 1H), 3.96-4.15 (m, 2H), 3.65 (br t, J=6.6 Hz, 2H), 2.64-2.71 (m, 1H), 2.62 (br t, J=6.6 Hz, 2H), 2.23 (br s, 3H), 2.14 (ddd, J=13.8, 8.3, 5.6 Hz, 1H), 1.30-1.40 (m, 1H), 1.13 (t, J=7.0 Hz, 3H), 1.06 (br d, J=6.4 Hz, 3H), 0.98 (br d, J=6.4 Hz, 3H); MS (ES, m/z) 583 [M+H⁺].

Example 59—Compound #263

3-(5-(1-(5-(2-Chloro-4-(trifluoromethyl)phenyl)-4-(trifluoromethyl)-1H-indazol-1-yl)-3-methylbut-yl)picolinamido)propanoic Acid

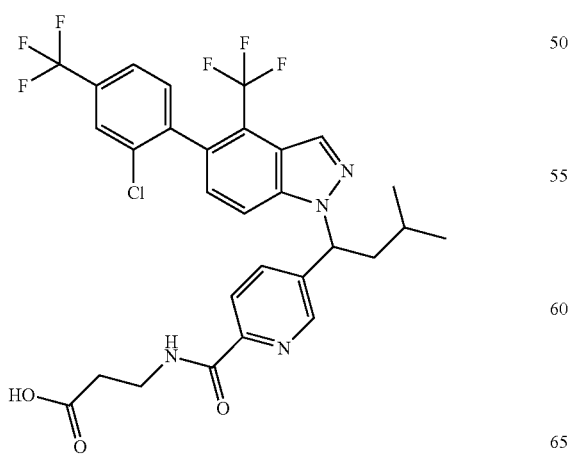

¹H NMR (CHLOROFORM-d) δ 8.56 (s, 1H), 8.39 (br t, J=5.5 Hz, 1H), 8.21 (s, 1H), 8.14 (d, J=8.3 Hz, 1H), 7.89 (br d, J=7.6 Hz, 1H), 7.82 (s, 1H), 7.64 (s, 2H), 7.51 (d, J=7.1 Hz, 1H), 7.34 (d, J=7.1 Hz, 1H), 5.75 (dd, J=8.9, 6.5 Hz, 1H), 3.69-3.77 (br d, J=5.4 Hz, 2H), 2.65-2.77 (m, 2H), 2.48-2.58 (m, 1H), 2.04-2.16 (m, 1H), 1.33-1.42 (m, 1H), 1.21 (t, J=7.1 Hz, 2H), 0.99 (d, J=6.6 Hz, 3H), 0.93 (d, J=6.4 Hz, 3H); MS (ES, m/z) 627 [M+H⁺].

Example 60—Compound #246

3-(5-(3-Methyl-1-(5-(2-methyl-4-(trifluoromethyl)phenyl)-4-(trifluoromethyl)-2H-indazol-2-yl)butyl)picolinamido)propanoic Acid

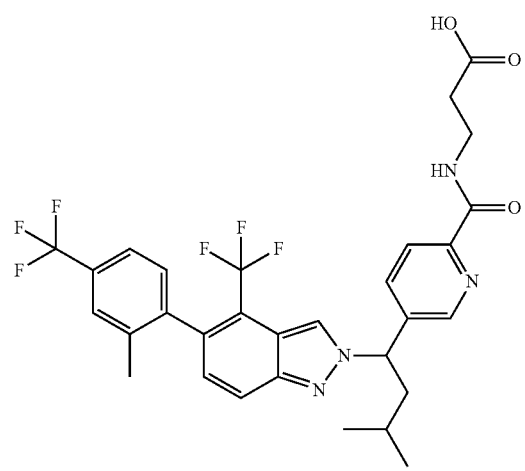 [SMILES: Cc1cc(C(F)(F)F)ccc1-c1ccc2nn(C(CC(C)C)c3ccc(C(=O)NCCC(=O)O)nc3)cc2c1C(F)(F)F]

¹H NMR (MeOH) b 8.73 (d, J=1.5 Hz, 1H), 8.70 (d, J=1.2 Hz, 1H), 8.00-8.06 (m, 2H), 7.64 (s, 1H), 7.53-7.61 (m, 2H), 7.43-7.53 (m, 2H), 7.27 (d, J=7.1 Hz, 1H), 6.02 (dd, J=10.1, 5.7 Hz, 1H), 3.63 (t, J=6.7 Hz, 2H), 2.56-2.64 (m, 3H), 2.17 (s, 3H), 2.08 (ddd, J=14.1, 8.2, 5.6 Hz, 1H), 1.21-1.36 (m, 1H), 1.01 (d, J=6.6 Hz, 3H), 0.91 (d, J=6.6 Hz, 3H).

Example 61—Compound #190

3-(4-(1-(5-(2,4-Dichlorophenyl)-4-methyl-2H-indazol-2-yl)-3-methylbutyl)benzamido)propanoic Acid

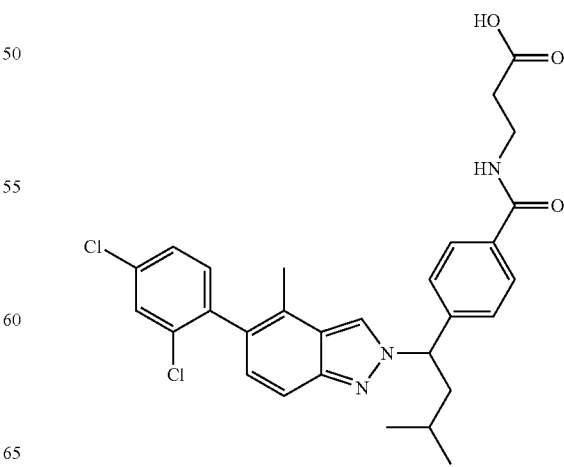

¹H NMR (400 MHz, CHLOROFORM-d) δ 8.01 (d, J=5.1 Hz, 1H), 7.74 (d, J=8.1 Hz, 2H), 7.58 (d, J=8.8 Hz, 1H), 7.43-7.53 (m, 3H), 7.23-7.34 (m, 1H), 7.18 (dd, J=2.3, 8.2 Hz, 1H), 7.05 (d, J=8.8 Hz, 1H), 6.83-6.95 (m, 1H), 5.73-5.86 (m, 1H), 3.72 (q, J=6.0 Hz, 2H), 2.70 (t, J=5.6 Hz, 2H), 2.43-2.60 (m, 1H), 2.26 (s, 3H), 2.14 (d, J=7.1 Hz, 1H), 1.46 (br. s., 1H), 0.98 (d, J=6.6 Hz, 3H), 1.01 (d, J=6.6 Hz, 3H) (The proton of carboxylic acid is not shown.); MS: 539 (M⁺+1).

Example 62—Compound #148

3-(4-(1-(5-(2-Chloro-4-methylphenyl)-4-methyl-2H-indazol-2-yl)-3-methylbutyl)benzamido)propanoic Acid

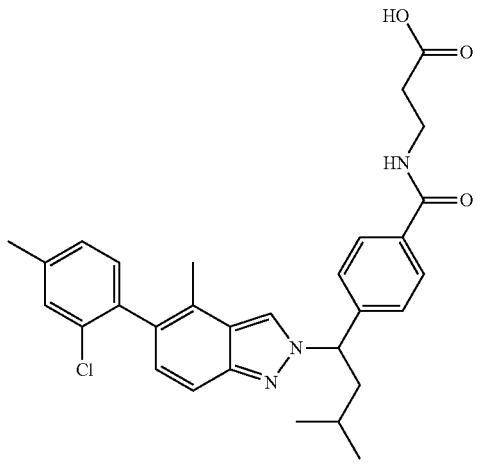

¹H NMR (400 MHz, CHLOROFORM-d) δ 8.01 (s, 1H), 7.73 (d, J=8.1 Hz, 2H), 7.57 (d, J=8.8 Hz, 1H), 7.45 (d, J=8.1 Hz, 2H), 7.32 (s, 1H), 7.22-7.30 (m, 1H), 7.08-7.22 (m, 2H), 6.92 (t, J=6.1 Hz, 1H), 5.81 (dd, J=6.6, 9.0 Hz, 1H), 3.71 (q, J=5.8 Hz, 2H), 2.69 (t, J=5.6 Hz, 2H), 2.46-2.59 (m, 1H), 2.34-2.46 (m, 6H), 2.14 (dt, J=6.9, 13.8 Hz, 1H), 1.36-1.53 (m, 1H), 0.97 (d, J=6.6 Hz, 3H), 1.01 (d, J=6.6 Hz, 3H) (The proton of carboxylic acid is not shown.); MS: 519 (M⁺+1).

Example 63—Compound #143

3-(4-(1-(5-(2,4-Dimethylphenyl)-4-methyl-2H-indazol-2-yl)-3-methylbutyl)benzamido)propanoic Acid

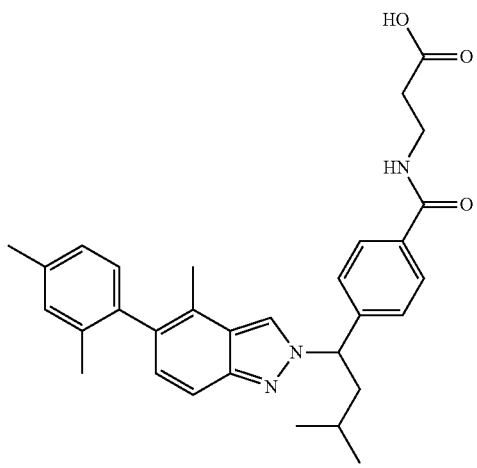 [SMILES: Cc1ccc(-c2ccc3nn(C(CC(C)C)c4ccc(C(=O)NCCC(=O)O)cc4)cc3c2C)c(C)c1]

¹H NMR (400 MHz, CHLOROFORM-d) δ 7.98 (d, J=4.6 Hz, 1H), 7.74 (d, J=8.1 Hz, 2H), 7.40-7.62 (m, 3H), 6.88-7.16 (m, 5H), 5.71-5.92 (m, 1H), 3.71 (q, J=5.6 Hz, 2H), 2.68 (t, J=5.5 Hz, 2H), 2.44-2.59 (m, 1H), 2.37 (s, 3H), 2.21 (s, 3H), 2.08-2.19 (m, 1H), 2.03 (s, 3H), 1.36-1.55 (m, 1H), 0.97 (d, J=6.6 Hz, 3H), 1.01 (d, J=6.6 Hz, 3H) (The proton of carboxylic acid is not shown.); MS: 499 (M⁺+1).

Example 64—Compound #149

3-(4-(1-(5-(3-Chloro-4-(trifluoromethyl)phenyl)-4-methyl-2H-indazol-2-yl)-3-methylbutyl)benzamido) Propanoic Acid

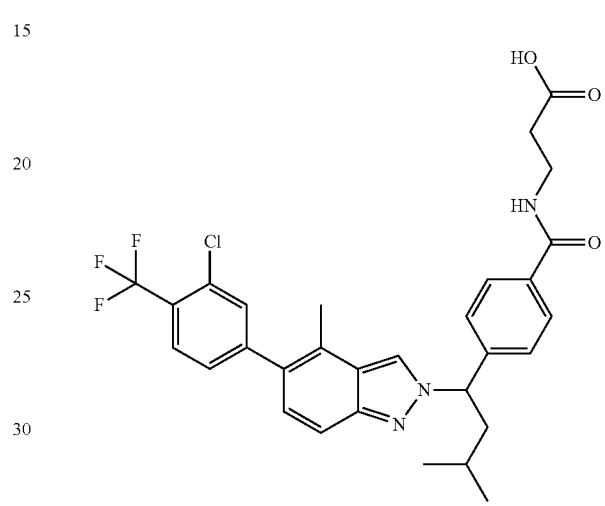

¹H NMR (400 MHz, CHLOROFORM-d) δ 8.04 (s, 1H), 7.73 (d, J=7.6 Hz, 3H), 7.62 (d, J=8.8 Hz, 1H), 7.40-7.55 (m, 3H), 7.33 (d, J=8.1 Hz, 1H), 7.16 (d, J=8.8 Hz, 1H), 6.88 (t, J=5.7 Hz, 1H), 5.71-5.86 (m, 1H), 3.71 (q, J=5.8 Hz, 2H), 2.69 (t, J=5.5 Hz, 2H), 2.46-2.62 (m, 1H), 2.44 (s, 3H), 2.15 (dt, J=7.1, 14.2 Hz, 1H), 1.35-1.53 (m, 1H), 1.01 (d, J=6.6 Hz, 3H), 0.97 (d, J=6.6 Hz, 3H) (The proton of carboxylic acid is not shown.); MS: 573 (M⁺+1).

Example 65—Compound #105

3-(4-(1-(5-(2-Chloro-4-methylphenyl)-4-methyl-1H-indazol-1-yl)-3-methylbutyl)benzamido)propanoic Acid

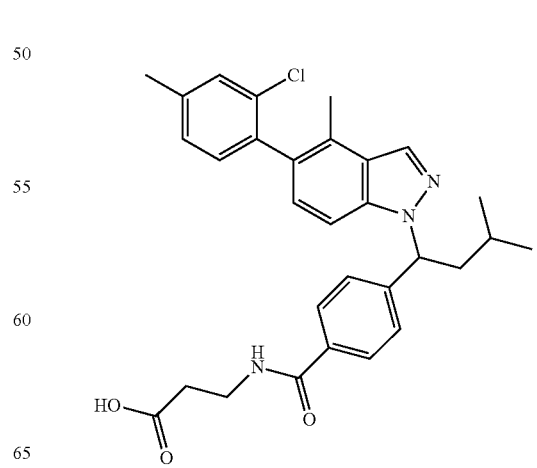

¹H NMR (400 MHz, CHLOROFORM-d) δ 8.13 (s, 1H), 7.62-7.74 (m, J=8.3 Hz, 2H), 7.33-7.43 (m, J=8.1 Hz, 2H), 7.15-7.33 (m, 4H), 7.10 (d, J=7.6 Hz, 1H), 6.68-6.78 (m, 1H), 5.71 (dd, J=5.6, 10.0 Hz, 1H), 3.68 (q, J=6.0 Hz, 2H), 2.60-2.76 (m, 3H), 2.50 (s, 3H), 2.42 (s, 3H), 2.01-2.12 (m, 1H), 1.45 (d, J=8.1 Hz, 1H), 0.97 (t, J=6.1 Hz, 6H); MS: 519 (M⁺+1).

Example 66—Compound #177

3-(4-(1-(5-(2,4-Dimethylphenyl)-4-methyl-1H-indazol-1-yl)-3-methylbutyl)benzamido)Propanoic Acid

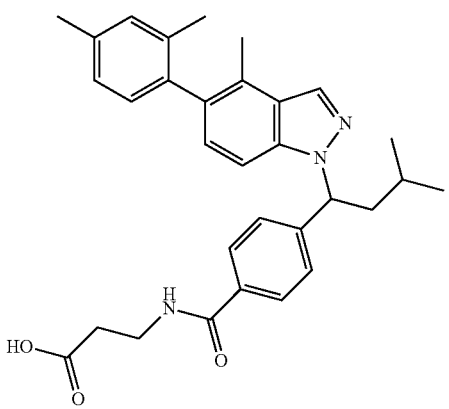 [SMILES: Cc1ccc(-c2ccc3c(cnn3C(CC(C)C)c3ccc(C(=O)NCCC(=O)O)cc3)c2C)c(C)c1]

¹H NMR (400 MHz, CHLOROFORM-d) δ 8.11 (s, 1H), 7.68 (dd, J=5.6, 7.8 Hz, 2H), 7.40 (d, J=8.3 Hz, 1H), 7.44 (d, J=8.3 Hz, 1H), 7.16-7.23 (m, 1H), 7.06-7.14 (m, 2H), 6.99-7.06 (m, 2H), 6.75 (d, J=4.9 Hz, 1H), 5.71 (dd, J=5.6, 9.8 Hz, 1H), 3.69 (q, J=5.8 Hz, 2H), 2.68 (t, J=5.6 Hz, 3H), 2.23-2.44 (m, 6H), 2.05-2.16 (m, 1H), 2.03-1.97 (m, 3H), 1.50 (br. s., 1H), 0.92-1.04 (m, 6H) (The proton of carboxylic acid is not shown.); MS: 499 (M⁺+1).

Example 67—Compound #223

3-(4-(1-(5-(2-Chloro-4-fluorophenyl)-1H-indazol-1-yl)-4,4,4-trifluorobutyl)benzamido)propanoic acid

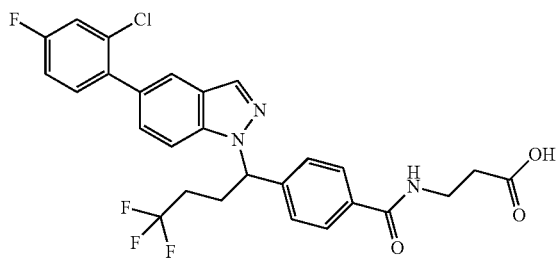 [SMILES: O=C(O)CCNC(=O)c1ccc(C(CCC(F)(F)F)n2ncc3cc(-c4ccc(F)cc4Cl)ccc32)cc1]

Step A: Methyl 4-(4,4,4-trifluorobutyl)benzoate

NiI₂.xH₂O (87.7 mg, 0.198 mol), 1,2-bis(diphenylphosphino)benzene (42.6 mg, 0.093 mmol), 4,4-di-tert-butyl-2,2'-dipyridyl (25.4 mg, 0.093 mol), methyl 4-iodobenzoate (500 mg, 1.85 mmol), 1-iodo-4,4,4-trifluorobutane (454.1 mg, 1.85 mmol) were transferred to a 5 ml microwave vial equipped with a magnetic stir bar. The vial was then capped with a rubber septum and purged with argon gas. DMPU (2 ml), pyridine (1 drop) were injected into the vial. Manganese powder (204 mg, 3.7 mmol) was added and the vial was placed under microwave irradiation at 120° C. for 60 min. The mixture was diluted with water, extracted with ethyl acetate. The organic layer was concentrated and the residue was purified by flash column chromatography on silica gel (EtOAc/heptane: 0>>>10%>>>20%) to yield a white solid. ¹H NMR (CHLOROFORM-d) δ: 7.98 (d, J=8.1 Hz, 2H), 7.24 (s, 2H), 3.91 (s, 3H), 2.75 (t, J=7.6 Hz, 2H), 2.00-2.19 (m, 2H), 1.85-1.98 (m, 2H).

Step B: Methyl 4-(1-bromo-4,4,4-trifluorobutyl)benzoate

A mixture of methyl 4-(4,4,4-trifluorobutyl)benzoate (589 mg, 2.39 mmol), NBS (468.3 mg, 2.63 mmol) and BPO (57.9 mg, 0.24 mmol) in 25 ml of CCl₄ was stirred at 86° C. for 4 h, then cooled to room temperature. The precipitate was filtered off, then washed with dichloromethane. The filtrate was concentrated and the residue was purified by flash column chromatography on silica gel (EtOAc/heptane: 0>>>10%>>>15%) to yield a residue. ¹H NMR (CHLOROFORM-d) δ: 8.02-8.06 (m, 2H), 7.45-7.49 (m, 2H), 4.96 (dd, J=9.2, 5.3 Hz, 1H), 3.93 (s, 3H), 2.44-2.57 (m, 1H), 2.32-2.43 (m, 2H), 2.07-2.28 (m, 1H).

Step C: Methyl 4-(1-(5-bromo-1H-indazol-1-yl)-4,4,4-trifluorobutyl)benzoate

A mixture of methyl 4-(1-bromo-4,4,4-trifluorobutyl)benzoate (437.4 mg, 1.35 mmol), 5-bromoindazole (291.6 mg, 1.48 mmol) and K₂CO₃ (371.9 mg, 2.69 mmol) in 2 ml of DMF was stirred at 50° C. for 16 hours. The resulting mixture was diluted with water, extracted with ethyl acetate. The organic layer was washed with brine, dried over Na₂SO₄, filtered and concentrated. The residue was purified by flash column chromatography on silica gel (EtOAc/heptane: 0>>>10%>>>20%) to yield two products: methyl 4-(1-(5-bromo-1H-indazol-1-yl)-4,4,4-trifluorobutyl)benzoate (350 mg, 59%) and methyl 4-(1-(5-bromo-2H-indazol-2-yl)-4,4,4-trifluorobutyl)benzoate (the N-1 substituted compound). ¹H NMR (CHLOROFORM-d) δ: 8.05-8.06 (m, 1H), 7.97 (d, J=8.3 Hz, 2H), 7.89 (d, J=1.5 Hz, 1H), 7.40 (dd, J=8.9, 1.6 Hz, 1H), 7.31 (d, J=8.3 Hz, 2H), 7.19 (d, J=8.8 Hz, 1H), 5.64 (dd, J=10.3, 5.1 Hz, 1H), 3.88 (s, 3H), 2.89-3.08 (m, 1H), 2.46-2.62 (m, 1H), 2.10-2.24 (m, 2H).

and methyl 4-(1-(5-bromo-2H-indazol-2-yl)-4,4,4-trifluorobutyl)benzoate (the N-2 substituted compound). ¹H NMR (CHLOROFORM-d) δ: 8.02 (d, J=8.3 Hz, 2H), 7.91 (s, 1H), 7.78 (d, J=1.2 Hz, 1H), 7.63 (d, J=9.0 Hz, 1H), 7.41 (d, J=8.3 Hz, 2H), 7.35 (dd, J=9.0, 1.7 Hz, 1H), 5.49-5.70 (m, 1H), 3.90 (s, 3H), 2.84-3.03 (m, 1H), 2.47-2.67 (m, 1H), 2.01-2.17 (m, 2H).

Step D: 4-(1-(5-Bromo-1H-indazol-1-yl)-4,4,4-trifluorobutyl)benzoic Acid

To a solution of methyl 4-(1-(5-bromo-1H-indazol-1-yl)-4,4,4-trifluorobutyl)benzoate (the N-1 substituted compound, 350 mg, 0.79 mmol) in TH/MeOH (7 ml, v/v=2:5) was added 2 ml of 1N NaOH and the resulting mixture was kept stirring at room temperature for 16 h. The solvent was removed under reduced pressure and the residue was acidified with 1N HCl and the extracted with ethyl acetate. The organic layer was dried, the drying agent was filtered off and the solvent was removed under reduced pressure to yield a white solid. m/z (MH+): 427.0.

Step E: tert-Butyl 3-(4-(1-(5-bromo-1H-indazol-1-yl)-4,4,4-trifluorobutyl)benzamido)propanoate A mixture of 4-(1-(5-bromo-1H-indazol-1-yl)-4,4,4-trifluorobutyl)benzoic acid (346.5 mg, 0.81 mmol), tert-butyl 3-aminopropanoate (176.8 mg, 0.97 mmol), EDC (202.1 g, 1.05 mmol), HOBt (124.2 mg, 0.81 mmol) and DIEA (314.5 mg, 2.43 mmol) in THF (6 ml) was stirred at room temperature for 16 h. The resulting mixture was diluted with water, extracted with ethyl acetate. The combined organic layer was washed with brine, dried over $Na_2SO_4$, filtered and concentrated under reduced pressure. The resulting residue was purified by flash column chromatography on silica gel (EtOAc/heptanes: 0>>>20%>>>30%) to yield a residue. $^1$H NMR (CHLOROFORM-d) δ: 8.05 (s, 1H), 7.88 (d, J=1.7 Hz, 1H), 7.69 (d, J=8.3 Hz, 2H), 7.40 (dd, J=8.9, 1.6 Hz, 1H), 7.31 (d, J=8.3 Hz, 2H), 7.19 (d, J=8.8 Hz, 1H), 6.85 (br t, J=5.7 Hz, 1H), 5.63 (dd, J=10.1, 5.3 Hz, 1H), 3.65 (q, J=6.0 Hz, 2H), 2.84-3.09 (m, 1H), 2.45-2.61 (m, 3H), 2.04-2.23 (m, 2H), 1.44 (s, 9H).

Step F: tert-Butyl 3-(4-(1-(5-(2-chloro-4-fluorophenyl)-1H-indazol-1-yl)-4,4,4-trifluorobutyl)benzamido)propanoate A mixture of tert-butyl 3-(4-(1-(5-bromo-1H-indazol-1-yl)-4,4,4-trifluorobutyl)benzamido)propanoate (80 mg, 0.14 mmol), 2-chloro-4-fluorophenyl boronic acid (32.7 mg, 0.19 mmol), $PdCl_2$(dppf) (10.6 mg, 0.014 mmol), $K_2CO_3$ (2N, 0.14 ml) in 5 ml of 1,4-dioxane was stirred at 85° C. for 16 h. The solvent was removed under reduced pressure and the residue was purified by flash column chromatography on silica gel (EtOAc/heptane: 0>>>10%>>>35%) to yield a white foam. $^1$H NMR (CHLOROFORM-d) δ: 8.15 (s, 1H), 7.69-7.75 (m, 3H), 7.36-7.41 (m, 3H), 7.29-7.35 (m, 1H), 7.23 (dd, J=8.6, 2.4 Hz, 1H), 7.04 (td, J=8.3, 2.7 Hz, 1H), 6.84 (br t, J=5.6 Hz, 1H), 5.60-5.79 (m, 1H), 3.59-3.69 (m, 2H), 2.96-3.08 (m, 1H), 2.50-2.62 (m, 3H), 2.10-2.25 (m, 2H), 1.44 (s, 9H).

Step G: 3-[[4-[1-[5-(2-Chloro-4-fluoro-phenyl)indazol-1-yl]-4,4,4-trifluoro-butyl]benzoyl]amino]propanoic Acid To a solution of tert-butyl 3-(4-(1-(5-(2-chloro-4-fluorophenyl)-1H-indazol-1-yl)-4,4,4-trifluorobutyl)benzamido)propanoate (57 mg, 0.094 mmol) in 2 ml of DCM was added 1 ml of TFA and the mixture was stirred at room temperature for 4 hours. The solvent was removed under reduced pressure and the residue was purified by Gilson HPLC to yield the title compound as a white solid.

$^1$H NMR (CHLOROFORM-d) δ: 8.15 (s, 1H), 7.73 (s, 1H), 7.69 (d, J=8.1 Hz, 2H), 7.33-7.41 (m, 4H), 7.30 (dd, J=8.6, 6.1 Hz, 1H), 7.22 (dd, J=8.6, 2.4 Hz, 1H), 7.03 (td, J=8.3, 2.6 Hz, 1H), 6.80-6.96 (m, 1H), 5.53-5.82 (m, 1H), 3.66 (q, J=5.8 Hz, 2H), 2.93-3.05 (m, 1H), 2.65 (br t, J=5.7 Hz, 2H), 2.48-2.59 (m, 1H), 2.08-2.22 (m, 2H). m/z (MH+): 548.0.

The following compounds (as shown in Examples 68-97 below) were similarly prepared according to the procedures described above, selecting and substituting a suitably substituted boronic acid in the Suzuki coupling step.

Example 68—Compound #8

3-[[4-[1-[5-(4-Chloro-2-methyl-phenyl)indazol-2-yl]-4,4,4-trifluoro-butyl]benzoyl]amino]propanoic Acid

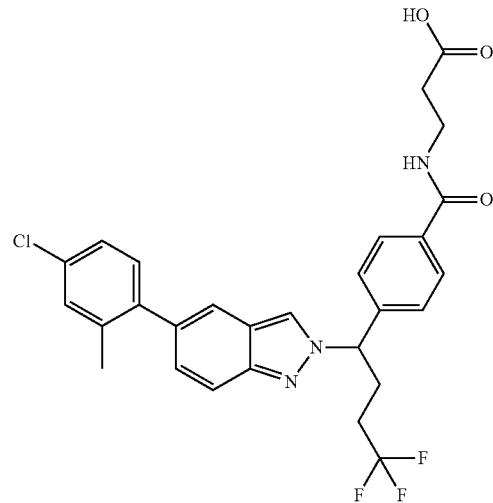 [SMILES: Cc1cc(Cl)ccc1-c1ccc2nn(C(CCC(F)(F)F)c3ccc(C(=O)NCCC(=O)O)cc3)cc2c1]

$^1$H NMR (CHLOROFORM-d) δ: 9.79-10.09 (m, 1H), 8.01 (s, 1H), 7.73 (br dd, J=8.4, 4.5 Hz, 3H), 7.37-7.56 (m, 4H), 7.11-7.32 (m, 4H), 5.71 (br dd, J=9.5, 5.9 Hz, 1H), 3.67 (br d, J=5.4 Hz, 2H), 2.85-3.05 (m, 1H), 2.61-2.73 (m, 2H), 2.54 (td, J=14.5, 6.1 Hz, 1H), 2.22 (s, 3H), 2.05-2.15 (m, 2H). m/z (MH+): 544.2.

Example 69—Compound #111

3-[[4-[1-[5-[3-Chloro-4-(trifluoromethyl)phenyl]indazol-1-yl]-4,4,4-trifluoro-butyl]benzoyl]amino] propanoic Acid

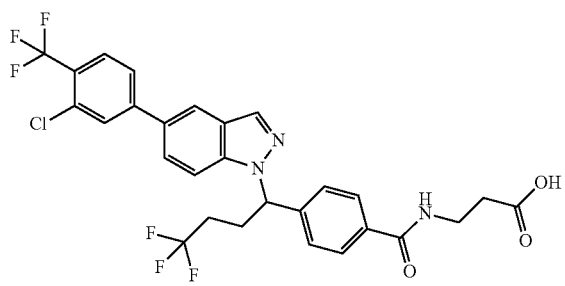 [SMILES: O=C(O)CCNC(=O)c1ccc(C(CCC(F)(F)F)n2ncc3cc(-c4ccc(C(F)(F)F)c(Cl)c4)ccc32)cc1]

$^1$H NMR (CHLOROFORM-d) δ: 8.18 (s, 1H), 7.92 (s, 1H), 7.65-7.77 (m, 5H), 7.51-7.59 (m, 2H), 7.40 (d, J=8.8 Hz, 1H), 7.34 (d, J=8.1 Hz, 2H), 6.94 (br s, 1H), 5.70 (br d, J=4.9 Hz, 1H), 3.65 (br d, J=5.6 Hz, 2H), 2.90-3.06 (m, 1H), 2.63 (br t, J=5.4 Hz, 2H), 2.48-2.59 (m, 1H), 2.08-2.23 (m, 2H). m/z (MH+): 598.0.

Example 70—Compound #40

3-[[4-[1-[5-(4-Chloro-2-methyl-phenyl)indazol-1-yl]-4,4,4-trifluoro-butyl]benzoyl]amino]propanoic Acid

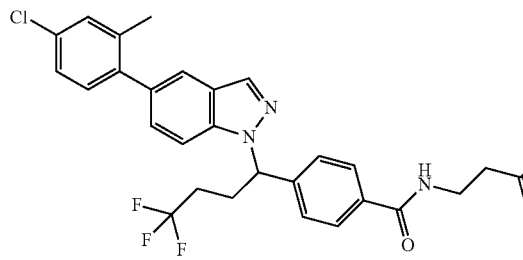

$^1$H NMR (CHLOROFORM-d) δ: 8.57-8.91 (m, 1H), 8.13 (s, 1H), 7.69 (br d, J=8.1 Hz, 2H), 7.61 (s, 1H), 7.35 (br dd, J=8.1, 5.9 Hz, 3H), 7.26 (br dd, J=5.6, 1.7 Hz, 2H), 7.19 (br dd, J=8.1, 2.0 Hz, 1H), 7.11-7.16 (m, 1H), 6.98 (br d, J=5.1 Hz, 1H), 5.59-5.85 (m, 1H), 3.66 (br d, J=4.9 Hz, 2H), 2.91-3.07 (m, 1H), 2.65 (br d, J=4.9 Hz, 2H), 2.48-2.59 (m, 1H), 2.21 (s, 3H), 2.09-2.19 (m, 2H). m/z (MH+): 544.2.

Example 71—Compound #167

3-[[4-[1-[5-[2-Chloro-4-(trifluoromethyl)phenyl]indazol-1-yl]-4,4,4-trifluoro-butyl]benzoyl]amino]propanoic Acid

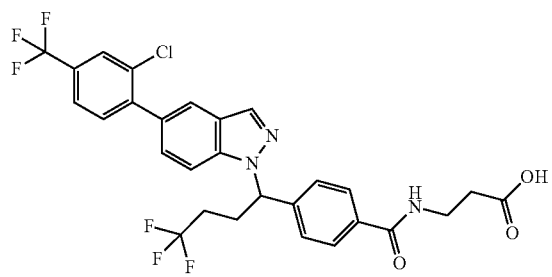 [SMILES: O=C(O)CCNC(=O)c1ccc(C(CCC(F)(F)F)n2ncc3cc(-c4ccc(C(F)(F)F)cc4Cl)ccc32)cc1]

$^1$H NMR (CHLOROFORM-d) δ: 8.18 (s, 1H), 7.80 (s, 1H), 7.75 (s, 1H), 7.69 (br d, J=8.1 Hz, 2H), 7.57 (br d, J=8.1 Hz, 1H), 7.33-7.50 (m, 5H), 7.06-7.22 (m, 1H), 6.92 (br t, J=5.7 Hz, 1H), 5.71 (br dd, J=10.3, 5.1 Hz, 1H), 3.67 (br d, J=5.4 Hz, 2H), 2.92-3.08 (m, 1H), 2.62-2.72 (m, 2H), 2.55 (td, J=13.6, 7.3 Hz, 1H), 2.08-2.25 (m, 2H). m/z (MH+): 598.0.

Example 72—Compound #112

3-[[4-[1-[5-(2,4-Dichlorophenyl)indazol-1-yl]-4,4,4-trifluoro-butyl]benzoyl]amino]propanoic Acid

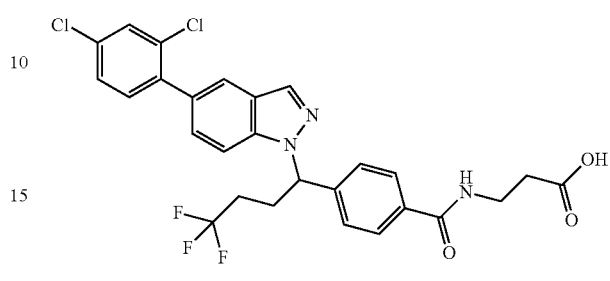

$^1$H NMR (CHLOROFORM-d) δ: 8.16 (s, 1H), 7.75 (s, 1H), 7.69 (br d, J=8.1 Hz, 2H), 7.49 (br d, J=2.0 Hz, 1H), 7.34-7.45 (m, 4H), 7.26-7.32 (m, 2H), 6.76-6.99 (m, 1H), 5.69 (br dd, J=9.9, 5.0 Hz, 1H), 3.68 (br d, J=5.4 Hz, 2H), 2.94-3.12 (m, 1H), 2.67 (br d, J=5.4 Hz, 2H), 2.48-2.61 (m, 1H), 2.10-2.27 (m, 2H). m/z (MH+): 564.0.

Example 73—Compound #224

3-[[4-[1-[5-(2,4-Dichlorophenyl)indazol-2-yl]-4,4,4-trifluoro-butyl]benzoyl]amino]propanoic Acid

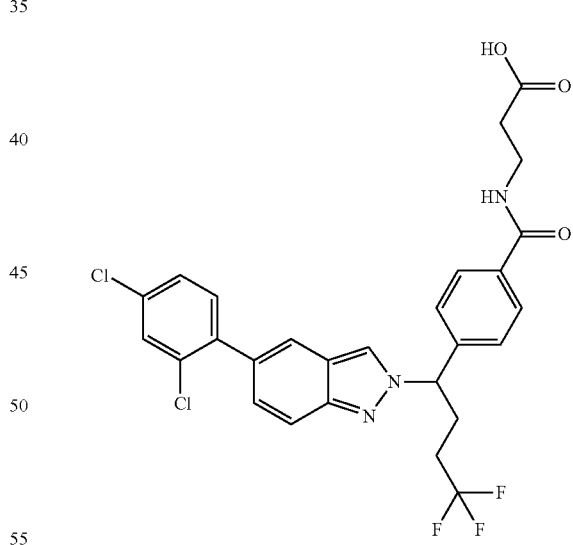

$^1$H NMR (CHLOROFORM-d) δ: 9.72 (br s, 1H), 8.01 (s, 1H), 7.74 (br dd, J=18.7, 8.4 Hz, 4H), 7.62 (s, 1H), 7.48 (br d, J=0.7 Hz, 1H), 7.32-7.45 (m, 3H), 7.27-7.31 (m, 1H), 7.01-7.17 (m, 1H), 5.68 (br dd, J=9.7, 5.7 Hz, 1H), 3.67 (br d, J=5.4 Hz, 2H), 2.83-3.03 (m, 1H), 2.65 (br t, J=5.4 Hz, 2H), 2.53 (td, J=14.5, 6.0 Hz, 1H), 2.02-2.17 (m, 2H). m/z (MH+): 564.0.

Example 74—Compound #75

3-[[4-[4,4,4-Trifluoro-1-[5-[4-(trifluoromethyl)phenyl]indazol-1-yl]butyl]benzoyl]amino]propanoic Acid

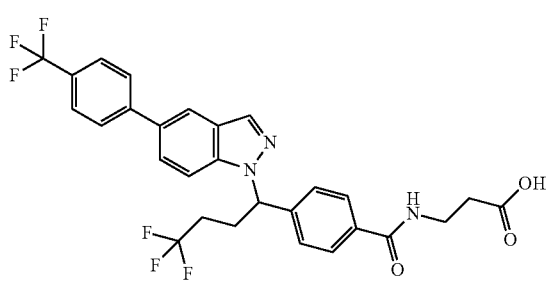 [SMILES: O=C(O)CCNC(=O)c1ccc(C(CCC(F)(F)F)n2ncc3cc(-c4ccc(C(F)(F)F)cc4)ccc32)cc1]

¹H NMR (CHLOROFORM-d) δ: 8.18 (s, 1H), 7.93 (s, 1H), 7.64-7.72 (m, 6H), 7.54-7.61 (m, 1H), 7.32-7.43 (m, 3H), 6.82-6.92 (m, 1H), 5.69 (dd, J=10.3, 5.1 Hz, 1H), 3.66 (q, J=5.9 Hz, 2H), 2.88-3.09 (m, 1H), 2.64 (br t, J=5.7 Hz, 2H), 2.46-2.60 (m, 1H), 2.07-2.21 (m, 2H). m/z (MH+): 564.2.

Example 75—Compound #44

3-[[4-[4,4,4-Trifluoro-1-[5-[2-methyl-4-(trifluoromethyl)phenyl]indazol-1-yl]butyl]benzoyl]amino]propanoic Acid

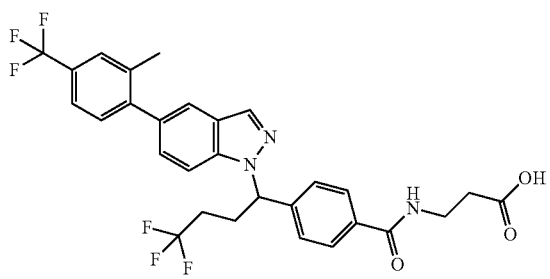 [SMILES: Cc1cc(C(F)(F)F)ccc1-c1ccc2c(cnn2C(CCC(F)(F)F)c2ccc(C(=O)NCCC(=O)O)cc2)c1]

¹H NMR (CHLOROFORM-d) δ: 8.15 (s, 1H), 7.62-7.74 (m, 3H), 7.53 (s, 1H), 7.48 (br d, J=8.1 Hz, 1H), 7.37 (br d, J=8.3 Hz, 3H), 7.30 (br dd, J=13.2, 8.3 Hz, 2H), 6.83-6.97 (m, 1H), 5.60-5.80 (m, 1H), 3.67 (q, J=5.5 Hz, 2H), 2.92-3.10 (m, 1H), 2.66 (br t, J=5.5 Hz, 2H), 2.49-2.61 (m, 1H), 2.29 (s, 3H), 2.08-2.23 (m, 2H). m/z (MH+): 578.2.

Example 76—Compound #11

3-[[4-[1-[5-(Benzofuran-2-yl)indazol-1-yl]-4,4,4-trifluoro-butyl]benzoyl]amino]propanoic Acid

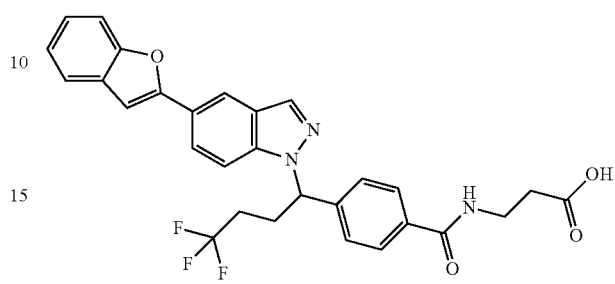

¹H NMR (CHLOROFORM-d) δ: 8.24 (s, 1H), 8.15 (s, 1H), 7.78 (d, J=8.8 Hz, 1H), 7.65 (br d, J=8.1 Hz, 2H), 7.54 (dd, J=21.2, 7.5 Hz, 2H), 7.19-7.36 (m, 5H), 6.96 (s, 1H), 6.82-6.90 (m, 1H), 5.63 (br dd, J=10.0, 4.9 Hz, 1H), 3.63 (br d, J=5.4 Hz, 2H), 2.89-3.03 (m, 1H), 2.61 (br s, 2H), 2.50 (br d, J=7.6 Hz, 1H), 2.06-2.20 (m, 2H). m/z (MH+):536.2.

Example 77—Compound #115

3-[[4-[1-[5-(Benzothiophen-2-yl)indazol-1-yl]-4,4,4-trifluoro-butyl]benzoyl]amino]propanoic Acid

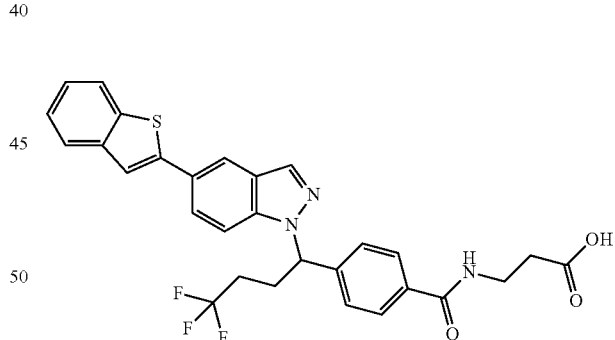

¹H NMR (CHLOROFORM-d) δ: 8.17 (s, 1H), 8.05 (s, 1H), 7.81 (br s, 1H), 7.74-7.79 (m, 1H), 7.70 (br d, J=8.1 Hz, 3H), 7.50 (s, 1H), 7.30-7.39 (m, 5H), 6.66-6.80 (m, 1H), 5.68 (br s, 1H), 4.12 (q, J=7.0 Hz, 2H), 3.70 (br d, J=6.1 Hz, 2H), 3.00 (br s, 1H), 2.69 (br s, 2H), 2.55 (br d, J=7.3 Hz, 1H), 2.16 (br d, J=8.8 Hz, 2H). m/z (MH+): 552.2.

Example 78—Compound #76

3-[[4-[4,4,4-Trifluoro-1-[5-[4-(trifluoromethoxy)phenyl]indazol-1-yl]butyl]benzoyl]amino]propanoic Acid

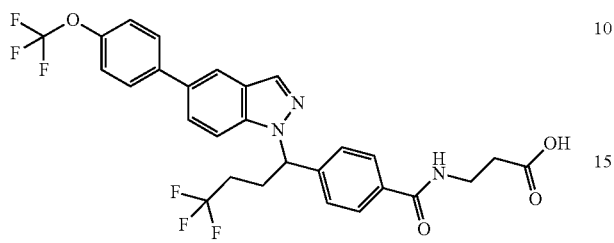

$^1$H NMR (CHLOROFORM-d) δ: 7.87 (s, 1H), 7.67 (d, J=8.1 Hz, 2H), 7.50-7.60 (m, 3H), 7.31-7.40 (m, 3H), 7.25-7.30 (m, 2H), 6.87 (br t, J=6.0 Hz, 1H), 5.68 (dd, J=10.1, 5.0 Hz, 1H), 3.65 (q, J=5.8 Hz, 2H), 2.92-3.07 (m, 1H), 2.63 (br t, J=5.6 Hz, 2H), 2.46-2.59 (m, 1H), 2.07-2.21 (m, 2H). m/z (MH+): 580.2.

Example 79—Compound #45

3-[[4-[1-[5-(3,5-Dichlorophenyl)indazol-1-yl]-4,4,4-trifluoro-butyl]benzoyl]amino]propanoic Acid

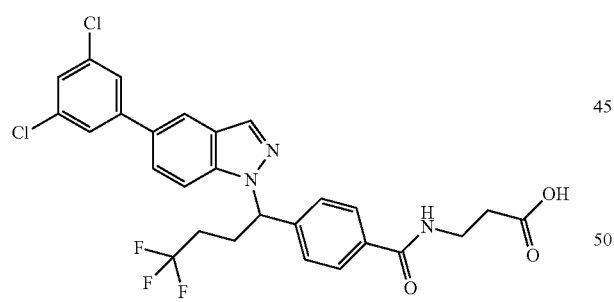

$^1$H NMR (CHLOROFORM-d) δ: 8.16 (s, 1H), 7.87 (d, J=1.0 Hz, 1H), 7.68 (d, J=8.3 Hz, 2H), 7.46-7.52 (m, 1H), 7.43 (d, J=1.7 Hz, 2H), 7.30-7.40 (m, 4H), 6.89 (br t, J=6.0 Hz, 1H), 5.68 (dd, J=10.1, 5.3 Hz, 1H), 3.66 (q, J=5.9 Hz, 2H), 2.89-3.05 (m, 1H), 2.64 (br t, J=5.6 Hz, 2H), 2.47-2.59 (m, 1H), 2.08-2.22 (m, 2H). m/z (MH+): 564.0.

Example 80—Compound #50

3-[[4-[4,4,4-Trifluoro-1-[5-[2-methyl-4-(trifluoromethyl)phenyl]indazol-2-yl]butyl]benzoyl]amino]propanoic Acid

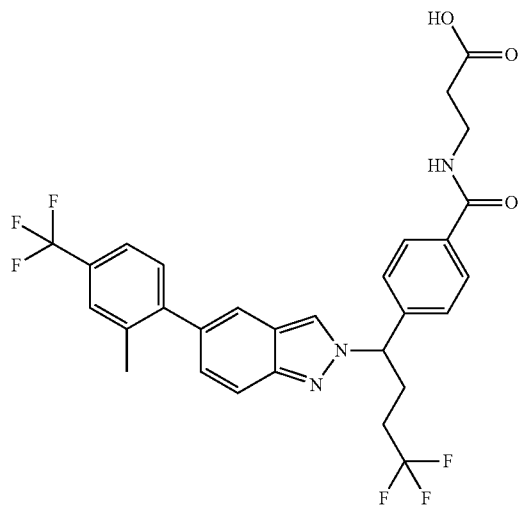 [SMILES: Cc1cc(C(F)(F)F)ccc1-c1ccc2nn(C(CCC(F)(F)F)c3ccc(C(=O)NCCC(=O)O)cc3)cc2c1]

$^1$H NMR (CHLOROFORM-d) δ: 8.03 (s, 1H), 7.72-7.82 (m, 3H), 7.53 (s, 2H), 7.46 (br d, J=8.3 Hz, 3H), 7.34 (d, J=7.8 Hz, 1H), 7.26-7.29 (m, 1H), 7.02-7.13 (m, 1H), 6.94-7.01 (m, 1H), 5.73 (dd, J=9.5, 5.9 Hz, 1H), 3.70 (q, J=5.9 Hz, 2H), 2.87-3.02 (m, 1H), 2.68 (t, J=5.7 Hz, 2H), 2.52-2.64 (m, 1H), 2.32 (s, 3H), 2.07-2.18 (m, 2H). m/z (MH+): 578.2.

Example 81—Compound #16

3-[[4-[1-[5-[2-Chloro-4-(trifluoromethyl)phenyl]indazol-2-yl]-4,4,4-trifluoro-butyl]benzoyl]amino]propanoic Acid

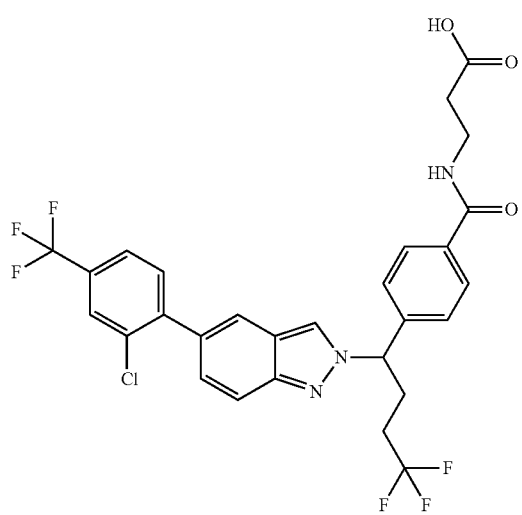 [SMILES: O=C(O)CCNC(=O)c1ccc(C(CCC(F)(F)F)n2cc3cc(-c4ccc(C(F)(F)F)cc4Cl)ccc3n2)cc1]

$^1$H NMR (CHLOROFORM-d) δ: 8.05 (s, 1H), 7.80 (d, J=8.8 Hz, 1H), 7.74 (d, J=8.1 Hz, 3H), 7.67 (s, 1H), 7.56 (s,

1H), 7.42-7.51 (m, 3H), 7.38 (dd, J=8.9, 1.6 Hz, 1H), 6.97 (t, J=6.0 Hz, 1H), 5.71 (dd, J=9.8, 5.9 Hz, 1H), 5.51-5.67 (m, 1H), 3.70 (q, J=6.0 Hz, 2H), 2.84-3.02 (m, 1H), 2.68 (t, J=5.7 Hz, 2H), 2.49-2.62 (m, 1H), 2.04-2.19 (m, 2H). m/z (MH+): 598.0.

Example 82—Compound #122

3-[[4-[1-[5-(Benzothiophen-2-yl)indazol-2-yl]-4,4,4-trifluoro-butyl]benzoyl]amino]propanoic Acid

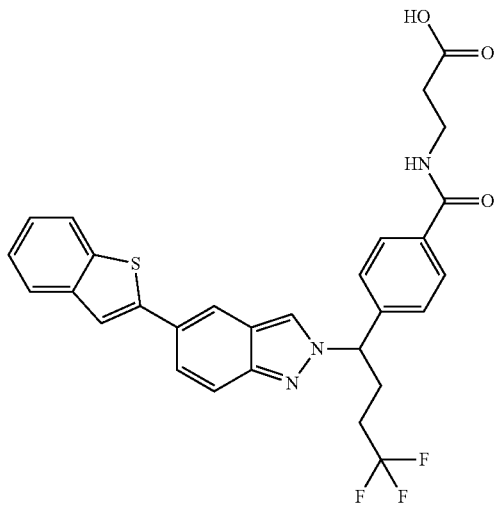 [SMILES: O=C(O)CCNC(=O)c1ccc(C(CCC(F)(F)F)n2cc3cc(-c4cc5ccccc5s4)ccc3n2)cc1]

$^1$H NMR (METHANOL-d$_4$) δ: 8.45 (s, 1H), 8.05 (s, 1H), 7.75-7.86 (m, 5H), 7.70-7.75 (m, 1H), 7.66 (s, 1H), 7.54 (d, J=8.3 Hz, 2H), 7.25-7.38 (m, 2H), 5.87 (dd, J=9.8, 5.9 Hz, 1H), 3.60 (t, J=7.0 Hz, 2H), 2.85-3.00 (m, 1H), 2.53-2.66 (m, 3H), 2.16-2.34 (m, 1H), 1.97-2.12 (m, 1H). m/z (MH+): 552.2.

Example 83—Compound #25

3-[[4-[3-Methyl-1-[6-methyl-5-[4-(trifluoromethyl)phenyl]indazol-1-yl]butyl]benzoyl]amino]propanoic Acid

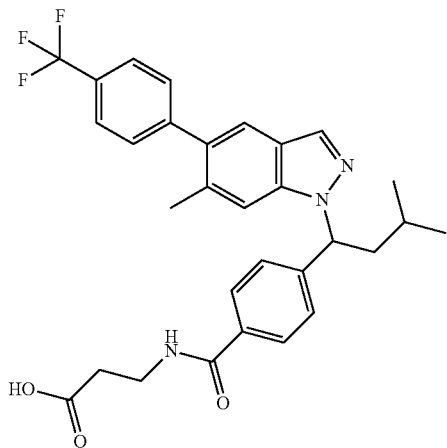 [SMILES: Cc1cc2c(cnn2C(CC(C)C)c2ccc(C(=O)NCCC(=O)O)cc2)cc1-c1ccc(C(F)(F)F)cc1]

$^1$H NMR (CHLOROFORM-d) δ: 8.07 (s, 1H), 7.67 (br t, J=8.7 Hz, 4H), 7.52 (s, 1H), 7.39 (br dd, J=16.8, 7.9 Hz, 4H), 6.99 (br t, J=5.7 Hz, 1H), 5.72 (br dd, J=9.8, 5.4 Hz, 1H), 3.66 (br d, J=5.6 Hz, 2H), 2.60-2.72 (m, 3H), 2.30 (s, 3H), 2.01-2.07 (m, 1H), 1.39-1.54 (m, 1H), 0.97 (br t, J=7.5 Hz, 6H). m/z (MH+): 538.2.

Example 84—Compound #134

3-[[4-[3-Methyl-1-[6-methyl-5-[4-(trifluoromethyl)phenyl]indazol-2-yl]butyl]benzoyl]amino]propanoic Acid

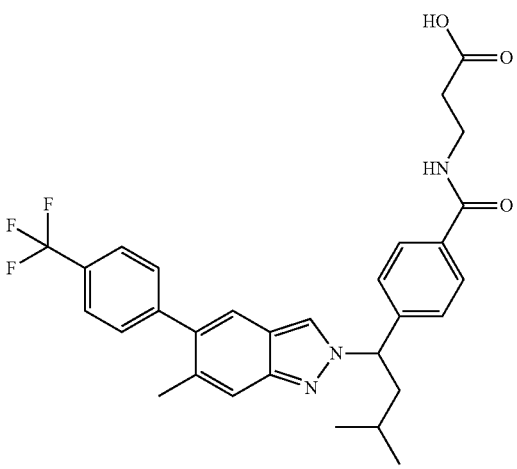

$^1$H NMR (CHLOROFORM-d) δ: 8.00 (s, 1H), 7.72 (d, J=8.3 Hz, 2H), 7.66 (d, J=8.3 Hz, 2H), 7.59 (s, 1H), 7.39-7.47 (m, 5H), 7.06 (br t, J=5.9 Hz, 1H), 5.81 (dd, J=9.0, 6.6 Hz, 1H), 3.69 (q, J=5.8 Hz, 2H), 2.67 (t, J=5.7 Hz, 2H), 2.44-2.54 (m, 1H), 2.26 (s, 3H), 2.09-2.15 (m, 1H), 1.38-1.50 (m, 1H), 0.97 (dd, J=15.9, 6.6 Hz, 6H). m/z (MH+): 538.2.

Example 85—Compound #93

3-[[4-[3-Methyl-1-[6-methyl-5-[2-methyl-4-(trifluoromethyl)phenyl]indazol-1-yl]butyl]benzoyl]amino]propanoic Acid

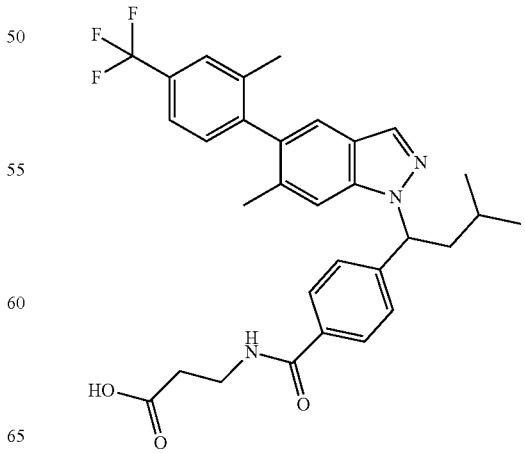

¹H NMR (CHLOROFORM-d) δ: 9.58-10.35 (m, 1H), 8.06 (s, 1H), 7.70 (dd, J=8.1, 5.6 Hz, 2H), 7.36-7.54 (m, 5H), 7.15-7.36 (m, 2H), 6.99 (br d, J=2.7 Hz, 1H), 5.72 (dd, J=9.7, 5.7 Hz, 1H), 3.62-3.74 (m, 2H), 2.62-2.74 (m, 3H), 2.04-2.10 (m, 7H), 1.42-1.58 (m, 1H), 0.94-1.04 (m, 6H). m/z (MH+): 552.15.

Example 86—Compound #174

3-[[4-[1-[5-(Benzothiophen-2-yl)-6-methyl-indazol-1-yl]-3-methyl-butyl]benzoyl]amino]propanoic Acid

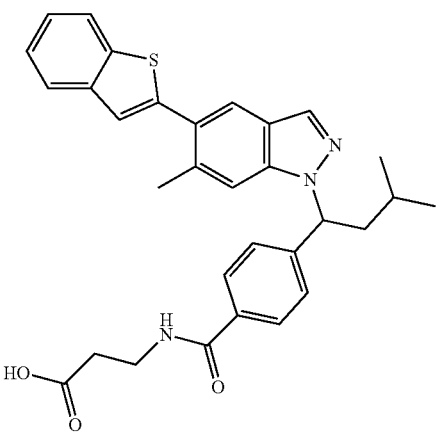 [SMILES: Cc1cc2c(cnn2C(CC(C)C)c2ccc(C(=O)NCCC(=O)O)cc2)cc1-c1cc2ccccc2s1]

¹H NMR (CHLOROFORM-d) δ: 8.07 (s, 1H), 7.75-7.84 (m, 3H), 7.68 (d, J=8.3 Hz, 2H), 7.26-7.40 (m, 6H), 7.19 (s, 1H), 6.93 (br t, J=6.0 Hz, 1H), 5.71 (dd, J=10.0, 5.4 Hz, 1H), 3.67 (q, J=5.9 Hz, 2H), 2.62-2.73 (m, 3H), 2.51 (s, 3H), 2.01-2.07 (m, 1H), 1.43-1.52 (m, 1H), 0.91-1.01 (m, 6H). m/z (MH+): 526.0.

Example 87—Compound #158

3-[[4-[1-[5-(5-Fluorobenzothiophen-2-yl)-6-methyl-indazol-1-yl]-3-methyl-butyl]benzoyl]amino]propanoic Acid

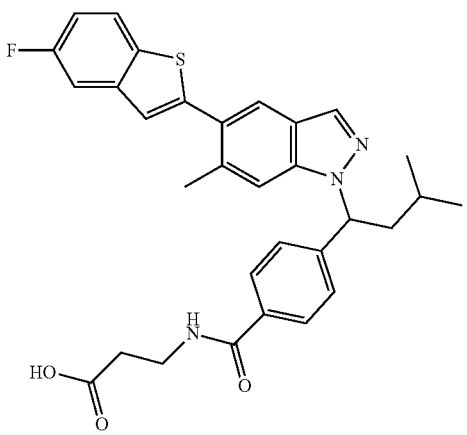 [SMILES: Cc1cc2c(cnn2C(CC(C)C)c2ccc(C(=O)NCCC(=O)O)cc2)cc1-c1cc2cc(F)ccc2s1]

¹H NMR (CHLOROFORM-d) δ: 8.07 (s, 1H), 7.79 (s, 1H), 7.71-7.77 (m, 1H), 7.68 (d, J=8.3 Hz, 2H), 7.43 (dd, J=9.5, 2.4 Hz, 1H), 7.37 (d, J=8.3 Hz, 2H), 7.27 (s, 1H), 7.15 (s, 1H), 7.05-7.11 (m, 1H), 6.90 (t, J=6.0 Hz, 1H), 5.71 (dd, J=9.9, 5.5 Hz, 1H), 3.63-3.72 (m, 2H), 2.63-2.68 (m, 3H), 2.48-2.54 (m, 3H), 2.02-2.06 (m, 1H), 1.43-1.51 (m, 1H), 0.95-1.02 (m, 6H). m/z (MH+): 544.2.

Example 88—Compound #94

3-[[4-[1-[5-[2-Chloro-4-(trifluoromethyl)phenyl]-6-methyl-indazol-1-yl]-3-methyl-butyl]benzoyl]amino]propanoic Acid

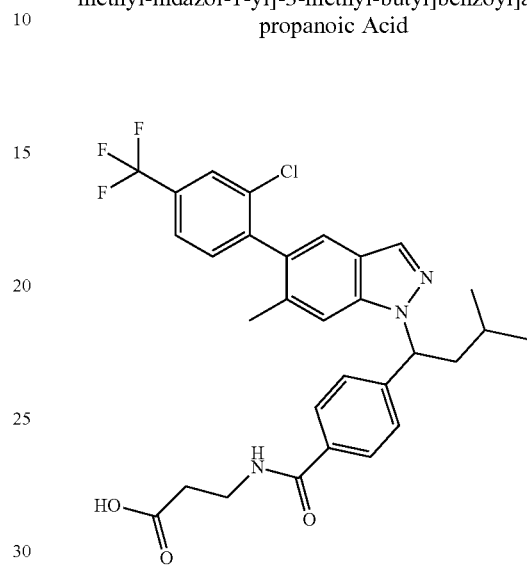

¹H NMR (CHLOROFORM-d) δ: 8.06 (s, 1H), 7.72-7.76 (m, 1H), 7.65-7.72 (m, 2H), 7.53-7.61 (m, 1H), 7.31-7.48 (m, 4H), 7.25-7.29 (m, 1H), 6.86 (br s, 1H), 5.70 (br dd, J=8.9, 6.0 Hz, 1H), 3.68 (br d, J=5.4 Hz, 2H), 2.67 (br t, J=5.5 Hz, 2H), 2.60-2.72 (m, 1H), 2.18 (d, J=5.9 Hz, 3H), 2.06-2.12 (m, 1H), 1.42-1.57 (m, 1H), 0.94-1.03 (m, 6H). m/z (MH+): 572.10.

Example 89—Compound #95

3-[[4-[1-[5-[2-Chloro-4-(trifluoromethyl)phenyl]-6-methyl-indazol-2-yl]-3-methyl-butyl]benzoyl]amino]propanoic Acid

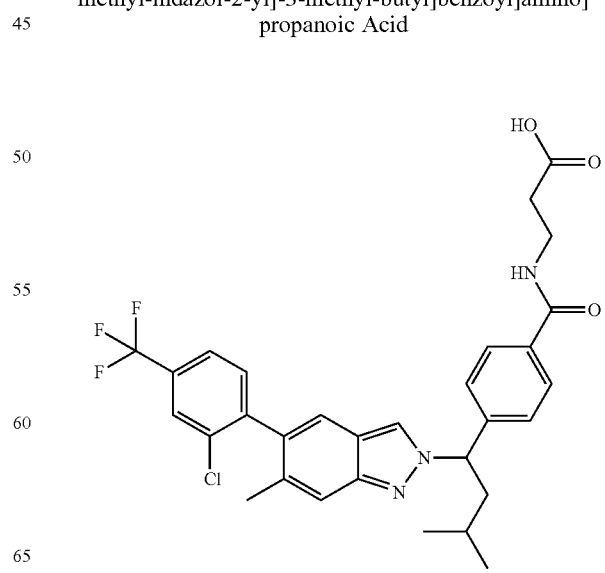

¹H NMR (CHLOROFORM-d) δ: 9.41-9.94 (m, 1H), 7.92-8.08 (m, 1H), 7.67-7.77 (m, 3H), 7.61 (s, 2H), 7.33-7.45 (m, 4H), 7.04-7.17 (m, 1H), 5.80 (br t, J=7.2 Hz, 1H), 3.69 (br d, J=5.1 Hz, 2H), 2.67 (br t, J=5.1 Hz, 2H), 2.48 (dt, J=13.6, 6.8 Hz, 1H), 2.14 (m, 4H), 1.43 (dt, J=13.0, 6.2 Hz, 1H), 0.97 (dd, J=14.4, 6.6 Hz, 6H). m/z (MH+): 572.10.

Example 90—Compound #54

3-[[4-[3-Methyl-1-[6-methyl-5-[2-methyl-4-(trifluoromethyl)phenyl]indazol-2-yl]butyl]benzoyl]amino]propanoic Acid

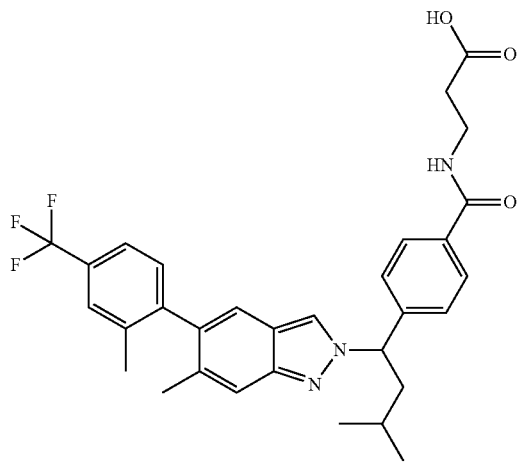

¹H NMR (CHLOROFORM-d) δ: 8.84-9.42 (m, 1H), 7.94-8.03 (m, 1H), 7.73 (br d, J=7.6 Hz, 2H), 7.59 (s, 1H), 7.52 (s, 1H), 7.40-7.49 (m, 3H), 7.32 (s, 1H), 7.22 (d, J=7.6 Hz, 1H), 7.12-7.19 (m, 1H), 5.69-5.91 (m, 1H), 3.69 (br d, J=4.4 Hz, 2H), 2.66 (br s, 2H), 2.44-2.56 (m, 1H), 2.05-2.15 (m, 7H), 1.40-1.49 (m, 1H), 0.97 (dd, J=14.9, 6.6 Hz, 6H). m/z (MH+): 552.15.

Example 91—Compound #261

3-[[4-[1-[6-Chloro-5-[2-methyl-4-(trifluoromethyl)phenyl]indazol-1-yl]-3-methyl-butyl]benzoyl]amino]propanoic Acid

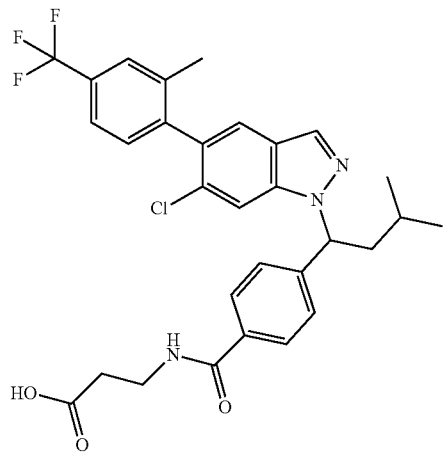 [SMILES: Cc1cc(C(F)(F)F)ccc1-c1cc2cnn(C(CC(C)C)c3ccc(C(=O)NCCC(=O)O)cc3)c2cc1Cl]

¹H NMR (CHLOROFORM-d) δ: 9.55 (br s, 1H), 8.09 (s, 1H), 7.67-7.76 (m, 2H), 7.36-7.57 (m, 6H), 7.19-7.30 (m, 1H), 6.95 (br s, 1H), 5.67 (dd, J=9.4, 5.7 Hz, 1H), 3.69 (br d, J=5.1 Hz, 2H), 2.60-2.73 (m, 3H), 2.08-2.20 (m, 4H), 1.40-1.58 (m, 1H), 0.88-1.04 (m, 6H). m/z (MH+): 572.10.

Example 92—Compound #30

3-[[4-[1-[6-Chloro-5-[2-methyl-4-(trifluoromethyl)phenyl]indazol-2-yl]-3-methyl-butyl]benzoyl]amino]propanoic Acid

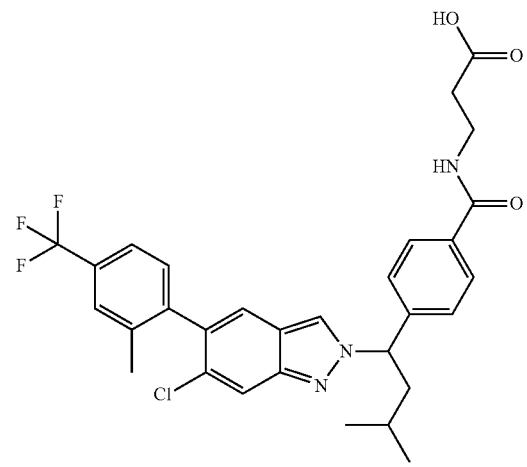 [SMILES: Cc1cc(C(F)(F)F)ccc1-c1cc2cn(C(CC(C)C)c3ccc(C(=O)NCCC(=O)O)cc3)nc2cc1Cl]

¹H NMR (CHLOROFORM-d) δ: 8.04 (br s, 1H), 7.87 (s, 1H), 7.74 (br d, J=7.6 Hz, 2H), 7.40-7.55 (m, 5H), 7.21-7.26 (m, 1H), 6.99-7.15 (m, 1H), 5.76 (br t, J=6.6 Hz, 1H), 3.69 (br d, J=4.2 Hz, 2H), 2.67 (br s, 2H), 2.45-2.57 (m, 1H), 2.10-2.20 (m, 4H), 1.36-1.50 (m, 1H), 0.98 (dd, J=14.4, 6.6 Hz, 6H). m/z (MH+): 572.10.

Example 93—Compound #33

3-[[5-[1-[6-Chloro-5-[2-chloro-4-(trifluoromethyl)phenyl]indazol-2-yl]-3-methyl-butyl]pyridine-2-carbonyl]amino]propanoic Acid

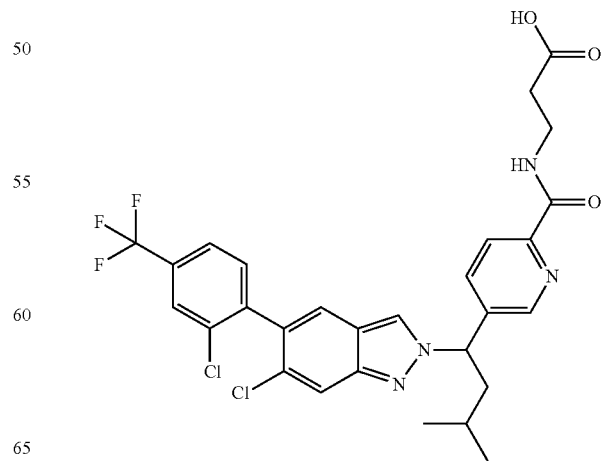

¹H NMR (CHLOROFORM-d) δ: 8.60 (t, J=1.8 Hz, 1H), 8.46 (t, J=6.2 Hz, 1H), 8.16 (d, J=8.1 Hz, 1H), 8.09 (dd, J=3.2, 1.0 Hz, 1H), 7.86-7.94 (m, 2H), 7.75 (s, 1H), 7.55-7.62 (m, 1H), 7.53 (s, 1H), 7.37-7.45 (m, 1H), 5.78 (br d, J=3.4 Hz, 1H), 3.75 (q, J=6.3 Hz, 2H), 2.71 (t, J=6.1 Hz, 2H), 2.59 (ddd, J=14.4, 9.1, 5.9 Hz, 1H), 2.11-2.19 (m, 1H), 1.37-1.48 (m, 1H), 0.95-1.08 (m, 6H). m/z (MH+): 593.0.

Example 94—Compound #140

3-[[5-[1-[6-Chloro-5-(4-chloro-2-methyl-phenyl)indazol-2-yl]-3-methyl-butyl]pyridine-2-carbonyl]amino]propanoic Acid

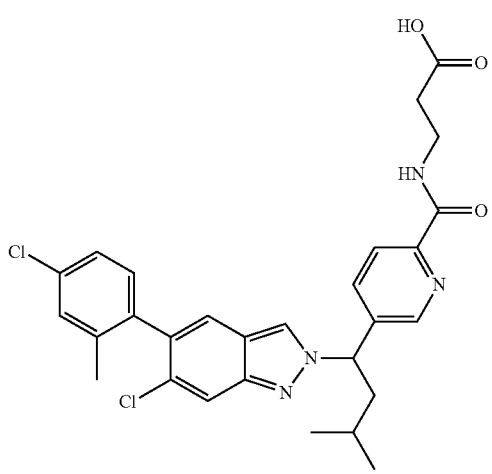 [SMILES: Cc1cc(Cl)ccc1-c1cc2cn(C(CC(C)C)c3ccc(C(=O)NCCC(=O)O)nc3)nc2cc1Cl]

¹H NMR (CHLOROFORM-d) δ: 8.60 (s, 1H), 8.46 (t, J=6.4 Hz, 1H), 8.16 (d, J=8.1 Hz, 1H), 8.04 (dd, J=2.4, 0.7 Hz, 1H), 7.90 (ddd, J=8.0, 5.4, 2.2 Hz, 1H), 7.85 (s, 1H), 7.45 (s, 1H), 7.20 (dt, J=8.1, 2.3 Hz, 2H), 7.03-7.10 (m, 1H), 5.78 (dt, J=9.4, 5.7 Hz, 1H), 3.75 (q, J=6.3 Hz, 2H), 2.71 (t, J=6.1 Hz, 2H), 2.58 (dddd, J=13.8, 9.7, 5.9, 3.7 Hz, 1H), 2.07-2.18 (m, 4H), 1.36-1.51 (m, 1H), 0.93-1.06 (m, 6H). m/z (MH+): 539.2.

Example 95—Compound #102

3-[[5-[1-[6-Chloro-5-(4-chloro-2-methyl-phenyl)indazol-1-yl]-3-methyl-butyl]pyridine-2-carbonyl]amino]propanoic Acid

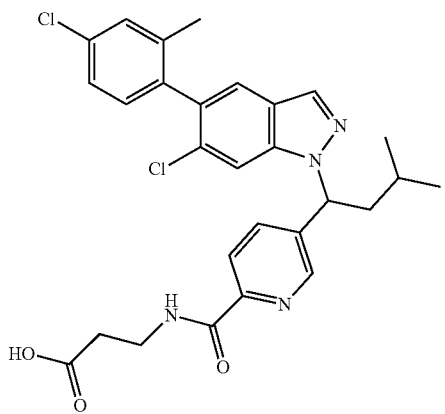 [SMILES: Cc1cc(Cl)ccc1-c1cc2cnn(C(CC(C)C)c3ccc(C(=O)NCCC(=O)O)nc3)c2cc1Cl]

¹H NMR (CHLOROFORM-d) δ: 9.52-10.58 (m, 1H), 8.54-8.64 (m, 1H), 8.45-8.52 (m, 1H), 8.05-8.17 (m, 2H), 7.81-7.93 (m, 1H), 7.50-7.58 (m, 2H), 7.16-7.31 (m, 2H), 7.00-7.13 (m, 1H), 5.57-5.85 (m, 1H), 3.74 (q, J=6.0 Hz, 2H), 2.65-2.75 (m, 3H), 2.07-2.14 (m, 4H), 1.41-1.58 (m, 1H), 0.99 (dt, J=8.6, 6.7 Hz, 6H). m/z (MH+): 541.2.

Example 96—Compound #176

3-[[5-[1-[6-Chloro-5-[2-methyl-4-(trifluoromethyl)phenyl]indazol-2-yl]-3-methyl-butyl]pyridine-2-carbonyl]amino]propanoic Acid

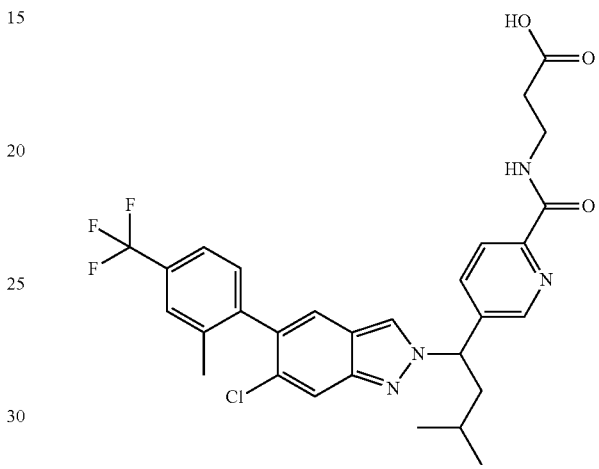

¹H NMR (CHLOROFORM-d) δ: 8.61 (br s, 1H), 8.49 (br t, J=5.9 Hz, 1H), 8.16 (br d, J=8.1 Hz, 1H), 8.07 (d, J=2.4 Hz, 1H), 7.83-7.95 (m, 2H), 7.42-7.55 (m, 3H), 7.25-7.29 (m, 1H), 5.68-5.89 (m, 3H), 3.75 (q, J=5.9 Hz, 2H), 2.71 (t, J=5.9 Hz, 2H), 2.52-2.65 (m, 1H), 2.17 (d, J=7.6 Hz, 3H), 1.43 (dsxt, J=13.2, 6.5 Hz, 1H), 0.93-1.07 (m, 6H). m/z (MH+): 573.2.

Example 97—Compound #146

3-[[5-[1-[6-Chloro-5-[2-methyl-4-(trifluoromethyl)phenyl]indazol-1-yl]-3-methyl-butyl]pyridine-2-carbonyl]amino]propanoic Acid

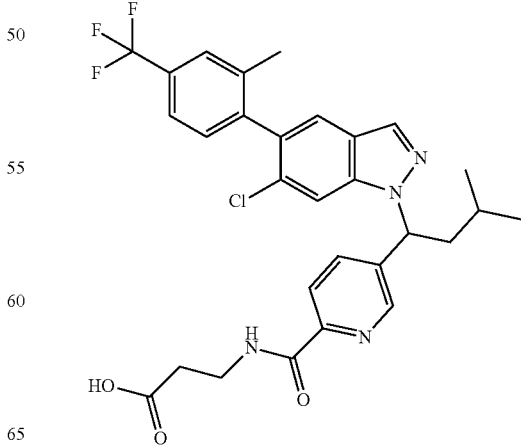

¹H NMR (CHLOROFORM-d) δ: 8.81 (br s, 1H), 8.49-8.65 (m, 2H), 8.08-8.20 (m, 2H), 7.90 (ddd, J=20.9, 8.2, 1.7 Hz, 1H), 7.43-7.60 (m, 4H), 7.19-7.31 (m, 1H), 5.63-5.83 (m, 1H), 3.75 (q, J=6.1 Hz, 2H), 2.64-2.81 (m, 3H), 2.05-2.21 (m, 4H), 1.48 (br dd, J=13.3, 6.7 Hz, 1H), 0.91-1.06 (m, 6H). m/z (MH+): 573.2.

Example 98—Compound #253

3-[[4-[(1S)-3-Methyl-1-[6-methyl-5-[2-methyl-4-(trifluoromethyl)phenyl]indazol-1-yl]butyl]benzoyl]amino]propanoic Acid

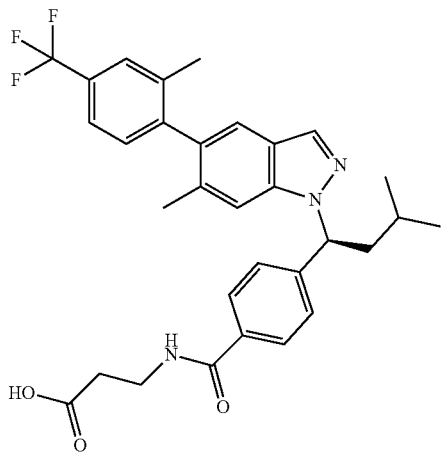 [SMILES: Cc1cc(C(F)(F)F)ccc1-c1cc2cnn([C@@H](CC(C)C)c3ccc(C(=O)NCCC(=O)O)cc3)c2cc1C]

Step A: Ethyl 4-(3-methylbutanoyl)benzoate 4-(Ethoxycarbonyl)phenyl-zinc iodide (100 mL of a 0.5 M solution in THF, 50 mmol) was added slowly to a stirred solution of dichlorbis(triphenylphosphine)palladium (II) (1403 mg) in THF (50 mL) at 0° C. under argon. After 20 min, 3-methylbutanoyl chloride (6.03 g, 50 mmol) was added dropwise and the resulting mixture was stirred at 0° C. for 2 hours, then poured into 1N HCl and extracted with EtOAc three times. The combined extracts were washed with aq. NaHCO₃, brine, dried (Na₂SO₄), filtered and concentrated under reduced pressure. The resulting residue was purified by flash column chromatography on silica gel (EtOAc/heptane: 0>>>5%) to yield a colorless oil initially, which upon standing became a white solid. ¹H NMR (CHLOROFORM-d) δ: 8.10-8.14 (m, 2H), 7.99 (d, J=8.6 Hz, 2H), 4.41 (q, J=7.2 Hz, 2H), 2.86 (d, J=6.8 Hz, 2H), 2.30 (dquin, J=13.4, 6.7 Hz, 1H), 1.42 (t, J=7.2 Hz, 3H), 1.01 (d, J=6.6 Hz, 6H).

Step B: (R)-Ethyl 4-(1-hydroxy-3-methylbutyl)benzoate

A solution of (S)—CH₃—CBS (743 mg, 2.68 mmol) in anhydrous THF (20 ml), cooled to 0° C. was treated with borane dimethylsulfide (16.8 ml, 2M in THF) and the resulting mixture was stirred for 25 min at 0° C. A solution of ethyl 4-(3-methylbutanoyl)benzoate (6.28 g, 26.8 mmol) in THF (20 ml) was added slowly to the reaction mixture, which was kept stirring for 2.5 hours, allowing the resulting mixture to warm to room temperature. The resulting mixture was then quenched with MeCOH and allowed to stir for 25 min and the solvent was removed under reduced pressure. The residue was diluted with EtOAc, washed with 1N HCl and brine, dried over Na₂SO₄ and concentrated. The resulting residue was purified by flash column chromatography on silica gel (EtOAc/heptane: 0>>>20%) to yield a colorless. ¹H NMR (CHLOROFORM-d) δ: 8.02 (d, J=7.8 Hz, 2H), 7.41 (d, J=8.1 Hz, 2H), 4.81 (br s, 1H), 4.37 (q, J=7.1 Hz, 2H), 1.93 (d, J=3.4 Hz, 1H), 1.72 (br s, 2H), 1.48 (s, 1H), 1.39 (t, J=7.1 Hz, 3H), 0.96 (d, J=6.1 Hz, 6H).

Step C: (R)-Ethyl 4-(3-methyl-1-((methylsulfonyl)oxy)butyl)benzoate

To a dichloromethane solution (70 ml) of (R)-ethyl 4-(1-hydroxy-3-methylbutyl)benzoate (4.46 g, 18.9 mmol) and trimethylamine (3.94 ml, 28.31 mmol) at −10° C. was added mesyl chloride (2.05 ml, 26.4 mmol) dropwise. The resulting mixture was stirred at −10° C. for 4 hours, partitioned between 0.1 N HCl and DCM. The organic layers were combined, washed with aq. NaHCO₃, brine, dried over Na₂SO₄, filtered and the filtrate was concentrated under reduced pressure to yield a light orange gel, which crystalized with the help of heptane, to a white solid (96.43% ee).

Step D: (S)-Ethyl 4-(3-methyl-1-(6-methyl-5-(2-methyl-4-(trifluoromethyl)phenyl)-1H-indazol-1-yl)butyl)benzoate and (S)-Ethyl 4-(3-methyl-1-(6-methyl-5-(2-methyl-4-(trifluoromethyl)phenyl)-2H-indazol-2-yl)butyl)benzoate To a mixture of 5-(2-chloro-4-(trifluoromethyl)phenyl)-6-methyl-1H-indazole (4.10 g, 13.19 mmol) and sodium hydride (527.7 mg, 13.19 mmol) was added 15 ml of anhydrous DMF under argon at room temperature and the resulting mixture was kept stirring for 40 min at room temperature under argon. The resulting mixture was cooled to 0° C. and (R)-ethyl 4-(3-methyl-1-((methylsulfonyl)oxy)butyl)benzoate (4.56 g, 14.5 mmol) in 15 ml of DMF was added dropwise. Upon the completion of the addition, the reaction mixture was kept stirring at room temperature under argon for additional 3 hours, quenched with 0.1 N HCl, extracted with ethyl acetate. The combined extracts were washed with brine, dried over Na₂SO₄ and the solvent was evaporated under reduced pressure. The resulting residue was purified by flash column chromatography on silica gel (EtOAc/heptane: 0>>>5%>>>15%) to yield two isomers, both of which were white foam solids.

The first isomer was (S)-ethyl 4-(3-methyl-1-(6-methyl-5-(2-methyl-4-(trifluoromethyl)phenyl)-1H-indazol-1-yl)butyl)benzoate (The N-1 substituted compound, 3.12 g, yield: 46.5% with >98% ee). ¹H NMR (CHLOROFORM-d) δ: 8.02-8.06 (m, 1H), 7.94-8.01 (m, 2H), 7.40 (s, 5H), 7.14-7.25 (m, 2H), 5.71 (dd, J=9.5, 5.9 Hz, 1H), 4.34 (q, J=7.1 Hz, 2H), 2.64-2.78 (m, 1H), 2.03-2.14 (m, 7H), 1.45-1.55 (m, 1H), 1.36 (t, J=7.1 Hz, 3H), 0.96-1.05 (m, 6H). m/z (MH+): 509.2. The second isomer was (S)-ethyl 4-(3-methyl-1-(6-methyl-5-(2-methyl-4-(trifluoromethyl)phenyl)-2H-indazol-2-yl)butyl)benzoate (the N-2 substituted compound, 1.83 g, yield: 27.3% with 99.2% ee). $^1$H NMR (CHLOROFORM-d) δ: 7.98-8.04 (m, 2H), 7.93-7.97 (m, 1H), 7.59-7.65 (m, 1H), 7.50-7.54 (m, 1H), 7.42-7.50 (m, 3H), 7.32 (s, 1H), 7.24 (m, 1H), 5.65-5.78 (m, 1H), 4.36 (q, J=7.3 Hz, 2H), 2.50-2.62 (m, 1H), 2.05-2.18 (m, 7H), 1.47 (br dd, J=12.7, 5.9 Hz, 1H), 1.37 (t, J=7.1 Hz, 3H), 1.00 (dd, J=14.1, 6.5 Hz, 6H). m/z (MH+): 509.2.

Step E: (S)-4-(3-Methyl-1-(6-methyl-5-(2-methyl-4-(trifluoromethyl)phenyl)-1H-indazol-1-yl)butyl)benzoic Acid To a solution of (S)-ethyl 4-(3-methyl-1-(6-methyl-5-(2-methyl-4-(trifluoromethyl)phenyl)-1H-indazol-1-yl)butyl)benzoate (3.12 g, 6.14 mmol) in THF (40 ml)/MeOH (30 ml) was added NaOH (12.3 ml, 3N) and the resulting mixture was stirred at room temperature for 3 hours. The solvents were removed under reduced pressure and the residue was acidified with 1N HCl, extracted with ethyl acetate, dried over Na$_2$SO$_4$, filtered and concentrated to yield a white solid. m/z (MH+): 481.2.

Step F: (S)-Methyl 3-(4-(3-methyl-1-(6-methyl-5-(2-methyl-4-(trifluoromethyl)phenyl)-1H-indazol-1-yl)butyl)benzamido)propanoate To a mixture of (S)-4-(3-methyl-1-(6-methyl-5-(2-methyl-4-(trifluoromethyl)phenyl)-1H-indazol-1-yl)butyl)benzoic acid (2.94 g, 6.12 mmol), methyl 3-aminopropanoate (1.11 g, 7.95 mmol), EDC (1.52 g, 7.95 mmol) and HOBt (937 mg, 6.12 mmol) in 35 ml of dichloromethane was added diisopropyl ethylamine (3.20 ml, 18.4 mmol) and the reaction mixture was stirred at room temperature for 48 hours. The resulting mixture was diluted with 1N HCl, extracted with ethyl acetate. The combined organic layer was washed with brine, dried over Na$_2$SO$_4$, filtered and the resulting residue was purified by flash column chromatography on silica gel (EtOAc/heptane: 0>>>10%>>>40%) to yield a white foam solid (99.1% ee). $^1$H NMR (CHLOROFORM-d) δ: 8.03 (s, 1H), 7.70 (t, J=6.7 Hz, 2H), 7.35-7.57 (m, 5H), 7.16-7.25 (m, 2H), 6.68-6.86 (m, 1H), 5.59-5.79 (m, 1H), 3.66-3.75 (m, 5H), 2.65-2.74 (m, 1H), 2.63 (t, J=5.7 Hz, 2H), 2.03-2.16 (m, 7H), 1.45-1.57 (m, 1H), 0.95-1.04 (m, 6H). m/z (MH+): 567.6.

Step G: 3-[[4-[(1S)-3-Methyl-1-[6-methyl-5-[2-methyl-4-(trifluoromethyl)phenyl]indazol-1-yl]butyl]benzoyl]amino]propanoic Acid To a solution of (S)-Methyl 3-(4-(3-methyl-1-(6-methyl-5-(2-methyl-4-(trifluoromethyl)phenyl)-1H-indazol-1-yl)butyl)benzamido)propanoate (2.95 g, 5.22 mmol) in 18 ml of THF/MeOH (2:1 v/v) was added 12 ml of 3N NaOH and the mixture was stirred at room temperature for 4 hours. The solvents were removed under reduced pressure and the residue was purified by flash column chromatography on silica gel to yield the title compound as a white solid.

$^1$H NMR (CHLOROFORM-d) δ: 8.05 (s, 1H), 7.64-7.74 (m, 2H), 7.35-7.55 (m, 5H), 7.15-7.30 (m, 2H), 6.99 (br s, 1H), 5.71 (br dd, J=9.4, 5.7 Hz, 1H), 3.67 (br d, J=5.6 Hz, 2H), 2.59-2.71 (m, 3H), 2.01-2.14 (m, 7H), 1.49 (td, J=13.0, 6.5 Hz, 1H), 0.89-1.03 (m, 6H). m/z (MH+): 552.4.

The following compounds (as shown in Examples 99-100 below) was similarly prepared according to the procedure described in Examples 98, selecting and substituting a suitably substituted indazole starting material.

Example 99—Compound #248

3-[[4-[(1S)-3-Methyl-1-[6-methyl-5-[2-methyl-4-(trifluoromethyl)phenyl]indazol-2-yl]butyl]benzoyl]amino]propanoic Acid

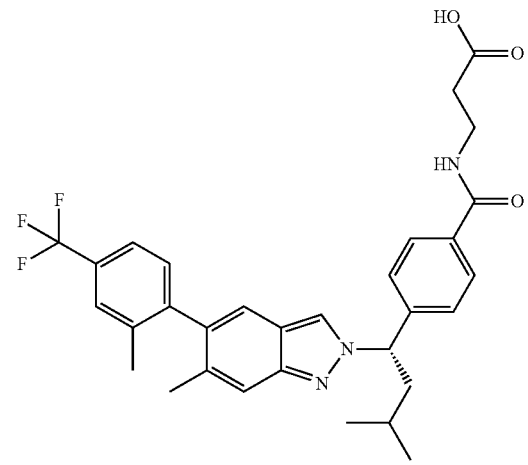 [SMILES: Cc1cc(C(F)(F)F)ccc1-c1cc2cn([C@@H](CC(C)C)c3ccc(C(=O)NCCC(=O)O)cc3)nc2cc1C]

$^1$H NMR (CHLOROFORM-d) δ: 7.98 (d, J=4.9 Hz, 1H), 7.73 (d, J=7.8 Hz, 2H), 7.59 (s, 1H), 7.51 (s, 1H), 7.40-7.49 (m, 3H), 7.32 (s, 1H), 7.21 (d, J=7.8 Hz, 1H), 7.15 (br t, J=5.1 Hz, 1H), 5.83 (br s, 1H), 3.61-3.77 (m, 2H), 2.66 (br t, J=5.6 Hz, 2H), 2.44-2.63 (m, 1H), 2.07 (d, J=17.1 Hz, 7H), 1.44 (dquin, J=13.2, 6.5 Hz, 1H), 0.97 (dd, J=15.0, 6.5 Hz, 6H). m/z (MH+): 552.40.

Example 100—Compound #241

(S)-3-(4-(1-(5-(2-Chloro-4-(trifluoromethyl)phenyl)-4-methyl-1H-indazol-1-yl)-3-methylbutyl)benzamido)propanoic Acid

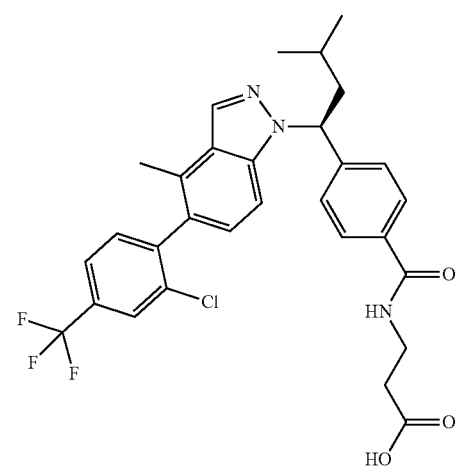 [SMILES: Cc1c(-c2ccc(C(F)(F)F)cc2Cl)ccc2c1cnn2[C@@H](CC(C)C)c1ccc(C(=O)NCCC(=O)O)cc1]

¹H NMR (METHANOL-d₄) δ: 8.24 (s, 1H), 7.84 (d, J=4.6 Hz, 1H), 7.63-7.77 (m, 3H), 7.40-7.56 (m, 4H), 7.14 (dd, J=8.7, 3.5 Hz, 1H), 5.93 (dd, J=10.3, 5.1 Hz, 1H), 3.54-3.66 (m, 2H), 2.66-2.78 (m, 1H), 2.60 (t, J=7.0 Hz, 2H), 2.35 (s, 3H), 1.98-2.13 (m, 1H), 1.35-1.55 (m, 1H), 0.98 (dt, J=14.8, 7.3 Hz, 6H). m/z (MH+): 571.80.

Example 101—Compound #85

3-[[4-[(1R)-1-[5-[2-Chloro-4-(trifluoromethyl)phenyl]indazol-1-yl]-3-methyl-butyl]benzoyl]amino]propanoic Acid

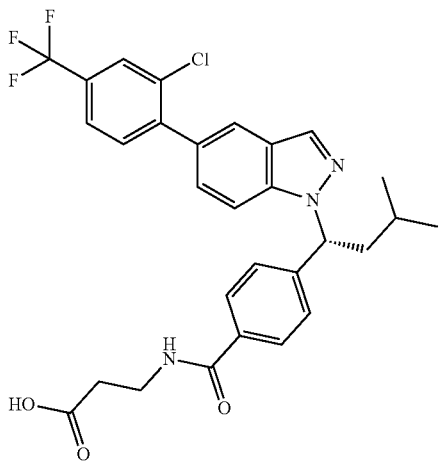 [SMILES: CC(C)C[C@H](c1ccc(C(=O)NCCC(=O)O)cc1)n1ncc2cc(-c3ccc(C(F)(F)F)cc3Cl)ccc21]

Step A: Methyl 4-(1-hydroxy-3-methylbutyl)benzoate

To a solution of methyl 4-formylbenzoate (9.32 g, 56.8 mmol) in 40 ml of anhydrous THF was added isobutylmagnesium bromide (2N, 31.2 ml) at 0° C. under nitrogen and the mixture was stirred for 2 hours. The resulting mixture was quenched with aqueous NH₄Cl, extracted with ethyl acetate. The organic layer was washed with brine, dried over Na₂SO₄, filtered, and concentrated. The resulting residue was purified by flash column chromatography on silica gel (EtOAc/heptane: 0>>>20%) to yield a colorless oil.

Step B: Methyl 4-(3-methylbutanoyl)benzoate

To a solution of methyl 4-(1-hydroxy-3-methylbutyl)benzoate (4.50 g, 20.24 mmol) in dichloromethane (100 ml) was added PCC (4.80 g, 22.27 mmol) in portions. The mixture was allowed to stir at room temperature for 3 hours and the reaction was monitored by TLC. Upon complete conversion, the reaction mixture was passed through a pad of CELITE. The filtrate was concentrated and the residue was purified by flash column chromatography on silica gel (EtOAc/heptane: 0>>>10%) to yield a white solid. ¹H NMR (CHLOROFORM-d) δ: 8.12 (d, J=8.6 Hz, 2H), 8.00 (d, J=8.3 Hz, 2H), 3.95 (s, 3H), 2.86 (d, J=6.8 Hz, 2H), 2.20-2.44 (m, 1H), 1.01 (d, J=6.6 Hz, 6H).

Step C: (S)-Methyl 4-(1-hydroxy-3-methylbutyl)benzoate

The DIP-Cl (−) (1.60 g, 4.99 mmol) was dissolved in anhydrous THF (18 ml) and cooled to −78° C. under nitrogen. To the mixture was then added 4-(3-methylbutanoyl)benzoate (1.0 g, 4.54 mmol) in 2 ml of THF dropwise and the reaction mixture was slowly warmed up to room temperature and kept stirring for a total 16 hours. The resulting mixture was quenched with MeCOH, followed by the addition of 3 ml of conc. HCl (37%), and the mixture was stirred at room temperature for 1 h. The resulting mixture was diluted with water and extracted with ethyl acetate. The extracts were combined and washed with brine, dried, filtered, and concentrated. The resulting residue was purified by flash column chromatography on silica gel (EtOAc/heptane: 0>>>20%) to yield a colorless oil (97.5% ee). ¹H NMR (CHLOROFORM-d) δ: 8.02 (d, J=8.1 Hz, 2H), 7.42 (d, J=8.1 Hz, 2H), 4.82 (dt, J=8.3, 4.1 Hz, 1H), 3.91 (s, 3H), 1.87 (d, J=3.7 Hz, 1H), 1.68-1.79 (m, 2H), 1.45-1.56 (m, 1H), 0.96 (d, J=6.4 Hz, 6H).

Step D: (R)-Methyl 4-(1-(5-(2-chloro-4-(trifluoromethyl)phenyl)-1H-indazol-1-yl)-3-methylbutyl)benzoate To a mixture of (S)-Methyl 4-(1-hydroxy-3-methylbutyl)benzoate (49.9 mg, 0.22 mmol), 5-(2-chloro-4-(trifluoromethyl)phenyl)-1H-indazole (66.6 mg, 0.22 mmol), triphenylphosphine (83.3 mg, 0.31 mmol) in 0.8 ml of THF was added DIEA (67.6 mg, 0.31 mmol) and the mixture was stirred at 65° C. for 16 h. The solvent was removed under reduced pressure and the residue was purified by flash column chromatography on silica gel to yield a residue. ¹H NMR (CHLOROFORM-d) δ: 8.15 (s, 1H), 7.97 (br d, J=7.8 Hz, 2H), 7.77 (br d, J=12.5 Hz, 2H), 7.57 (br d, J=8.1 Hz, 1H), 7.38-7.51 (m, 5H), 5.75 (br dd, J=9.4, 5.7 Hz, 1H), 3.88 (s, 3H), 2.64-2.80 (m, 1H), 2.01-2.17 (m, 1H), 1.40-1.54 (m, 1H), 0.99 (br t, J=5.1 Hz, 6H).

Step E: (R)-tert-butyl 3-(4-(1-(5-(2-chloro-4-(trifluoromethyl)phenyl)-1H-indazol-1-yl)-3-methylbutyl)benzamido)propanoate (R)-Methyl 4-(1-(5-(2-chloro-4-(trifluoromethyl)phenyl)-1H-indazol-1-yl)-3-methylbutyl)benzoate (46 mg, 0.10 mmol) was first hydrolyzed into its acid (20 mg) in the presence of NaOH. The resulting acid (20 mg, 0.041 mmol) was mixed with tert-butyl 3-aminopropanoate (9.7 mg, 0.053 mmol), EDC (10.2 mg, 0.05 mmol) and HOBt (6.3 mg, 0.041 mmol). To the mixture was then added 1.5 ml of THF, followed by the addition of DIEA (15.9 mg, 0.12 mmol) and the reaction mixture was stirred at room temperature for 16 hours. The resulting mixture was concentrated and the residue was purified by flash column chromatography on silica gel (EtOAc/heptane: 0>>>30%) to yield a white solid. ¹H NMR (METHANOL-d₄) δ: 8.19 (s, 1H), 7.83 (d, J=8.8 Hz, 2H), 7.69-7.76 (m, 3H), 7.66 (s, 1H), 7.57-7.63 (m, 1H), 7.46 (d, J=8.3 Hz, 3H), 5.84-6.05 (m, 1H), 3.56 (t, J=7.0 Hz, 2H), 2.64-2.79 (m, 1H), 2.53 (t, J=6.8 Hz, 2H), 1.99-2.13 (m, 1H), 1.43-1.49 (m, 1H), 1.42 (s, 9H), 0.98 (dd, J=15.7, 6.6 Hz, 6H).

Step F: 3-[[4-[(1R)-1-[5-[2-Chloro-4-(trifluoromethyl)phenyl]indazol-1-yl]-3-methyl-butyl]benzoyl]amino]propanoic Acid (R)-tert-Butyl 3-(4-(1-(5-(2-chloro-4-(trifluoromethyl)phenyl)-1H-indazol-1-yl)-3-methylbutyl)benzamido)propanoate (24.5 mg, 0.04 mmol) was dissolved in 2 ml of DCM, to which was added 0.5 ml of TFA and the mixture was stirred at room temperature for 4 hours and the solvent was removed under reduced pressure. The residue was purified by Gilson HPLC to yield the title compound as a white foam.

¹H NMR (METHANOL-d₄) δ: 8.19 (s, 1H), 7.83 (br d, J=8.6 Hz, 2H), 7.64-7.77 (m, 4H), 7.61 (s, 1H), 7.46 (br d, J=8.1 Hz, 3H), 5.96 (br dd, J=10.3, 5.1 Hz, 1H), 3.59 (t, J=6.8 Hz, 2H), 2.65-2.76 (m, 1H), 2.60 (t, J=7.0 Hz, 2H), 2.02-2.11 (m, 1H), 1.42 (dt, J=13.1, 6.5 Hz, 1H). m/z (MH+): 558.2.

The following compounds (as shown in Examples 102-111 below) were similarly prepared according to the procedures described in Examples 98 and 101, selecting and substituting a suitably substituted indazole starting material.

Example 102—Compound 145

(R)-3-(4-(1-(4-Methoxy-5-(2-methyl-4-(trifluoromethyl)phenyl)-1H-indazol-1-yl)-3-methylbutyl)benzamido)propanoic Acid

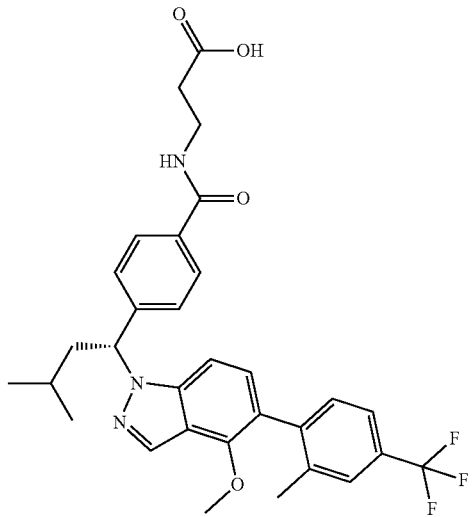 [SMILES: COc1c(-c2ccc(C(F)(F)F)cc2C)ccc2c1cnn2[C@H](CC(C)C)c1ccc(C(=O)NCCC(=O)O)cc1]

¹H NMR (CHLOROFORM-d) δ: 8.28 (s, 1H), 7.69 (br d, J=6.6 Hz, 2H), 7.37-7.54 (m, 4H), 7.26-7.33 (m, 1H), 7.07 (s, 2H), 6.89 (br s, 1H), 5.70 (br dd, J=9.3, 5.6 Hz, 1H), 3.99 (s, 3H), 3.68 (br s, 2H), 2.66 (br s, 3H), 2.19 (br d, J=7.8 Hz, 4H), 1.48 (br s, 1H), 0.98 (br d, J=5.6 Hz, 6H). m/z (MH+): 568.20.

Example 103—Compound #229

3-[[4-[(1R)-3-Methyl-1-[6-methyl-5-[4-(trifluoromethyl)phenyl]indazol-1-yl]butyl]benzoyl]amino]propanoic Acid

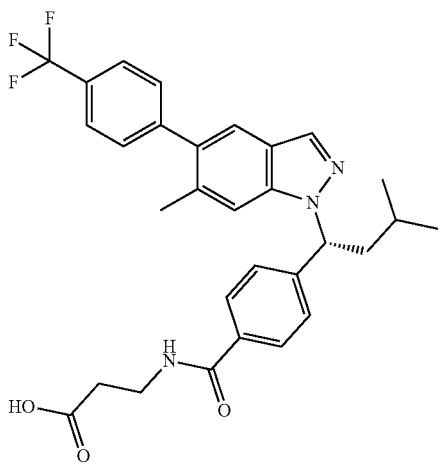 [SMILES: Cc1cc2c(cnn2[C@H](CC(C)C)c2ccc(C(=O)NCCC(=O)O)cc2)cc1-c1ccc(C(F)(F)F)cc1]

¹H NMR (CHLOROFORM-d) δ: 8.06 (s, 1H), 7.67 (t, J=7.7 Hz, 4H), 7.53 (s, 1H), 7.40 (dd, J=13.6, 7.9 Hz, 4H), 6.81 (br t, J=5.7 Hz, 1H), 5.71 (dd, J=9.8, 5.4 Hz, 1H), 3.69 (q, J=5.7 Hz, 2H), 2.60-2.74 (m, 3H), 2.31 (s, 3H), 2.01-2.13 (m, 1H), 1.42-1.54 (m, 1H), 0.98 (t, J=6.5 Hz, 6H). m/z (MH+): 538.2.

Example 104—Compound #90

3-[[4-[(1S)-1-[5-[2-Chloro-4-(trifluoromethyl)phenyl]indazol-1-yl]-3-methyl-butyl]benzoyl]amino]propanoic Acid

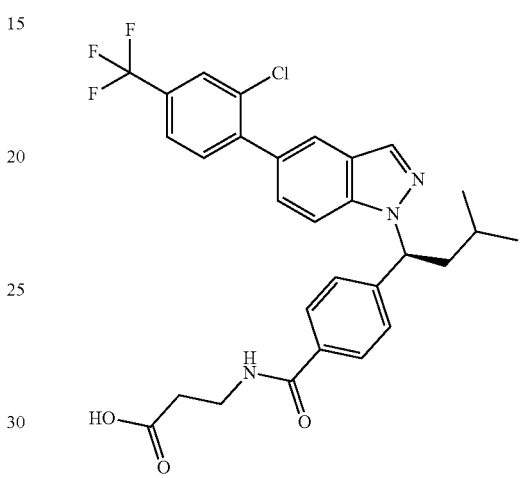

¹H NMR (CHLOROFORM-d) δ: 8.15 (s, 1H), 7.73-7.79 (m, 2H), 7.68 (d, J=8.3 Hz, 2H), 7.54-7.59 (m, 1H), 7.46 (d, J=13.2 Hz, 2H), 7.38-7.43 (m, 3H), 6.84-6.92 (m, 1H), 5.74 (dd, J=9.8, 5.6 Hz, 1H), 3.67 (q, J=6.0 Hz, 2H), 2.60-2.72 (m, 3H), 2.09-2.13 (m, 1H), 1.43-1.52 (m, 1H), 0.97 (t, J=6.2 Hz, 6H). m/z (MH+): 558.2.

Example 105—Compound #191

3-[[4-[(1R)-1-[5-[2-Chloro-4-(trifluoromethyl)phenyl]-4-methoxy-indazol-2-yl]-3-methyl-butyl]benzoyl]amino]propanoic Acid

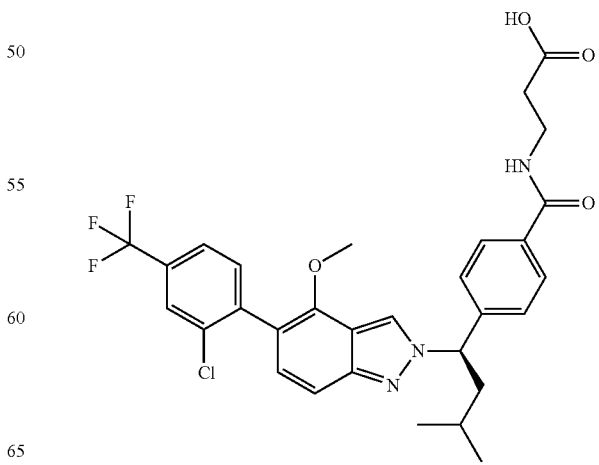

¹H NMR (CHLOROFORM-d) δ: 8.13-8.33 (m, 1H), 7.71-7.80 (m, 3H), 7.57 (br d, J=8.1 Hz, 1H), 7.44-7.52 (m, 4H), 7.17 (d, J=8.6 Hz, 1H), 7.02 (br s, 1H), 5.91 (br t, J=7.6 Hz, 1H), 3.84 (s, 3H), 3.74 (br s, 2H), 2.72 (br s, 2H), 2.41-2.53 (m, 1H), 2.20 (dt, J=14.0, 7.1 Hz, 1H), 1.44-1.54 (m, 1H), 1.01 (br t, J=7.7 Hz, 6H). m/z (MH+): 588.2.

Example 106—Compound #150

3-[[4-[(1S)-1-[5-[2-Chloro-4-(trifluoromethyl)phenyl]-4-methoxy-indazol-2-yl]-3-methyl-butyl]benzoyl]amino]propanoic Acid

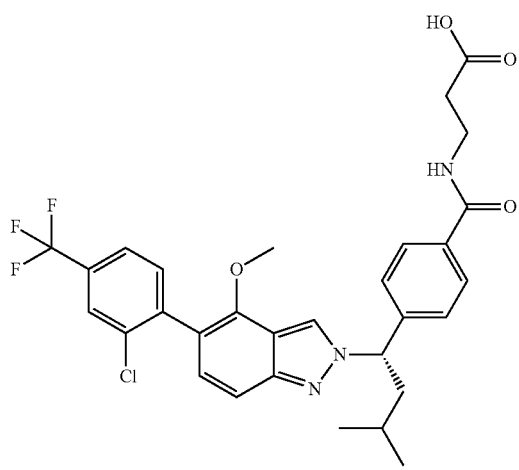

¹H NMR (CHLOROFORM-d) δ: 8.10-8.31 (m, 1H), 7.67-7.79 (m, 3H), 7.40-7.61 (m, 6H), 6.97-7.16 (m, 2H), 5.70-5.90 (m, 1H), 3.85 (s, 3H), 3.67 (br s, 2H), 2.61-2.72 (m, 2H), 2.43-2.56 (m, 1H), 2.09-2.21 (m, 1H), 1.36-1.54 (m, 1H), 0.99 (br dd, J=13.0, 6.4 Hz, 6H). m/z (MH+): 588.2.

Example 107—Compound #201

3-[[4-[(1S)-1-[5-[2-Chloro-4-(trifluoromethyl)phenyl]-4-methoxy-indazol-1-yl]-3-methyl-butyl]benzoyl]amino]propanoic Acid

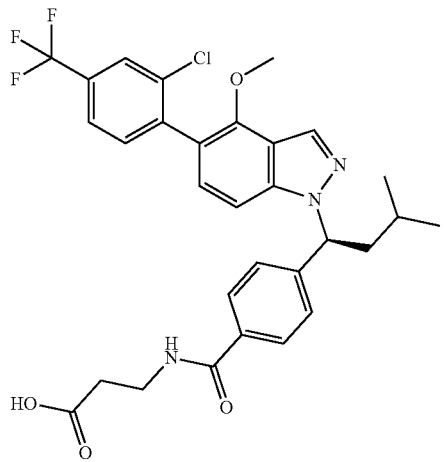 [SMILES: COc1c(-c2ccc(C(F)(F)F)cc2Cl)ccc2c1cnn2[C@@H](CC(C)C)c1ccc(C(=O)NCCC(=O)O)cc1]

¹H NMR (CHLOROFORM-d) δ: 8.30 (s, 1H), 7.73 (s, 3H), 7.51-7.57 (m, 1H), 7.41 (br d, J=5.6 Hz, 3H), 7.10 (br d, J=9.3 Hz, 2H), 6.71-6.87 (m, 1H), 5.69 (br dd, J=9.3, 5.9 Hz, 1H), 4.09 (s, 3H), 3.69 (br s, 2H), 2.58-2.75 (m, 3H), 2.09 (br d, J=6.1 Hz, 1H), 1.48 (br s, 1H), 0.98 (br d, J=5.9 Hz, 6H). m/z (MH+): 588.2.

Example 108—Compound #192

3-[[4-[(1S)-1-[4-Methoxy-5-[2-methyl-4-(trifluoromethyl)phenyl]indazol-1-yl]-3-methyl-butyl]benzoyl]amino]propanoic Acid

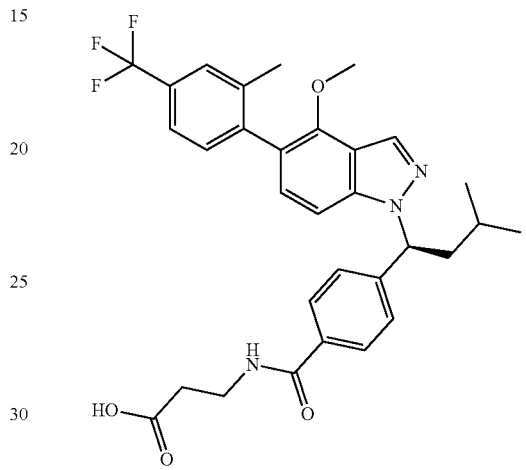

¹H NMR (CHLOROFORM-d) δ: 8.28 (s, 1H), 7.69 (br d, J=7.6 Hz, 2H), 7.37-7.54 (m, 4H), 7.27-7.34 (m, 1H), 7.07 (s, 2H), 6.87 (br s, 1H), 5.69 (br dd, J=9.4, 5.7 Hz, 1H), 3.99 (s, 3H), 3.68 (br s, 2H), 2.59-2.74 (m, 3H), 2.06-2.27 (m, 4H), 1.49 (br s, 1H), 0.98 (br d, J=6.1 Hz, 6H). m/z (MH+): 568.2.

Example 109—Compound #180

3-[[4-[(1S)-1-[5-[2-Chloro-4-(trifluoromethyl)phenyl]-4-methyl-indazol-2-yl]-3-methyl-butyl]benzoyl]amino]propanoic Acid

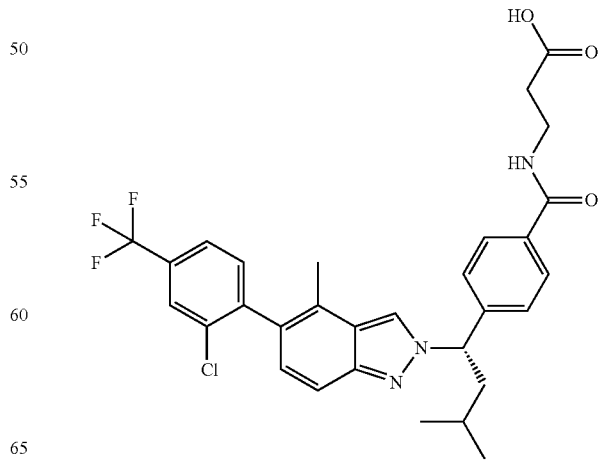

¹H NMR (CHLOROFORM-d) δ: 9.67 (br s, 1H), 8.07 (d, J=4.9 Hz, 1H), 7.67-7.78 (m, 3H), 7.58 (dd, J=15.3, 8.4 Hz, 2H), 7.34-7.44 (m, 3H), 7.23 (br s, 1H), 7.04 (d, J=8.8 Hz, 1H), 5.77 (br s, 1H), 3.63 (br d, J=5.1 Hz, 2H), 2.60 (br s, 2H), 2.50 (dt, J=13.3, 6.5 Hz, 1H), 2.27 (s, 3H), 2.11 (dt, J=13.8, 6.9 Hz, 1H), 1.37-1.51 (m, 1H), 0.96 (dd, J=16.1, 6.6 Hz, 6H). m/z (MH+): 572.2.

Example 110—Compound #196

3-[[4-[(1S)-1-[5-[2-Chloro-4-(trifluoromethyl)phenyl]-6-methyl-indazol-1-yl]-3-methyl-butyl]benzoyl]amino]propanoic Acid

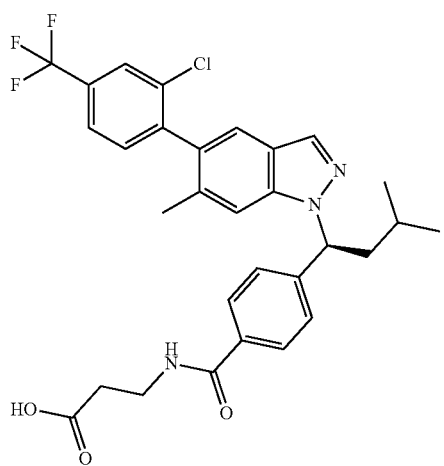 [SMILES: Cc1cc2c(cnn2[C@@H](CC(C)C)c2ccc(C(=O)NCCC(=O)O)cc2)cc1-c1ccc(C(F)(F)F)cc1Cl]

¹H NMR (CHLOROFORM-d) δ: 8.06 (s, 1H), 7.65-7.77 (m, 3H), 7.57 (t, J=8.3 Hz, 1H), 7.31-7.49 (m, 4H), 7.25 (br s, 1H), 6.76 (br s, 1H), 5.67-5.73 (m, 1H), 3.70 (q, J=5.5 Hz, 2H), 2.61-2.72 (m, 3H), 2.18 (d, J=5.6 Hz, 3H), 2.05 (m, 1H), 1.40-1.59 (m, 1H), 0.93-1.04 (m, 6H). m/z (MH+): 572.2.

Example 111—Compound #156

3-[[4-[(1S)-3-Methyl-1-[4-methyl-5-[2-methyl-4-(trifluoromethyl)phenyl]indazol-2-yl]butyl]benzoyl]amino]propanoic Acid

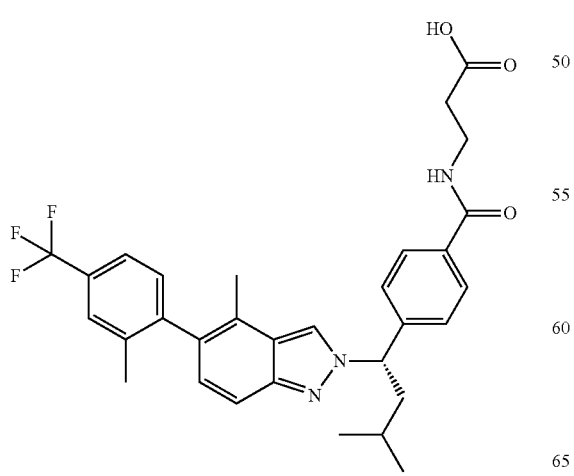

¹H NMR (CHLOROFORM-d) δ: 9.97-10.54 (m, 1H), 8.09 (d, J=3.7 Hz, 1H), 7.75 (d, J=7.8 Hz, 2H), 7.59 (d, J=8.8 Hz, 1H), 7.53 (s, 1H), 7.48 (br d, J=7.8 Hz, 3H), 7.17-7.28 (m, 2H), 7.04 (d, J=8.8 Hz, 1H), 5.87 (br s, 1H), 3.63-3.74 (m, 2H), 2.66 (br t, J=5.6 Hz, 2H), 2.47-2.59 (m, 1H), 2.21 (s, 3H), 2.13-2.19 (m, 1H), 2.11 (s, 3H), 1.40-1.51 (m, 1H), 0.99 (dd, J=14.4, 6.6 Hz, 6H). m/z (MH+): 552.3.

The following compounds (as shown in Examples 112-120 below) were similarly prepared according to the procedures described in Examples 5 and 6, selecting and substituting a suitably substituted arylalkyl bromides and indazoles as starting materials.

Example 112—Compound #214

3-[[5-[3-Methyl-1-[6-methyl-5-[2-methyl-4-(trifluoromethyl)phenyl]indazol-1-yl]butyl]pyridine-2-carbonyl]amino]propanoic Acid

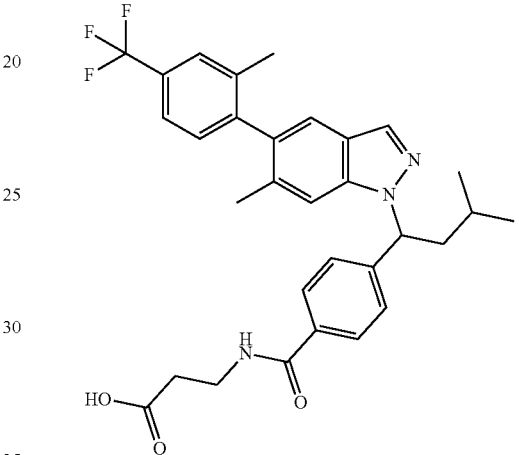

¹H NMR (CHLOROFORM-d) δ: 9.98 (br s, 1H), 8.43-8.64 (m, 2H), 8.14 (t, J=7.1 Hz, 1H), 8.06 (s, 1H), 7.88 (br dd, J=20.5, 8.1 Hz, 1H), 7.44-7.57 (m, 2H), 7.42 (s, 1H), 7.15-7.34 (m, 2H), 5.76 (br dd, J=8.9, 6.0 Hz, 1H), 3.75 (q, J=5.8 Hz, 2H), 2.65-2.78 (m, 3H), 2.05-2.15 (m, 7H), 1.43-1.59 (m, 1H), 0.95-1.08 (m, 6H). m/z (MH+): 553.2.

Example 113—Compound #187

3-[[5-[3-Methyl-1-[6-methyl-5-[2-methyl-4-(trifluoromethyl)phenyl]indazol-2-yl]butyl]pyridine-2-carbonyl]amino]propanoic Acid

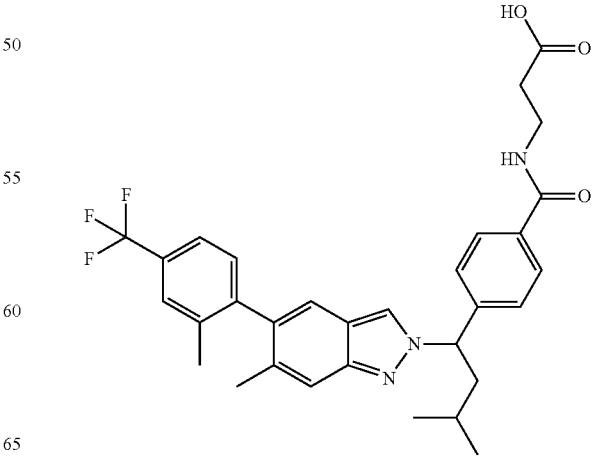

¹H NMR (CHLOROFORM-d) δ: 8.62 (s, 1H), 8.50 (br t, J=6.0 Hz, 1H), 8.16 (d, J=8.1 Hz, 1H), 8.01 (d, J=4.2 Hz, 1H), 7.88 (br d, J=8.1 Hz, 1H), 7.60 (s, 1H), 7.46-7.55 (m, 2H), 7.33 (s, 1H), 7.15-7.26 (m, 1H), 5.83 (br s, 1H), 3.76 (q, J=5.7 Hz, 2H), 2.71 (br t, J=5.9 Hz, 2H), 2.52-2.64 (m, 1H), 2.07-2.17 (m, 7H), 1.40-1.53 (m, 1H), 1.00 (dd, J=16.9, 6.6 Hz, 6H). m/z (MH+): 553.2.

Example 114—Compound #259

3-[[5-[1-[5-[2-Chloro-4-(trifluoromethyl)phenyl]-6-methyl-indazol-1-yl]-3-methyl-butyl]pyridine-2-carbonyl]amino]propanoic Acid

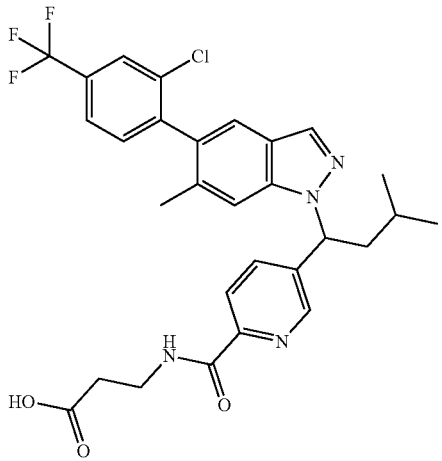 [SMILES: Cc1cc2c(cnn2C(CC(C)C)c2ccc(C(=O)NCCC(=O)O)nc2)cc1-c1ccc(C(F)(F)F)cc1Cl]

¹H NMR (CHLOROFORM-d) δ: 10.01 (br s, 1H), 8.57 (br d, J=15.9 Hz, 1H), 8.49 (br d, J=4.4 Hz, 1H), 8.01-8.20 (m, 2H), 7.87 (br dd, J=26.4, 8.1 Hz, 1H), 7.74 (br d, J=6.6 Hz, 1H), 7.57 (br t, J=8.2 Hz, 1H), 7.47 (s, 1H), 7.26-7.42 (m, 2H), 5.76 (br dd, J=9.0, 5.9 Hz, 1H), 3.75 (br d, J=5.6 Hz, 2H), 2.61-2.81 (m, 3H), 2.20 (br d, J=4.6 Hz, 3H), 2.10 (s, 1H), 1.38-1.62 (m, 1H), 0.93-1.08 (m, 6H). m/z (MH+): 573.2.

Example 115—Compound #242

3-[[5-[1-[5-[2-Chloro-4-(trifluoromethyl)phenyl]-6-methyl-indazol-2-yl]-3-methyl-butyl]pyridine-2-carbonyl]amino]propanoic Acid

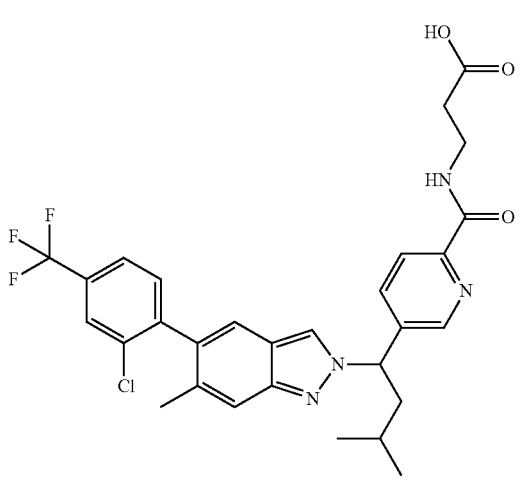 [SMILES: Cc1cc2nn(C(CC(C)C)c3ccc(C(=O)NCCC(=O)O)nc3)cc2cc1-c1ccc(C(F)(F)F)cc1Cl]

¹H NMR (CHLOROFORM-d) δ: 10.31-11.33 (m, 1H), 8.62 (br s, 1H), 8.51 (br s, 1H), 8.15 (br d, J=8.1 Hz, 1H), 8.04 (br s, 1H), 7.88 (br d, J=7.8 Hz, 1H), 7.74 (br s, 1H), 7.52-7.66 (m, 2H), 7.31-7.49 (m, 2H), 5.74-5.98 (m, 1H), 3.76 (br d, J=5.6 Hz, 2H), 2.72 (br d, J=4.9 Hz, 2H), 2.51-2.64 (m, 1H), 2.10-2.27 (m, 4H), 1.44 (br d, J=6.8 Hz, 1H), 0.99 (br dd, J=17.0, 6.2 Hz, 6H). m/z (MH+): 573.2.

Example 116—Compound #56

3-(4-(1-(5-(4-(tert-Butyl)phenyl)-1H-indazol-1-yl)butyl)benzamido)propanoic Acid

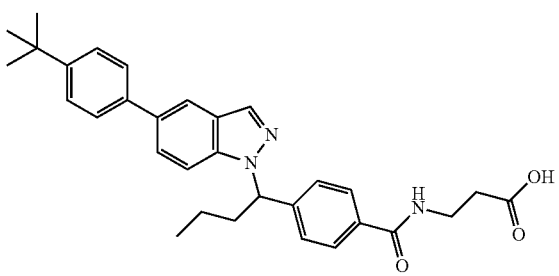 [SMILES: CCCC(c1ccc(C(=O)NCCC(=O)O)cc1)n1ncc2cc(-c3ccc(C(C)(C)C)cc3)ccc21]

¹H NMR (400 MHz, CDCl₃) δ 8.17 (s, 1H), 7.91 (s, 1H), 7.71-7.73 (m, 2H), 7.50-7.63 (m, 5H), 7.41-7.47 (m, 2H), 6.80-6.81 (m, 1H), 5.65-5.71 (m, 1H), 3.71-3.77 (m, 2H), 2.65-2.73 (m, 3H), 2.27-2.33 (m, 1H), 1.33 (s, 9H), 0.97-1.02 (m, 3H). (ES, m/z) 498 [M+H]+.

Example 117—Compound #22

3-(4-(1-(5-(4-(tert-Butyl)phenyl)-2H-indazol-2-yl)butyl)benzamido)propanoic Acid

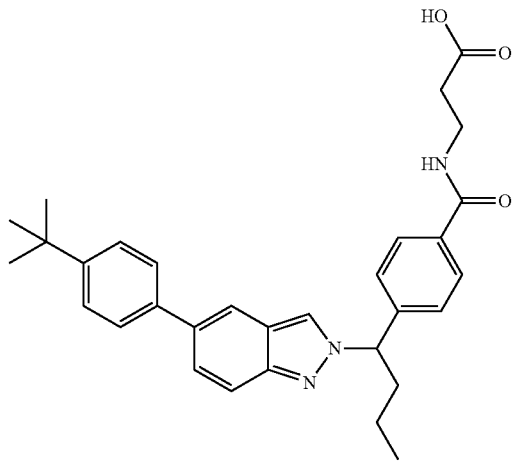 [SMILES: CCCC(c1ccc(C(=O)NCCC(=O)O)cc1)n1cc2cc(-c3ccc(C(C)(C)C)cc3)ccc2n1]

¹H NMR (400 MHz, CDCl₃) δ 8.11 (s, 1H), 7.81-7.84 (m, 2H), 7.58-7.73 (m, 3H), 7.46-7.55 (m, 6H), 6.93-6.94 (m, 1H), 5.85 (s, 1H), 3.74 (s, 2H), 2.72 (s, 2H), 2.54 (s, 1H), 2.32 (s, 1H), 1.39 (s, 9H), 1.01 (t, J=6.6 Hz, 3H). (ES, m/z) 498 [M+H]+.

Example 118—Compound #23

3-(4-(1-(5-(4-(tert-Butyl)phenyl)-1H-indazol-1-yl)-4-methylpentyl)benzamido)propanoic Acid

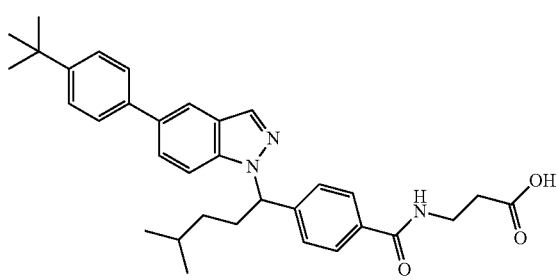 [SMILES: CC(C)CCC(c1ccc(C(=O)NCCC(=O)O)cc1)n1ncc2cc(-c3ccc(C(C)(C)C)cc3)ccc21]

$^1$H NMR (300 MHz, CDCl$_3$) δ 8.16 (s, 1H), 7.91 (s, 1H), 7.69-7.72 (m, 2H), 7.40-7.62 (m, 8H), 6.75 (s, 1H), 5.60 (m, 1H), 3.71-3.73 (m, 2H), 2.65-2.73 (m, 3H), 2.29-2.36 (m, 1H), 1.62-1.64 (m, 1H), 1.39 (s, 9H), 1.19-1.24 (m, 2H), 0.90 (dd, J=3.6 Hz, 6.3 Hz, 6H). (ES, m/z) 526 [M+H]+.

Example 119—Compound #227

3-(4-(1-(5-(4-(tert-Butyl)phenyl)-2H-indazol-2-yl)-4-methylpentyl)benzamido)propanoic Acid

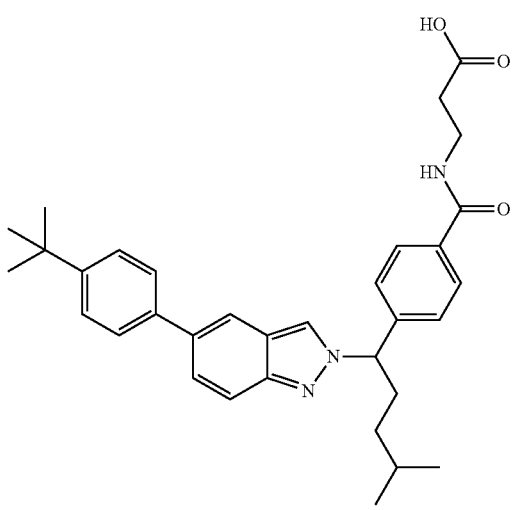 [SMILES: CC(C)CCC(c1ccc(C(=O)NCCC(=O)O)cc1)n1cc2cc(-c3ccc(C(C)(C)C)cc3)ccc2n1]

$^1$H NMR (300 MHz, CDCl$_3$) δ 8.22 (s, 1H), 7.87 (s, 1H), 7.70-7.80 (m, 4H), 7.42-7.57 (m, 7H), 7.03 (s, 1H), 5.76-5.79 (m, 1H), 3.71-3.72 (m, 2H), 2.70 (s, 2H), 1.62-1.66 (m, 1H), 1.38 (s, 9H), 1.17-1.28 (m, 2H), 0.88-0.91 (m, 6H). (ES, m/z) 526 [M+H]+.

Example 120—Compound #24

3-(4-(1-(5-(4-(tert-Butyl)phenyl)-1H-indazol-1-yl)-2-cyclohexylethyl)benzamido)propanoic Acid

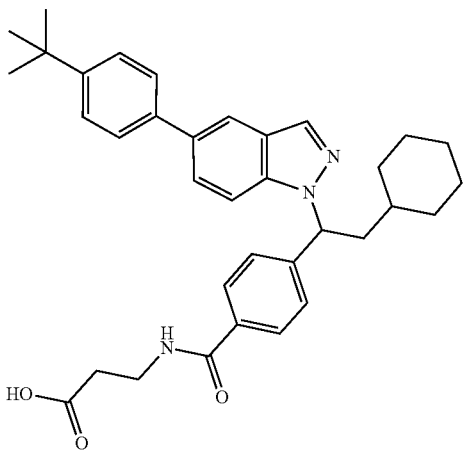 [SMILES: CC(C)(C)c1ccc(-c2ccc3c(cnn3C(CC3CCCCC3)c3ccc(C(=O)NCCC(=O)O)cc3)c2)cc1]

Step A:

Into a 250-mL 3-necked round-bottom flask purged and maintained with an inert atmosphere of nitrogen, was placed magnesium (420 mg, 17.50 mmol, 1.10 equiv), a solution of (2-bromoethyl)cyclohexane (3 g, 15.71 mmol, 1.00 equiv) in tetrahydrofuran (50 mL). The solution was refluxed for 3 hours, then cooled to room temperature. Into another 250-mL 3-necked round-bottom flask purged and maintained with an inert atmosphere of nitrogen, was placed a solution of trimethyl borate (2.46 g, 23.65 mmol, 1.50 equiv) in tetrahydrofuran (50 mL) with stirring at −78° C. To this mixture was added the above prepared solution. The resulting mixture was stirred for 3 hours at room temperature. To the resulting mixture was then added KHF$_2$ (4.926 g, 63.15 mmol, 4.00 equiv) and water (80 mL). The resulting solution was stirred overnight at room temperature. The solvent was removed under reduced pressure. The residue was washed with 3×100 mL of propan-2-one and the resulting filtrate was then concentrated under vacuum to yield potassium (2-cyclohexylethyl)trifuoroborate as a white solid.

Step B:

Into a 100-mL round-bottom flask purged and maintained with an inert atmosphere of nitrogen, was placed a solution of methyl 4-bromobenzoate (740 mg, 3.44 mmol, 1.00 equiv) in 1,4-dioxane (30 mL), a solution of potassium (2-cyclohexylethyl)trifuoroborate (950 mg, 4.36 mmol, 1.30 equiv) in water (15 mL), Cs$_2$CO$_3$ (2.77 g, 8.50 mmol, 2.50 equiv), Pd(dppf)Cl$_2$ (270 mg, 0.34 mmol, 0.10 equiv). The resulting solution was stirred overnight at 105° C. in an oil bath. The resulting solution was extracted with 3×30 mL of ethyl acetate after cooling. The combined organic layers were washed with 2×30 mL of sodium chloride, dried over anhydrous sodium sulfate and concentrated under vacuum. The residue was purified by chromatography over a silica gel column with PE/EA (3:1) to yield methyl 4-(2-cyclohexylethyl) benzoate as a light yellow oil. (ES, m/z) 247 [M+H]$^+$ Step C:

Into a 50-mL round-bottom flask, was placed a solution of methyl 4-(2-cyclohexylethyl) benzoate (800 mg, 3.25 mmol, 1.00 equiv) in CCl$_4$ (20 mL), NBS (580 mg, 3.26 mmol, 1.00 equiv), benzoic peroxyanhydride (7 mg, 0.03 mmol, 0.01 equiv). The resulting solution was stirred for 2 hrs at reflux in an oil bath and then cooled to room temperature. The solids were filtered out. The filtrate was concentrated under vacuum. The residue was applied onto a silica gel column and eluted with PE/EA (3:1) to yield methyl 4-(1-bromo-2-cyclohexylethyl) benzoate as s yellow oil. (ES, m/z) 326 [M+H]+

Step D:

Into a 25-mL round-bottom flask, was placed a solution of methyl 4-(1-bromo-2-cyclohexylethyl)benzoate (200 mg, 0.62 mmol, 1.15 equiv) in N,N-dimethylformamide (10 mL), 5-(4-tert-butylphenyl)-1H-indazole (140 mg, 0.56 mmol, 1.00 equiv), $Cs_2CO_3$ (270 mg, 0.83 mmol, 1.50 equiv). The resulting solution was stirred overnight at 60° C. in an oil bath and then quenched by the addition of 25 ml of water. The resulting solution was extracted with 3×30 mL of ethyl acetate. The combined organic layers were washed with 2×20 mL of sodium chloride, dried over anhydrous sodium sulfate. The residue was applied onto a silica gel column and eluted with ethyl acetate/petroleum ether (1:50-20:1) to yield a first yellow oil (the N-1 substituted compound) and a second yellow oil (the N-2 substituted compound) (ES, m/z) 495 [M+H]+

Step E:

Into a 25-mL round-bottom flask, was placed a solution of methyl 4-(2-(5-(4-tert-butylphenyl)-1H-indazol-1-yl)-2-cyclohexylethyl) benzoate (106 mg, 0.21 mmol, 1.00 equiv) in tetrahydrofuran/MeOH (8/2 mL), a solution of $LiOH.H_2O$ (90 mg, 2.14 mmol, 10.00 equiv) in water (2 mL). The resulting solution was stirred for 3 h at room temperature. The pH value of the solution was adjusted to 2 with 2 N HCl. The resulting mixture was extracted with 3×30 mL of ethyl acetate. The combined organic layers were washed with 2×20 mL of sodium chloride, dried over anhydrous sodium sulfate and concentrated under vacuum to yield 4-(2-(5-(4-tert-butylphenyl)-1H-indazol-1-yl)-2-cyclohexylethyl) benzoic acid as a yellow oil. (ES, m/z) 481 [M+H]+

Step F:

Into a 25-mL round-bottom flask, was placed a solution of 4-(2-(5-(4-tert-butylphenyl)-1H-indazol-1-yl)-2-cyclohexylethyl) benzoic acid (90 mg, 0.19 mmol, 1.20 equiv) in N,N-dimethylformamide (10 mL), HATU (152 mg, 0.40 mmol, 2.00 equiv). To the mixture was then added\DIEA (103 mg, 0.80 mmol, 4.00 equiv) and ethyl 3-aminopropanoate hydrochloride (30 mg, 0.20 mmol, 1.00 equiv). The resulting solution was stirred for 1 h at room temperature, then diluted with water and extracted with 2×30 mL of ethyl acetate. The combined organic layers were washed with 2×20 mL of sodium chloride, dried over anhydrous sodium sulfate and concentrated under vacuum. The residue was applied onto a silica gel column and eluted with PE/EA (3:1) to yield ethyl 3-(4-(2-(5-(4-tert-butylphenyl)-1H-indazol-1-yl)-2-cyclohexylethyl) benzamido) propanoate as a yellow oil. (ES, m/z) 580 [M+H]+

Step G:

Into a 25-mL round-bottom flask, was placed a solution of ethyl 3-(4-(1-(5-(4-tert-butylphenyl)-1H-indazol-1-yl)-2-cyclohexylethyl) benzamido)propanoate (80 mg, 0.14 mmol, 1.00 equiv) in tetrahydrofuran/MeOH (4/1 mL), a solution of $LiOH.H_2O$ (59 mg, 1.40 mmol, 10.00 equiv) in water (1 mL). The resulting solution was stirred for 3 h at room temperature. The pH value of the solution was adjusted to 2 with 2N HCl. The resulting solution was extracted with 3×15 mL of ethyl acetate. The combined organic layers were washed with 2×15 mL of brine and concentrated under vacuum. The resulting residue was purified by Prep-HPLC with the following conditions (1 #-Waters 2767-1): Column, SunFire Prep C18, 5 um, 19*150 mm; mobile phase: water in 0.05% TFA and $CH_3CN$ (50% $CH_3CN$ up to 75% in 10 min, up to 100% in 2 min, down to 50% in 2 min); Detector, UV 254 nm to yield 3-(4-(1-(5-(4-tert-butylphenyl)-1H-indazol-1-yl)-2-cyclohexylethyl)benzamido)propanoic acid as a white solid.

$^1$H NMR (400 MHz, $CDCl_3$) δ 8.14 (s, 1H), 7.90 (s, 1H), 7.60-7.69 (m, 2H), 7.54-7.58 (m, 3H), 7.47-7.49 (m, 2H), 7.41-7.43 (m, 3H), 6.76 (s, 1H), 5.77-5.80 (m, 1H), 3.69-3.71 (s, 2H), 2.62-2.69 (m, 2H), 2.12-2.17 (m, 1H), 1.76-1.87 (m, 2H), 1.61-1.69 (m, 3H), 1.39 (s, 9H), 1.05-1.18 (m, 6H). (ES, m/z) 552 [M+H]+.

The following compounds (as shown in Examples 121-123 below) were similarly prepared according to the procedure described in Examples 120, selecting and substituting a suitably substituted arylalkyl bromide starting material.

Example 121—Compound #228

3-(4-(1-(5-(4-(tert-Butyl)phenyl)-2H-indazol-2-yl)-2-cyclohexylethyl)benzamido)propanoic Acid

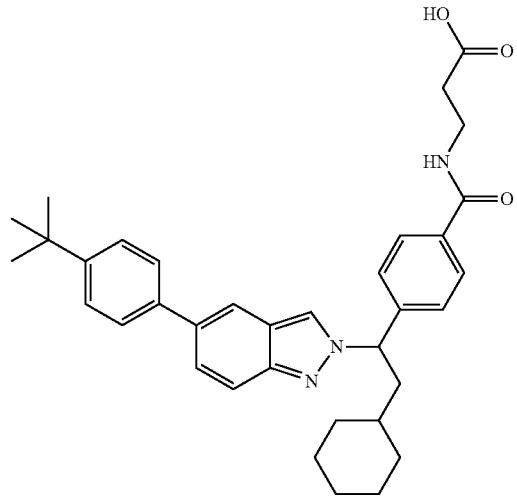 [SMILES: CC(C)(C)c1ccc(-c2ccc3nn(C(CC4CCCCC4)c4ccc(C(=O)NCCC(=O)O)cc4)cc3c2)cc1]

$^1$H NMR (400 MHz, $CDCl_3$) δ (ppm): 8.05 (s, 1H), 7.78-7.81 (m, 2H), 7.72-7.74 (m, 2H), 7.56-7.60 (m, 2H), 7.48-7.50 (m, 2H), 7.42-7.44 (m, 2H), 6.90-6.93 (m, 1H), 5.83-5.87 (m, 1H), 3.71-3.74 (m, 2H), 2.68-2.71 (m, 2H), 2.47-2.54 (m, 1H), 2.13-2.20 (m, 1H), 1.86-1.89 (m, 1H), 1.62-1.78 (m, 4H), 1.39 (s, 9H), 1.16-1.37 (m, 6H). LC-MS (ES, m/z) 552 [M+H]+

Example 122—Compound #239

3-(4-(3-Cyclobutyl-1-(5-(4-(trifluoromethyl)phenyl)-1H-indazol-1-yl)propyl)benzamido)propanoic Acid

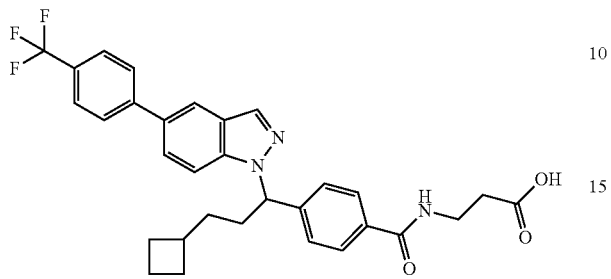

¹H NMR (300 MHz, CD₃OD) δ: 8.21 (s, 1H), 8.09 (s, 1H), 7.85 (d, J=8.1 Hz, 2H), 7.72-7.76 (m, 6H), 7.44 (d, J=8.1 Hz, 2H), 5.82-5.86 (m, 1H), 3.60 (t, J=6.9 Hz, 2H), 2.59-2.64 (m, 3H), 2.15-2.45 (m, 2H), 2.05-2.10 (m, 2H), 1.79-1.90 (m, 2H), 1.25-1.50 (m, 4H). LC-MS (ES, m/z) 550 [M+H]+.

Example 123—Compound #215

3-(4-(3-Cyclobutyl-1-(5-(4-(trifluoromethyl)phenyl)-2H-indazol-2-yl)propyl)benzamido)propanoic Acid

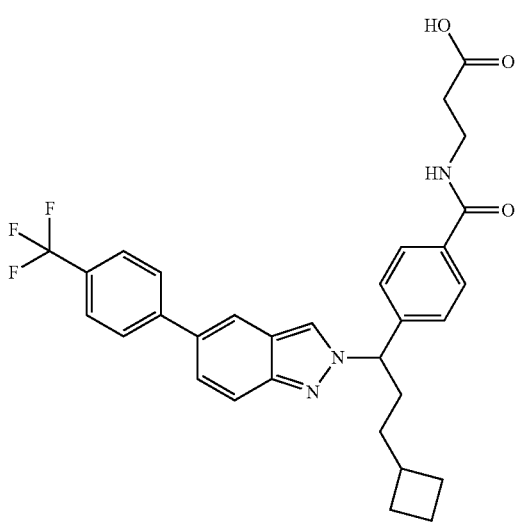 [SMILES: O=C(O)CCNC(=O)c1ccc(C(CCC2CCC2)n2cc3cc(-c4ccc(C(F)(F)F)cc4)ccc3n2)cc1]

¹H NMR (300 MHz, CD₃OD) δ: 8.50 (s, 1H), 8.03 (s, 1H), 7.73-7.88 (m, 7H), 7.65-7.68 (m, 1H), 7.51 (d, J=8.1 Hz, 2H), 5.72-5.77 (m, 1H), 3.61 (t, J=6.9 Hz, 2H), 2.62 (t, J=6.9 Hz, 2H), 2.41-2.54 (m, 1H), 2.27-2.41 (m, 2H), 2.08-2.18 (m, 2H), 1.78-1.90 (m, 2H), 1.57-1.63 (m, 2H), 1.40-1.50 (m, 1H), 1.25-1.35 (m, 1H). LC-MS (ES, m/z) 550 [M+H]+.

Example 124—Compound #185

3-(4-(3-Fluoro-3-methyl-1-(5-(4-(trifluoromethyl)phenyl)-1H-indazol-1-yl)butyl)benzamido)propanoic Acid

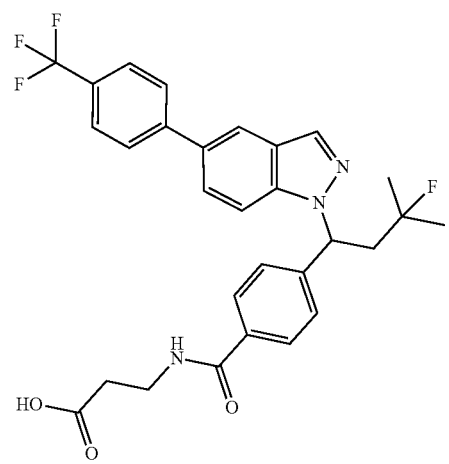 [SMILES: CC(C)(F)CC(c1ccc(C(=O)NCCC(=O)O)cc1)n1ncc2cc(-c3ccc(C(F)(F)F)cc3)ccc21]

Step A:

Into a 1000-mL round-bottom flask, was placed a solution of 4-formylbenzoic acid (22 g, 146.67 mmol, 2.00 equiv) in tetrahydrofuran (650 mL), dimethyl 2-oxopropylphosphonate (10 g, 60.24 mmol, 1.00 equiv), a solution of potassium carbonate (27.6 g, 200.00 mmol, 2.00 equiv) in water (160 mL). The resulting solution was stirred overnight at room temperature and the reaction was then quenched by the addition of 250 mL of water. The pH value of the solution was adjusted to 2 with 2 N HCl. The resulting solution was extracted with 2×150 mL of ethyl acetate. The combined organic layers were washed with 3×100 mL of brine, dried over anhydrous sodium sulfate and concentrated under vacuum to yield (E)-4-(3-oxobut-1-enyl)benzoic acid as a white solid.

Step B:

Into a 1000-mL round-bottom flask, was placed a solution of (E)-4-(3-oxobut-1-enyl)benzoic acid (10 g, 52.63 mmol, 1.00 equiv) in ethyl acetate (800 mL), palladium on carbon (10 g). H₂ was introduced into the above solution. The resulting solution was stirred overnight at room temperature. The reaction progress was monitored by LCMS. The solids were filtered out. The filtrate was concentrated under vacuum to yield 4-(3-oxobutyl)benzoic acid as a white solid.

Step C:

Into a 100-mL 3-necked round-bottom flask purged and maintained with an inert atmosphere of nitrogen, was placed a solution of 4-(3-oxobutyl)benzoic acid (3000 mg, 15.62 mmol, 1.00 equiv) in tetrahydrofuran (120 mL), followed by addition of CH₃MgBr (3M) (14.6 mL) at −10° C. The resulting solution was stirred overnight at room temperature and the reaction was then quenched by the addition of water at 0° C. The pH value of the solution was adjusted to 2 with 1 N HCl. The resulting solution was extracted with 2×25 mL of ethyl acetate. The combined organic layers were washed with 2×20 mL of brine, dried over Na₂SO₄ and concentrated under vacuum. The residue was applied onto a silica gel column and eluted with petroleum ether: EtOAc (20:1) to yield 4-(3-hydroxy-3-methylbutyl)benzoic acid as a white solid.

Step D:

Into a 150-mL round-bottom flask, was placed a solution of 4-(3-oxobutyl)benzoic acid (3000 mg, 15.62 mmol, 1.00 equiv) in methanol (80 mL), sulfuric acid (0.5 mL). The resulting solution was heated to reflux overnight in an oil bath. The reaction was then quenched by the addition of water (20 ml). The resulting solution was extracted with 3×25 mL of ethyl acetate. The combined organic layers were washed with 3×30 mL of brine, dried over anhydrous sodium sulfate and concentrated under vacuum. The residue was applied onto a silica gel column and eluted with ethyl acetate/petroleum ether (1/50) to yield methyl 4-(3-oxobutyl)benzoate as light yellow oil.

Step E:

Into a 250-mL round-bottom flask, was placed a solution of methyl 4-(3-hydroxy-3-methylbutyl)benzoate (1500 mg, 6.76 mmol, 1.00 equiv) in CC 4 (100 mL), NBS (1260 mg, 7.08 mmol, 1.05 equiv), $(C_6H_5CO)_2O_2$ (5 mg, 0.02 mmol). The resulting solution was heated to reflux for 1 h in an oil bath before the resulting mixture was cooled to room temperature. The solids were filtered out. The filtrate was concentrated under vacuum. The residue was applied onto a silica gel column and eluted with petroleum ether:EtOAc (100:1) to yield methyl 4-(1-bromo-3-hydroxy-3-methylbutyl)benzoate as yellow oil.

Step F:

Into a 25-mL round-bottom flask, was placed a solution of methyl 4-(1-bromo-3-hydroxy-3-methylbutyl)benzoate (515 mg, 1.72 mmol, 2.00 equiv) in N,N-dimethylformamide (5 mL), 5-(4-(trifluoromethyl)phenyl)-1H-indazole (250 mg, 0.95 mmol, 1.00 equiv), $Cs_2CO_3$ (622 mg, 1.91 mmol, 2.00 equiv). The resulting solution was stirred overnight at 60° C. in an oil bath and the reaction was then quenched by the addition of 25 mL of water. The resulting solution was extracted with 3×25 of ethyl acetate. The combined organic layers were washed with 3×25 mL of brine, dried over sodium sulfate and concentrated under vacuum. The residue was applied onto a silica gel column and eluted with petroleum ether:EtOAc (20:1) to yield a mixture of methyl 4-(3-hydroxy-3-methyl-1-(5-(4-(trifluoromethyl)phenyl)-1H-indazol-1-yl)butyl)benzoate (the N-1 substituted compound) as a first light yellow oil; and methyl 4-(3-hydroxy-3-methyl-1-(5-(4-(trifluoromethyl)phenyl)-2H-indazol-2-yl)butyl)benzoate (the N-2 substituted compound) as a second light yellow oil.

Step G:

Into a 10-mL round-bottom flask, was placed methyl 4-(3-hydroxy-3-methyl-1-(5-(4-(trifluoromethyl)phenyl)-1H-indazol-1-yl)butyl)benzoate (112 mg, 0.23 mmol, 1.00 equiv). To the mixture was then added DAST (0.12 mL) at −78° C. The resulting solution was stirred overnight at room temperature and the reaction was then quenched by the addition of water at 0° C. The resulting solution was extracted with 2×10 mL of dichloromethane. The combined organic layers were washed with 2×5 mL of brine, dried over anhydrous sodium sulfate and concentrated under vacuum. The residue was applied onto a silica gel column and eluted with ethyl acetate/petroleum ether (1:50) to yield methyl 4-(3-fluoro-3-methyl-1-(5-(4-(trifluoromethyl)phenyl)-1H-indazol-1-yl)butyl)benzoate as light yellow oil.

Step H:

Into a 10-mL round-bottom flask, was placed a solution of methyl 4-(3-fluoro-3-methyl-1-(5-(4-(trifluoromethyl)phenyl)-1H-indazol-1-yl)butyl)benzoate (45 mg, 0.09 mmol, 1.00 equiv) in tetrahydrofuran/MeOH (4/1 mL), $LiOH.H_2O$ (39 mg, 0.93 mmol, 10.00 equiv) in water (1 ml). The resulting solution was stirred for 2 h at room temperature and the reaction was then quenched by the addition of water (25 ml). The pH value of the solution was adjusted to 2 with 2 N HCl. The resulting solution was extracted with 2×5 mL of ethyl acetate. The combined organic layers were washed with 2×5 mL of brine, dried over anhydrous sodium sulfate and concentrated under vacuum to yield 4-(3-fluoro-3-methyl-1-(5-(4-(trifluoromethyl)phenyl)-1H-indazol-1-yl)butyl)benzoic acid as light yellow oil.

Step I:

Into a 50-mL round-bottom flask, was placed a solution of 4-(3-fluoro-3-methyl-1-(5-(4-(trifluoromethyl)phenyl)-1H-indazol-1-yl)butyl)benzoic acid (65 mg, 0.14 mmol, 1.00 equiv) in N,N-dimethylformamide (3 mL), ethyl 3-aminopropanoate hydrochloride (25.4 mg, 0.17 mmol, 1.20 equiv), HATU (105 mg, 0.28 mmol, 2.00 equiv), DIPEA (71.4 mg, 0.55 mmol, 4.00 equiv). The resulting solution was stirred overnight at room temperature and the reaction was then quenched by the addition of 15 mL of water. The resulting solution was extracted with 2×50 mL of ethyl acetate. The combined organic layers were washed with 3×25 mL of brine, dried over anhydrous sodium sulfate and concentrated under vacuum. The residue was purified by a silica gel column with petroleum ether:EtOAc (20:1) to yield ethyl 3-(4-(3-fluoro-3-methyl-1-(5-(4-(trifluoromethyl)phenyl)-1H-indazol-1-yl)butyl)benzamido)propanoate as a light yellow oil.

Step J:

Into a 10-mL round-bottom flask, was placed a solution of ethyl 3-(4-(3-fluoro-3-methyl-1-(5-(4-(trifluoromethyl)phenyl)-1H-indazol-1-yl)butyl)benzamido)propanoate (50 mg, 0.09 mmol, 1.00 equiv) in tetrahydrofuran/MeOH (8/2 mL), a solution of $LiOH.H_2O$ (37 mg, 0.88 mmol, 10.00 equiv) in water (2 mL). The resulting solution was stirred for 30 min at room temperature. The pH value of the solution was adjusted to 2 with 2N HCl. The resulting solution was extracted with 3×20 mL of ethyl acetate. The combined organic layers were washed with 2×20 mL of brine, dried over sodium sulfate and concentrated under vacuum. The resulting residue was purified by Prep-HPLC with the following conditions (1 #-Waters 2767-1): Column, SunFire Prep $C_{18}$, 5 um, 19*150 mm; mobile phase: water in 0.05% TFA and $CH_3CN$ (50% $CH_3CN$ up to 75% in 10 min, up to 100% in 2 min, down to 50% in 2 min); Detector, UV 254 nm to yield 3-(4-(3-fluoro-3-methyl-1-(5-(4-(trifluoromethyl)phenyl)-1H-indazol-1-yl)butyl)benzamido)propanoic acid as a white solid.

$^1$H NMR (400 MHz, $CD_3OD$) δ: 8.22 (s, 1H), 8.09 (s, 1H), 7.82-7.87 (m, 2H), 7.74-7.79 (m, 6H), 7.50 (d, J=8.4 Hz, 2H), 6.12-6.17 (m, 1H), 3.60 (t, J=6.9 Hz, 2H), 3.32-3.44 (m, 1H), 2.61 (t, J=6.9 Hz, 2H), 2.50-2.56 (m, 1H), 1.35 (d, J=21.3 Hz, 3H), 1.10 (d, J=21.3 Hz, 3H). LC-MS (ES, m/z) 542 [M+H]+

The following compound (as shown in Example 125 below) was similarly prepared according to the procedure described in Examples 124 STEPS G-J, reacting methyl 4-(3-hydroxy-3-methyl-1-(5-(4-(trifluoromethyl)phenyl)-2H-indazol-2-yl)butyl)benzoate (the N-2 substituted compound prepared in STEP F as the second light yellow oil).

Example 125—Compound #256

3-(4-(3-Fluoro-3-methyl-1-(5-(4-(trifluoromethyl)phenyl)-2H-indazol-2-yl)butyl)benzamido)propanoic acid

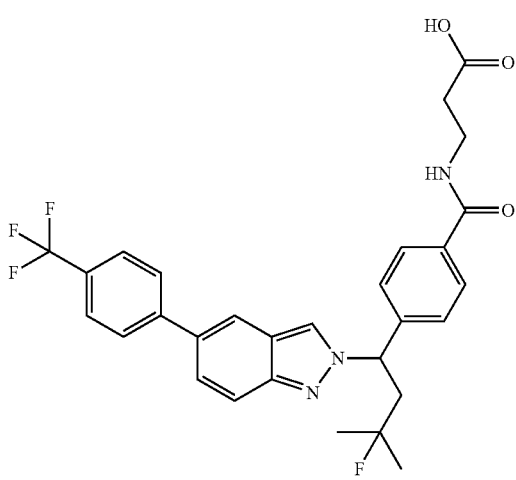 [SMILES: CC(C)(F)CC(c1ccc(C(=O)NCCC(=O)O)cc1)n1cc2cc(-c3ccc(C(F)(F)F)cc3)ccc2n1]

$^1$H NMR (400 MHz, CD$_3$OD) δ: 8.58 (s, 1H), 8.02 (s, 1H), 7.81-7.87 (m, 2H), 7.74-7.93 (m, 4H), 7.65-7.68 (m, 1H), 7.55-7.56 (m, 2H), 6.10-6.13 (m, 1H), 3.60 (t, J=6.8 Hz, 2H), 3.25-3.32 (m, 2H), 2.59-2.68 (m, 3H), 1.35 (d, J=16.2 Hz, 3H), 1.19 (d, J=16.2 Hz, 3H). LC-MS (ES, m/z) 542 [M+H]$^+$.

Example 126—Compound #101

3-(4-((4-(Trifluoromethyl)phenyl)(5-(4-(trifluoromethyl)phenyl)-1H-indazol-1-yl)methyl)benzamido)propanoic acid

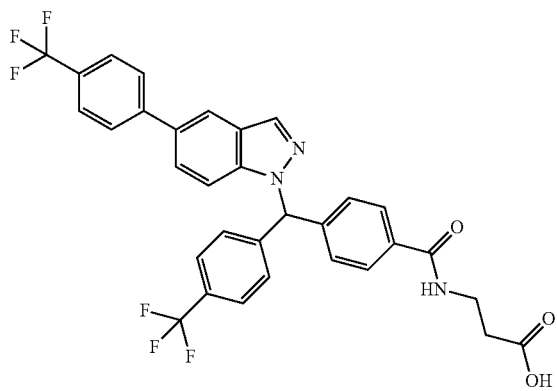 [SMILES: O=C(O)CCNC(=O)c1ccc(C(c2ccc(C(F)(F)F)cc2)n2ncc3cc(-c4ccc(C(F)(F)F)cc4)ccc32)cc1]

Step A:

Into a 500-mL round-bottom flask purged and maintained with an inert atmosphere of nitrogen, was placed a solution of 4-(trifluoromethyl)phenylboronic acid (3.72 g, 19.580 mmol, 1.50 equiv) in 1,4-dioxane (90 mL), methyl 4-(bromomethyl)benzoate (3.00 g, 13.100 mmol, 1.00 equiv), Pd(PPh$_3$)$_4$ (1.50 g, 1.300 mmol, 0.10 equiv), a solution of CsF (5.00 g, 32.890 mmol, 2.50 equiv) in water (45 mL). The resulting solution was stirred overnight at 105° C. in an oil bath and the reaction was then quenched by the addition of 200 mL of water. The resulting solution was extracted with 3×100 mL of EtOAc. The combined organic layers were washed with 3×200 mL of brine, dried over anhydrous sodium sulfate and concentrated under vacuum. The residue was applied onto a silica gel column and eluted with ethyl acetate/petroleum ether (50:1) to yield methyl 4-(4-(trifluoromethyl)benzyl)benzoate as a light yellow oil. LC-MS: (ES, m/z): 295.1 [M+H]+.

Step B:

Into a 250-mL round-bottom flask, was placed a solution of methyl 4-(4-(trifluoromethyl)benzyl)benzoate (1400 mg, 4.760 mmol, 1.00 equiv) in CCl$_4$ (150 mL), NBS (1530 mg, 8.600 mmol, 1.80 equiv), benzoyl peroxide (10 mg, 0.040 mmol). The resulting solution was heated to reflux for 2 hrs in an oil bath before the resulting mixture was cooled to room temperature. The solids were filtered out and the filtrate was concentrated under vacuum. The residue was applied onto a silica gel column and eluted with PE:EA (100:1) to yield methyl 4-(bromo(4-(trifluoromethyl)phenyl)methyl)benzoate as a yellow oil. LC-MS: (ES, m/z): 373.0 [M+H]$^+$.

Step C:

Into a 50-mL round-bottom flask, was placed a solution of methyl 4-(bromo(4-(trifluoromethyl)phenyl)methyl)benzoate (430 mg, 1.150 mmol, 1.50 equiv) in CH$_3$CN (30 mL), 5-(4-(trifluoromethyl)phenyl)-1H-indazole (200 mg, 0.760 mmol, 1.00 equiv), potassium carbonate (213 mg, 1.540 mmol, 2.00 equiv). The resulting solution was heated to reflux overnight in an oil bath. The reaction was then quenched by the addition of 25 mL of water. The resulting solution was extracted with 3×25 ml of ethyl acetate. The combined organic layers were washed with 3×25 mL of brine, dried over sodium sulfate and concentrated under vacuum. The residue was applied onto a silica gel column and eluted with PE:EA (20:1) to yield a mixture of methyl 4-((4-(trifluoromethyl)phenyl)(5-(4-(trifluoromethyl)phenyl)-1H-indazol-1-yl)methyl)benzoate (the N-1 substituted compound) as a first white solid LC-MS: (ES, m/z): 555.1 [M+H]$^+$;

and methyl 4-((4-(trifluoromethyl)phenyl)(5-(4-(trifluoromethyl)phenyl)-2H-indazol-2-yl)methyl)benzoate (the N-2substituted compound) as a second white solid. LC-MS: (ES, m/z): 555.1 [M+H]$^+$.

Step D:

Into a 50-mL round-bottom flask, was placed a solution of methyl 4-((4-(trifluoromethyl)phenyl)(5-(4-(trifluoromethyl)phenyl)-1H-indazol-1-yl)methyl)benzoate (300 mg, 0.540 mmol, 1.00 equiv) in tetrahydrofuran/MeOH (4/1 mL), a solution of LiOH.H$_2$O (227 mg, 5.400 mmol, 10.00 equiv) in water (1 mL) was added. The resulting solution was stirred for 3 h at room temperature. The pH value of the solution was adjusted to 2 with 2 N HCl. The resulting solution was extracted with 3×30 mL of ethyl acetate. The combined organic layers were washed with 3×50 mL of brine, dried over anhydrous sodium sulfate and concentrated under vacuum to yield 4-((4-(trifluoromethyl)phenyl)(5-(4-(trifluoromethyl)phenyl)-1H-indazol-1-yl)methyl)benzoic acid as a yellow oil. LC-MS: (ES, m/z): 541.1 [M+H]$^+$.

Step E:

Into a 50-mL round-bottom flask, was placed a solution of 4-((4-(trifluoromethyl)phenyl)(5-(4-(trifluoromethyl)phenyl)-1H-indazol-1-yl)methyl)benzoic acid (320 mg, 0.590 mmol, 1.00 equiv) in N,N-dimethylformamide (8 mL), ethyl 3-aminopropanoate hydrochloride (108.8 mg, 0.710 mmol, 1.20 equiv), HATU (450.4 mg, 1.190 mmol, 2.00 equiv), DIPEA (305.8 mg, 2.370 mmol, 4.00 equiv). The resulting solution was stirred overnight at room temperature and the reaction was then quenched by the addition of 15 mL of water. The resulting solution was extracted with 2×50 mL of ethyl acetate. The combined organic layers were washed with 3×25 mL of brine, dried over anhydrous sodium sulfate and concentrated under vacuum. The residue was purified by a silica gel column with PE:EA (20:1) to yield ethyl 3-(4-((4-(trifluoromethyl)phenyl)(5-(4-(trifluoromethyl)phenyl)-1H-indazol-1-yl)methyl)benzamido)propanoate as a white solid. LC-MS: (ES, m/z): 640.2 [M+H]$^+$.

Step F:

Into a 50-mL round-bottom flask, was placed a solution of ethyl 3-(4-((4-(trifluoromethyl)phenyl)(5-(4-(trifluoromethyl)phenyl)-1H-indazol-1-yl)methyl)benzamido)propanoate (150 mg, 0.230 mmol, 1.00 equiv) in tetrahydrofuran/MeOH (4/1 mL), a solution of LiOH.H$_2$O (99 mg, 2.300 mmol, 10.00 equiv) in water (1 mL) was added. The resulting solution was stirred for 2 h at room temperature. The pH value of the solution was adjusted to 2 with 2 N HCl. The resulting solution was extracted with 3×50 mL of ethyl acetate. The combined organic layers were washed with 3×50 mL of brine, dried over anhydrous sodium sulfate and concentrated under vacuum. The resulting residue was purified by Prep-HPLC with the following conditions (1 #-Waters 2767-1): Column, SunFire Prep C18, 5 um, 19*150 mm; mobile phase: water with 0.05% TFA and CH$_3$CN (50% CH$_3$CN up to 75% in 10 min, up to 100% in 2 min, down to 50% in 2 min); Detector, UV 254 nm to yield 3-(4-((4-(trifluoromethyl)phenyl)(5-(4-(trifluoromethyl)phenyl)-1H-indazol-1-yl)methyl)benzamido)propanoic acid as a white solid.

$^1$H NMR (300 MHz, CD$_3$OD) δ 8.13 (s, 1H), 8.13 (s, 1H), 7.67-7.88 (m, 10H), 7.44-7.46 (m, 3H), 7.35-7.38 (m, 2H), 3.63 (t, J=6.6 Hz, 2H), 2.66 (t, J=6.6 Hz, 2H). LC-MS: (ES, m/z) 612.2 [M+H]$^+$.

The following compound (as shown in Example 127 below) was similarly prepared according to the procedures described in Examples 126 STEP D-F, substituting methyl 4-((4-(trifluoromethyl)phenyl)(5-(4-(trifluoromethyl)phenyl)-2H-indazol-2-yl)methyl)benzoate (the N-2substituted compound, prepared as the second white solid in STEP C.

Example 127—Compound #66

3-(4-((4-(Trifluoromethyl)phenyl)(5-(4-(trifluoromethyl)phenyl)-2H-indazol-2-yl)methyl)benzamido)propanoic acid

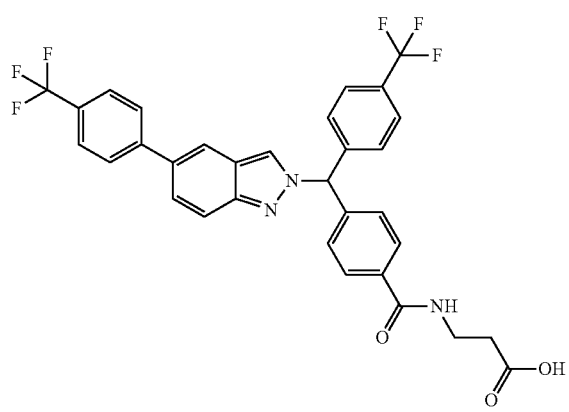 [SMILES: O=C(O)CCNC(=O)c1ccc(C(c2ccc(C(F)(F)F)cc2)n2cc3cc(-c4ccc(C(F)(F)F)cc4)ccc3n2)cc1]

$^1$H NMR (300 MHz, CD$_3$OD) δ 8.31 (s, 1H), 8.03 (s, 1H), 7.80-7.88 (m, 4H), 7.67-7.76 (m, 6H), 7.34-7.43 (m, 5H), 3.64 (t, J=6.7 Hz, 2H), 2.64 (t, J=6.7 Hz, 2H). LC-MS: (ES, m/z) 612.2 [M+H]+.

The following compound (as shown in Example 128 below) was similarly prepared according to the procedures described in Examples 5, substituting 1-methyl-4-(4,4,5,5-tetramethyl-1,3,2-dioxaborolan-2-yl)-1H-pyrazole in the Suzuki coupling step.

Example 128—Compound #12

3-(4-(3-Methyl-1-(5-(1-methyl-1H-pyrazol-4-yl)-1H-indazol-1-yl)butyl)benzamido)propanoic acid

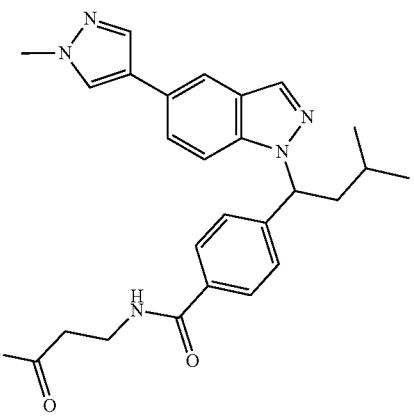

$^1$H NMR (CHLOROFORM-d) δ: 8.10 (s, 1H), 7.81-7.93 (m, 1H), 7.60-7.81 (m, 4H), 7.30-7.46 (m, 4H), 6.89 (br t, J=6.0 Hz, 1H), 5.72 (dd, J=10.0, 5.6 Hz, 1H), 4.00 (s, 3H), 3.68 (q, J=5.9 Hz, 2H), 2.60-2.72 (m, 3H), 2.01-2.12 (m, 1H), 1.44 (dquin, J=13.5, 6.7 Hz, 1H), 0.96 (t, J=6.5 Hz, 6H). MS (m/z): 460.2

Additional compounds of the present invention were similarly prepared according to the general synthesis schemes and examples described herein, selecting and substituting suitable reagents, starting materials and reactants, as would be readily recognized by those skilled in the art.

Biological Example 1—Prophetic Example

Inhibition $^{125}$I-Glucagon Binding to Membranes from HEK293 Cells Expressing the Human Glucagon Receptor (GCGR)

Full-length human GCGR (Accession Number: NM000160) subcloned into pcDNA3.1 is stably transfected into HEK293 cells (hGluc-1HEK) and maintained under G418 selection (500 μg/mL). Cell cultures are maintained in DMEM/F12 media supplemented with 10% FBS and 1% GlutaMax™ Supplement (Available from ThermoFisher Scientific, catalog #35050061). Membranes are prepared from these cells as follows: cells are harvested from T225 flasks and re-suspended in hypotonic lysis buffer, 50 mM HEPES pH 7.4 supplemented with Complete Protease inhibitors (Boehringer Mannheim, Indianapolis, Ind.). Cells are dounced 20 times on ice and spun at 700×g to remove nuclei and unlysed cells. The resulting pellet is re-suspended in hypotonic lysis buffer and the above step is repeated. Supernatants from the low speed centrifugation are combined and subsequently spun at 100K×g for 1 hr at 4° C. The resulting pellet is re-suspended in buffer containing 50 mM HEPES pH 7.4 and 10% sucrose, and the protein concentration is adjusted at 1 mg/mL as determined in the Pierce™ BCA Protein Assay Kit (Available from ThermoFisher Scientific, Catalog #23225). Membranes are aliquoted and stored at −80° C. The binding assay is performed by a filtration method in a 384 well format. Membranes at a final protein concentration of 6 μg/well are incubated with $^{125}$I-glucagon at 0.3 nM and in the presence of compound for 2 hours at room temperature in a total reaction volume of 40 μL per well. Assay buffer consists of 50 mM HEPES, pH 7.4, 5 mM $MgCl_2$, 1 mM $CaCl_2$ and 0.2% BSA. 30 μL of the reaction is then transferred to PEI treated filter plates and followed by filter aspiration. Plates are then washed 5× and allowed to dry at room temperature overnight. The next day the bottom of the plate is covered with seal tape and scintillant was added. Total counts retained by the filters are quantified with a Top Count instrument. $IC_{50}$'s are generated by using a non-linear regression macro driven in Excel and converted to $K_i$'s.

Biological Example 2

$IC_{50}$ Values in Cellular Functional Assays: cAMP Readout

Full-length human GCGR (Accession Number: NM000160) subcloned into pcDNA3.1 was stably transfected into HEK293 cells (hGluc-1HEK) and maintained under G418 selection (500 μg/mL). Cell cultures were maintained in DMEM/F12 media supplemented with 10% FBS and 1% GlutaMax™ Supplement (Available from ThermoFisher Scientific, catalog #35050061). Glucagon stimulated cAMP was quantified using LANCE technology as per manufacturer instructions. On the day of the experiment, spent media was removed and cells were washed with Hank's Buffered Saline solution (HBSS), and cells harvested with non-enzymatic cell dissociation solution, then washed once with HBSS. Cells were re-suspended in stimulation buffer at a concentration of 0.83×10$^6$ cells/ml and cAMP detection antibody was added. 6 μl/well of this solution was then dispensed in a 384 well plate (cell density 5000 cells/well). Test compound was serially diluted in DMSO and 50 nl were dispensed on top of the cell solution and allowed to incubate for 30 minutes. 6 μl of a 2× glucagon solution (final concentration in assay 100 pM) was then added and the reaction was terminated after 5 minutes with the addition of detection mix. The resulting mixture was incubated, protected from light for 1.5 h. cAMP levels were quantified by TR-FRET in an EnVision instrument against a known standard. $IC_{50}$'s were generated by using a non-linear regression macro driven in Excel and converted to $K_i$ values.

Representative compounds of the present invention were tested according to the procedures as described in Biological Example 2, with results as listed in Table 3, below.

TABLE 3

Biological Assay Results

| ID No. | Inhibition of cAMP Ki (μM) |
|---|---|
| 1 | 0.090, 0.159 |
| 2 | 0.700 |
| 4 | 1.100 |

TABLE 3-continued

Biological Assay Results

| ID No. | Inhibition of cAMP Ki (μM) |
|---|---|
| 5 | 0.600 |
| 7 | 0.800 |
| 8 | 0.059 |
| 9 | 0.190 |
| 10 | 0.285 |
| 11 | 0.175 |
| 12 | 2.300 |
| 13 | 0.076 |
| 14 | 0.447 |
| 15 | 0.265 |
| 16 | 0.065 |
| 17 | >5.2 |
| 18 | 0.014, 0.044 |
| 19 | 0.047, 0.049 |
| 20 | 0.025 |
| 21 | 0.092 |
| 22 | 0.800 |
| 23 | 0.144 |
| 24 | 0.114 |
| 25 | 0.102 |
| 26 | 0.045 |
| 27 | 0.105 |
| 28 | 0.260 |
| 29 | 0.060 |
| 30 | 0.044 |
| 31 | 0.120 |
| 32 | 0.330 |
| 33 | 0.070 |
| 34 | 0.086 |
| 36 | 0.430 |
| 37 | 0.062, 0.130 |
| 38 | 0.650 |
| 39 | 0.210 |
| 40 | 0.490 |
| 41 | 0.086 |
| 43 | 0.175 |
| 44 | 0.160 |
| 45 | 1.650 |
| 46 | 0.750 |
| 47 | 0.092 |
| 48 | 0.470 |
| 49 | 2.600 |
| 50 | 0.047 |
| 51 | 0.750 |
| 53 | 0.105 |
| 54 | 0.019 |
| 55 | 0.115 |
| 56 | 0.650 |
| 57 | 0.170 |
| 59 | 0.155 |
| 60 | 0.300 |
| 61 | 0.052 |
| 62 | 0.230 |
| 63 | 0.028 |
| 64 | 0.037 |
| 65 | 0.240 |
| 66 | 0.600 |
| 67 | 0.245 |
| 68 | 2.800 |
| 70 | 0.260 |
| 71 | 0.190 |
| 72 | >2.6 |
| 73 | 0.062 |
| 74 | 0.255 |
| 75 | 0.235 |
| 76 | 0.700 |
| 77 | 0.135 |
| 78 | 0.035 |
| 79 | 0.500 |
| 80 | 0.340 |
| 82 | >1.3 |
| 83 | 0.336 |
| 84 | 0.085 |
| 85 | 1.269 |
| 86 | 0.136 |
| 88 | 0.255 |

TABLE 3-continued

Biological Assay Results

| ID No. | Inhibition of cAMP Ki (μM) |
|---|---|
| 89 | 0.130 |
| 90 | 0.085 |
| 91 | 0.125 |
| 92 | 0.063 |
| 93 | 0.036 |
| 94 | 0.026 |
| 95 | 0.052 |
| 96 | 0.092 |
| 98 | 0.083 |
| 99 | 0.145 |
| 100 | 0.550 |
| 101 | 0.800 |
| 102 | 0.550 |
| 103 | 0.100 |
| 104 | 0.145 |
| 105 | 0.800 |
| 108 | 1.345 |
| 111 | >1.3 |
| 112 | 0.410 |
| 113 | 0.420 |
| 114 | 0.650 |
| 115 | 0.140 |
| 116 | 0.750 |
| 117 | 1.000 |
| 118 | 2.250 |
| 119 | >2.6 |
| 120 | 0.058 |
| 121 | 0.700 |
| 122 | 0.125 |
| 123 | >5.2 |
| 126 | 0.280 |
| 127 | 0.310 |
| 128 | 0.199 |
| 129 | 0.088 |
| 131 | 0.310 |
| 132 | 0.230 |
| 133 | 0.092 |
| 134 | 0.195 |
| 135 | 0.100 |
| 136 | 0.135 |
| 137 | 0.022 |
| 138 | 0.100 |
| 139 | 0.200 |
| 140 | 0.125 |
| 141 | 0.115 |
| 142 | 0.850 |
| 143 | 0.024 |
| 144 | 0.484 |
| 145 | 1.850 |
| 146 | 0.160 |
| 147 | 0.040 |
| 148 | 0.057 |
| 149 | 0.070 |
| 150 | 0.035 |
| 151 | 0.090 |
| 152 | 0.120 |
| 153 | 0.042 |
| 154 | 0.013 |
| 155 | 0.009 |
| 156 | 0.022 |
| 157 | 0.250 |
| 158 | 0.190 |
| 159 | 0.155 |
| 160 | 0.120 |
| 161 | 3.200 |
| 163 | 0.465 |
| 164 | >5.2 |
| 165 | 1.350 |
| 167 | 0.270 |
| 168 | 0.191 |
| 170 | 0.245 |
| 171 | 0.133 |
| 172 | 0.260 |
| 173 | 0.265 |
| 174 | 0.190 |
| 175 | 0.265 |
| 176 | 0.050 |
| 177 | 0.485 |
| 178 | 0.022 |
| 179 | 0.024 |
| 180 | 0.025, 0.020, 0.025 |
| 182 | 0.070 |
| 183 | 0.350 |
| 184 | 0.071 |
| 185 | 0.430 |
| 186 | 0.275 |
| 187 | 0.030 |
| 188 | 0.165 |
| 189 | 0.199 |
| 190 | 0.025 |
| 191 | 0.035 |
| 192 | 0.022 |
| 193 | 0.155 |
| 194 | 0.210 |
| 195 | 0.042 |
| 196 | 0.032 |
| 197 | 0.015 |
| 198 | 0.060 |
| 199 | 0.310 |
| 200 | 0.080 |
| 201 | 0.030 |
| 202 | 1.100 |
| 203 | 0.075 |
| 204 | 0.021 |
| 205 | 0.057 |
| 207 | 0.017 |
| 208 | 0.175 |
| 209 | 0.361 |
| 210 | 0.365 |
| 211 | 0.085 |
| 212 | 0.090 |
| 213 | 0.075 |
| 214 | 0.032 |
| 215 | 0.210 |
| 219 | >5.2 |
| 220 | 0.120 |
| 221 | 2.900 |
| 222 | 0.800 |
| 223 | 0.950 |
| 224 | 0.110 |
| 225 | 0.150 |
| 226 | 0.242 |
| 227 | 0.330 |
| 228 | 0.130 |
| 229 | 1.550 |
| 230 | 0.280 |
| 231 | 0.095 |
| 232 | 0.019 |
| 233 | 0.024 |
| 234 | 0.275 |
| 235 | >5.2 |
| 236 | 0.012 |
| 237 | 0.160 |
| 238 | 0.210 |
| 239 | 0.260 |
| 240 | 0.200 |
| 241 | 0.042 |
| 242 | 0.065 |
| 243 | 2.400 |
| 244 | 0.200 |
| 245 | 0.210 |
| 246 | >5.2 |
| 247 | 0.037 |
| 248 | 0.025 |
| 249 | 0.042 |
| 250 | 0.055 |
| 251 | 0.650 |
| 252 | 0.271 |
| 253 | 0.014 |
| 254 | 0.090 |
| 255 | 0.550 |
| 256 | 0.200 |

TABLE 3-continued

Biological Assay Results

| ID No. | Inhibition of cAMP Ki (μM) |
|---|---|
| 257 | 0.026 |
| 258 | 0.065 |
| 259 | 0.037 |
| 260 | 0.135 |
| 261 | 0.105 |
| 262 | NT* |
| 263 | NT* |

*NT indicates that the compound was not tested.

Biological Example 3

Glucagon Challenge In Vivo Assay Measuring Blood Glucose

The efficacy of a glucagon receptor antagonist was evaluated using a normal dog glucagon challenge test. Male beagle dogs were overnight fasted prior to the study. Test compound (at 3 mg/kg and 10 mg/kg for Compound #196 and at 10 mg/kg for Compounds #180, #248 and #253) or vehicle (0.5% hydroxypropyl methylcellulose) was dosed via oral gavage. Ninety minutes later, the dogs (1.5 years old, ~9 Kg) were submitted to a glucagon challenge test by a single intramuscular injection of glucagon (Glucagon, rDNA origin, Eli Lilly, Indianapolis, Ind.) at dose of 5 g/kg. Blood glucose levels were determined at times −10 min, 0 min (on challenge), 10 min, 20 min, 30 min, and 60 min after glucagon injection.

The measured blood glucose levels showed that, compared with vehicle treated group, treatment with Compound #180 markedly reduced blood glucose levels during glucagon challenge time and this effect last for more than 60 min. Compound #196, Compound #180, and Compound #253 at 10 mg/kg significantly inhibited GCG-mediated increases in blood glucose (23.9%, 28.9%, and 17.1% inhibition vs vehicle, respectively). Compound #248 exhibited only 15% inhibition versus vehicle treated animals. Compound #196 at 3 mg/kg had a tendency effect on GCG-mediated increases in blood glucose (measured as 5.9% inhibition).

Formulation Example 1—Prophetic Example

Solid, Oral Dosage Form

As a specific embodiment of an oral composition, 100 mg of the Compound #253 prepared as in Example 101 is formulated with sufficient finely divided lactose to provide a total amount of 580 to 590 mg to fill a size O hard gel capsule.

Formulation Example 2—Prophetic Example

Solid, Oral Dosage Form

As a specific embodiment of an oral composition, 100 mg of the Compound #180 prepared as in Example 110 is formulated with sufficient finely divided lactose to provide a total amount of 580 to 590 mg to fill a size O hard gel capsule.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

We claim:

1. A method for making a pharmaceutical composition the method comprising mixing a compound of formula (II)

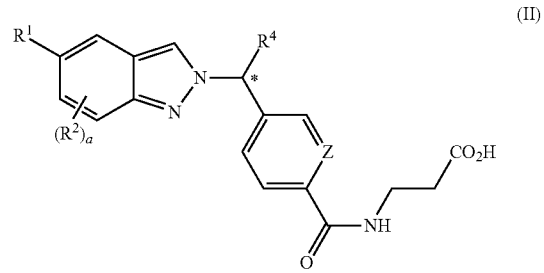

wherein
$R^1$ is selected from the group consisting of phenyl, —($C_{1-2}$alkyl)-phenyl, naphthyl, thienyl, benzofuranyl, benzothienyl, indazolyl, quinolinyl, pyrazolyl and pyridyl;
wherein the phenyl, naphthyl, thienyl, benzofuranyl, benzothienyl, indazolyl, quinolinyl, pyrazolyl or pyridyl whether alone or as part of a substituent group is optionally substituted with one to more substituents independently selected from the group consisting of halogen, $C_{1-6}$alkyl, fluorinated $C_{1-4}$alkyl, $C_{1-4}$alkoxy and fluorinated $C_{1-4}$alkoxy;
a is in integer from 0 to 2;
each $R^2$ is independently selected from the group consisting of halogen, $C_{1-4}$alkyl, fluorinated $C_{1-4}$alkyl, $C_{1-4}$alkoxy and fluorinated $C_{1-4}$alkoxy;
$R^4$ is selected from the group consisting of $C_{1-6}$alkyl, fluorinated $C_{1-4}$alkyl, —($C_{1-2}$alkyl)-O—($C_{1-4}$alkyl), $C_{3-6}$cycloalkyl, —($C_{1-2}$alkyl)-$C_{3-6}$cycloalkyl, phenyl and —($C_{1-2}$alkyl)-phenyl;
wherein the phenyl, whether alone or as part of a substituent group is optionally substituted with one or more substituents independently selected from the group consisting of halogen, $C_{1-6}$alkyl, fluorinated $C_{1-4}$alkyl, $C_{1-4}$alkoxy and fluorinated $C_{1-4}$alkoxy;
Z is selected from the group consisting of CH and N;
or a stereoisomer or pharmaceutically acceptable salt thereof;
and a pharmaceutically acceptable carrier.

2. The method of claim 1, wherein
$R^1$ is selected from the group consisting of phenyl, —($C_{1-2}$alkyl)-phenyl, naphthyl, thienyl, benzofuranyl, benzothienyl, indazolyl, quinolinyl, pyrazolyl and pyridyl;
wherein the phenyl, naphthyl, thienyl, benzofuranyl, benzothienyl, indazolyl, quinolinyl, pyrazolyl or pyridyl whether alone or as part of a substituent group is optionally substituted with one to two substituents independently selected from the group consisting of halogen, $C_{1-6}$alkyl, fluorinated $C_{1-2}$alkyl, $C_{1-4}$alkoxy and fluorinated $C_{1-2}$alkoxy;
a is in integer from 0 to 2;
each $R^2$ is independently selected from the group consisting of halogen, $C_{1-2}$alkyl, fluorinated $C_{1-2}$alkyl, $C_{1-2}$alkoxy and fluorinated $C_{1-2}$alkoxy;
$R^4$ is selected from the group consisting of $C_{1-6}$alkyl, fluorinated $C_{1-4}$alkyl, —($C_{1-2}$alkyl)-O—($C_{1-4}$alkyl), $C_{3-6}$cycloalkyl, —($C_{1-2}$alkyl)-$C_{3-6}$cycloalkyl, phenyl and —($C_{1-2}$alkyl)-phenyl;

wherein the phenyl, whether alone or as part of a substituent group is optionally substituted with one or to two substituents independently selected from the group consisting of halogen, $C_{1-6}$alkyl, fluorinated $C_{1-2}$alkyl, $C_{1-4}$alkoxy and fluorinated $C_{1-2}$alkoxy;

Z is selected from the group consisting of CH and N;

or a stereoisomer or pharmaceutically acceptable salt thereof.

3. The method of claim 1, wherein $R^1$ is selected from the group consisting of phenyl, naphthyl, thienyl, benzofuranyl, benzothienyl, pyrazolyl, indazolyl and quinolinyl;

wherein the phenyl, naphthyl, benzofuranyl, benzothienyl, pyrazolyl or indazolyl is optionally substituted with one to two substituents independently selected from the group consisting of halogen, $C_{1-6}$alkyl, fluorinated $C_{1-2}$alkyl, $C_{1-2}$alkoxy and fluorinated $C_{1-2}$alkoxy;

a is an integer from 0 to 1;

$R^2$ is selected from the group consisting of halogen, $C_{1-2}$alkyl, fluorinated $C_{1-2}$alkyl and $C_{1-2}$alkoxy;

$R^4$ is selected from the group consisting of $C_{1-6}$alkyl, fluorinated $C_{1-6}$alkyl, —($C_{1-2}$alkyl)-O—($C_{1-2}$alkyl), $C_{3-6}$cycloalkyl, —($C_{1-2}$alkyl)-$C_{3-6}$cycloalkyl, phenyl and ($C_{1-2}$alkyl)-phenyl;

wherein the phenyl is optionally substituted with a substituent selected from the group consisting of halogen, $C_{1-2}$alkyl or fluorinated $C_{1-2}$alkyl;

Z is selected from the group consisting of CH and N;

or a stereoisomer or pharmaceutically acceptable salt thereof.

4. The method of claim 1, wherein $R^1$ is selected from the group consisting of 4-t-butyl-phenyl, 2,4-dimethyl-phenyl, 4-trifluoromethyl-phenyl, 2,4-dichloro-phenyl, 2-chloro-4-methyl-phenyl, 2-methyl-4-chloro-phenyl, 2-chloro-4-trifluoromethyl-phenyl, 2-methyl-4-trifluoromethyl-phenyl, 3-chloro-4-trifluoromethyl-phenyl, naphth-2-yl, 6-methoxy-naphth-2-yl, thien-3-yl, benzofuran-2-yl, benzothien-2-yl, 5-fluoro-benzothien-2-yl, 6-fluoro-benzothien-2-yl, 5-methyl-benzothien-2-yl, 1-isopentyl-pyrazol-4-yl, 1-methyl-indazol-5-yl, 1-methyl-indazol-6-yl, quinolin-3-yl and quinolin-6-yl;

a is an integer from 0 to 1;

$R^2$ is selected from the group consisting of 4-chloro, 4-methyl, 4-methoxy, 4-ethoxy, 4-trifluoromethyl, 6-chloro, 6-methyl and 7-methyl;

$R^4$ is selected from the group consisting of methyl, n-propyl, isobutyl, n-pentyl, isopentyl, 2,2-dimethyl-n-propyl, n-hexyl, 3,3,3-trifluoro-n-propyl, 3,3,4,4,4-pentafluoro-n-butyl, 2-fluoro-2-methyl-propyl, methoxy-ethyl-, cyclopropyl-methyl, cyclobutyl-methyl-, cyclobutyl-ethyl, cyclopentyl-methyl-, cyclopentyl-ethyl, cyclohexyl, cyclohexyl-methyl-, cyclohexyl-ethyl-, 4-trifluoromethyl-phenyl, phenylethyl- and 4-chloro-phenylethyl-;

Z is selected from the group consisting of CH and N;

or a stereoisomer or pharmaceutically acceptable salt thereof.

5. The method of claim 4, wherein $R^1$ is selected from the group consisting of 4-t-butyl-phenyl, 2,4-dimethyl-phenyl, 4-trifluoromethyl-phenyl, 2,4-dichloro-phenyl, 2-chloro-4-methyl-phenyl, 2-methyl-4-chloro-phenyl, 2-chloro-4-trifluoromethyl-phenyl, 2-methyl-4-trifluoromethyl-phenyl, 3-chloro-4-trifluoromethyl-phenyl, benzofuran-2-yl, benzothien-2-yl, 5-fluoro-benzothien-2-yl and 6-fluoro-benzothien-2-yl;

a is an integer from 0 to 1;

$R^2$ is selected from the group consisting of 4-chloro, 4-methyl, 4-methoxy, 4-ethoxy, 6-chloro and 6-methyl;

$R^4$ is selected from the group consisting of n-propyl, isobutyl, n-pentyl, isopentyl, 2,2-dimethyl-n-propyl, n-hexyl, 3,3,3-trifluoro-n-propyl, 3,3,4,4,4-pentafluoro-n-butyl, 2-fluoro-2-methyl-propyl, cyclopropyl-methyl, cyclobutyl-methyl-, cyclobutyl-ethyl, cyclopentyl-methyl-, cyclopentyl-ethyl, cyclohexyl, cyclohexyl-methyl-, cyclohexyl-ethyl, phenylethyl- and 4-chloro-phenylethyl-;

Z is selected from the group consisting of CH and N;

or a stereoisomer or pharmaceutically acceptable salt thereof.

6. A compound of claim 4, wherein $R^1$ is selected from the group consisting of 4-t-butyl-phenyl, 2,4-dimethyl-phenyl, 4-trifluoromethyl-phenyl, 2,4-dichloro-phenyl, 2-chloro-4-methyl-phenyl, 2-methyl-4-chloro-phenyl, 2-chloro-4-trifluoromethyl-phenyl, 2-methyl-4-trifluoromethyl-phenyl, 3-chloro-4-trifluoromethyl-phenyl, benzofuran-2-yl, benzothien-2-yl and 5-fluoro-benzothien-2-yl;

a is an integer from 0 to 1;

$R^2$ is selected from the group consisting of 4-chloro, 4-methyl, 4-methoxy, 4-ethoxy, 6-chloro and 6-methyl;

$R^4$ is selected from the group consisting of isobutyl, 2,2-dimethyl-n-propyl, n-hexyl, 3,3,3-trifluoro-n-propyl, cyclobutyl-methyl-, cyclopentyl-methyl-, cyclohexyl, cyclohexyl-methyl-, cyclohexyl-ethyl and 4-chloro-phenylethyl;

Z is selected from the group consisting of CH and N;

or a stereoisomer or pharmaceutically acceptable salt thereof.

7. The method of claim 4, wherein $R^1$ is selected from the group consisting of 4-t-butyl-phenyl, 2,4-dimethyl-phenyl, 4-trifluoromethyl-phenyl, 2,4-dichloro-phenyl, 2-methyl-4-chloro-phenyl, 2-chloro-4-trifluoromethyl-phenyl and 2-methyl-4-trifluoromethyl-phenyl;

a is an integer from 0 to 1;

$R^2$ is selected from the group consisting of 4-chloro, 4-methyl, 4-methoxy, 4-ethoxy, 6-chloro and 6-methyl;

$R^4$ is selected from the group consisting of isobutyl, 2,2-dimethyl-n-propyl, n-hexyl, 3,3,3-trifluoro-n-propyl, cyclohexyl-methyl- and cyclohexyl-ethyl;

Z is selected from the group consisting of CH and N;

or a stereoisomer or pharmaceutically acceptable salt thereof.

8. The method of claim 4, wherein $R^1$ is selected from the group consisting of 2,4-dichloro-phenyl, 2-methyl-4-chloro-phenyl, 2-chloro-4-trifluoromethyl-phenyl and 2-methyl-4-trifluoromethyl-phenyl;

a is an integer from 0 to 1;

$R^2$ is selected from the group consisting of 4-chloro, 4-methyl, 4-methoxy, 4-ethoxy and 6-methyl;

$R^4$ is selected from the group consisting of isobutyl and n-hexyl;

Z is selected from the group consisting of CH and N;

and stereoisomers and pharmaceutically acceptable salts thereof.

9. The method of claim 4, wherein the compound is selected from the group consisting of 3-[[4-[(1R)-1-[5-[2-chloro-4-(trifluoromethyl)phenyl]-4-methoxy-indazol-2-yl]-3-methyl-butyl]benzoyl]amino]propanoic acid;

3-[[4-[(1S)-1-[5-[2-chloro-4-(trifluoromethyl)phenyl]-4-methyl-indazol-2-yl]-3-methyl-butyl]benzoyl]amino]propanoic acid;

3-[[4-[(1S)-3-methyl-1-[6-methyl-5-[2-methyl-4-(trifluoromethyl)phenyl]indazol-2-yl]butyl]benzoyl]amino]propanoic acid;

and stereoisomers and pharmaceutically acceptable salts thereof.

10. The method of claim 1, wherein the carrier is selected from the group consisting of binders, suspending agents, lubricants, flavorants, sweeteners, preservatives, dyes, and coatings.

11. The method of claim 10, wherein said pharmaceutical composition is in an oral form.

12. The method of claim 11, wherein the oral form is a pill, tablet, caplet, capsule, granule, powder, solution, syrup, elixir, emulsion, or suspension.

* * * * *